US012129265B2

(12) United States Patent
Zaid et al.

(10) Patent No.: US 12,129,265 B2
(45) Date of Patent: Oct. 29, 2024

(54) THERAPEUTIC AGENTS AND USES THEREOF

(71) Applicant: Ankh Life Sciences Limited, Dublin (IE)

(72) Inventors: Gene H. Zaid, Hutchinson, KS (US); Thomas W. Burgoyne, Lake Zurich, IL (US)

(73) Assignee: Ankh Life Sciences Limited, Dublin (IE)

( * ) Notice: Subject to any disclaimer, the term of this patent is extended or adjusted under 35 U.S.C. 154(b) by 854 days.

(21) Appl. No.: 17/108,898

(22) Filed: Dec. 1, 2020

(65) Prior Publication Data

US 2022/0033417 A1 Feb. 3, 2022

Related U.S. Application Data

(63) Continuation of application No. 16/935,079, filed on Jul. 21, 2020, now abandoned.

(51) Int. Cl.
*C07D 519/00* (2006.01)
*A61P 35/00* (2006.01)

(52) U.S. Cl.
CPC ............ *C07D 519/00* (2013.01); *A61P 35/00* (2018.01)

(58) Field of Classification Search
CPC .. C07D 519/00; C07D 215/06; C07D 215/14; C07D 215/20; C07D 217/20; A61P 35/00
See application file for complete search history.

(56) References Cited

U.S. PATENT DOCUMENTS

| | | |
|---|---|---|
| 3,542,799 A | 11/1970 | Shavel et al. |
| 3,937,709 A | 2/1976 | Sevenet et al. |
| 4,011,330 A | 3/1977 | Giudicelli et al. |
| 4,631,323 A | 12/1986 | Jenekhe |
| 4,808,718 A | 2/1989 | Hartman et al. |
| 4,933,345 A | 6/1990 | Huth et al. |
| 5,095,020 A | 3/1992 | Hulkenberg et al. |
| 5,300,645 A | 4/1994 | Audia et al. |
| 5,332,746 A | 7/1994 | Hamminga et al. |
| 5,350,750 A | 9/1994 | Huth et al. |
| 5,576,460 A | 11/1996 | Buchwald et al. |

(Continued)

FOREIGN PATENT DOCUMENTS

| | | |
|---|---|---|
| CN | 101139347 | 3/2008 |
| CN | 101367802 | 2/2009 |

(Continued)

OTHER PUBLICATIONS

Aggarwal et al. "Anticancer Potential of Curcumin: Preclinical and Clinical Studies." Anticancer Research 23 (2003): 363-398.

(Continued)

*Primary Examiner* — Savitha M Rao
(74) *Attorney, Agent, or Firm* — Hovey Williams LLP; Crissa A. Cook

(57) ABSTRACT

Human therapeutic compositions are provided, comprising compounds including a plurality of fused polycyclic moieties and a linker moiety. In certain embodiments, the compounds are the reaction products of aldehyde and harmaline components. The compositions exhibit anti-cancer properties, especially against lymphoma, leukemia, pancreatic, endometrial, ovarian, gastric, breast, renal, cervical, head and neck, and myeloma cell lines.

7 Claims, 75 Drawing Sheets

(56) References Cited

U.S. PATENT DOCUMENTS

| | | |
|---|---|---|
| 5,604,236 A | 2/1997 | Jakubowski et al. |
| 5,792,799 A | 8/1998 | Sherman-Gold |
| 5,861,409 A | 1/1999 | Audia et al. |
| 6,114,350 A | 9/2000 | Randall et al. |
| 6,218,434 B1 | 4/2001 | Crooks et al. |
| 6,316,449 B1 | 11/2001 | Bratton et al. |
| 6,323,366 B1 | 11/2001 | Wolfe et al. |
| 6,350,757 B1 | 2/2002 | Goldstein et al. |
| 6,462,047 B1 | 10/2002 | Bombrun et al. |
| 6,664,272 B2 | 12/2003 | Snyder et al. |
| 6,720,331 B2 | 4/2004 | Yeh et al. |
| 6,790,979 B2 | 9/2004 | Lee et al. |
| 6,849,619 B2 | 2/2005 | Robichtaud et al. |
| 7,008,649 B2 | 3/2006 | Bessette et al. |
| 7,084,322 B2 | 8/2006 | Back et al. |
| 7,125,886 B2 | 10/2006 | Zhang et al. |
| 7,396,546 B2 | 7/2008 | Rosenbloom |
| 7,425,650 B1 | 9/2008 | Chuang |
| 7,507,425 B2 | 3/2009 | Rosenbloom |
| 7,550,479 B2 | 6/2009 | Orme et al. |
| 7,616,538 B2 | 11/2009 | Yang |
| 7,732,437 B2 | 6/2010 | Tegtmeier et al. |
| 7,955,718 B2 | 6/2011 | Kambe et al. |
| 7,981,939 B2 | 7/2011 | Zhou et al. |
| 7,998,971 B2 | 8/2011 | Barlow et al. |
| 8,039,025 B1 | 10/2011 | Zaid et al. |
| 8,076,352 B2 | 12/2011 | Cao et al. |
| 8,198,323 B2 | 6/2012 | Lee et al. |
| 8,268,854 B2 | 9/2012 | Cook et al. |
| 8,380,157 B2 | 2/2013 | Zhang et al. |
| 8,391,959 B2 | 3/2013 | Mardor et al. |
| 8,410,177 B2 | 4/2013 | Namboothiri et al. |
| 8,450,307 B2 | 5/2013 | Sargent et al. |
| 8,546,422 B2 | 10/2013 | Leblanc et al. |
| 8,557,991 B2 | 10/2013 | Muller et al. |
| 8,586,629 B2 | 11/2013 | De Groote |
| 8,691,801 B2 | 4/2014 | Guzman et al. |
| 8,735,154 B2 | 5/2014 | Berkland et al. |
| 8,741,853 B2 | 6/2014 | Steliou |
| 8,748,473 B2 | 6/2014 | McKnight et al. |
| 8,772,265 B2 | 7/2014 | Neven et al. |
| 8,772,311 B2 | 7/2014 | Wu et al. |
| 8,802,161 B2 | 8/2014 | Mazzio et al. |
| 8,815,840 B2 | 8/2014 | Purandare et al. |
| 8,841,264 B2 | 9/2014 | Raederstorff et al. |
| 8,952,158 B2 | 2/2015 | Ohmoto et al. |
| 9,006,246 B2 | 4/2015 | Ohata et al. |
| 9,034,865 B2 | 5/2015 | Chakravarty et al. |
| 9,034,880 B2 | 5/2015 | Hung et al. |
| 9,162,980 B2 | 10/2015 | McKnight et al. |
| 9,168,247 B2 | 10/2015 | Frederick et al. |
| 9,180,155 B2 | 11/2015 | Babish et al. |
| 9,193,957 B2 | 11/2015 | Chen et al. |
| 9,271,971 B2 | 3/2016 | Jain et al. |
| 9,290,476 B2 | 3/2016 | Leonard et al. |
| 9,402,834 B2 | 8/2016 | Zaid et al. |
| 9,404,130 B2 | 8/2016 | Ajkumar et al. |
| 9,593,115 B2 | 3/2017 | Barawkar et al. |
| 9,725,449 B2 | 8/2017 | Norris et al. |
| 9,907,786 B2 | 3/2018 | Zaid et al. |
| 10,011,614 B2 | 7/2018 | Wang et al. |
| 10,047,049 B2 | 8/2018 | Barel et al. |
| 10,072,009 B2 | 9/2018 | Bharate et al. |
| 10,086,000 B2 | 10/2018 | Fischer et al. |
| 10,092,550 B2 | 10/2018 | Zaid et al. |
| 10,125,114 B2 | 11/2018 | Bradner et al. |
| 10,138,242 B2 | 11/2018 | Sattler et al. |
| 10,442,803 B2 | 10/2019 | Rodgers et al. |
| 10,461,256 B2 | 10/2019 | Choi et al. |
| 10,471,049 B2 | 11/2019 | Zaid et al. |
| 10,487,086 B2 | 11/2019 | Corte et al. |
| 10,507,200 B1 | 12/2019 | Zaid et al. |
| 10,508,108 B2 | 12/2019 | Fischer et al. |
| 10,526,332 B2 | 1/2020 | Xu et al. |
| 10,532,043 B2 | 1/2020 | Zaid et al. |
| 10,576,067 B2 | 3/2020 | Zaid et al. |
| 10,577,324 B2 | 3/2020 | Wang et al. |
| 10,647,718 B2 | 5/2020 | Sauvageau et al. |
| 10,744,124 B2 | 8/2020 | Zaid et al. |
| 10,751,330 B2 | 8/2020 | Zaid et al. |
| 10,947,253 B2 * | 3/2021 | Blagg ............... C07D 215/06 |
| 2006/0167259 A1 | 7/2006 | Chao et al. |
| 2006/0217410 A1 | 9/2006 | Chen et al. |
| 2007/0027178 A1 | 2/2007 | Lee |
| 2007/0060644 A1 | 3/2007 | Vander Jagt et al. |
| 2007/0085059 A1 | 4/2007 | Mora-Gutierrez et al. |
| 2007/0142462 A1 | 6/2007 | Kennedy |
| 2008/0069899 A1 | 3/2008 | Jossang born Yanagida |
| 2008/0113042 A1 | 5/2008 | Chu et al. |
| 2008/0221221 A1 | 9/2008 | Zhou et al. |
| 2008/0241287 A9 | 10/2008 | Rosenbloom |
| 2009/0011991 A1 | 1/2009 | Shoji et al. |
| 2009/0087501 A1 | 4/2009 | Cummins |
| 2009/0093517 A1 | 4/2009 | Graulich et al. |
| 2009/0220624 A1 | 9/2009 | Larkins |
| 2009/0227619 A1 | 9/2009 | Wu et al. |
| 2010/0113478 A1 | 5/2010 | Gant et al. |
| 2010/0172916 A1 | 7/2010 | Gant et al. |
| 2010/0234396 A1 | 9/2010 | Fecher et al. |
| 2010/0234467 A1 | 9/2010 | Ottinger et al. |
| 2011/0002855 A1 | 1/2011 | Caldwell et al. |
| 2011/0067123 A1 | 3/2011 | Andersen et al. |
| 2011/0224205 A1 | 9/2011 | Chen et al. |
| 2011/0245503 A1 | 10/2011 | Santos et al. |
| 2011/0250129 A1 | 10/2011 | Pomper et al. |
| 2011/0287085 A1 | 11/2011 | Kurzrock et al. |
| 2011/0301130 A1 | 12/2011 | Melzer et al. |
| 2012/0053208 A1 | 3/2012 | Li et al. |
| 2012/0058208 A1 | 3/2012 | Jacob |
| 2012/0108500 A1 | 5/2012 | Sakane et al. |
| 2012/0108556 A1 | 5/2012 | Zaid et al. |
| 2012/0136154 A1 | 5/2012 | Hwang et al. |
| 2012/0237455 A1 | 9/2012 | Trivedi et al. |
| 2012/0251516 A1 | 10/2012 | Kenyon et al. |
| 2013/0116219 A1 | 5/2013 | Ellis et al. |
| 2013/0131127 A1 | 5/2013 | Chen et al. |
| 2013/0137705 A1 | 5/2013 | Jain et al. |
| 2013/0165470 A1 | 6/2013 | Isfort et al. |
| 2013/0190328 A1 | 7/2013 | Jain et al. |
| 2013/0231360 A1 | 9/2013 | Higgins et al. |
| 2013/0316027 A1 | 11/2013 | Chakrabortty et al. |
| 2014/0005220 A9 | 1/2014 | Frederick et al. |
| 2014/0024610 A1 | 1/2014 | Pisani et al. |
| 2014/0080832 A1 | 3/2014 | Patterson et al. |
| 2014/0107050 A1 | 4/2014 | Kim et al. |
| 2014/0221426 A1 | 8/2014 | Gerk et al. |
| 2014/0257170 A1 | 9/2014 | Diaz Alperi et al. |
| 2014/0271923 A1 | 9/2014 | Reid |
| 2014/0288068 A1 | 9/2014 | Ellies et al. |
| 2014/0295049 A1 | 10/2014 | Ragot et al. |
| 2014/0308212 A1 | 10/2014 | Zhang |
| 2015/0037389 A1 | 2/2015 | Ragot et al. |
| 2015/0315188 A1 | 11/2015 | Protter et al. |
| 2016/0031884 A1 | 2/2016 | Ohata et al. |
| 2016/0039845 A1 | 2/2016 | Wang et al. |
| 2016/0106687 A1 | 4/2016 | Zaid et al. |
| 2016/0106721 A1 | 4/2016 | Zaid et al. |
| 2016/0106722 A1 | 4/2016 | Zaid et al. |
| 2016/0159787 A1 | 6/2016 | Linz et al. |
| 2016/0213727 A1 | 7/2016 | Rohlfsen |
| 2016/0318928 A1 | 11/2016 | Norris et al. |
| 2016/0326166 A1 | 11/2016 | Wang et al. |
| 2017/0042865 A1 | 2/2017 | Zaid et al. |
| 2017/0042866 A1 | 2/2017 | Zaid et al. |
| 2017/0042867 A1 | 2/2017 | Zaid et al. |
| 2017/0105975 A1 | 4/2017 | Zaid et al. |
| 2017/0105976 A1 | 4/2017 | Zaid et al. |
| 2017/0216222 A1 | 8/2017 | Zaid et al. |
| 2017/0369507 A1 | 12/2017 | Christian et al. |
| 2018/0022747 A1 | 1/2018 | Meng et al. |
| 2018/0078535 A1 | 3/2018 | Zaid et al. |
| 2018/0155299 A1 | 6/2018 | Birudukota et al. |
| 2018/0251459 A1 | 9/2018 | Hubin et al. |
| 2018/0291020 A1 | 10/2018 | Haddach |

(56) References Cited

U.S. PATENT DOCUMENTS

| | | | |
|---|---|---|---|
| 2018/0297999 | A1 | 10/2018 | Boloor et al. |
| 2018/0319804 | A1 | 11/2018 | Lim et al. |
| 2019/0152970 | A1 | 5/2019 | Labadie et al. |
| 2019/0231756 | A1 | 8/2019 | Zaid et al. |
| 2019/0248785 | A1 | 8/2019 | Takahashi et al. |
| 2019/0292183 | A1 | 9/2019 | Zhang et al. |
| 2020/0055853 | A1 | 2/2020 | Ellies et al. |
| 2020/0085793 | A1 | 3/2020 | Crew et al. |
| 2020/0123167 | A1 | 4/2020 | Jain et al. |
| 2020/0140438 | A1 | 5/2020 | Blayo et al. |
| 2020/0147061 | A1 | 5/2020 | Zaid et al. |

FOREIGN PATENT DOCUMENTS

| | | |
|---|---|---|
| CN | 101475460 | 7/2009 |
| CN | 101434525 | 7/2012 |
| CN | 102640848 | 8/2012 |
| CN | 102675416 | 9/2012 |
| CN | 102796124 | 11/2012 |
| CN | 102886014 | 1/2013 |
| CN | 102993018 | 3/2013 |
| CN | 103394045 | 11/2013 |
| CN | 103536750 | 1/2014 |
| CN | 103656498 | 3/2014 |
| CN | 106977515 | 4/2017 |
| CN | 107880040 | 4/2018 |
| CN | 108191863 | 6/2018 |
| EP | 1336602 | 8/2003 |
| EP | 1368046 | 12/2003 |
| EP | 1634881 | 3/2006 |
| EP | 2050747 | 4/2009 |
| EP | 2151441 | 2/2010 |
| EP | 3091015 | 11/2016 |
| FR | 2869540 | 11/2005 |
| GB | 2304712 | 11/1995 |
| IN | 200100767 | 7/2005 |
| JP | S58162520 | 9/1983 |
| JP | 2002020278 | 1/2002 |
| JP | 2004075666 | 3/2004 |
| JP | 2008516954 | 5/2008 |
| NZ | 522055 | 7/2003 |
| TW | 201119663 | 6/2011 |
| WO | 2001085736 | 11/2001 |
| WO | 2002074319 | 9/2002 |
| WO | 2004106335 | 3/2006 |
| WO | 2005115470 | 3/2007 |
| WO | 2007073646 | 7/2007 |
| WO | 2007101863 | 9/2007 |
| WO | 2008053319 | 5/2008 |
| WO | 2008150899 | 12/2008 |
| WO | 2009003147 | 12/2008 |
| WO | 2009047298 | 4/2009 |
| WO | 2009051470 | 6/2009 |
| WO | 2009148623 | 12/2009 |
| WO | 2011041907 | 4/2011 |
| WO | 2011070299 | 6/2011 |
| WO | 2011133795 | 10/2011 |
| WO | 2013048355 | 4/2013 |
| WO | 2014153203 | 9/2014 |
| WO | 2014168925 | 10/2014 |
| WO | 2015006646 | 1/2015 |
| WO | 2015101206 | 7/2015 |
| WO | 2016064676 | 4/2016 |
| WO | 2016181220 | 11/2016 |
| WO | 2017146220 | 8/2017 |
| WO | 2020193996 | 10/2020 |
| WO | 2020214240 | 10/2020 |
| WO | 2021026016 | 2/2021 |
| WO | 2021191864 | 9/2021 |

OTHER PUBLICATIONS

Al-Shamma, et al. "Antimicrobial agents from higher plants." J. Natural Products 44.6 (1981): 745-747.

Ali et al. "In Vivo Anticancer Activity of Vanillin Semicarbazone." Asian Pac J Trop Biomed 2.6 (2012): 438-442.

Anand et al. "Biological Activities of Curcumin and its Analogues (Congeners) Made by Man and Mother Nature." Biochemical Pharmacology 76 (2008): 1590-1611.

Appendino, et al. "N-Acylvanillamides: Development of an Expeditious Synthesis and Discovery of New Acyl Templates for Powerful Activation of the Vanilloid Receptor." J. Med. Chem 45 (2002): 3739-3745.

Bae et al. "Cytotoxicity of Phenolic Compounds Isolated from Seeds of Safflower (Carthamus tinctorius L.) on Cancer Cell Lines." Food Sci. Biotechnol, 11.2 (2002): 140-146.

Bahl et al. "Variation in Yield of Curcumin and Yield and Quality of Leaf and Rhizome Essential Oils among Indian Land Races of Turmeric Curcuma longa L." Proc Indian Nat Sci Acad 80(1) (2014): 143-156.

Basic Pharmaceutical Textbooks Series 19 Medicinal Chemistry, Kagaku Dojan Co., Ltd., Jun. 1, 2009, first edition, first Printing, p. 397 to B. 410 (English Translation not available).

Basnet et al. "Curcumin: An Anti-Inflammatory Molecule from a Curry Spice on the Path to Cancer Treatment." Molecules 16 (2011): 4567-4598.

"Benaldehyde." Encyclopaedia Britannica last updated Jul. 22, 2008; available online at https://www.britannica.com/science/benzaldehyde.

Brierly et al. "Developments in Harmine Pharmacology—Implications for Ayahuasca Use and Drug-Dependence Treatment." Progress in Neuro-Psychopharmacology & Biological Psychiatry 39 (2012): 263-272.

Brobst et al. "The Free Base Extraction of Harmaline from Penganum harmala." American Journal of Undergraduate Research 8.2-3 (2009): 1-4.

Brophy et al. "Leaf essential oils of the genus Leptospermum (Myrtaceae) in eastern Australia. Part 6. Leptospermum polygalifolium and allies." Flavour Fragr. J. 15 (2000): 271-277.

Bucar et al. "Natural product isolation—how to get from biological material to pure compounds." Nat. Prod. Rep. 2013, 30, 525-545.

Cannon, J.G. "Burger's Medicinal Chemistry and Drug Discovery, Fifth Edition, vol. 1: Principles and Practice, Chapter Nineteen: Analog Design." Wiley-Interscience 1995, pp. 738-802.

Cao et al. "Design, Synthesis and 3D-QSAR of β-carboline Derivatives as Potent Antitumor Agents." European Journal of Medicinal Chemistry 45 (2010) 2503-2515.

Cao et al. "DNA binding properties of 9-substituted harmine derivatives." Biochemical and Biophysical Research Communications 338 (2005): 1557-1563.

Cao et al. "Synthesis and Structure-Activity Relationships of Harmine Derivatives as Potential Antitumor Agents." European Journal of Medicinal Chemistry 60 (2013): 135-143.

Chadha et al. "Indoles as therapeutics of interest in medicinal chemistry: Bird's eye view." European Journal of Medicinal Chemistry 134 (2017): 159-184.

Chanh. "Structure-Activity Relationship of Aerosols of Vanillin and of its Isomers and Derivatives on the Isolated Guinea-Pig Lungs." Arch. Int. Pharmacodyn. 149.1-2 (1964): 248-256.

Chatwichien et al. "Design, Synthesis and Biological Evaluation of β-Carboline Dimers Based on the Structure of Neokauluamine." Tetrahedron Lett. Jun. 3, 2015; 56(23): 3515-3517.

Chen et al. "Synthesis and Antitumor Activity of Feruloyl and Caffeoyl Derivatives." Bioorg. Med. Chem. Lett. 24 (2014): 4367-4371.

Dahmke et al. "Cooking Enhances Curcumin Anti-Cancerogenic Activity Through Pyrolytic Formation of Deketene Curcumin." Food Chemistry 151 (2014): 514-519.

Dalpozzo. "Strategies for the asymmetric functionalization of indoles: an update." Chem. Soc. Rev., 2015, 44, 742.

Deb et al. "Activity of Aspirin Analogues and Vanillin in a Human Colorectal Cancer Cell Line." Oncology Reports 26 (2011): 557-565.

Deters et al. "Different Curcuminoids Inhibit T-Lymphocyte Proliferation Independently of Their Radical Scavenging Activities." Pharmaceutical Research 25.8 (Aug. 2008): 1822-1827.

(56) References Cited

OTHER PUBLICATIONS

Du et al. Synthesis and Antitumor Activity of beta-carboline dimmers. In: The 9th Chinese National Conference on Chemical Biology, Aug. 28-31, 2015, pp. 1-222 [online]. Available online at http://or.nsfc.gov.cn/bitstream/00001903-5/401410/1/1000014265298.pdf#page=208>; p. 187, first paragraph; p. 187, figure 1.
Du et al. "Synthesis and biological evaluation of bivalent β-carbolines as potential anticancer agents." Med. Chem. Commun. 7 (2016): 636-645.
Durant et al. "Vanillins—a novel family of DNA-PK inhibitors." Nucleic Acids Research 31.19 (2003): 5501-5512.
El-Sharkawy et al. "New Approaches for the Synthesis and Antitumor Evaluation of Pyridine, Thieno[3,4-c]Pyridine, Pyrazolo[3,4-b]Pyridine and Pyrido[3,4-d]Pyridazine Derivatives." Eur. Chem. Bull., 2013, 2(8), 530-537.
Erowid Online Books: "Ayahuasca: alkaloids, plants, and analogs" by Keeper of the Trout; (online) downloaded Jan. 15, 2015, www.erowid.org/library/books_online/ayahuasca_apa/aya_sec1_harmine_occurrence.shtml.
Extended Search Report in European Patent Application Serial No. 17185821.0-1466, dated Oct. 27, 2017.
Extended Search Report in European Patent Application Serial No. 15853030.3-1112, dated Apr. 10, 2018.
Fang et al. "Antitumor Constituents from Alternanthera philoxeroides." Journal of Asian Natural Products Research 9.6 (2007): 511-515.
Francik et al. "Antioxidant Activity of β-Carboline Derivatives." Acta Pol Pharm, Drug Research 68.2 (2011); 185-189.
Frost et al. "β-Carboline Compounds, Including Harmine, Inhibit DYRK1A and Tau Phosphorylation at Multiple Alzheimer's Disease-Related Sites." PLoS One 6.5 (May 2011): 1-9.
Fuchs et al. "Structure-Activity Relationship Studies of Curcumin Analogues." Bioorg Med Chem Lett 19 (2009): 2065-2069.
Gao et al. "DH332, a Synthetic â-Carboline Alkaloid, Inhibits B Cell Lymphoma Growth by Activation of the Caspase Family." Asian Pac J Cancer Prev 15.9 (2014): 3901-390.
Goel et al. "Curcumin as "Curecumin": From kitchen to clinic." Biochemical Pharmacology 75 (2008): 787-809.
Gordon. "Oxidative Transformation of Curcumin: Products and Reaction Mechanisms." Dissertation, Vanderbilt University (2014).
Gu et al. "Synthesis and In Vitro Antitumor Activity of Novel Bivalent β-Carboline-3-carboxylic Acid Derivatives with DNA as a Potential Target." Int. J. Mol. Sci., 2018, 19 3179.
Guo et al. "Synthesis and preliminary evaluation of novel alkyl diamine linked bivalent β-carbolines as angiogenesis inhibitors." MedChemComm, Nov. 1, 2016, Issue 11, 2017-2183. Abstract only.
Guo et al. "Synthesis and structure-activity relationships of asymmetric dimeric β-carbolines derivatives as potential antitumor agents." European Journal of Medicinal Chemistry 147:10 2018, 253-265.
Hail, Jr. et al. "Examining the Role of Mitochondrial Respiration in Vanilloid-Induced Apoptosis." Journal of the National Cancer Institute 94.17 (Sep. 4, 2002): 1281-1292.
Hakkarainen, K.M. et al. "Prevalence and Perceived Preventability of Self-Reported Adverse Drug Events—A Population-Based Survey of 7,099 Adults." PLoS One 8.9 (2013): e73166.
Heger et al. "The Molecular Basis for the Pharmacokinetics and Pharmacodynamics of Curcumin and Its Metabolites in Relation to Cancer." Pharmacol Rev 66 (Jan. 2014): 222-307.
Huang et al. "Linking Proteomic and Transcriptional Data Through the Interactome and Epigenome Reveals a Map of Oncogene-induced Signaling." PloS Computational Biology 9.2 (Feb. 2013): 1-21.
Husbands et al. "β-carboline binding to imidazoline receptors." Drug and Alcohol Dependence 64 (2001) 203-208.
Ikeda et al. "3-Benzylamino-β-carboline derivatives induce apoptosis through G2/M arrest in human carcinoma cells HeLa S-3." European Journal of Medicinal Chemistry, 46 (2011) 636-646.
International Search Report and Written Opinion in PCT/US2015/055968, dated Jan. 8, 2016.

Tu "The B-Carboline Analog Mana-Hox Causes Mitotic Aberration by Interacting with DNA" Chemistry & Biology, 2005, vol. 12, pp. 1317-1324.
Hsiao "Mana-Hox displays anticancer activity against prostate cancer cells through tubulin depolymerization and DNA damage stress" Naunyn-Schmiedeberg's Arch Pharmacol, 2008, vol. 378, pp. 599-608.
Muller "Exciton Fission and Fusion in Bis(tetracene) Molecules with Different Covalent Linker Structures" JACS, 2007, vol. 129, pp. 14240-14250.
Peng "Structure-Activity Relationship and Mechanism of Action Studies of Manzamine Analogues for the Control of Neuroinflammation and Cerebral Infections" J. Med. Chem., 2010, vol. 53, pp. 61-76.
Shen "Synthesis of 1-Substituted Carbazolyl-1,2,3,4-tetrahydro and Carbazolyl-3,4-dihydro-β-carboline Analogs as Potential Antitumor Agents" Mar. Drugs, 2011, vol. 9, pp. 256-277.
Yadav "Telomerase Inhibition and Human Telomeric G-Quadruplex DNA Stabilization by a β-Carboline-Benzimidazole Derivative at Low Concentrations" Biochemistry, 2017, vol. 56, pp. 4392-4404 (abstract attached).
Zhu "Indole Alkaloids from Alocasia macrorrhiza" Chem. Pharm. Bull., 2012, vol. 60, pp. 670-673.
Weiqun, "β-Carbolines. 1. Synthesis of several new Bis-β-Carboline compounds" J. Chinese Pharm Sci., 1999, 8(3), pp. 177-179.
Charlet-Fagnere, "Syntheses of Large-Ring Bis-Indolic Dilactams" Tetrahedron Letters 40 (1999) 1685-1688.
Jiang, "Cytotoxic Bis-3,4-dihydro-β-carbolines and Bis-β-carbolines" J Enzyme Inhibition and Medicinal Chem. 2002 17:6, 369-374.
International Search Report and Written Opinion in corresponding PCT/IB2017/000529, dated Aug. 14, 2017.
Perkin, "Harmine and Harmaline, part. 1" J Chem Society Trans., 1912, 101, pp. 1775-1787.
O Fischer, "Über Harmin und Harmalin" Berichte Der Deutschen Chemischen Gesellschaft, 1914, 47(1), pp. 99-107 (English translation attached).
Rahman, "Synthesis of Gambirtannine Derivatives by Photocyclization of Enamine Intermediates" J Chem Society Trans., Perkin Transactions 1, 1982, 1, pp. 59-62.
Pouilhes, "6',7-Dihydrokeramamine C and analogues: synthesis and biological evaluation", Tetrahedron Letters, 2001, 42, pp. 8297-8299.
Cao, "Synthesis and cytotoxic activities of 1-benzylidine substituted beta-carboline derivatives", Bioorganic & Medicinal Chemistry Letters, 2008, 18(24), pp. 6558-6561.
International Search Report and Written Opinion in corresponding PCT/US2020/042933, dated Feb. 25, 2021.
Chen, "Design, Synthesis, and Biological Evaluation of Novel N-Acylhydrazone Bond Linked Heterobivalent 8-Carbolines as Potential Anticancer Agents", Molecules, 2019, 24, 2950.
Al Asmari, "Low-dose acute vanillin is beneficial against harmaline-induced tremors in rats" J Progress in Neurosurgery. 2017, 39(3), pp. 264-270 (abstract attached).
Zhou, "Research on a novel chitosan microsphere/scaffold system by double cross-linkers" Denial Materials Journal 2016; 35(6), pp. 862-868.
Li, "Development of drug-loaded chitosan-vanillin nanoparticles and its cytotoxicity against HT-29 cells" Drug Deliv, 2016, 23(1), pp. 30-35.
Abranyi-Balogh, "Synethsis of 1'-Aryl-1,3'-bi-β-carbolines and their saturated counterparts" Polycyclic Aromatic Compounds, 2018, 38(2), pp. 131-140.
Guo, "Synthesis and biological evaluation of novel N9-heterobivalent β-carbolines as angiogenesis inhibitors" J Enzyme Inhibition and Medicinal Chem., 2019, 34(1), pp. 375-387.
Al Asmari, "Vanillin a food additive ameliorates harmaline induced tremor in rats", J Neurology & Exper. Neuro., 2016, 2(1), 13 pages.
Akermark et al. "Palladium-Promoted Cyclization of Diphenyl Ether, Diphenylamine, and Related Compounds" J. Org. Chem., 1975, 40 (9), 1365-1367.

(56) References Cited

OTHER PUBLICATIONS

Deng et al. "Palladium-Catalyzed Oxidative Carbocyclizations" Eur. J. 2012, 18, 11498-11523.

Knolker "Synthesis of Biologically Active Carbazole Alkaloids Using Selective Transition-metal-catalyzed Coupling Reactions" Chemistry Letters 2009, 38(1) 8-13.

Hostyn et al. Synthesis of a-Carbolines Starting from 2,3-Dichloropyridines and Substituted Anilines Adv. Synth. Catal. 2008, 350, 2653-2660.

Laha et al. "One-Pot Synthesis of r-Carbolines via Sequential Palladium-Catalyzed Aryl Amination and Intramolecular Arylation" J. Org. Chem. 2009, 74, 3152-3155.

Mineno et al. "Rapid access to diverse α-carbolines through sequential transition metal catalyzed amination and direct C—H arylation" Tetrahedron 70 (2014) 5550-5557.

Mineno et al. "Integrated cross-coupling strategy for an α-carboline-based Aurora B kinase inhibitor" J Org Chem. Feb. 6, 2015; 80(3); 1564-8.

Muci et al. "Practical Palladium Catalysts for C—N and C—O Bond Formation" Cross-Coupling Reactions vol. 219 of the series Topics in Current Chemistry, 2002, pp. 131-209.

Panunzio et al. "Palladium-Catalyzed Heteroaromatic Couplings Mediated by Microwave Irradiation" Synthetic Communications, 2007 37: 4239-4244.

Raposo et al. "Synthesis of highly substituted diphenylacetamides and diphenylsulfonamides by the Goldberg coupling reaction" J. Chem. Research (S), 2000, 156-158.

Wadsworth et al. "A review of the synthesis of α-carbolines" European Journal of Medicinal Chemistry 2015, 97 816-829.

Tiruveedhula et al. "Synthesis of aza and carbocyclic β-carbolines for the treatment of alcohol abuse. Regiospecific solution to the problem of 3,6-disubstituted β- and aza-β-carboline specificity" J.Org. Biomol. Chem., 2015, 13, 10705.

Venkatesh, et al. "Palladium-Catalyzed Intramolecular N-Arylation of Heteroarenes: A Novel and Efficient Route to Benzimidazo[1,2-a]quinolines" J. Org. Chem. 2006, 71, 1280-1283.

Watanabe et al. "Palladium-Catalyzed Direct Synthesis of Carbazoles via One-Pot N-Arylation and Oxidative Biaryl Coupling: Synthesis and Mechanistic Study" J. Org. Chem. 2009, 74, 4720-4726.

Yogo et al. "Synthesis of Some Carbazolequinone Alkaloids and Their Analogues. Facile Palladium-Assisted Intramolecula Ring Closure of Arylamino-1, 4-benzequinones Carbazole-1,4-quinones" Chem, Pharm. Bull. 1991, 39 (2) 328-334.

International Search Report and Written Opinion in PCT/IB2016/000723, dated Sep. 5, 2016.

International Search Report and Written Opinion in PCT/IB2016/000723, dated Nov. 21, 2016.

International Search Report and Written Opinion in PCT/US2017/059299, dated Jan. 29, 2018.

International Search Report and Written Opinion in PCT/US2018/033018, dated Sep. 14, 2018.

International Search Report and Written Opinion in PCT/US2018/038533, dated Sep. 18, 2018.

International Search Report and Written Opinion in PCT/US2018/066814, dated Feb. 12, 2019.

International Search Report and Written Opinion in PCT/US2019/032510, dated Sep. 3, 2019.

Karin et al. "The IKK NF-κB System: A Treasure Trove for Drug Development." Nature Reviews/Drug Discovery 3 (2004): 17-26.

Kaur et al. "Antimalarials from nature." Bioorganic & Medicinal Chemistry, Article in Press. (2009) 28 pages.

Ketron et al. "Oxidative Metabolites of Curcumin Poison Human Type II Topoisomerases." Biochemistry 52:1 (2013): 221-227.

Khader et al. "Thymoquinone: an emerging natural drug with a wide range of medical applications." Iran J Basic Med Sci 2014; 17:950-957.

Wang et al. "Stability of Curcumin in Buffer Solutions and Characterization of its Degradation Products." Journal of Pharmaceutical and Biomedical Analysis 15 (1997): 1867-1876.

Wilken et al. "Curcumin: A review of anti-cancer properties and therapeutic activity in head and neck squamous cell carcinoma." Molecular Cancer 10:12 (2011): 1-19. Found online at http://www.molecular-cancer.com/content/10/1/12.

Wright et al. "Bioactivity of Turmeric-Derived Curcuminoids and Related Metabolites in Breast Cancer." Curr Pharm Des. 19.34 (2013): 6218-6225.

Wu et al. "Discovering Natural Product Modulators to Overcome Multidrug Resistance in Cancer Chemotherapy." Curr Pharm Biotechnol. 12.4 (Apr. 2011): 609-620.

Yan et al. "Induction of Apoptosis and Autophagic Cell Death by the Vanillin Derivative 6-bromine-5-hydroxy-4-methoxybenzaldehyde Is Accompanied by the Cleavage of Dna-pkcs and Rapid Destruction of C-myc Oncoprotein in Hepg2 Cells." Cancer Letters 252 (2007): 280-289.

Zeng et al. "Cytotoxic and Insecticidal Activities of Derivatives of Harmine, a Natural Insecticidal Component Isolated from Peganum harmala." Molecules 15 (2010): 7775-7791.

Zhang, Hao et al. "Harmine Induces Apoptosis and Inhibits Tumor Cell Proliferation, migration and Invasion Through Down-regulation of Cyclooxygenase-2expression in Gastric Cancer." Phytomedicine 21 (2014): 348-355.

Zhang, Xiao-Fei et al. "Synthesis and mechanisms of action of novel harmine derivatives as potential antitumor agents." Scientific Reports 6:33204 (2016): 1-16.

Zhang, Yimao et al. "Identification of Inhibitors of ABCG2 by a Bioluminescence Imaging-Based High-Throughput Assay." Cancer Res 69 (2009): 5867-5876.

Zuo et al. "Synthesis, cytotoxicity of new 4-aryilidene curcumin analogs and their multi-functions in inhibition of both NF-κB and Akt signalling." European Journal of Medicinal Chemistry 55 (2012): 346-357.

AbuKhader, M.M.. "Thymoquinone in the Clinical Treatment of Cancer: Fact or Fiction?" Pharmacogn Review. Jul.-Dec. 7, 2013(14):117-120.

Yin et al. "Synthesis of bivalent ligands of β-Carboline-3-carboxylates via a palladium-catalyzed homocoupling process." Tetrahedron Letters 46 (2005) 6363-6368.

Booth et al. "GZ17-6.02 initiates DNA damage causing autophagosome-dependent HDAC degradation resulting in enhanced anti-PD1 checkpoint inhibitory antibody efficacy," J Cell Physiol. 235:11; 8098-8113. 2020 (abstract attached).

Dai et al. "Beta-Carboline alkaloid monomers and dimers: Occurrence, structrual diversity, and biological activities," European Journal of Medicinal Chemistry, 2018, vol. 157, pp. 622-656.

Danziger et al. "Automated site-directed drug design: a general algorithm for knowledge acquisition about hydrogen-bonding regions at protein surfaces," Proc. R. Soc. Lond. 236 (1989), 101-113 (abstract attached).

Hamer. "Some derivatives of methylenediquinaldine and their relationship to the carbocyanines." Journal of the Chemical Society, Transactions 123 (1923): 246-59 (abstract attached).

Jin et al. "Bronsted acid catalyzed synthesis of 1,3-di (2-quinolyl)propane derivatives via tandem C(sp3)-H functionalization." Tetrahedron 69.32 (2013): 6579-6584.

Kitanovic et al. "a Deadly Organometallic Luminescent Probe: Anticancer Activity of a Re' Bisquinoline Complex," Chem. Eur. J. 2014, vol. 20, pp. 2496-2507.

Manoharan et al. "Curcumin: a Wonder Drug as a Preventive Measure for COVID19 Management." Ind J Clin Biochem 35.3 (Jul.-Sep. 2020): 373-375.

Misra et al. "Studies in potential amebicides. XVI. Synthesis of some quinaldinyl and biquinolypropane derivatives and their reduction products." Journal of the Indian Chemical Society 39 (1962): 321-24.

Naseri et al. "The Antiuviral Effects of Curcumin Nanomicelles on the Attachment and Entry of Hepatitis C Virus." Iranian J Virol 11.2 (2017): 29-35.

Rook et al. "Bivalent β-Carbolines as Potential Multitarget Anti-Alzheimer Agents." J. Med. Chem. 2020, 53, 3611-3617.

(56) References Cited

OTHER PUBLICATIONS

Roshdyn et al. "EGYVIR: An immunomodulatory herbal extract with potent antiviral activity against SARS-Co-V-2." PLoS One 15.11 (2020):1-19; e0241739. https://doi.org/10,1371/journal.pone. 0241739.
Skidmore et al. "Quinoline series. I. Addition reactions of quinaldine and lepidine." Journal of the Chemical Society (1959): 1641-5.
Song, et al. "β-Carbolines as Specific Inhibitors of Cyclin-Dependent Kinases." Bioorganic & Medicinal Chemistry Letters 12 (2002 1129-1132.
Sotiropoulou et al. "Chemical Approaches to Targeting Drug Resistance in Cancer Stem Cells." Drug Discovery Today 19.10 (Oct. 2014): 1547-1562.
Villalta-Romero et al. "Identification of New Snake Venom Metalloproteinase Inhibitors Using Compound Screening and Rational Peptide Design," ACS Med. Chem. Lett. 2012, 3, 540-543; found online at pubs.acs.org/acsmedchemlett.
Wang, et al. "Synthesis of carbon-11-labeled bivalent β-carbolines as new PET agents for imaging of cholinesterase in Alzheimer's disease." Applied Radiation and Isotopes, 69 (2011) 678-685.
West et al. "A novel plant-derived compound is synergistic with 5-fluorouracil and has increased apoptotic activity through autophagy in the treatment of actinic keratoses." Journal of Dermatological Treatment, 2020, DOI: 10.1080/09546634.2020.1764905.
International Search Report and Written Opinion in PCT/US2019/ 027002, dated Jul. 5, 2019.
International Search Report and Written Opinion in PCT/US2020/ 044567, dated Jan. 4, 2021.
International Search Report and Written Opinion in PCT/US2021/ 40880, dated Nov. 17, 2021.
International Search Report and Written Opinion in PCT/US2020/ 067583, dated Mar. 30, 2021.
International Search Report and Written Opinion in PCT/US2021/ 064888, dated Mar. 9, 2022.
PubChem-CID 102496256 Create Date: Dec. 28, 2015; pp. 1-7. Found online at https://pubchem.ncbi.nlm.nih.gov/compound/ 102496256, Nov. 30, 2020.
PubChem Compound Summary—Harmaline; found online at https:// pubchem.ncbi.nim.nih.gov/compound/3564 on Jun. 10, 2019.
PubChem Compound Summary—Thymoquinone; found online at https://pubchem.ncbi.nim.nih.gov/compound/10281 on Jun. 10, 2019.
PubChem-CID 132563536 Create Date: Apr. 8, 2018; pp. 1-7. Found online at https://pubchem.ncbi.nlm.nih.gov/compound/ 132563536, Nov. 30, 2020.
PubChem-CID 46708588 Create Date: Jul. 26, 2010; pp. 1-8. Found online at https://pubchem.ncbi.nlm.nih.gov/compound/46708588, Nov. 30, 2020.
PubChem-CID 72163367 Create Date: Dec. 2, 2013; pp. 1-7. Found online at https://pubchem.ncbi.nlm.nih.gov/compound/72163367, Nov. 30, 2020.
Khlifi et al. "Composition and Anti-Oxidant, Anti-Cancer and Anti-Inflammatory Activities of Artemisia herba-alba, *Ruta chalpensis* L. and *Peganum harmala* L." Food Chem Toxicol 55 (2013): 202-208.
Kumar et al. "A Review on the Vanillin Derivatives Showing Various Biological Activities." International Journal of PharmTech Research 4.1 (Jan.-Mar 2012): 266-279.
Kumavat et al. "Degradation Studies of Curcumin." International Journal of Pharmacy Review and Research 3.2 (2013): 50-55.
Kurien et al. "Heat-solubilized Curry Spice Curcumin Inhibits Antibody-Antigen Interaction in In Vitro Studies: A Possible Therapy to Alleviate Autoimmune Disorders." Mol. Nutr. Food Res. 54 (2010): 1202-1209.
Kurien et al. "Improving the Solubility and Pharmacological Efficacy of Curcumin by Heat Treatment." ASSAY and Drug Development Technologies 5.4 (2007): 567-576.
Lamoral-Theys et al. "Simple Di- and Trivanillates Exhibit Cytostatic Properties Toward Cancer Cells Resistant to Pro-Apoptotic Stimuli." Bioorganic & Medicinal Chemistry 18 (2010): 3823-3833.

Li et al. "Metabolites Identification of Harmane in Vitro/in Vivo in Rats by Ultra-performance Liquid Chromatography Combined with Electrospray Ionization Quadrupole Time-of-flight Tandem Mass Spectrometry." Journal of Pharmaceutical and Biomedical Analysis 92 (2014): 53-62.
Li et al. "DH334, a β-carboline Anti-Cancer Drug, Inhibits the CDK Activity of Budding Yeast." Cancer Biology and Therapy 6.8 (2007): 1204-1210.
Liang et al. "Exploration and Synthesis of Curcumin Analogues with Improved Structural Stability Both In Vitro and In Vivo as Cytotoxic Agents." Bioorganic & Medicinal Chemistry 17 (2009): 2623-2631.
Lin et al. "Antitumor Agents 247. New 4-ethoxycarbonylethyl Curcumin Analogs as Potential Antiandrogenic Agents." Bioorganic & Medicinal Chemistry 14 (2006): 2527-2534.
Lin et al. "Antitumor Agents 250. Design and Synthesis of New Curcumin Analogs as Potential Anti-Prostate Cancer Agents." J Med Chem 49.13 (Jun. 29, 2006): 3963-3972.
Lirdprapamongkol et al. "Vanillin Suppresses In Vitro Invasion and In Vivo Metastasis of Mouse Breast Cancer Cells." European Journal of Pharmaceutical Sciences 25 (2005): 57-65.
Lirdprapamongkol et al. "Vanillin Suppresses Metastatic Potential of Human Cancer Cells through PI3K Inhibition and Decreases Angiogenesis in Vivo." J. Agric. Food Chem. 57 (2009): 3055-3063.
Liu, G et al. "Protection Against Damaged DNA in the Single Cell by Polyphenols." Pharmazie 57.12 (Dec. 2002): 852-854 (Abstract attached).
Liu, H et al. "Harmine hydrochloride inhibits akt phosphorylation and depletes the pool of cancer stem cells of glioblastoma." J Neurooncol 2013, 112:39-48.
Luo et al. "Anti-cancer Effects of JKA97 Are Associated with Its Induction of Cell Apoptosis via a Bax-dependent and p53-independent Pathway." The Journal of Biological Chemistry 283. 13, (2008), 8624-8633.
Mani et al. "Alterations of Chemotherapeutic Pharmacokinetic Profiles by Drug-Drug Interactions." Expert Opin. Drug Metabl. Toxicol 5.2 (2009): 109-130.
Matsuda et al. "Studies of Cuticle Drugs from Natural Sourses. II. Inhibitory Effects of Prunus Plants on Melanin Bioshynthesis." Biological and Pharmaceutical Bulletin 17.10 (1994): 1417-1420.
McKenna et al. "Ultra-Violet Mediated Cytotoxic Activity of B-Carboline Alkaloids." Phytochemistry 20:5 (1981): 1001-1004.
Moloudizargari et al. "Pharmacological and Therapeutic Effects of Peganum Harmala and Its Main Alkaloids." Pharmacogn Rev. 7.14 (Jul.-Dec. 2013): 199-212.
Nagatsu et al. "Tyrosinase Inhibitory and Anti-Tumor Promoting Activities of Compounds Isolated from Safflower (*Carthamus tinctorius* L.) and Cotton (*Gossypium hirsutum* L.) Oil Cakes." Natural Product Research 14.3 (2000): 153-158.
Nekkanti et al. "Targeting DNA Minor Groove by Hybrid Molecules as Anticancer Agents." Current Medicinal Chemistry, 2017, 24 2887-2907 (abstract attached).
Nidhina et al. "Vanillin Induces Adipocyte Differentiation in 3T3-L1 Cells by Activating Extracellular Signal Regulated Kinase 42/44." Life Sciences 88 (2011): 75-680.
Obach, R.S. "Drug-Drug Interactions: An Important Negative Attribute in Drugs." Drugs Today 39.5 (2003): 308-338 (Abstract attached).
Office Action dated Nov. 20, 2018, in SN U.S. Appl. No. 16/013,504, filed Jun. 20, 2018.
Ohori et al. "Synthesis and Biological Analysis of New Curcumin Analogues Bearing an Enhanced Potential for the Medicinal Treatment of Cancer." Mol Cancer Ther 5.10 (2006): 2563-2571.
Padhye et al. "Perspectives on Chemopreventive and Therapeutic Potential of Curcumin Analogs in Medicinal Chemistry." Mini Rev Med Chem. 10.5 (May 2010): 372-387.
Paramapojn et al. "Quantitative Analysis of Curcuminoids in Curcuma Zedoaria Rhizomes in Thailand by Hplc Method." ISHS Acta Horticulturae 786: International Workshop on Medicinal and Aromatic Plants; downloaded Apr. 27, 2015; available online at http:// www.actahort.org/books/786/786_18.htm.

(56) References Cited

OTHER PUBLICATIONS

Patel, P.S. et al. "A Study of Potential Adverse Drug-Drug Interactions Among Prescribed Drugs in a Medicine Outpatient Department of a Tertiary Care Teaching Hospital." J. Basic Clin. Pharm. 5.2 (2014): 44-48.

Pedroso et al. "Effect of the O-Methyl Catechols Apocynin, Curcumin and Vanillin on the Activity of Tamoxifen." Journal of Enzyme Inhibition and Medicinal Chemistry 28.4 (Aug. 2013): 734-740—Abstract only.

Ponra et al. "Bronsted acid-promoted synthesis of common heterocycles and related bio-active and functional molecules." RSC Adv. 2016, 6, 37784.

PubChem-CID 84053302 Create Date: Oct. 20, 2014; pp. 1-10; p. 3, Fig. Found online at https://pubchem.ncbi.nlm.nih.gov/compound/84053302, Aug. 10, 2018.

Rani et al. "The Potential Role of Curcumin in Cancer Prevention and Treatment." RRJPPS 2:3 (2013): 1-4.

Rashan. "In Vitro Study of the Antiviral Activity of Some β-Carboline Alkaloids." Fitoterapia LXI:2 (1990): 153-155.

Reddy et al. "Synthesis of Semi-Synthetic Chalcones from the Isolated Intermediate Aldehydes of the roots of Decalepis hemiltonii." Asian Journal of Chemistry 21:5 (2009); 3855-3860.

Rescigno et al. "Vanilloid Derivatives as Tyrosinase Inhibitors Driven by Virtual Screen-Based QSAR Models." Drug Test Analysis 3 (2011): 176-191.

Réus et al. "Harmine and Imipramine Promote Antioxidant Activities in Prefrontal Cortex and Hippocampus." Oxidative Medicine and Cellular Longevity 3:5 (Sep./Oct. 2010): 325-331.

Sagnou, et al. "Evaluation of naturally occurring curcuminoids and related compounds against mosquito larvae." Acta Tropica 123 (2012): 190-195.

Samundeeswari et al. "Design and synthesis of novel phenyl-1,4-beta-carboline-hybrid molecules as potential anticancer agents." European Journal of Medical Chemistry 128 (2017) 123-139.

Sandur et al. "Curcumin, demethoxycurcumin, bisdemethoxycurcumin, tetrahycrocurcumin and turmerones differentially regulate anti-inflammatory and anti-proliferative responses through a ROS-independent mechanism." Carcinogenesis 28:8 (2007): 1765-1773.

Sasidharan et al. "Comparative Chemical Composition and Antimicrobial Composition Activity Fresh and Dry Ginger Oils (Zingiber Officinale Roscoe)." Int J Curr Pharm Res 2:4 (2010): 40-43.

Shahwar et al. "Microbial Transformation of Vanillin Isolated from Melia azedarach to Vanillyl Alcohol followed by Protease Inhibition and Antioxidant Activity." J.Chem.Soc.Pak., 33:5 (2011): 715-719.

Sharma et al. "Imidazole Derivatives Show Anticancer Potenti,al by Inducing Apoptosis and Cellular Senescence." Med. Chem. Commun. 5 (2014): 175.

Shen et al. "The pharmacology of curcumin: is it the degradation products?" Trends in Molecular Medicine 18.3 (2012): 138-144.

Shetty et al. "Eliminating the Heart from the Curcumin Molecule: Monocarbonyl Curcumin Mimics (MACs)." Molecules 20 (2015): 249-292.

Spenser. "A Synthesis of Harmaline." Can. J. Chem. 37 (1959): 1851-1858.

Takeuchi et al. "Benzaldehyde as a Carcinostatic Princple in Figs." Agric. Biol. Chem. 42.7 (1978): 1449-1451.

Van Sickle et al. "Inhibition of Cholesterol Synthesis by Cyclopropylamine Derivatives of Squalene in human Hepatoblastoma Cells in Culture." Lipids (1992): 157-160.

Vusovich et al. "Comparison of Vanillin and Isovanillin Photolysis in Aqueous Solutions." Russian Physics Journal 56.11 (Mar. 2014): 1287-1291.

Waghule, T., Gorantla, S., Rapalli, V.K. et al. Emerging Trends in Topical Delivery of Curcumin Through Lipid Nanocarriers: Effectiveness in Skin Disorders. AAPS PharmSciTech 21, 284 (2020). https://doi.org/10.1208/s12249-020-01831-9 (abstract attached).

Extended Search Report in corresponding European Patent Application Serial No. 20946050.0, dated Mar. 27, 2024.

\* cited by examiner

THERAPEUTIC AGENTS AND USES THEREOF

CROSS-REFERENCE TO RELATED APPLICATION

This is a continuation of U.S. patent application Ser. No. 16/935,079 filed Jul. 21, 2020, which is incorporated by reference herein in its entirety.

BACKGROUND OF THE INVENTION

Field of the Invention

The present invention relates to chemotherapeutics for treatment of humans, and especially for the treatment of human cancers, and corresponding methods for the treatment of humans suffering from cancers or other maladies. The invention further provides dosage forms and regimens for administration to human patients, and methods of formulating and administering such dosage forms to yield improvements in treatment outcomes. More particularly, the invention is concerned with the administration of specific chemotherapeutic dosage forms (e.g., liquid mixtures, capsules, pills, or tablets) comprising compounds or agents having a plurality of fused polycyclic moieties linked or tethered by means of an appropriate linker. In certain embodiments, compounds having plural β-carboline component moieties and a single linker moiety are provided.

Description of Related Art

Cancer is a generic term for a large group of diseases that can affect any part of the body. Other terms used are malignant tumors and neoplasms. One defining feature of cancer is the rapid creation of abnormal cells that grow beyond their usual boundaries, and which can then invade adjoining parts of the body and spread to other organs. This process is referred to as metastasis. Metastases are the major cause of death from cancer.

The transformation from a normal cell into a tumor cell is a multistage process, typically a progression from a pre-cancerous lesion to malignant tumors. These changes are the result of the interaction between a person's genetic factors and three categories of external agents, including:
- physical carcinogens, such as ultraviolet and ionizing radiation
- chemical carcinogens, such as asbestos, components of tobacco smoke, aflatoxin (a food contaminant) and arsenic (a drinking water contaminant)
- biological carcinogens, such as infections from certain viruses, bacteria, or parasites.

Some examples of infections associated with certain cancers:
- Viruses: hepatitis B and liver cancer, Human Papilloma Virus (HPV) and cervical cancer, and human immunodeficiency virus (HIV) and Kaposi sarcoma.
- Bacteria: *Helicobacter pylori* and stomach cancer.
- Parasites: schistosomiasis and bladder cancer.

Aging is another fundamental factor for the development of cancer. The incidence of cancer rises dramatically with age, most likely due to a buildup of risks for specific cancers that increase with age. The overall risk accumulation is combined with the tendency for cellular repair mechanisms to be less effective as a person grows older.

Tobacco use, alcohol use, low fruit and vegetable intake, and chronic infections from hepatitis B (HBV), hepatitis C virus (HCV) and some types of Human Papilloma Virus (HPV) are leading risk factors for cancer in low- and middle-income countries. Cervical cancer, which is caused by HPV, is a leading cause of cancer death among women in low-income countries. In high-income countries, tobacco use, alcohol use, and being overweight or obese are major risk factors for cancer.

The most common cancer treatment modalities are surgery, chemotherapy, and radiation treatments. All of these techniques have significant drawbacks in terms of side effects and patient discomfort. For example, chemotherapy may result in significant decreases in white blood cell count (neutropenia), red blood cell count (anemia), and platelet count (thrombocytopenia). This can result in pain, diarrhea, constipation, mouth sores, hair loss, nausea, and vomiting.

Biological therapy (sometimes called immunotherapy, biotherapy, or biological response modifier therapy) is a relatively new addition to the family of cancer treatments. Biological therapies use the body's immune system, either directly or indirectly, to fight cancer or to lessen the side effects that may be caused by some cancer treatments.

During chemotherapies involving multiple-drug treatments, adverse drug events are common, and indeed toxicities related to drug-drug interactions are one of the leading causes of hospitalizations in the US. Obach, R. S. "Drug-Drug Interactions: An Important Negative Attribute in Drugs." *Drugs Today* 39.5 (2003): 308-338. In fact, in any single-month period, one-fifth of all surveyed adults in the USA reported an adverse drug response. Hakkarainen, K. M. et al. "Prevalence and Perceived Preventability of Self-Reported Adverse Drug Events—A Population-Based Survey of 7,099 Adults." *PLoS One* 8.9 (2013): e73166. A large-scale study of adults aged 57-85 found that 29% were taking more than five prescription medications and nearly 5% were at risk of major adverse drug-drug interactions. In the field of oncology, a review of over 400 cancer patients determined that 77% were taking drugs that were considered to have a moderately severe potential for adverse drug interactions, and 9% had major adverse drug interactions. Ghalib, M. S. et al. "Alterations of Chemotherapeutic Pharmocokinetic Profiles by Drug-Drug Interactions." *Expert Opin. Drug Metabl. Toxicol* 5.2 (2009): 109-130.

Such interactions are a global health problem, and the WHO has determined that negative drug interactions are leading causes of morbidity and mortality around the world, with up to 7% of all hospitalizations in the US due to negative drug interactions. A recent survey of a single hospital shows that 83% of hospitalized patients were prescribed drug combinations with the potential to cause adverse reactions. Patel, P. S. et al. "A Study of Potential Adverse Drug-Drug Interactions Among Prescribed Drugs in a Medicine Outpatient Department of a Tertiary Care Teaching Hospital." *J. Basic Clin. Pharm.* 5.2 (2014): 44-48.

Examples of famous negative drug interactions include the development of rhabdomyolysis, a severe muscle disease, when taking Simvastatin with Amiodarone. As a result, the FDA introduced a warning on the drug label about the interaction. The calcium channel blocker Mibefradif, taken for high blood pressure, was removed from the market because of the harmful interaction with drugs that work on the electrical activity of the heart.

U.S. Pat. No. 8,039,025 describes cancer treatments in the form of extracts of *Arum palaestinum* Boiss, supplemented with individual amounts of β-sitosterol, isovanillin, and linoleic acid, and this patent is incorporated by reference herein in its entirety.

U.S. Pat. No. 9,402,834, issued Aug. 2, 2016, describes anti-cancer compositions containing various components in mixtures, such as curcumin, harmine, and isovanillin component mixtures, or component mixtures containing curcumin/harmine, curcumin/isovanillin, and harmine/isovanillin components.

Despite the immense amount of worldwide research and efforts to stem the tide of cancer and its side effects, the disease in its many manifestations continues to be a huge problem. Therefore, any new cancer treatment having a curative affect and/or the ability to ameliorate cancer symptoms and improve the lifestyle of patients is highly significant and important.

SUMMARY OF THE INVENTION

The present invention provides compositions which may be used as improved chemotherapeutics for treatment of humans, and especially in the treatment of human cancers, and corresponding methods for preparing such compositions and use thereof. Generally speaking, the chemotherapeutics of the invention comprise (or consist essentially of, or consist of) one or more compounds and related versions thereof. Thus, as used herein in the present specification and claims, a defined "therapeutic compound" or "compound" means the defined compound per se, as well as the dimers, isomers, tautomers, derivatives, solvates, metabolites, esters, metal complexes (e.g., Cu, Fe, Zn, Pt, V), prodrugs, and salts thereof. Hence, "dimers" refers to a molecule or molecular complex made up of two identical molecules linked together by bonds that can be strong or weak (e.g., covalent or hydrogen bonds); "isomers" refers to each of two or more compounds with the same formula but with at different arrangement of atoms, and includes structural isomers and stereoisomers (e.g., geometric isomers and enantiomers); "tautomers" refers to two or more isometric compounds that exist in equilibrium, such as keto-enol and imine and enamine tautomers; "derivatives" refers to compounds that can be imagined to arise or actually be synthesized from a defined parent compound by replacement of one atom with another atom or a group of atoms; "solvates" refers to interaction with a defined compound with a solvent to form a stabilized solute species; "metabolites" refers to a defined compound which has been metabolized in vivo by digestion or other bodily chemical processes; and "prodrugs" refers to defined compound which has been generated by a metabolic process. The compounds can be directly used in partial or essentially completely purified forms, or can be modified as indicated above. The compounds may be in crystalline or amorphous forms, and may be lyophilized.

The invention also provides new methods for treatment of cancers by administration of appropriate quantities of compositions comprising therapeutic compounds as described herein. Hence, the compositions are particularly designed for use in the treatment of cancers, and the compositions can be used for the manufacture of medicaments for anti-cancer therapeutic applications. In addition, the invention provides compositions for the treatment of cancers comprising administering therapeutically effective amounts of the new compositions, prepared by processes known per se, with a pharmaceutically acceptable carrier.

A "chemotherapeutic," "chemotherapeutic agent," or simply "therapeutic agent," as used herein refers to one or more of the compounds described herein as useful in the treatment of human conditions, especially human cancers. Chemotherapeutics may be cytostatic, selectively toxic, or destructive of cancerous tissue and/or cells, including cancer stem cells, but also include indiscriminately cytotoxic compounds used in cancer treatments.

The therapeutic compounds or agents of the invention have been found to be effective in the treatment of a number of human cancer cells, and especially lymphoma, leukemia, pancreatic, endometrial, ovarian, gastric, breast, renal, cervical, head and neck, and myeloma.

The compounds or agents of the invention broadly comprise a plurality of fused polycyclic moieties linked or tethered by an appropriate linker; preferably, there are two tricyclic moieties. The polycyclic moieties each include at least one N-containing ring. β-carboline moieties are particularly useful in the invention, such as harmaline or similar moieties. In certain embodiments, a pair of β-carboline moieties are bonded by means of a linker moiety, and specifically through a single atom forming at least a part of the overall linker. The reaction products of β-carboline compounds and aldehyde compounds yield a number of useful anti-cancer compounds in accordance with the invention. While the compounds per se of the invention not a part of anti-cancer compositions do not include compounds made up of the reaction product of two harmaline moieties or two harmine moieties, with a linker moiety of benzaldehyde of p-nitro benzaldehyde, the anti-cancer compositions of the invention (which normally include at least one other agent, component, or compound) and treatment methods do embrace such compounds.

BRIEF DESCRIPTION OF THE DRAWINGS

FIG. 120 is a graph illustrating cell growth as a function of the concentration of the confirmed 560 compound, in the MiaPaCa-2 pancreatic ductal adenocarcinoma cell proliferation assay described in Example 15;

FIG. 121 is a graph illustrating cell growth as a function of the concentration of the confirmed 562 compound, in the S2-007 pancreatic ductal adenocarcinoma cell proliferation assay described in Example 15;

FIG. 122 is a graph illustrating cell growth as a function of the concentration of the confirmed 562 compound, in the MiaPaCa-2 pancreatic ductal adenocarcinoma cell proliferation assay described in Example 15;

FIG. 123 is a series of photographs depicting the colony formations as a function of the concentration of the confirmed 560 compound, in the S2-007 pancreatic ductal adenocarcinoma cell colony formation assay described in Example 16;

FIG. 124 is a series of photographs depicting the colony formations as a function of the concentration of the confirmed 560 compound, in the MiaPaCa-2 pancreatic ductal adenocarcinoma cell colony formation assay described in Example 16;

FIG. 125 is a series of photographs depicting the colony formations as a function of the concentration of the confirmed 562 compound, in the S2-007 pancreatic ductal adenocarcinoma cell colony formation assay described in Example 16;

FIG. 126 is a series of photographs depicting the colony formations as a function of the concentration of the confirmed 562 compound, in the MiaPaCa-2 pancreatic ductal adenocarcinoma cell colony formation assay described in Example 16;

FIG. 127 is a further series of photographs depicting the colony formations as a function of the concentration of the confirmed 562 compound, in the MiaPaCa-2 pancreatic ductal adenocarcinoma cell colony formation assay described in Example 16;

Figure 128:
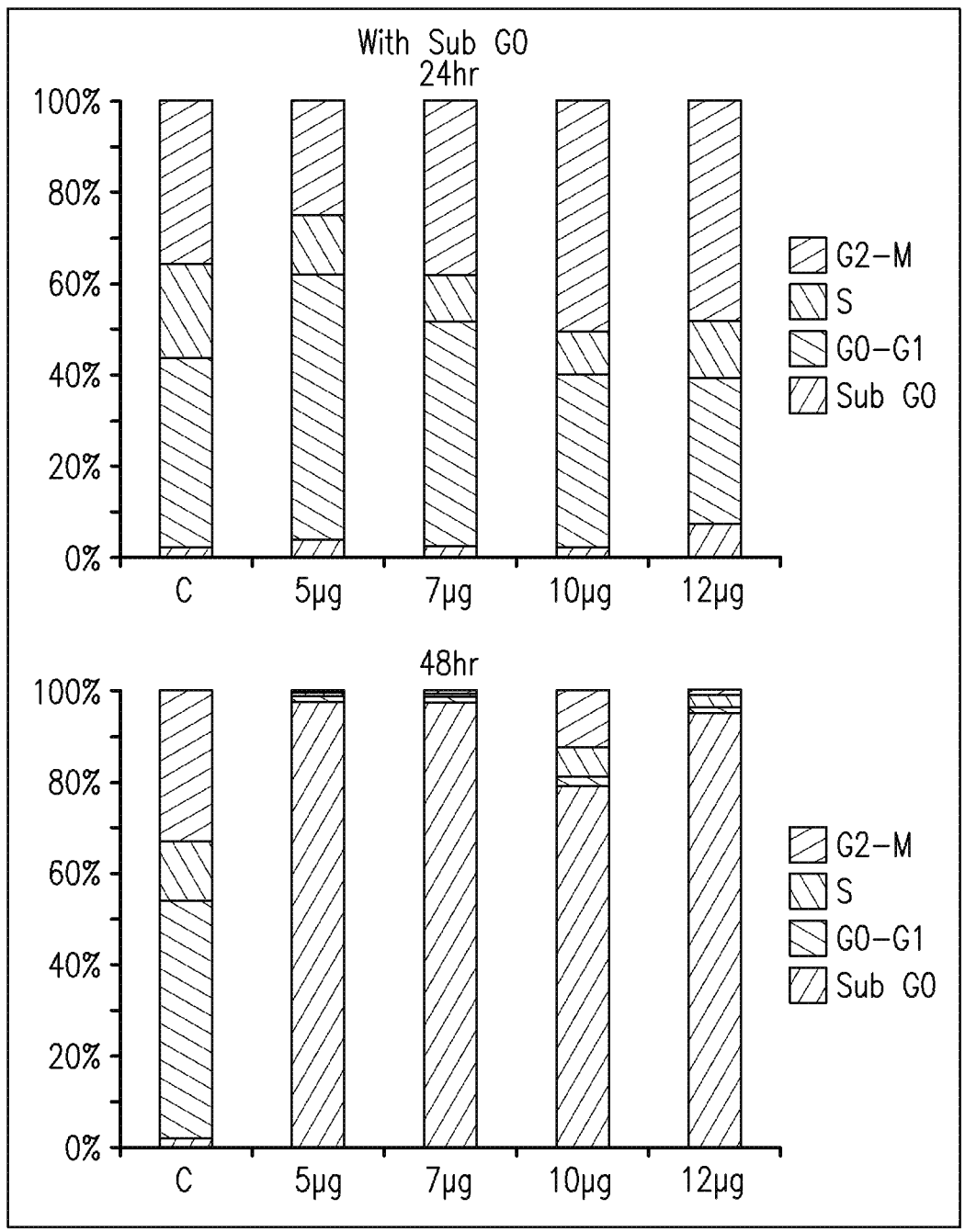
Figure 128A:
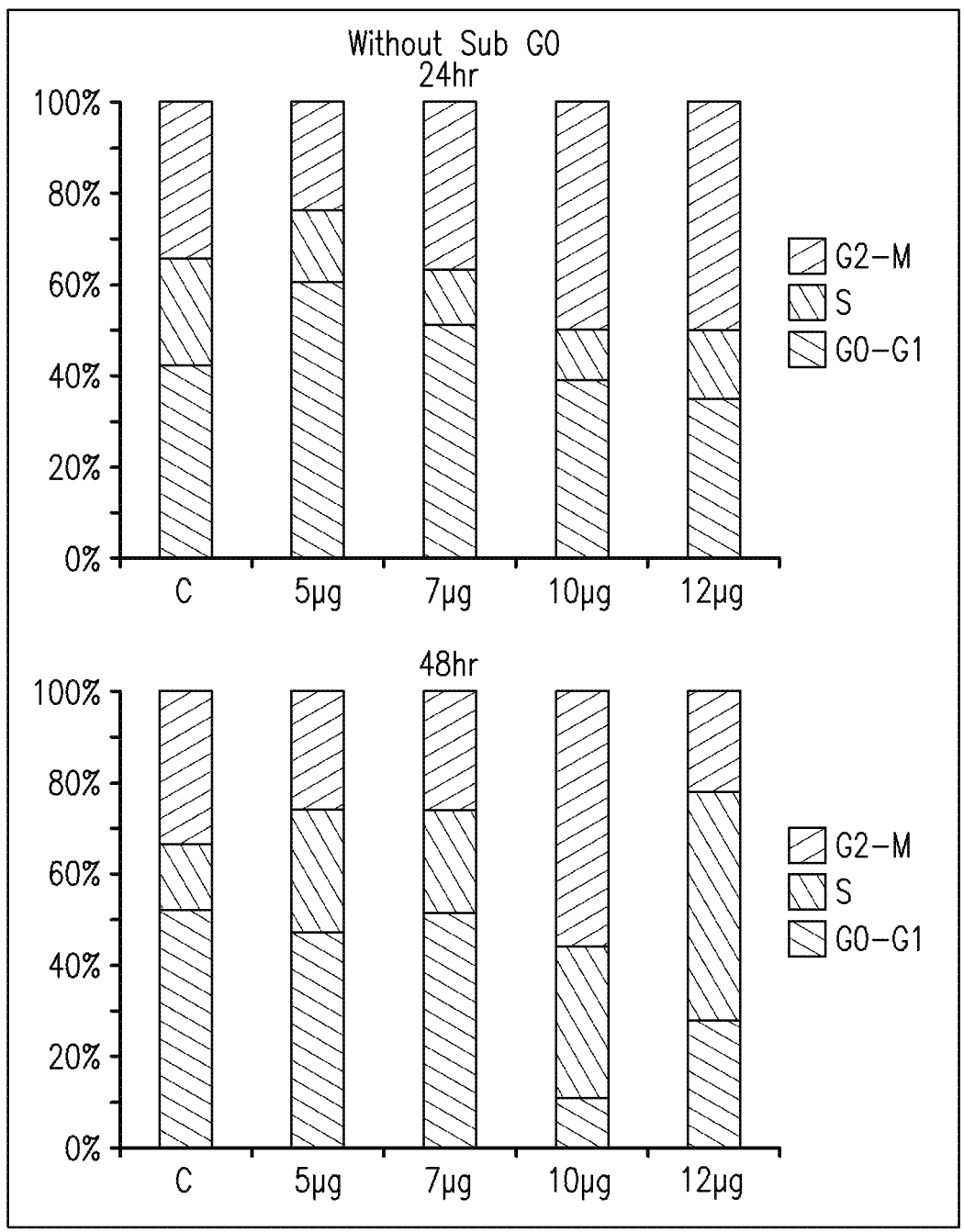
Figure 129:
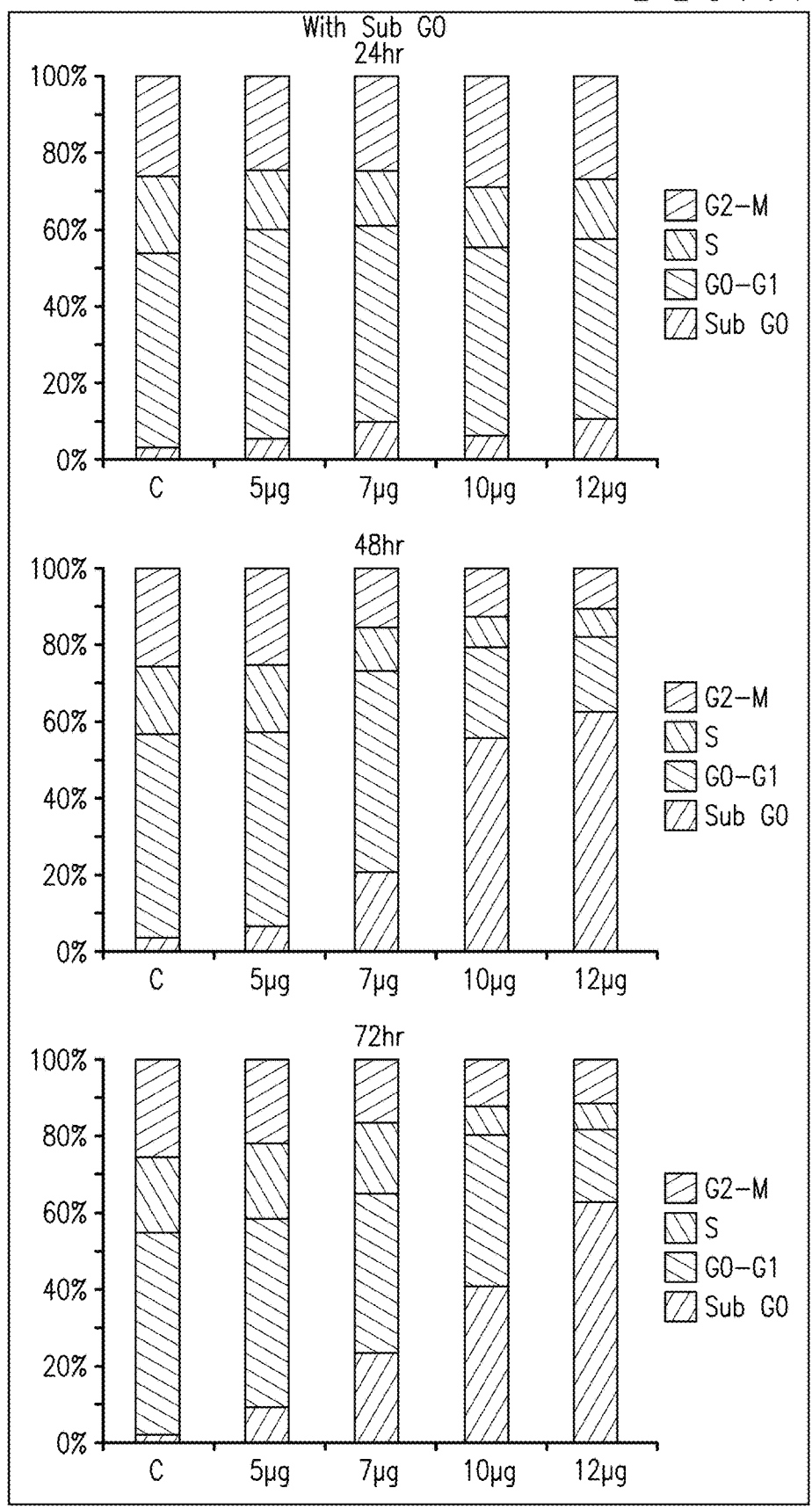
Figure 129A:
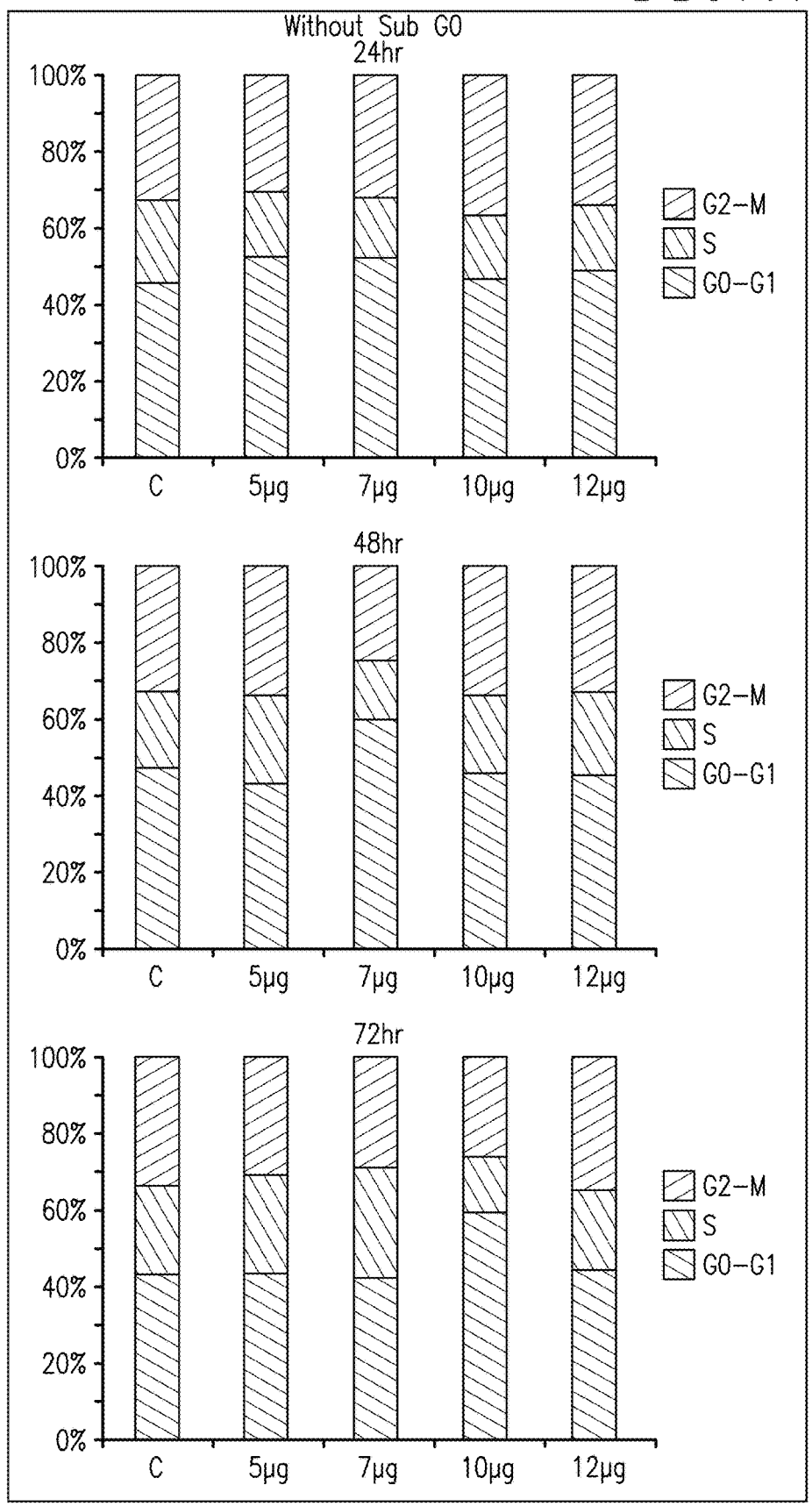
Figure 130:
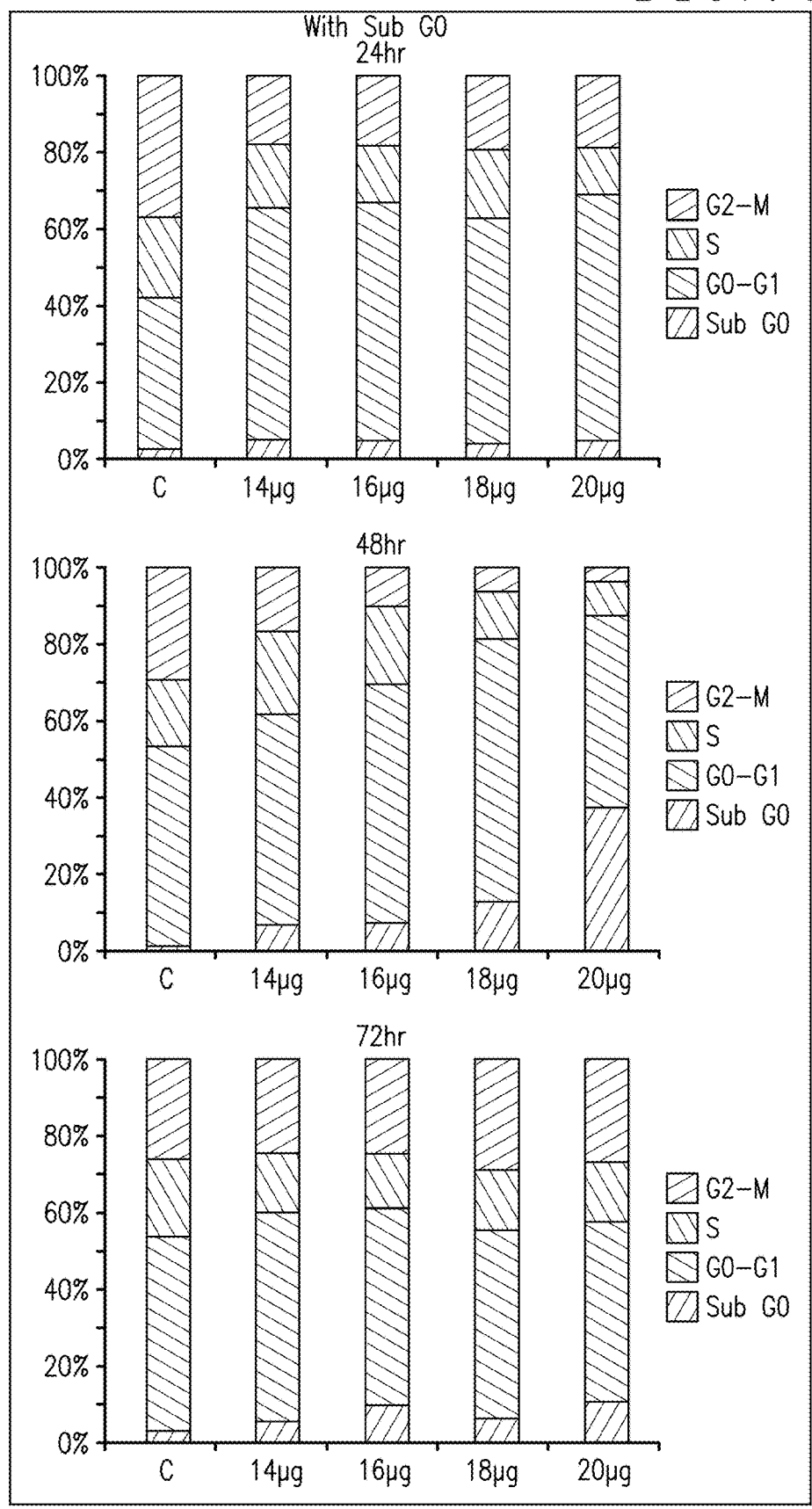
Figure 130A:
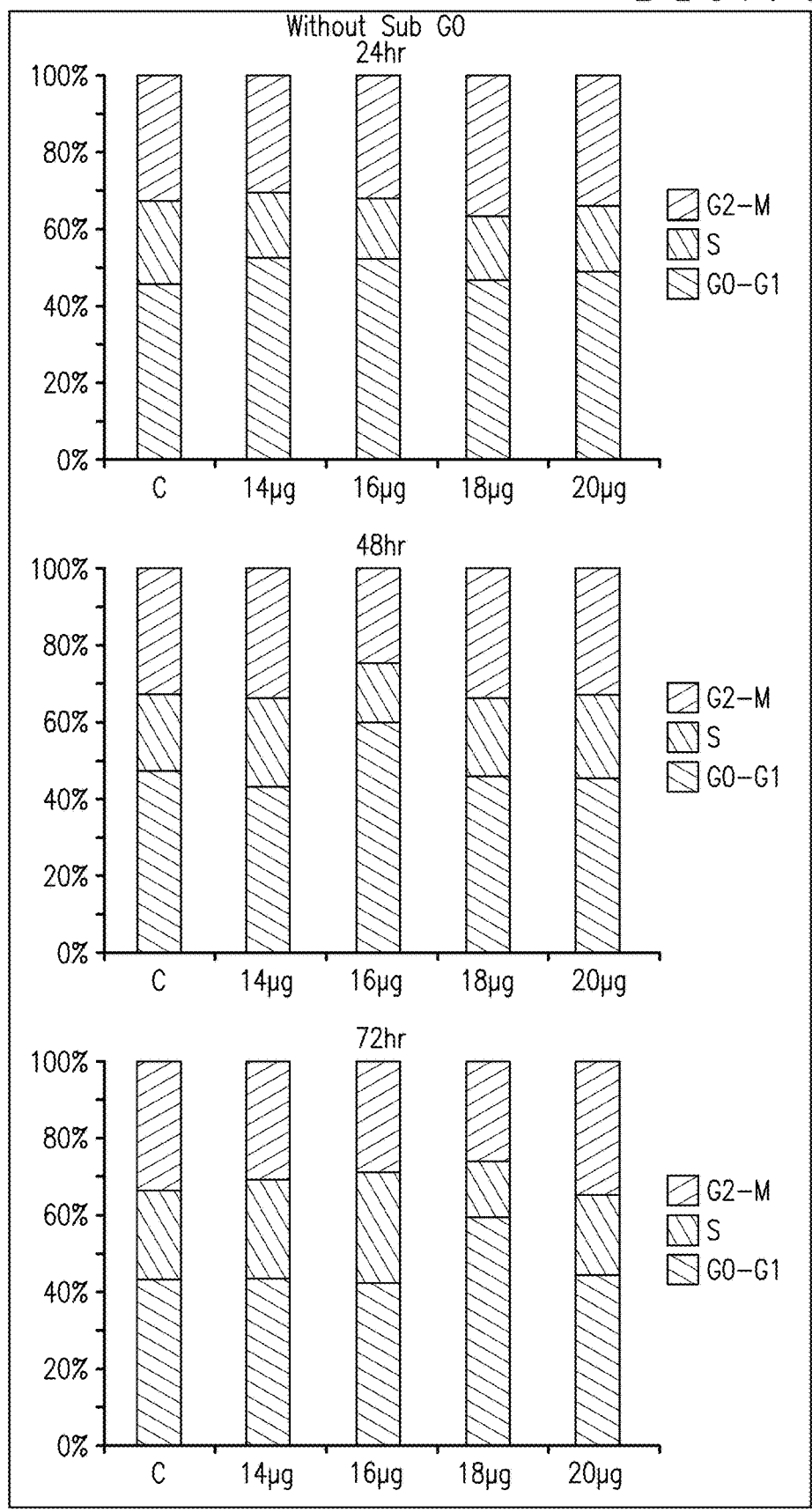
Figure 131:
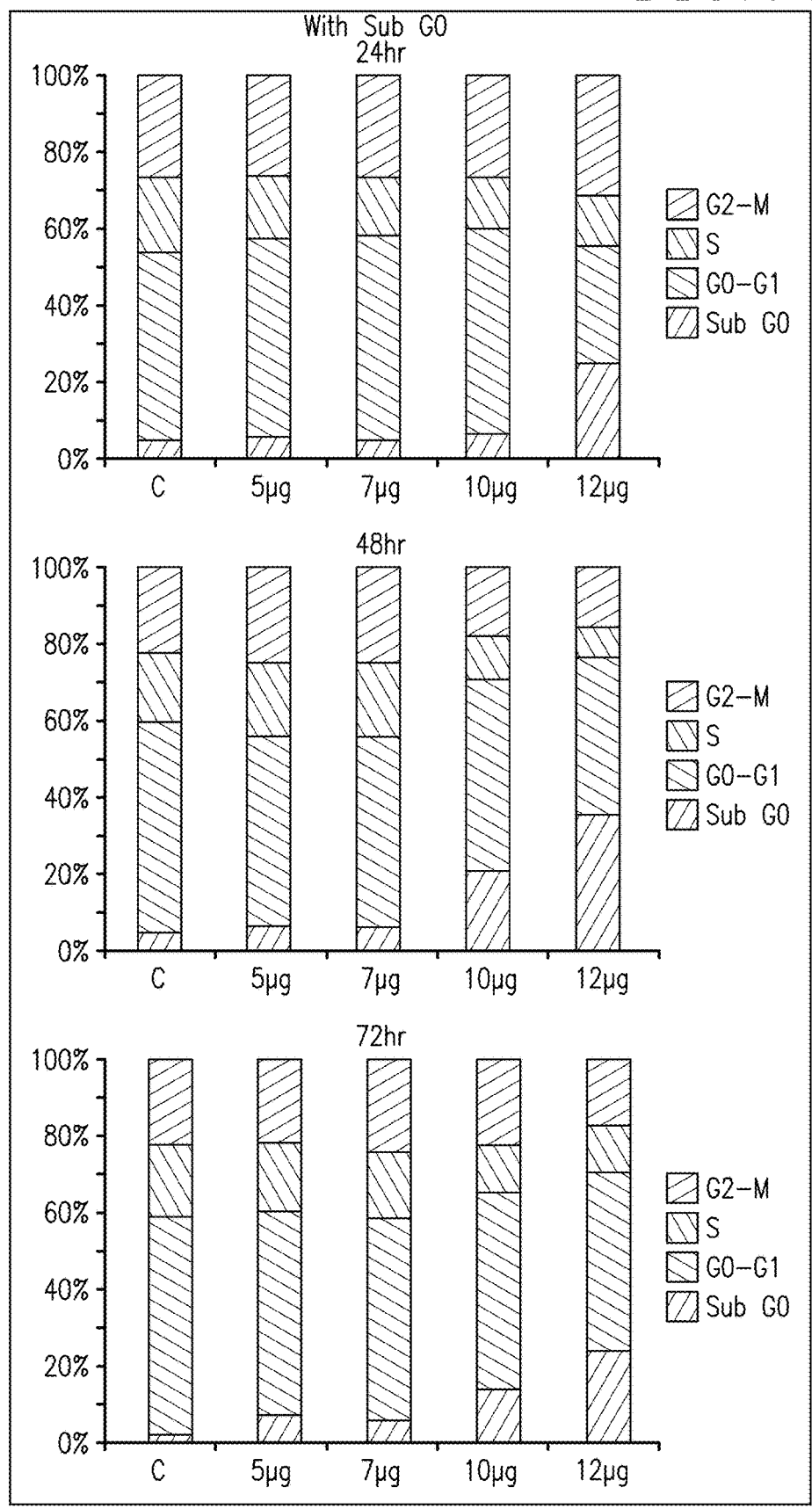
Figure 131A:
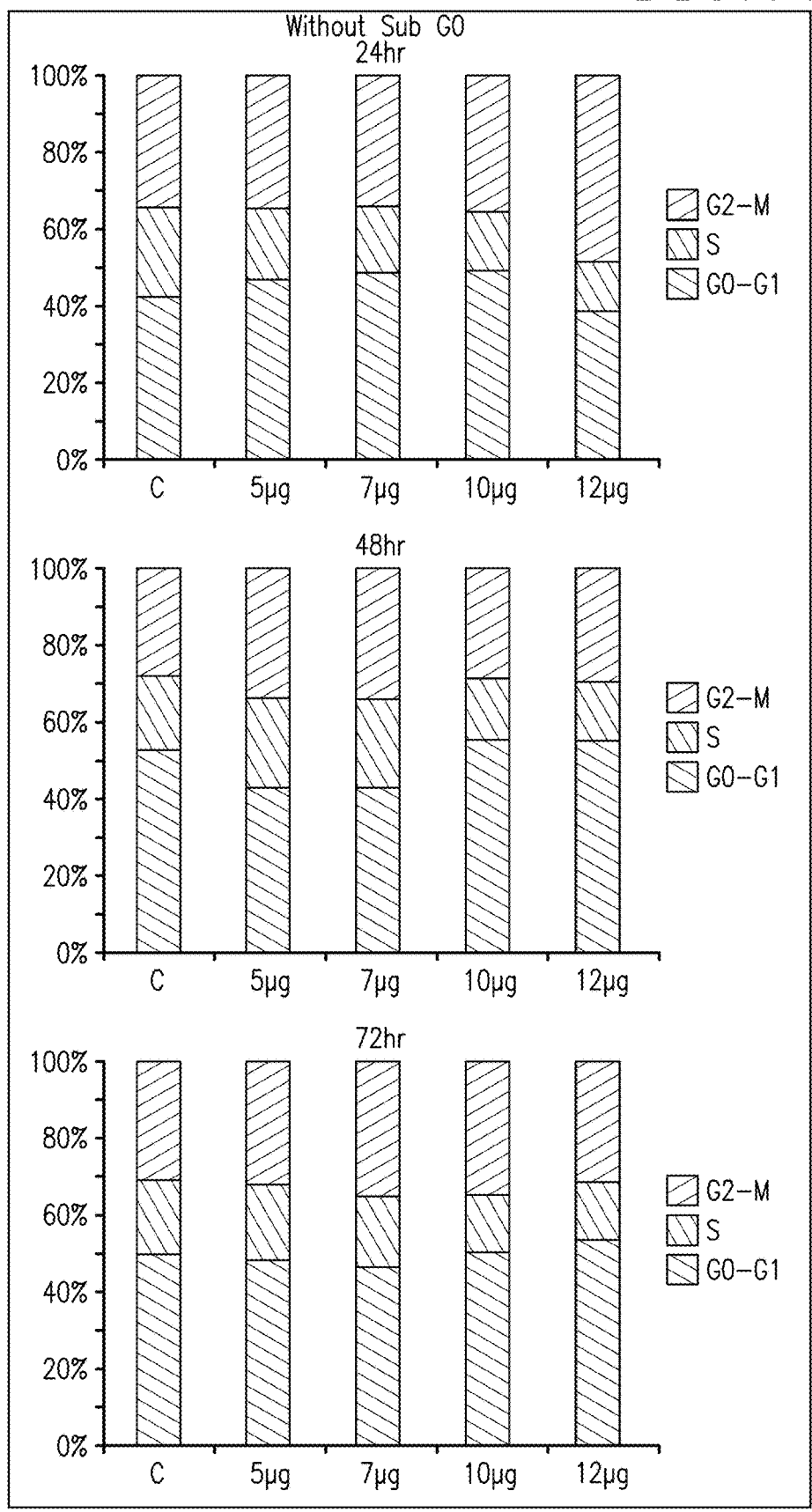

FIG. 128 is a set of bar graphs illustrating the results of a cell cycle assay using the confirmed 560 compound with S2-007 cells over 24 and 48 hours, as described in Example 17, with Sub G0;

FIG. 128A is a set of bar graphs illustrating the results of a cell cycle assay using the confirmed 560 compound with S2-007 cells over 24 and 48 hours, as described in Example 17, without Sub G0;

FIG. 129 is a set of bar graphs illustrating the results of a cell cycle assay using the confirmed 560 compound with MiaPaCa-2 cells over 24, 48, and 72 hours, as described in Example 17, with Sub G0;

FIG. 129A is a set of bar graphs illustrating the results of a cell cycle assay using the confirmed 560 compound with MiaPaCa-2 cells over 24, 48, and 72 hours, as described in Example 17, without Sub G0;

FIG. 130 is a set of bar graphs illustrating the results of a cell cycle assay using the confirmed 562 compound with S2-007 cells over 24, 48, and 72 hours, as described in Example 17, with Sub G0;

FIG. 130A is a set of bar graphs illustrating the results of a cell cycle assay using the confirmed 562 compound with S2-007 cells over 24, 48, and 72 hours, as described in Example 17, without Sub G0;

FIG. 131 is a set of bar graphs illustrating the results of a cell cycle assay using the confirmed 562 compound with MiaPaCa-2 cells over 24, 48, and 72 hours, as described in Example 17, with Sub G0; and FIG. 131A is a set of bar graphs illustrating the results of a cell cycle assay using the confirmed 562 compound with MiaPaCa-2 cells over 24, 48, and 72 hours, as described in Example 17, without Sub G0.

DETAILED DESCRIPTION OF THE PREFERRED EMBODIMENTS

The therapeutic agents of the invention are used in therapeutically effective amounts, i.e., amounts that will elicit the biological or medical response of a tissue, system, or subject that is being sought, and in particular to elicit some desired therapeutic effect against a variety of human diseases, and especially cancers; in the case of cancers, the agents operate by preventing and/or inhibiting proliferation and/or survival of cancerous cells, including cancer stem cells, and/or by slowing the progression of cancers. Those skilled in the art recognize that an amount may be considered therapeutically effective even if the condition is not totally eradicated or prevented, but it or its symptoms and/or effects are improved or alleviated partially in the subject. Of course, the appropriate makeup of the agents hereof and dosing regimens using such agents will depend on the particular cancer being treated, the extent of the disease, and other factors related to the patient as determined by those skilled in the art. Hence, the terms "therapeutic" or "treat," as used herein, refer to products or processes in accordance with the invention that are intended to produce a beneficial change in an existing condition (e.g., cancerous tissue, tumor size, metastases, etc.) of a subject, such as by reducing the severity of the clinical symptoms and/or effects of the condition, and/or reducing the duration of the symptoms/effects of a subject.

Additional ingredients may be included with the chemotherapeutic agents of the invention for administration to the subject. Such additional ingredients include, other active agents, preservatives, buffering agents, salts, carriers, excipients, diluents, or other pharmaceutically acceptable ingredients. The active agents that could be included in the compositions include antiviral, antibiotic, or other anticancer compounds; the latter could include the compounds described in PCT application serial number PCT/US2015/055968, such as curcumin, harmine, and isovanillin, and metabolites, dimers, derivatives, isomers, enantiomers (both D and L), tautomers, esters, complexes and salts of any of the foregoing.

The therapeutic agents of the invention give significant and unexpected therapeutic results, particularly in the context of anti-cancer results. In use, a therapeutically effective amount of an agent or composition in accordance with the invention is administered to a subject in need thereof. Such may comprise a single unit dosage or, more usually, periodic (e.g., daily) administration of lower dosages over time.

The dosages may be administered in any convenient manner, such as by oral, rectal, nasal, ophthalmic, parenteral (including intraperitoneal, gastrointestinal, intrathecal, intravenous, cutaneous (e.g., dermal patch), subcutaneous (e.g., injection or implant), or intramuscular) administrations. The dosage forms of the invention may be in the form of liquids, gels, suspensions, solutions, or solids (e.g., tablets, pills, or capsules). Moreover, therapeutically effective amounts of the agents of the invention may be co-administered with other chemotherapeutic agent(s), where the two products are administered substantially simultaneously or in any sequential manner.

Levels of dosing using the compositions of the invention are quite variable owing to factors such as the patient's age, patient's physical condition, weight, the type of condition(s) being treated (e.g., specific cancer(s)), and the severity of the conditions. In general, however, regardless of the dosage form or route of administration employed, such as liquid solutions or suspensions, capsules, pills, or tablets, via oral, parenteral, or injection, the compositions should be dosed of from about 5 to 2000 mg per day, and more usually from about 100-800 mg per day. Such dosages may be based on a single administration per day, but more usually multiple administrations per day.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

As used herein, pharmaceutically acceptable salts with reference to the therapeutic compounds of the present invention mean salts of the compounds which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucametacin acid, gluconic acid, glutamic acid, glycolic acid, heptanoic acid, hexanoic acid, hydroxynaphthoic acid, lactic acid, laurylsulfuric acid, maleic acid, malic acid, malonic acid, Mandela acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutyl acetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use*, P. H. Stahl & C. G. Wermuth eds., ISBN 978-3-90639-058-1 (2008).

In preparing the compounds of the invention, use should be made of starting ingredients of relatively high purity, typically at least about 90% by weight pure, and more preferably at least about 98% by weight pure. The use of naturally occurring sources for the ingredients is generally not appropriate or desirable, because these naturally occurring products may contain relatively small amounts of the desired components and/or have potentially interfering compounds therein. Moreover, use of low-purity ingredients often leads to little or no compounds in accordance with the invention.

Thus, the preferred starting compounds or components of the invention are either synthetically derived or derived from one or more naturally occurring product(s) which have been significantly modified so as to contain at least about 90% by weight (more preferably at least about 98% by weight) of the desired component. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product.

As used herein, the terms "alkyl," "alkenyl," "alkynyl," mean and are intended to cover straight, branched chain, and cyclic groups. "Amines" means and is intended to cover primary, secondary, and tertiary amines. "Sulfur groups" means and is intended to cover thiols, sulfides, disulfides, and sulfoxides. "Derivative" means and is intended to cover compounds, moieties, and/or groups which are substituted with atoms, groups, or side chains which do not materially degrade (e.g., no more than about 20%, preferably no more than about 10%, degradation) of the performance of the compound, moiety, or group as compared with the unsubstituted versions thereof.

As indicated, certain preferred compounds or agents of the invention comprise a pair of fused polycyclic moieties, each including an N-containing ring, where the fused polycyclic moieties are bound or linked by a single tether or linker moiety, which are schematically illustrated as

PCM1—L—PCM2 where PCM1 and PCM2 are the fused polycyclic moieties (which may be the same or different), where L is the tether or linker. As indicated by this schematic, the linker L may be attached to PCM1 and PCM2 at any position on any ring thereof, and the bonding sites need not be the same for both PCM1 and PCM2. The fused polycyclic and linker moieties are described below.

The Fused Polycyclic Compounds or Moieties

The fused polycyclic moieties of the invention are derived or synthesized from starting ingredients which yield compounds or moieties having the following generalized structure:

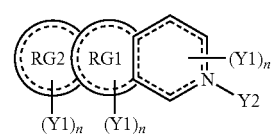

I where one of the terminal rings is a 6-membered ring including at least one N heteroatom at any valence-permitted position(s) around the 6-membered ring (the single N-atom illustrated in Structure I is exemplary only, both in terms of the position of the N-atom, and the number of N-atoms). This 6-membered ring may be aryl in character (e.g., a pyrido ring), or non-aryl (e.g., a piperidine ring), or contain multiple N-atoms (e.g., a piperazine ring). Further with respect to Structure I, RG1 is fused with the terminal 6-membered N-atom-containing ring and has from 5-8 atoms (as used herein, "fused" refers to the fact that the fused rings share 2 adjacent atoms or, in other words, 1 covalent bond). Ring RG2 may be nothing (i.e., the moiety is bicyclic) and, if present, ring RG2 is fused with ring RG1 and with the terminal six-membered ring, and has from 5-8 atoms. In both RG1, RG2 (where present), and the six-membered N-containing ring, the majority of ring atoms in each case are carbon atoms. However, these rings may also include one or more heteroatoms, such as S, O, or N.

The interior dotted lines illustrated in RG1 and RG2 represent the fact that the individual rings may have one or more double bonds and may be aryl or non-aryl in character. As indicated, in the six-member N-atom-containing ring, the N-atom(s) may be at any permitted position around the ring, and the dotted lines represent that the six-membered ring may have 1, 2, or 3 double bonds. The n subscript on each Y1 represents the fact that there may be single or multiple substituents at any permitted position(s) around the six-membered N-atom-containing ring, RG1, and/or RG2; preferably, each n is independently either 1, 2, or 3. Each Y1 and Y2 is independently selected from the group consisting of nothing, OH, C1-C12 (preferably C1-C$_4$) alkyl, alkenyl, and alkynyl groups, C1-C12 (preferably C1-C4) alkoxy and alkoxyphenyl groups, aryl and aryloxy groups, aldehyde and carbaldehyde groups, amines, nitro groups, nitrile groups, C2-C6 carboxylic acid groups, boronic groups, sulfur groups, and amino acids, where any of the aforementioned may be substituted with N, S, O, B, or halogen atoms.

Exemplary bicyclic compounds corresponding to the moieties in accordance with Structure I may include quinoline and derivatives thereof, purine and derivatives thereof, as well as quinolin-2-amine, 6-bromo-2-methylquinoline, 2-hydroxy-4-methylquinoline, 4-chloro-7-methoxyquinoline, 8-quinolineboronic acid, quinoxaline, 8-aminoisoquinoline, 5-chloro-3-methylbenzothiothene, 4-nitroquinoline-N-oxide, 1-methylisoquinoline, 7-methylquinoline, 6,7-dimethoxyquinazoline-2,4-dione, 6-chloroquinoline, 1-chloroisoquinoline, 4-chloroquinoline, 8-chloroquinoline, isocarbostyril, 8-hydroxyquinoline-5-sulfonic acid, isoquinoline N-oxlide, 6-fluoroquinaldine, 2-chloroquinoline-3-carbaldehyde, 5-nitroisoquinoline, 2,6-dimethylquinoline, 3-hydroxyquinoline, 2-methyl-6-quinolinecarboxylic acid, 6-bromoisoquinoline, 8-mercaptoquinoline hydrochloride, quinoline-4-carboxylic acid, 6-bromoquinoline, 7-bromoquinoline, 6-nitroquinoline, decahydroquinoline, 4-hydroxyquinoline, 8-methylquinoline, 3-hydroxy-2-methyl-4-quinolinecarboxylic acid, 6-quinolinecarboxylic acid, 3-quinolinecarboxylic acid, 2-hydroxy-4-quinolinecarboxylic acid, 2,4-dimethylquinoline, 1-isoquinolinecarbonitrile, 7-chloro-2-methylquinoline, 1-methyl-3,4-dihydroisoquinoline, 4-methyl-6H,7H-thieno[3,2-c]pyridine, 7-methyl-4H, 5H-thieno[2,3-c]pyridine, 1-ethyl-3,4-dihydroisoquinoline, 5-methyl-7,8-dihydro-1,6-naphthyridine, 1,4-dimethyl-3,4-dihydro-2,7-naphthyridine, 5-methyl-7,8-dihydro-1,6-naphthyridine, and 4-methyl-6,7-dihydrothienol[3,2-c]pyridine.

A variety of fused tricyclic compounds corresponding to the moieties in accordance with Structure I are also useful in the invention. One class of fused tricyclic compounds are O-carboline compounds and derivatives thereof, having a tricyclic ring system, e.g., a bicycle made up of a six-membered benzene ring and a fused five-membered pyrrole ring, with a terminal N-containing ring fused with the intermediate pyrrole ring. Exemplary O-carbolines include tryptoline, pinoline, harmane, harmine, harmaline, tetrahydroharmaline, and 9-methyl-β-carboline. Harmaline is in some instances preferred for use in the invention.

Harmaline (7-methoxy-1-1-methyl-4,9-dihydro-3H-pyrido[3,4-b]indole) is a fluorescent psychoactive alkaloid from the group of harmala alkaloids and O-carbolines, and occurs in various plants, such as *Peganum harmala*. Harmaline is identified as CAS #304-21-2, and exists in two tautomeric forms:

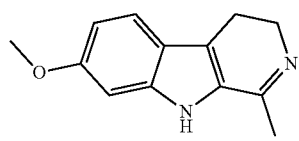

7-methoxy-1-methyl-4,9-dihydro-
3H-pyrido[3,4-b]indole
Chemical Formula: C$_{13}$H$_{14}$N$_2$O
Exact Mass: 214.11

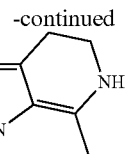

7-methoxy-1-methyl-3,4-dihydro-
2H-pyrido[3,4-b]indole
Chemical Formula: C$_{13}$H$_{14}$N$_2$O
Exact Mass: 214.11

As used herein, "harmaline" refers to either or both tautomers. Other harmaline components are described below.

Some harmaline components have the structure

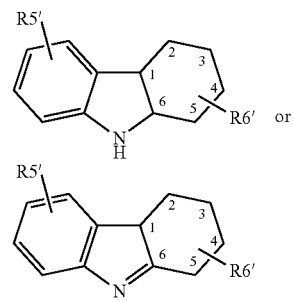

where the numbered 6-member fused ring is a N-heterocycle with a single N atom at any of the positions 2-5, and the R6' substituents may be located at any ring position; R5' is H, OH, C1-C12 (preferably C1-C$_4$) alkoxy, aryloxy (e.g., benzyloxy or phenoxy), carboxy, biphenyl, nitro, carboxylate; and R6' is H, OH, C1-C12 (preferably C1-C$_4$) alkyls, or a C1-C12 (preferably C1-C4) carboxylic acid.

Representative compounds of this type include harmaline and the following:

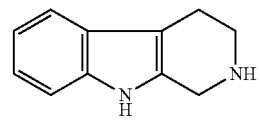

1,2,3,4-Tetrahydro-
9H-pyrido[3,4-b]indole
(THβC)

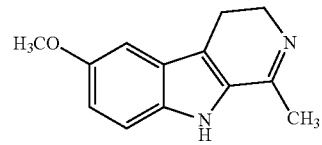

6-methoxy-1-methyl-3,4-dihydro-
2H-yrido[3,4-b]indole
(6-Methoxyharmalan)

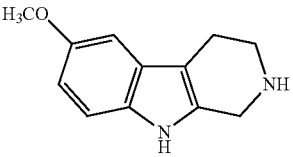

6-Methoxy-1,2,3,4-tetrahydro-
9H-pyrido[3,4-b]indole
(pinoline)

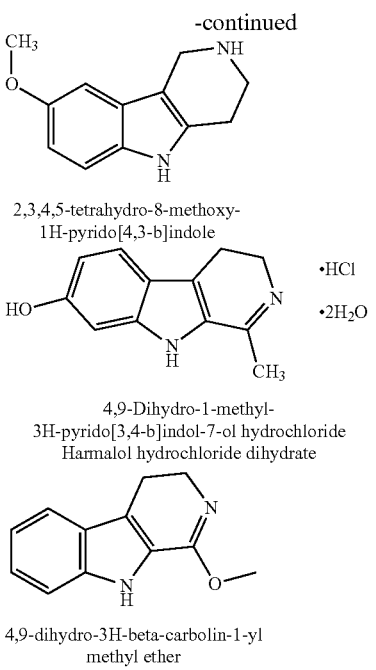

2,3,4,5-tetrahydro-8-methoxy-
1H-pyrido[4,3-b]indole 4,9-Dihydro-1-methyl-
3H-pyrido[3,4-b]indol-7-ol hydrochloride
Harmalol hydrochloride dihydrate 4,9-dihydro-3H-beta-carbolin-1-yl
methyl ether In the foregoing representative compounds, any methoxy substituent may be replaced by a C2-C4 alkoxy group, or by a phenoxy group.

The Linker Compounds and Moieties

Each linker L provides two bonding branches from a single atom forming at least a part of the linker moiety. Thus, the linker moiety may present an effective "V" or "Y" configuration, with the single atom at the lower vertex (as depicted in Structure II below) with the two bonding branches respectively bonded to the fused polycyclic moieties. Thus, a linker may be a single methylene group (CH2), where the fused polycyclic moieties are bonded to the carbon atom of the methylene group to present an effective "V" configuration. In like manner, the linker may comprise a pair of alkyl groups with an intermediate carbon atom such as CH3-C-CH3, so that the fused polycyclic moieties are bonded to the intermediate carbon atom. Thus, preferred linkers include multiple atoms, one of which is the bonding atom for the fused polycyclic moieties. The single bonding atom of the linkers may be selected from non-metals, and especially atoms of carbon, nitrogen, oxygen, fluorine, phosphorous, sulfur, chlorine, bromine, and iodine. Metal atoms, such as Pt, are normally less preferred. In addition, the bonding between the single atom and the bonding branches may be classical covalent bonding, meaning that each atom participating in the bonding contributes at least one electron as a part of a molecular orbital. However, typical metal bonding, such as coordinate or dative bonding, is generally less favored.

It will be appreciated that linker compounds or moieties serve to separate the fused polycyclic moieties forming a part of the compounds of the invention and may also contribute to the morphology and/or steric characteristics of the complete compounds. As used herein, and in keeping with conventional linker nomenclature, the entirety of any multiple-atom linker moiety between the fused polycyclic moieties is considered to be the "linker," without any artificial separation of such a multiple-atom linker moiety, where one atom of the linker moiety is deemed to be the "linker" and with the remainder of the linker moiety not being considered as a part of the "linker." For example, if a propyl moiety is used as the linker moiety where two fused polycyclic moieties are bonded to respectively bonded to the terminal carbons of the propyl moiety, it would be inappropriate and not in keeping with the invention to deem one of the terminal CH2 to methylene groups as the linker, while disregarding the presence of the remaining CH2-CH2 group as a part of the linker.

In certain preferred compounds of the invention, the fused tricyclic moieties are bonded to the linker through a single atom, and wherein this single atom is the carbon atom of a methine group. A "methine group" is defined by the *Illustrated Glossary of Organic Chemistry* as a portion of a molecular structure equivalent to methane minus three hydrogen atoms, i.e., a CH group. A methine group is to be contrasted with a "methylene group" defined as a portion of a molecular structure equivalent to methane minus two hydrogen atoms, or a CH2 group.

Some linker moieties may be derived from aldehydes, where both of the fused polycyclic moieties are bonded to the carbonyl carbon of the aldehyde functional group, thereby presenting an effective "Y" configuration. In certain embodiments, appropriate aldehyde linker moieties are characterized by a six-membered ring with an attached aldehyde functional group, of the following structure.

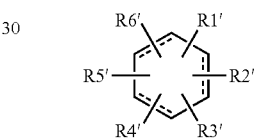

where the substituents may be located at any position around the ring. $R1'$ is a C1-C12 (preferably $C1-C_4$) aldehyde, $R2'$-$R5'$ are independently and selectively taken from the group consisting of H, OH, C1-C12 (preferably C1-C4) alkyl groups, C2-C12 (preferably C2-C5) alkenyl groups, C1-C12 (preferably C1-C4) alkoxy groups, C1-C12 (preferably C1-C4) aldehyde groups, acetate, isobutyrate, phenyl, phenoxy, benzyloxy, C2-C12 (preferably $C2-C_6$) alkyl esters, halo (e.g., F, Br, I, Cl), primary and secondary amines, nitro, and mixtures thereof. The dotted bond lines in the six-membered ring represent that the six-membered ring may be cyclohexane, or have one, two, or three carbon-carbon double bonds (e.g., cyclohexene, cyclohexadiene, phenyl, or derivatives thereof).

Representative compounds of this type include vanillin, benzaldehyde, cinnamaldehyde, cuminaldehyde, orthovanillin, perillaldehyde, cyclohexanecarboxaldehyde, and the following:

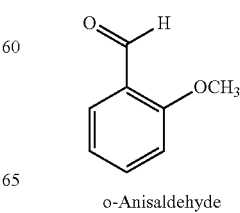

o-Anisaldehyde

-continued

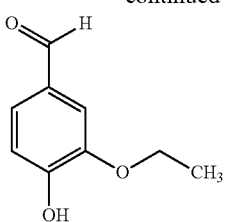

Ethyl Vanillin (3-Ethoxy-4-hydroxybenzaldehyde

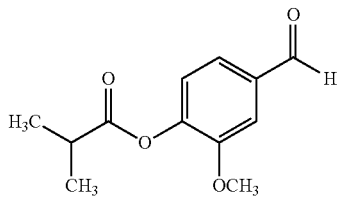

Vanillin Isobutyrate

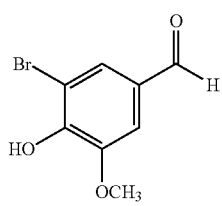

5-Bromovanillin

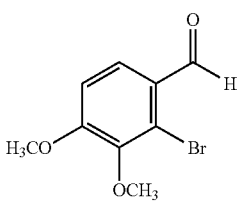

2-Bromo-3-hydroxy-4-methoxybenzaldehyde

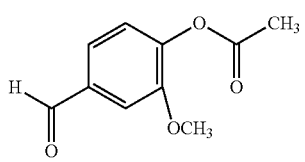

Vanillin acetate

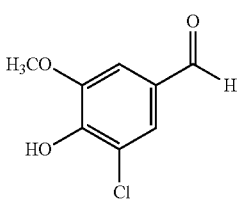

3-Chloro-4-hydroxy-5-methoxybenzaldehyde

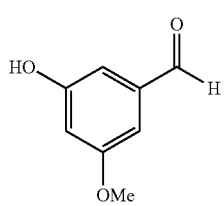

3-Hydroxy-5-methoxybenzaldehyde

-continued

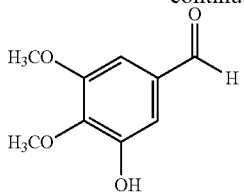

3,4-Dimethoxy-5-hydroxybenzaldehyde

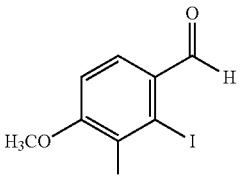   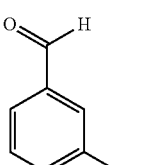

3-Hydroxy-2-iodo-4-methoxybenzaldehyde   m-Anisaldehyde

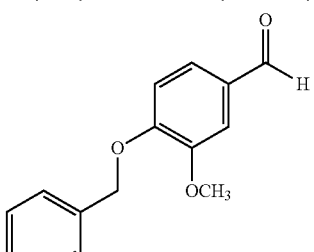

4-Benzyloxy-3-methoxybenzaldehyde

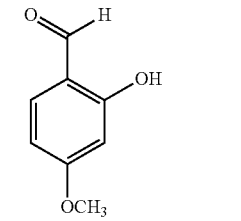   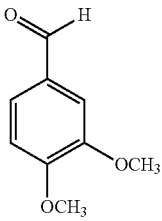

2-Hydroxy-4-methoxybenzaldehyde   Veratraldehyde

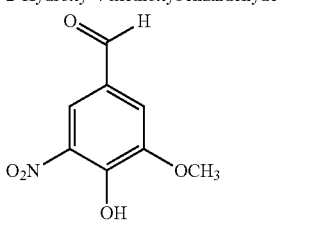

5-Nitrovanillin

Still further phenyl aldehydes useful in the invention as linkers include moieties of 2-methoxybenzaldehyde, 3-ethoxy-4-hydroxybenzaldehyde, 4-formyl-2-methoxyphenyl isobutyrate, 3,4-dimethoxybenzaldehyde, 4-hydroxy-3-methoxy-5-nitrobenzaldehyde, 4-formyl-2-methoxyphenyl acetate, 3-hydroxy-5-methoxybenzaldehyde, 2-hydroxy-4-methoxybenzaldehyde, 3-chloro-4-hydroxy-5-methoxybenzaldehyde, 4-(benzyloxy)-3-methoxybenzaldehyde, 3-hydroxy-4,5-dimethoxybenzaldehyde, 3-bromo-4-hydroxy-5-methoxybenzaldehyde, 2-bromo-3-hydroxy-4-methoxybenzaldehyde, 3-hydroxy-2-iodo-4-methoxybenzaldehyde, 3-methoxybenzaldehyde, 3-phenoxybenzaldehyde, 4-phenoxybenzaldehyde, [1,1'-biphenyl]-3-carbaldehyde, 4-fluoro-3-phenoxybenzaldehyde, 3-fluorobenzaldehyde, 4-fluorobenzaldehyde, 3,5-difluorobenzaldehyde, 2,4,5-trifluorobenzaldehyde, 2,3,4,5,6-pentafluorobenzaldehyde, 4-methylbenzaldehyde, terephthalaldehyde, 4-chlorobenzaldehyde, 4-(prop-1-en-2-yl)cyclohex-1-ene-1-carbaldehyde, 4-isopropylbenzaldehyde, and cyclohexanecarbaldehyde.

In other embodiments, aliphatic or alkenyl aldehydes may be used as linkers. Generally, such linkers are moieties of aldehydes, such as C1-C12 alkyl or C2-C12 alkenyl aldehydes, and include representative compounds such as (E)-hex-2-enal (C6H10O, Exact Mass: 98.07), 3-methylbutanal (isovaleraldehyde) (C5H10O, Exact Mass: 86.07), 3,7-dimethyloct-6-enal (citronellal) (C10H18O, Exact Mass: 154.14), 7-hydroxy-3,7-dimethyloctanal (hydroxycitronellal) (C10H20O2, Exact Mass: 172.15), and dodecyl aldehyde (C12H24O, Exact Mass: 184.18).

The Complete Compounds of the Invention

As noted previously, one generalized form of the compounds is set forth in the schematic representation

PCM1-L—PCM2.

Preferred species of this representation are set forth in the following Structure II

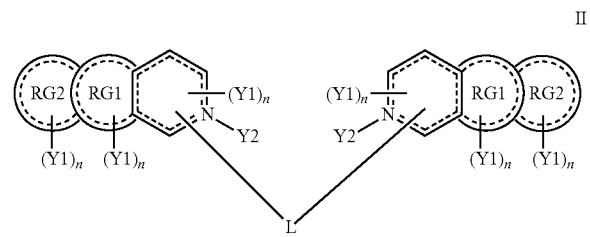

II where it will be seen that the intermediate tether or linker L is bonded to the six-membered, N-containing ring of the respective fused polycyclic moieties of Structure I, and specifically at a single atom forming a lower vertex and at least a part of the linker L. The bonding sites of the linker L to the fused polycyclic moieties may be at any permitted locations around the six-membered rings, including at the N-heteroatom (in which case Y2 would be nothing), and such bonding sites need not be the same for the respective polycyclic moieties. The six-membered terminal N-containing ring, RG1, RG2, the Y1 and Y2 substituents, and the n values, are those previously defined with respect to Structure I.

One class of compounds (Structure III below) has a central linker bonded to the N-containing B rings at respective positions at an ortho carbon atom relative to the nitrogen atom, where each of the β-carboline groups may independently be substituted or unsubstituted. "Substituted" with respect to the first moiety ring, and the β-carboline groups, means that these may be substituted at any position (and independently in the case of the respective β-carboline groups) with any substituent which does not materially degrade (e.g., no more than about 20%, preferably no more than about 10%, degradation) of the performance of the compound as compared with the unsubstituted version thereof More particularly, certain other compounds of this type have the generic Structure III:

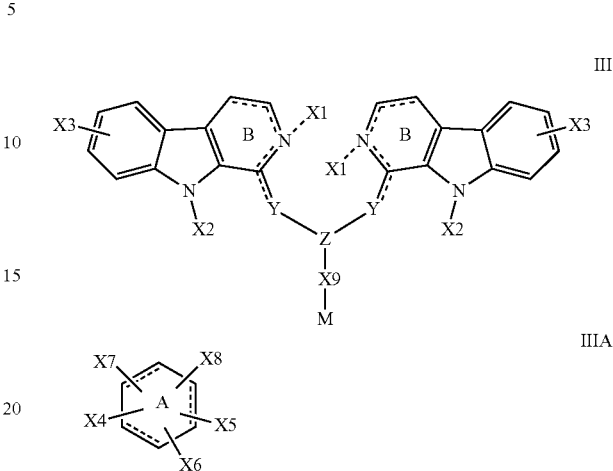

III

IIIA wherein each of X1, X2, X3, and X9, is independently selected from the group consisting of nothing, OH, C1-C12 alkyl, alkenyl, and alkynyl groups, C1-C12 alkoxy and alkoxyphenyl groups, aryl and aryloxy groups, aldehyde and carbaldehyde groups, amines, nitro groups, nitrile groups, C2-C6 carboxylic acid groups, boronic groups, sulfur groups, and amino acids, where any of the aforementioned may be substituted with N, S, O, B, or halogen atoms, Z contains the single bonding atom described above and is selected from the group consisting of C1-C12 alkyl, alkenyl, and alkynyl groups, C1-C12 alkoxy and alkoxyphenyl groups, aryl and aryloxy groups, aldehyde and carbaldehyde groups, amines, nitro groups, nitrile groups, C2-C6 carboxylic acid groups, boronic groups, sulfur groups, and amino acids, where any of the aforementioned may be substituted with N, S, O, B, or halogen atoms. Each X3 may be attached at any position around the corresponding terminal phenyl moieties of the β-carboline groups. Each Y is independently nothing (e.g., there is a direct bond between the two B rings, or Z may be directly coupled to one or both of the B rings), H, OH, C1-C12 (preferably C1-C4) alkyl, alkenyl, and alkynyl groups, C1-C12 (preferably C1-C4) alkoxy and alkoxyphenyl groups, aryl and aryloxy groups, aldehyde groups, amines, nitro groups, nitrile groups, C2-C6 carboxylic acid groups, boronic groups, sulfur groups, and amino acids, where any of the aforementioned may be substituted with N, S, O, B, or halogen atoms. Preferably, Y is a C1-C12 (preferably C1-C4) group composed of C, CH, and/or CH2 atoms or groups, and Z is C, CH, or CH2. X9 is preferably selected from the group consisting of nothing (e.g., M may be bonded to Z), C1-C12 (preferably C1-C4) alkyl groups, and C2-C12 (preferably C2-O5) alkenyl groups. M is selected from the group consisting of Structure IIIA, nothing, OH, C1-C12 (preferably C1-C4) alkyl, alkenyl, and alkynyl groups, C1-C12 (preferably C1-C4) alkoxy and alkoxyphenyl groups, aryl and aryloxy groups, aldehyde groups, amines, nitro groups, nitrile groups, C2-C6 carboxylic acid groups, boronic groups, sulfur groups, and amino acids, where any of the aforementioned may be substituted with N, S, O, B, or halogen atoms. Each X4, X5, X6, X7, and X8 of Structure IIIA is attached at any position around the A ring and is independently selected from the group consisting of nothing, OH, C1-C12 (preferably C1-C4)

alkyl, alkenyl, and alkynyl groups, C1-C12 (preferably C1-C4) alkoxy and alkoxyphenyl groups, aryl and aryloxy groups, aldehyde groups, amines, nitro groups, nitrile groups, C2-C6 carboxylic acid groups, boronic groups, sulfur groups, and amino acids, where any of the aforementioned may be substituted with N, S, O, B, or halogen atoms. The designation ---- in the A ring refers to the fact that there may optionally be 0, 1, 2, or 3 double bonds (e.g., the A ring may be cyclohexane, cyclohexene, cyclohexadiene, benzene, or derivatives thereof), and wherein the designation ---- in connection with the two B rings refers to the fact that there may optionally be: 1) one or two non-fused double bonds at one or two valence-permitted positions around either or both of the B rings, such as illustrations a-d below; 2) a double bond between either or both of the B rings and Y or Z, with or without an additional non-fused double bond at any valence-permitted position around the corresponding N-containing ring, such as illustrations e-g below. In instances of 2) where there is a double bond between the nitrogen atom of either N-containing ring and Y or Z, X1 may be nothing, such as illustrations a-c and g. However, if there is no such nitrogen double bond, the corresponding X1 is as defined above, and is preferably selected from the group consisting of H, OH, and C1-C12 (preferably C1-C4) alkyl groups, such as illustrations d-f; or 3) either or both of the B rings are free of non-fused double bonds, and each X1 is as set forth above, and is preferably from the group consisting of H, OH, and C1-C12 (more preferably C1-C4) alkyl groups.

In preferred instances where Z is a methine CH group, X9 is not nothing or H.

Set forth below are illustrations depicting certain exemplary double bond configurations of either or both of the B rings of the above Structure III.

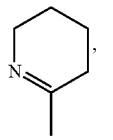

a

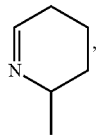

b

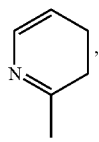

c

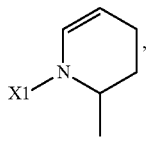

d

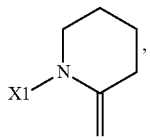

e

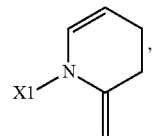

f

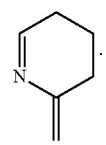

g

Advantageously, each X1 is nothing, each X2 is H, and each X3 is methoxy.

In certain embodiments of Structure III, M is the 1A ring, both of X1 are nothing, both of X3 are methoxy, 2 of X4, X5, X6, X7, and X8 are H, at least one of X4, X5, X6, X7, and X8 is selected from the group consisting of H, —OH, methoxy, ethoxy, phenoxy, C2-C5 alkenyl groups, F, and Cl, with the provisos that: 1) when one or more of X4, X5, X6, X7, and X8 is/are F or Cl, the remainder of X4, X5, X6, X7, and X8 are all H; 2) only one of X4, X5, X6, X7, and X8 may be phenoxy, and in such case, the remainder of X4, X5, X6, X7, and X8 are all H.

In other embodiments, certain compounds containing two harmaline moieties and a single phenyl moiety derived from a phenyl aldehyde compound are provided, having the general Structure IV:

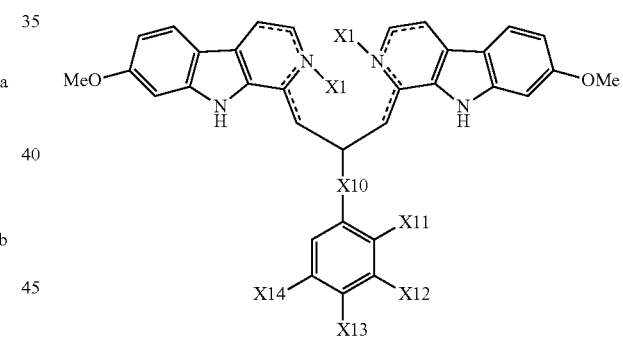

IV where X10 is —CH═CH—, X11, X12, X13, and X14 are each independently selected from the group consisting of H, —OH, methoxy, ethoxy, and phenoxy, F, and Cl, with the provisos that: 1) at least one of X12, X13, or X14 is H; 2) when one or more of X11, X12, X13, or X14 is/are F or Cl, the remainder of the X11, X12, X13, and X14 are all H; 3) a phenoxy group is present only at X12, and X11, X13, and X14 are all H, and 4) if a methoxy or ethoxy is present, at least one such methoxy or ethoxy must be at either the 2 or 3 position, wherein the designation ---- in connection with the two N-containing rings refers to the fact that there may optionally be: 1) one or two non-fused double bonds at one or two valence-permitted positions around either or both of the N-containing rings, such as illustrations a-c below; 2) a double bond between either or both of the N-containing rings and the adjacent carbon atoms, with or without an additional non-fused double bond at any valence-permitted position around the corresponding N-containing ring, such as illustration g below; or 3) either or both of the N-containing rings are free of non-fused double bonds, and each X1 is independently selected from the group consisting of H, OH, and C1-C12 (preferably C1-C4) alkyl groups.

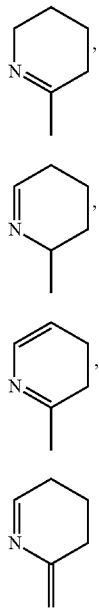

Where X10 is nothing and X11, X12, X13, and X14 are all H, the resultant structure is the 560 compound described in Example 12; where X10 is nothing, X11 is H, X12 is methoxy, X13 is —OH, and X14 is H, the resultant structure is the 562 compound described in Example 14; where X10 is nothing, X11 is —OH, X12 is methoxy, and X13 and X14 are both H, the resultant structure is the principal 523 compound described below; where X10 is nothing, X11, X13, and X14 are all H, and X12 is phenoxy, the resultant structure is the 594 compound described in Example 24; and where X10 is —CH═CH—, and all of X11, X12, X13, and X14 are H, the resultant structure is the 561 diharmaline compound set forth hereinafter as the primary compound of harmaline and cinnamaldehyde.

In other embodiments, certain compounds within the ambit of Structure IV containing two harmaline moieties and a single linker moiety are provided. These compounds are selected from the group consisting of

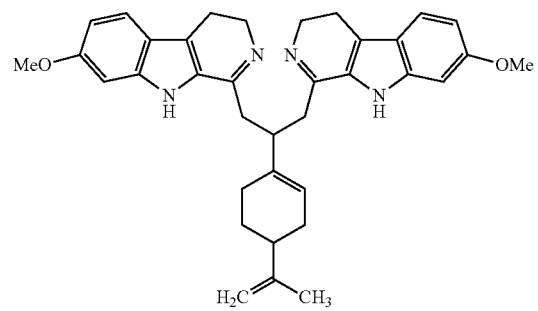

1,1'-(2-(4-(prop-1-en-2-yl)cyclohex-1-en-1-yl)propane-1,3-diyl)bis(7-methoxy-4,9-dihydro-3H-pyrido[3,4-b]indole)
Chemical Formula: $C_{36}H_{40}N_4O_2$
Exact Mass: 560.32 or

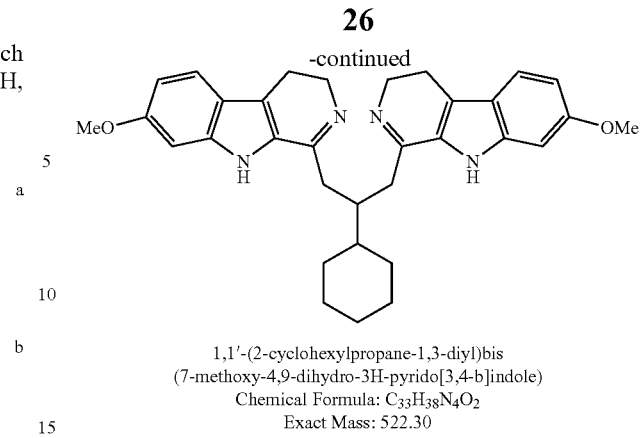

1,1'-(2-cyclohexylpropane-1,3-diyl)bis(7-methoxy-4,9-dihydro-3H-pyrido[3,4-b]indole)
Chemical Formula: $C_{33}H_{38}N_4O_2$
Exact Mass: 522.30

Synthesis of the Complete Compounds of the Invention

In preparing the compounds of the invention, use should be made of starting ingredients of relatively high purity, typically at least about 90% by weight pure, and more preferably at least about 98% by weight pure. The use of naturally occurring sources for the ingredients is generally not appropriate or desirable, because these naturally occurring products may contain relatively small amounts of the desired components and/or have potentially interfering compounds therein. Moreover, use of low-purity ingredients often leads to little or no compounds in accordance with the invention.

Thus, the preferred starting compounds or components of the invention are either synthetically derived or derived from one or more naturally occurring product(s) which have been significantly modified so as to contain at least about 90% by weight (more preferably at least about 98% by weight) of the desired component. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product.

One method of preparing the compounds of the invention, particularly where the linker moiety is derived from an aldehyde, involves the direct reaction between the aldehyde and the fused polycyclic compounds of interest. Hence, products produced by this method are reaction products of an aldehyde and the fused polycyclic compounds.

In carrying out the aldehyde reactions between the aldehyde and fused polycyclic compound(s), of whatever types, the weight ratios of the aldehyde component(s) to the fused polycyclic compound(s) in the reaction mixtures should range from about 0.5:1 to 25:1, more preferably from about 0.7:1 to 6:1, and most preferably from about 1.5:1 to 4:1. In terms of weight amounts, the amounts of the aldehyde component(s) should range from about 25-95% by weight, and the weight of amount of the fused polycyclic compound(s) should be from about 5-75% by weight, with the total weight of these reactants taken as 100% by weight. In most cases, it is preferred that the weight amount of the aldehyde component(s) should be present in a weight excess relative to the amount of the fused polycyclic compound(s).

The components are usually mixed with an organic solvent, such as a C1-C4 lower alcohol (e.g., methanol, ethanol, or propanol) and/or dimethyl sulfoxide (DMSO), and allowed to stand for a period (typically from about 12 hours-4 weeks) at a temperature ranging from about 20-60° C. at ambient pressures. Alternately, the mixture may be refluxed (e.g., 30 minutes-2 hours at 50-85° C. in ethanol or 30 minutes at 55° C. in methanol). The reaction products can then be recovered in either liquid or solid form. Depending upon the selected solvent, the reaction products may exhibit different colors, but this does not affect the anti-cancer properties of the reaction products. Moreover, the particular reaction conditions are generally not critical.

The production of effective esters, metal complexes, and pharmaceutically acceptable salts of the compounds is quite straightforward and well within the skill of the art. For example, salts may be formed by reacting the products with inorganic or organic acids.

The reactants, reaction ratios, reactant amounts, and reaction conditions set forth above are suitable for all of the aldehyde reactions in accordance with the invention, and skilled artisans can readily determine the optimums through routine experimentation.

In some cases using the aldehyde reaction, it may be difficult to determine the precise structure(s) of the reaction products. However, molecular weights of the active reaction products can be determined, and such are important criteria for the active products. Thus, important reaction products of benzaldehyde and harmaline have a molecular weight of approximately 516, whereas such reaction products of vanillin and harmaline have a molecular weight of approximately 562. "Approximately" in connection with the molecular weights referred to herein means the listed molecular weights plus or minus 5 weight units. Also, the molecular weights of reaction product derivatives (e.g., reduction products produced by hydrogenation, esters, or salts) would be somewhat different; but such weights are easily calculated in light of the nature of the derivatives. Hence, the preferred molecular weights recited herein are for the non-derivatized versions of the reaction products.

A second synthesis method may be used when it is desired to produce fused tricyclic compounds such as β-carboline and its derivatives. Generally speaking, this method involves reacting an indole alkyl amine with a diacid to produce an intermediate, followed by a ring-closure reaction to produce the final compound of interest.

A third reaction method, particularly useful for the production of compounds having fused bicyclic moieties bonded with a linker moiety, is illustrated below.

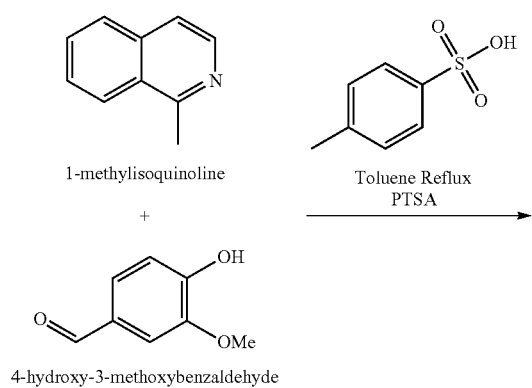

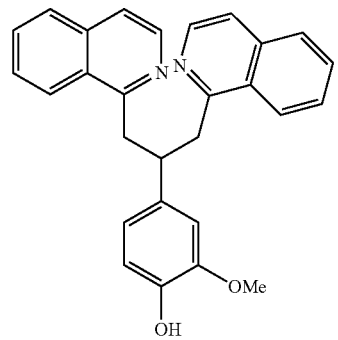

4-(1,3-di(isoquinlin-1-yl)propan-2-yl)-2-methoxyphenol

Benzaldehyde/Harmaline 560 Compounds

Benzaldehyde is a benzene ring with an aldehyde substituent, and is the primary constituent of bitter almond oil. It is identified by CAS #100-52-7.

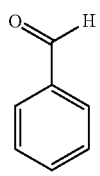

Benzaldehyde

The aldehyde reaction between benzaldehyde and harmaline is preferably carried out by mixing together the two components at a weight ratio of about 2:1 (benzaldehyde:harmaline). Ethanol is then added to give a final reaction mixture concentration of about 10:1000 mg/mL, more preferably from about 700:1000 mg/mL to form a dispersion. The vial is then capped, and the mixture within the vial is allowed to stand in a warm water bath of about 50° C. (more broadly, about 40-60° C.) for about 3 days (more broadly, about 1-10 days). The solid compound is then washed with water and methanol, giving a final product of about 90-95% by weight purity.

Certain compounds are formed with one moiety of harmaline and one moiety of benzaldehyde, one of which has a molecular weight of approximately 320. Other products also have one moiety of harmaline and one of benzaldehyde, but have a molecular weight of approximately 302, owing to loss of water attendant to the reaction. These products are set forth below.

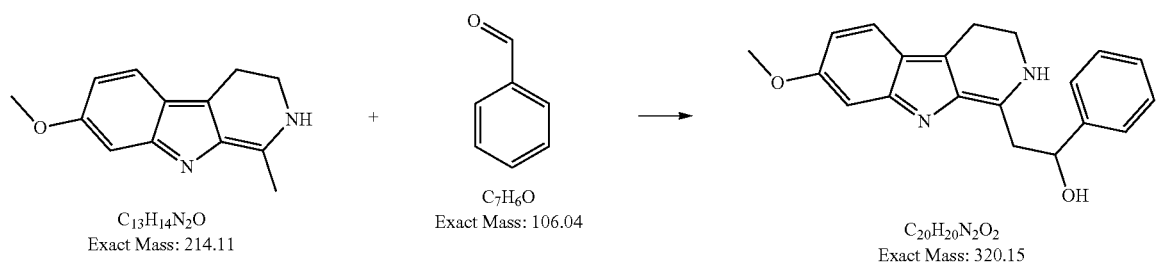
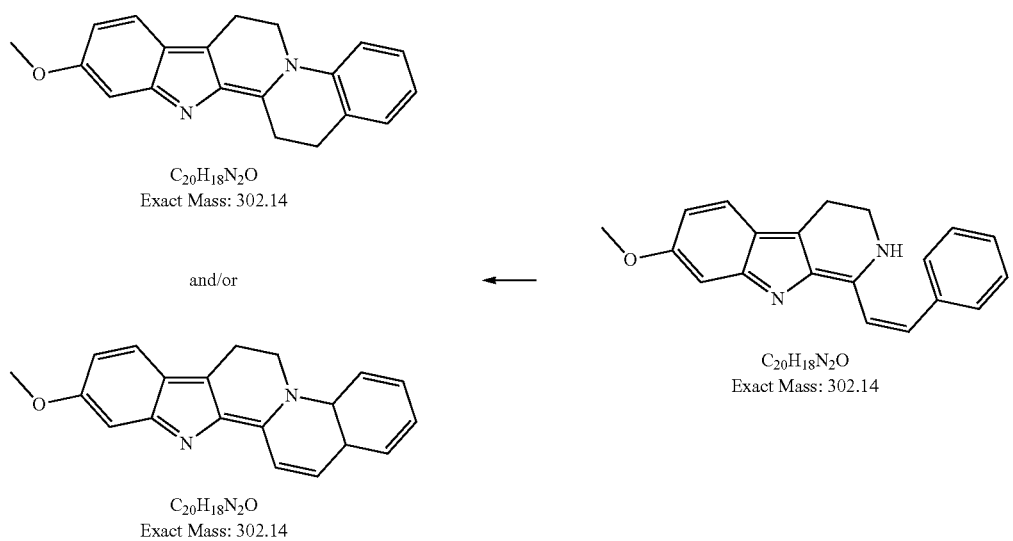
and/or
Further, useful compounds are formed with two harmaline moieties and a single linker moiety derived from benzaldehyde, with molecular weights of approximately 516, as follows.
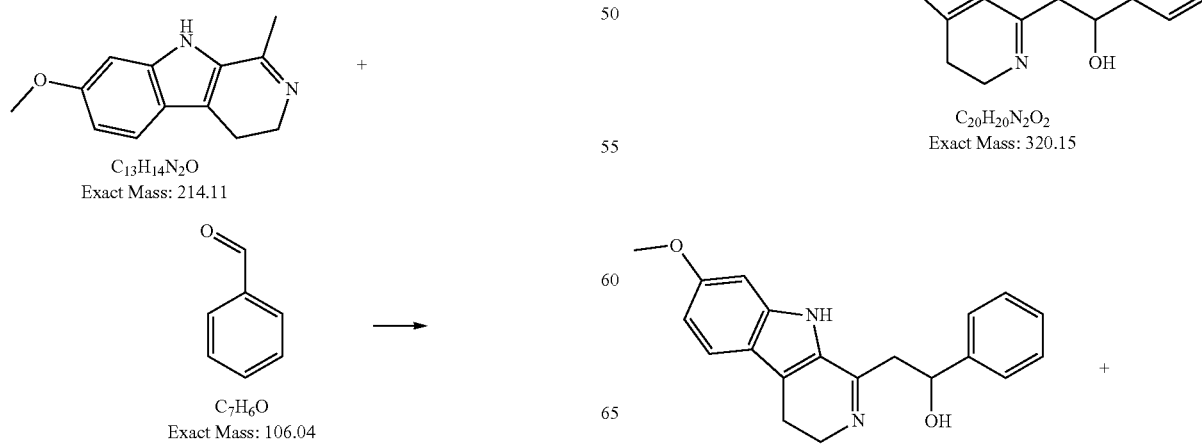
-continued

31
-continued
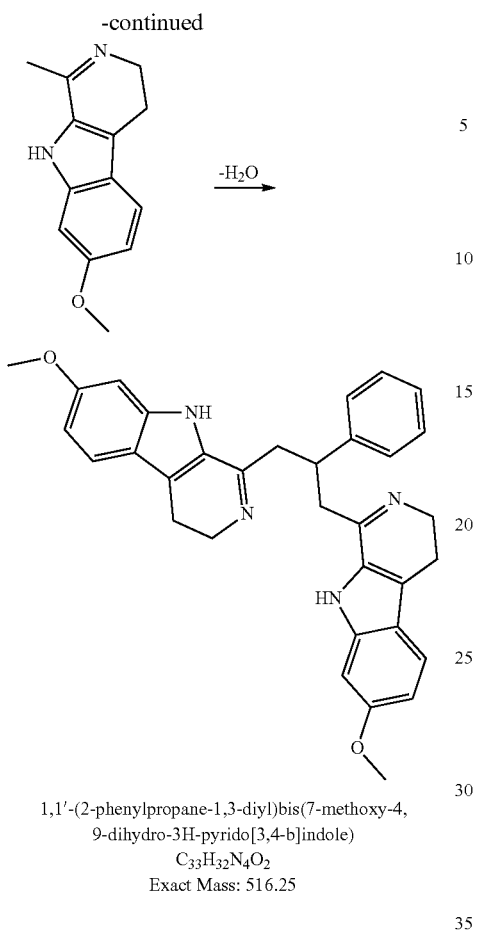
1,1'-(2-phenylpropane-1,3-diyl)bis(7-methoxy-4,
9-dihydro-3H-pyrido[3,4-b]indole)
$C_{33}H_{32}N_4O_2$
Exact Mass: 516.25
Other compounds containing one moiety of benzaldehyde and two harmaline moieties include the following.
32
-continued
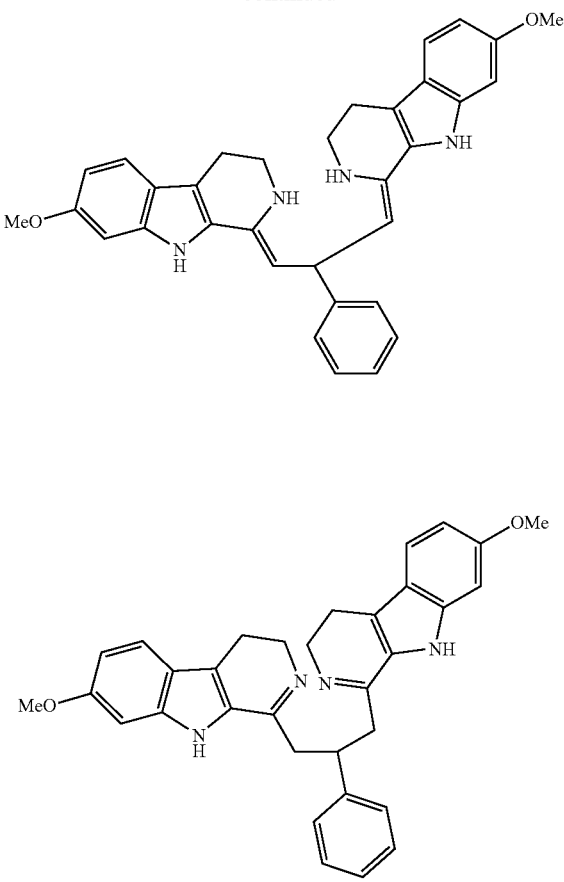
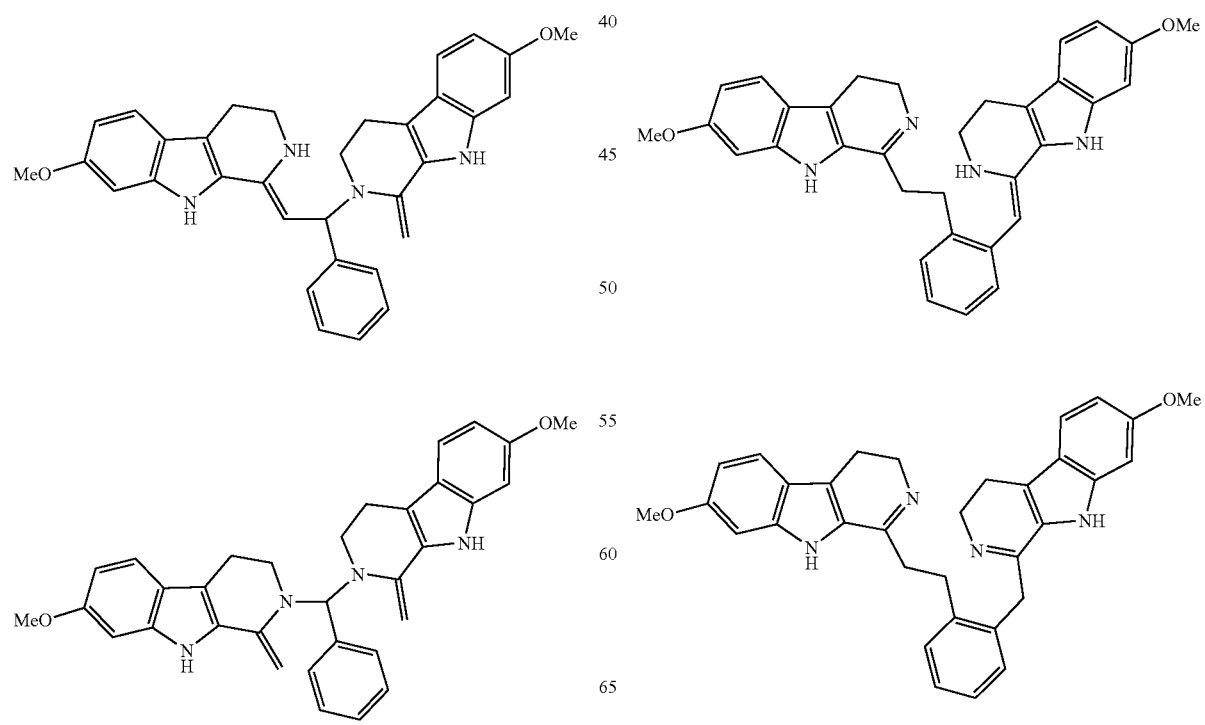

As explained in Example 12, a confirmed compound is

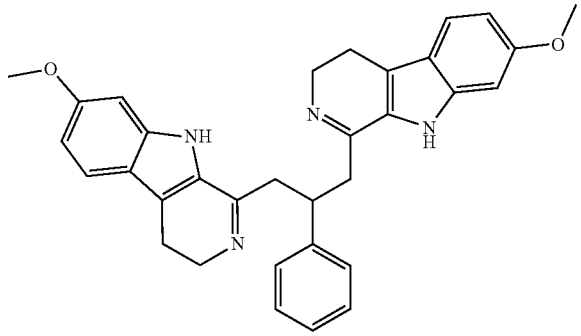

1,1'-(2-phenylpropane-1,3-diyl)bis(7-methoxy-4,9-dihydro-3H-pyrido
[3,4-b]indole)
Chemical Formula: $C_{33}H_{32}N_4O_2$
Molecular Weight: 516.65

An analog of the above compound has a molecular weight of 520.68 and is a reduced version wherein the nitrogen atoms of the two harmaline moieties are hydrogenated, eliminating the double bond therein, as set forth below:

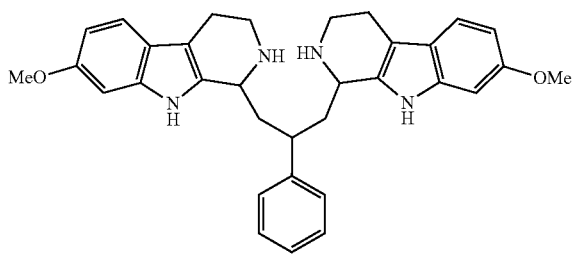

1,1'-(2-phenylpropane-1,3-diyl)bis(7-methoxy-2,3,4,9-tetrahydro-1H-pyrido
[3,4-b]indole)
Chemical Formula: $C_{33}H_{36}N_4O_2$
Exact Mass: 520.28
Molecular Weight: 520.68

More broadly, however, appropriate benzaldehyde/harmaline compounds include one or more of the structure:

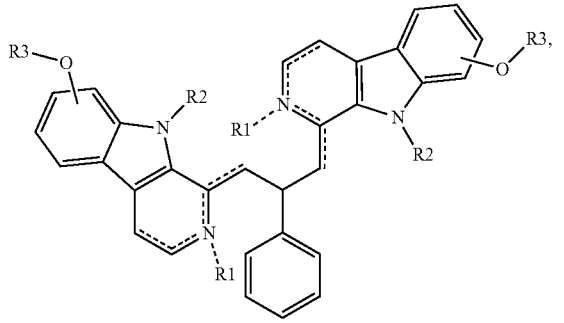

V and the dimers, isomers, and tautomers thereof, where the —O—R3 groups may be independently located at any position on the terminal phenyl groups, where each R1 is independently selected from the group consisting of nothing, H, OH, C1-C12 (preferably C1-C4) alkyl groups, and halogens (such as I and Br), each R2 is independently selected form the group consisting of H, OH, and C1-C12 (preferably C1-C4) alkyl groups, and halogens (such as I and Br), each R3 group is independently selected from the group consisting of C1-C12 (preferably C1-C4) alkyl groups, and substituted or unsubstituted phenyl groups, and wherein the designation ---- refers to the fact that there may optionally be: 1) one or two non-fused double bonds at one or two valence-permitted positions around either or both of the six-membered, N-containing rings, such as illustrations a-d below; 2) a double bond between either or both of the N-containing rings and the adjacent carbons of the central moiety, with or without an additional non-fused double bond at any valence-permitted position around the corresponding N-containing ring, such as illustrations e-g. In instances of 2) where there is a double bond between the nitrogen atom of either N-containing ring and an adjacent carbon atom thereof, R1 is nothing, such as illustrations a-c and g. However, if there is no such nitrogen double bond, the corresponding R1 is selected from the group consisting of H, OH, and C1-C12 (preferably C1-C4) alkyl groups, such as illustrations d-f; or 3) either or both of the B rings are free of non-fused double bonds, and each R1 is independently selected from the group consisting of H, OH, and C1-C12 (preferably C1-C4) alkyl groups.

Set forth below are illustrations depicting certain exemplary double bond configurations of either or both of the N-containing rings of Structure V.

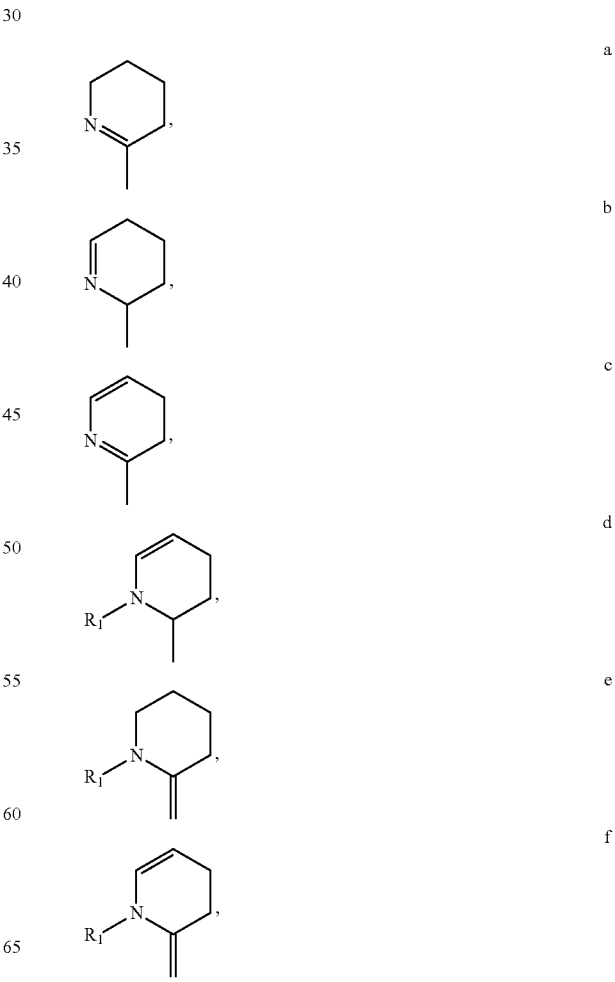

g

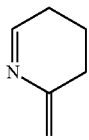

In other embodiments, the following compounds are useful

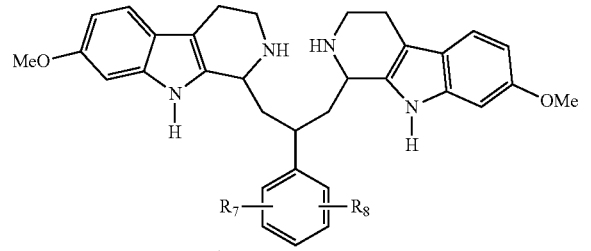

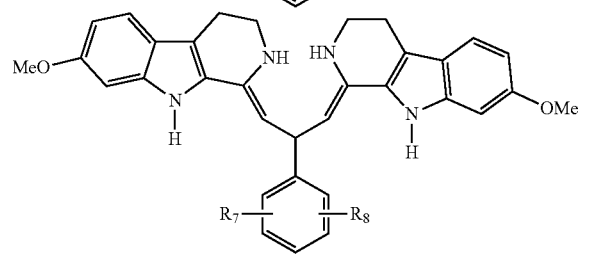

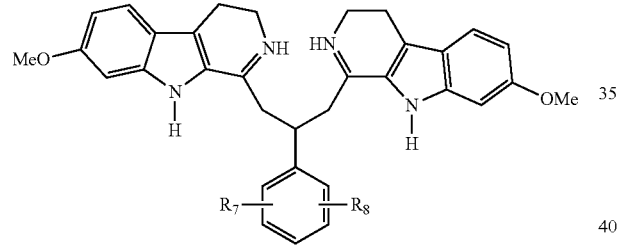

where R7 and R8 are attached at any position around the benzene ring and are independently selected from the group consisting of H, OH, and C1-C12 (preferably C1-C4) alkoxy groups, and where, preferably, R7 is OH, R8 is a C1-C12 (preferably C1-C4) alkoxy group.

Cinnamaldehyde/Harmaline 561 Compounds

Cinnamaldehyde occurs in the bark of cinnamon trees and is present in cis and trans isomers. It is identified by CAS #104-55-2.

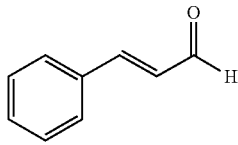

Cinnamaldehyde

These compounds are produced using the aldehyde reaction in the same fashion as the benzaldehyde/harmaline products using the aldehyde reactions, and have molecular weights of approximately 346, 328, and 542, as represented below. The MW 542 compound includes a first cinnamaldehyde moiety with two harmaline moieties bonded to the first moiety. The MW 346 compound is made up of a single cinnamaldehyde moiety and a single harmaline moiety, whereas the MW 328 product is a dehydrated version of the MW 346 product. The primary compound is the MW542 product.

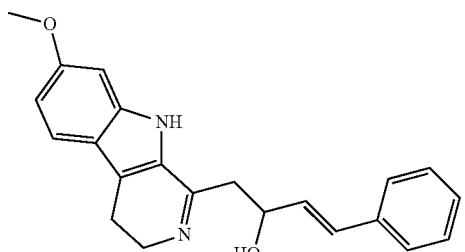

(E)-1-(7-methoxy-4,9-dihydro-3H-pyrido[3,4-b]indol-1-yl)-4-phenylbut-3-en-2-ol
Chemical Formula: $C_{22}H_{22}N_2O_2$
Exact Mass: 346.17

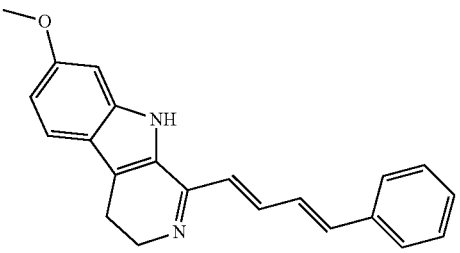

7-methoxy-1-((1E,3E)-4-phenylbuta-1,3-dien-1-yl)-4,9-dihydro-3H-pyrido[3,4-b]indole
Chemical Formula: $C_{20}H_{20}N_2O$
Exact Mass: 328.16

Primary:

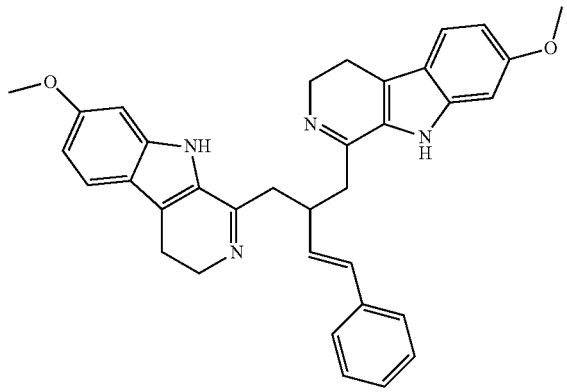

(E)-1,1'-(2-styrylpropane-1,3-diyl)bis(7-methoxy-4,9-dihydro-3H-pyrido[3,4-b]indole)
Chemical Formula: $C_{35}H_{34}N_4O_2$
Exact Mass: 542.27

Again, an analog of the above primary structure is a hydrogenated version wherein the N atoms of the two harmaline moieties are hydrogenated, eliminating the double bonds therein.

More broadly, however, appropriate cinnamaldehyde/harmaline compounds include one or more compounds of the structure:

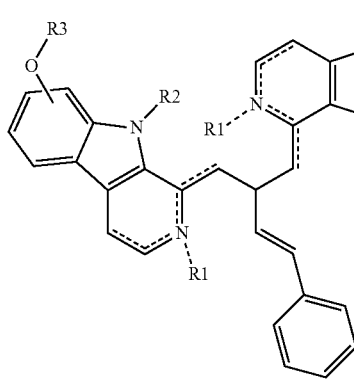

VI

c

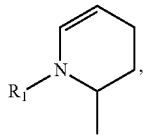

d

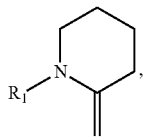

e

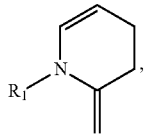

f

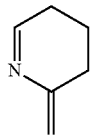

g and the dimers, isomers, and tautomers thereof, where the —O—R3 groups may be independently located at any position on the terminal phenyl groups, where each R1 is independently selected from the group consisting of nothing, H, OH, and C1-C12 (preferably C1-C4) alkyl groups, each R2 is independently selected form the group consisting of H, OH, and C1-C12 (preferably C1-C4) alkyl groups, each R3 group is independently selected from the group consisting of C1-C12 (preferably C1-C4) alkyl groups, and substituted or unsubstituted phenyl groups, and wherein the designation ---- refers to the fact that there may optionally be: 1) one or two non-fused double bonds at one or two valence-permitted positions around either or both of the six-membered, N-containing rings, such as illustrations a-d below; 2) a double bond between either or both of the N-containing rings and the adjacent carbons of the central moiety, with or without an additional non-fused double bond at any valence-permitted position around the corresponding N-containing ring, such as illustrations e-g. In instances of 2) where there is a double bond between the nitrogen atom of either N-containing ring and an adjacent carbon atom thereof, R1 is nothing, such as illustrations a-c and g. However, if there is no such nitrogen double bond, the corresponding R1 is selected from the group consisting of H, OH, and C1-C12 (preferably C1-C4) alkyl groups, such as illustrations d-f; or 3) either or both of the N-containing rings are free of non-fused double bonds and each R1 is independently selected from the group consisting of H, OH, and C1-C12 (preferably C1-C4) alkyl groups.

Set forth below are illustrations depicting certain exemplary double bond configurations of either or both of the N-containing rings of Structure VI.

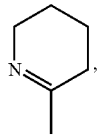

a

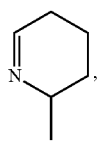

b

Vanillin/Harmaline 562 Compounds

The aldehyde reactions between vanillin and harmaline components, carried out in the same fashion as the benzaldehyde/harmaline reaction, yield products as set forth below.

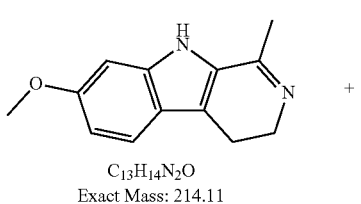

$C_{13}H_{14}N_2O$
Exact Mass: 214.11

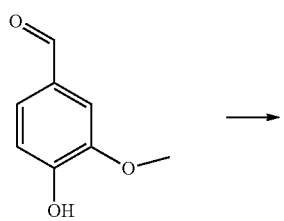

$C_8H_8O_3$
Exact Mass: 152.05

-continued

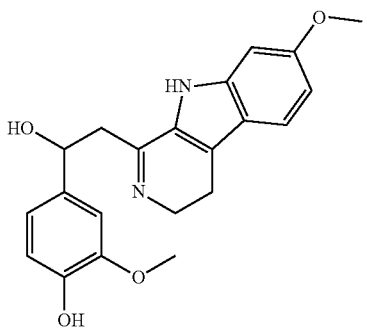

C₂₁H₂₂N₂O₄
Exact Mass: 366.16

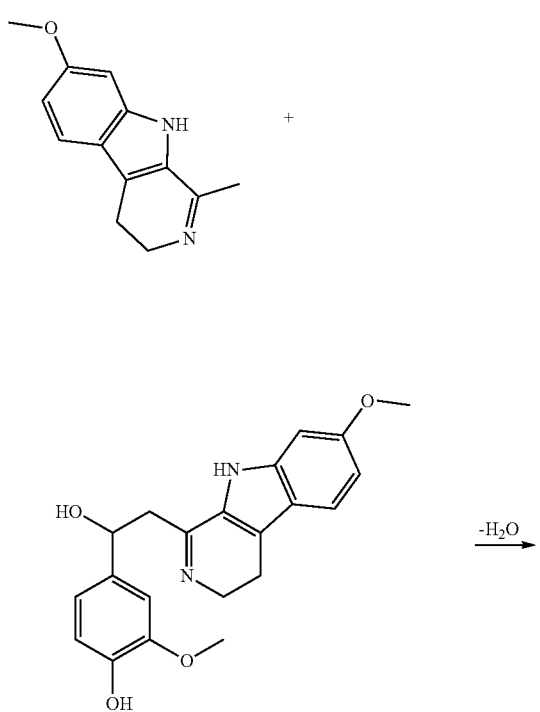

C₃₄H₃₄N₄O₄
Exact Mass: 562.26

As explained in Example 14, a confirmed vanillin/harmaline compound is

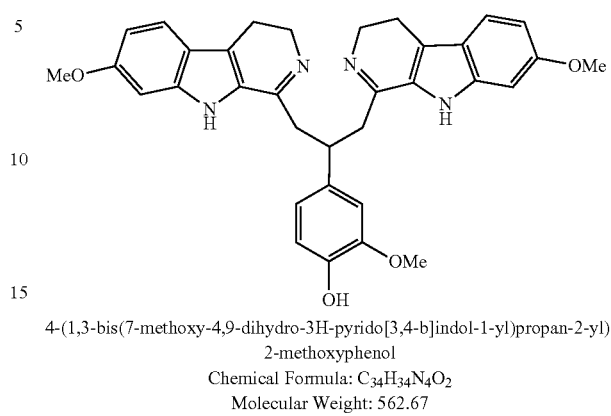

4-(1,3-bis(7-methoxy-4,9-dihydro-3H-pyrido[3,4-b]indol-1-yl)propan-2-yl)-2-methoxyphenol
Chemical Formula: C₃₄H₃₄N₄O₂
Molecular Weight: 562.67

An analog of the above structure involves hydrogenation of the N-containing ring nitrogen atoms and is set forth below:

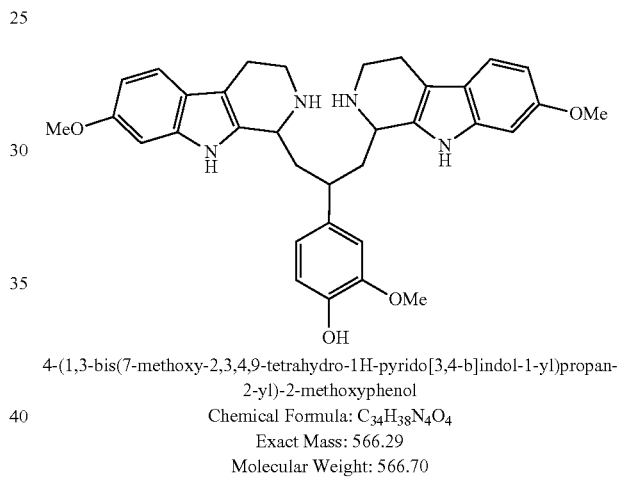

4-(1,3-bis(7-methoxy-2,3,4,9-tetrahydro-1H-pyrido[3,4-b]indol-1-yl)propan-2-yl)-2-methoxyphenol
Chemical Formula: C₃₄H₃₈N₄O₄
Exact Mass: 566.29
Molecular Weight: 566.70

More broadly, however, appropriate vanillin/harmaline compounds include one or more compounds of the structure:

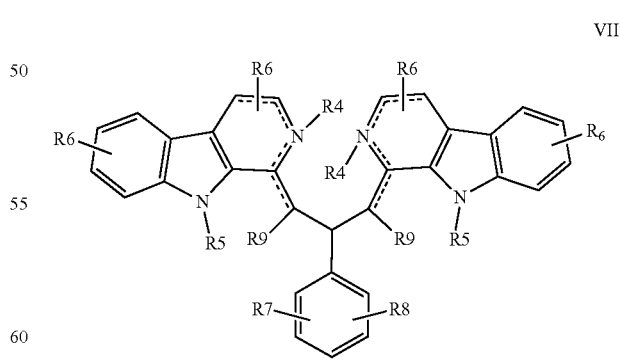

VII and the dimers, isomers, and tautomers thereof, where each R4 is independently selected from the group consisting of nothing, H, OH, and C1-C12 (preferably C1-C4) alkyl groups, each R5 is independently selected from the group consisting of H, OH, and C1-C12 (preferably C1-C4) alkyl

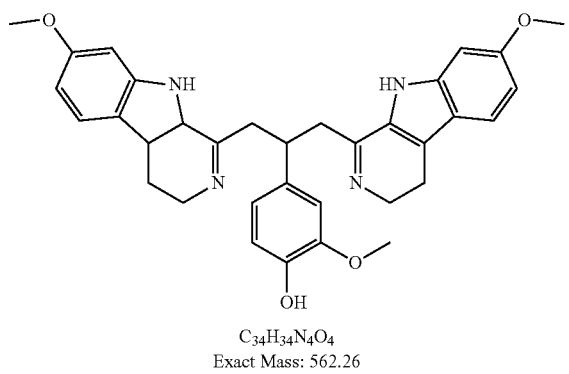

groups, each R6 group is independently located at any position around the corresponding terminal phenyl group, or at either of the two open positions of the two N-containing rings, and is selected from the group consisting of C1-C12 (preferably C1-C4) alkoxy groups, H, OH, and substituted or unsubstituted phenyl groups, R7 and R8 are attached at any position around the benzene ring and are independently selected from the group consisting of H, OH, and C1-C12 (preferably C1-C4) alkoxy groups, with the proviso that R7 and R8 are not both H, and where, preferably, R7 is OH, R8 is a C1-C12 (preferably C1-C4) alkoxy group, and each R9 is independently selected from the group consisting of H, OH, and C1-C12 (preferably C1-C4) alkyl groups, and wherein the designation ---- refers to the fact that there may optionally be: 1) zero, one, or two non-fused double bonds at one or two valence-permitted positions around either or both of the six-membered, N-containing rings, such as illustrations a'-d' below; 2) a double bond between either or both of the N-containing rings and the adjacent carbons of the central moiety, with or without an additional non-fused double bond at any valence-permitted position around the corresponding N-containing ring, such as illustrations e'-g' below. In instances of 2) where there is a double bond between the nitrogen atom of either N-containing ring and an adjacent carbon atom thereof, R4 is nothing, such as illustrations a'-c' and g' below. However, if there is no such nitrogen double bond, the corresponding R4 is selected from the group consisting of H, OH, and C1-C12 (preferably C1-C4) alkyl groups, such as illustrations d'-f; or 3) either or both of the N-containing rings are free of non-fused double bonds and each R4 is independently selected from the group consisting of H, OH, and C1-C12 (preferably C1-C4) alkyl groups.

Set forth below are illustrations depicting certain exemplary double bond configurations of either or both of the N-containing rings of Structure VII.

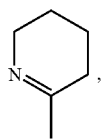

a'

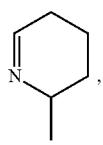

b'

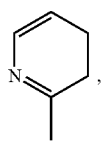

c'

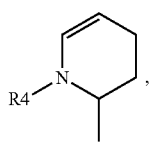

d'

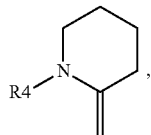

e'

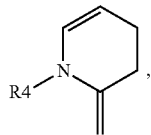

f'

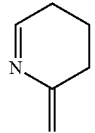

g'

An exemplary compound consistent with 3) above is a hydrogenated form of the preferred 562 compound having the structure

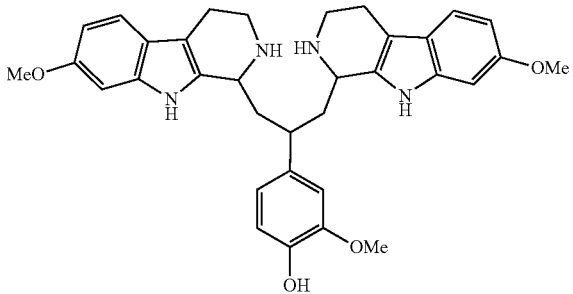

4-(1,3-bis(7-methoxy-2,3,4,9-tetrahydro-1H-pyrido[3,4-b]indol-1-yl)propan-2-yl)-2-methoxyphenol
Chemical Formula: $C_{34}H_{38}N_4O_4$
Exact Mass: 566.29
Molecular Weight: 566.70

Phenoxy Benzaldehyde/Harmaline 594 Compounds

As described in Example 24, the principal 594 compound has the following structure:

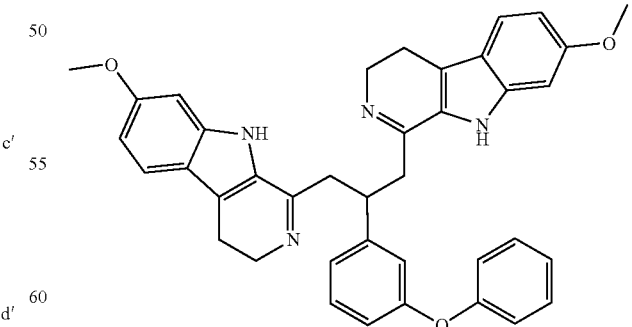

1,1'-(2-(3-phenoxyphenyl)propane-1,3-diyl)bis(7-methoxy-4,9-dihydro-3H-pyrido[3,4-b]indole)
Chemical Formula: $C_{39}H_{36}N_4O_3$
Exact Mass: 608.28

Orthovanillin/Harmaline 523 Compounds
Aldehyde reactions between orthovanillin and harmaline are quite diverse, and the resulting products are similarly variable. Four reaction schemes have been identified as potential candidates, as set forth below.
Scheme 1 Monomers
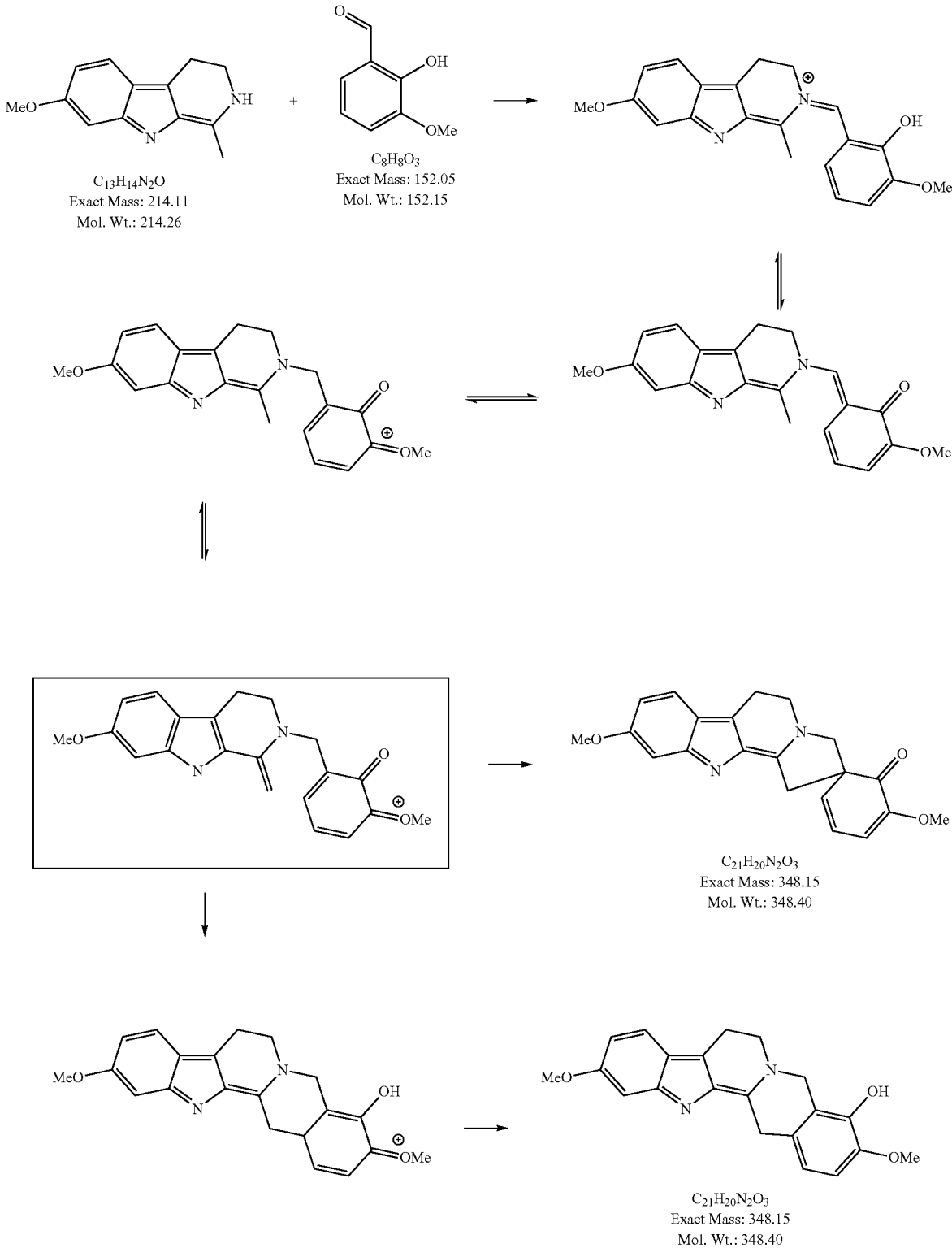

45
Scheme 1 Dimers
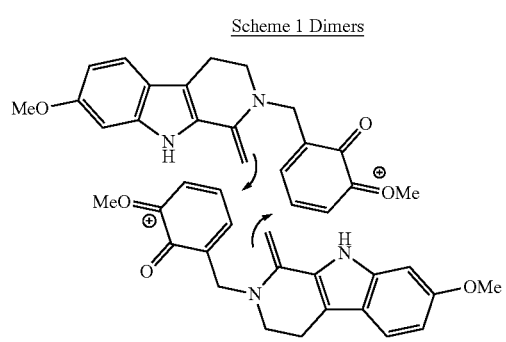
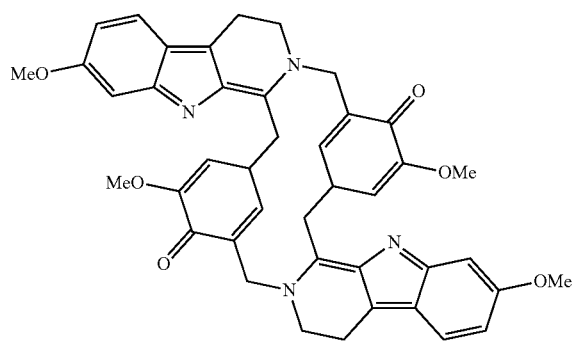
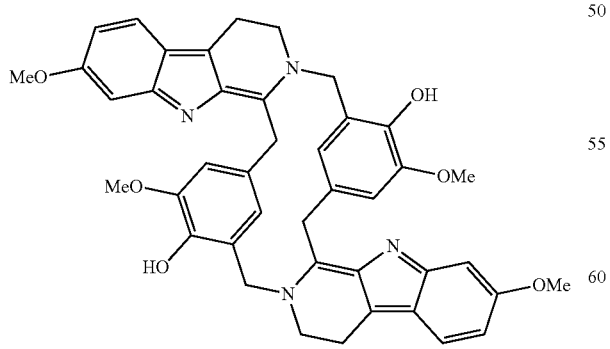
C$_{42}$H$_{40}$N$_4$O$_6$
Exact Mass: 696.29
Mol. Wt.: 696.79
46
-continued
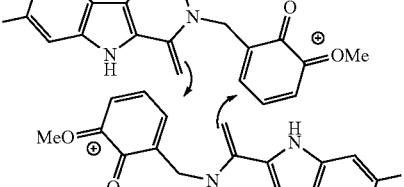
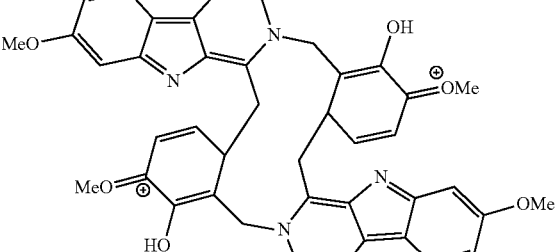
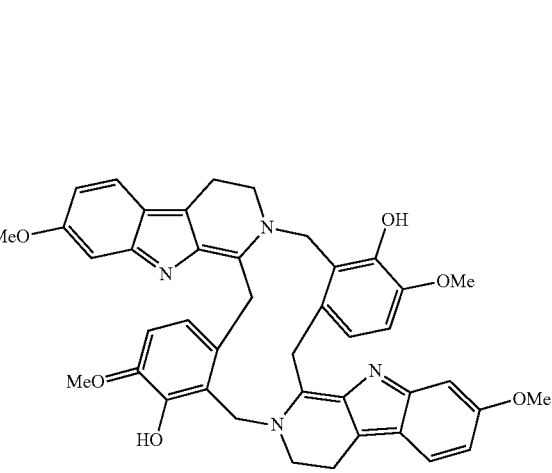
C$_{42}$H$_{40}$N$_4$O$_6$
Exact Mass: 696.29
Mol. Wt.: 696.79

Scheme 1 Trimers
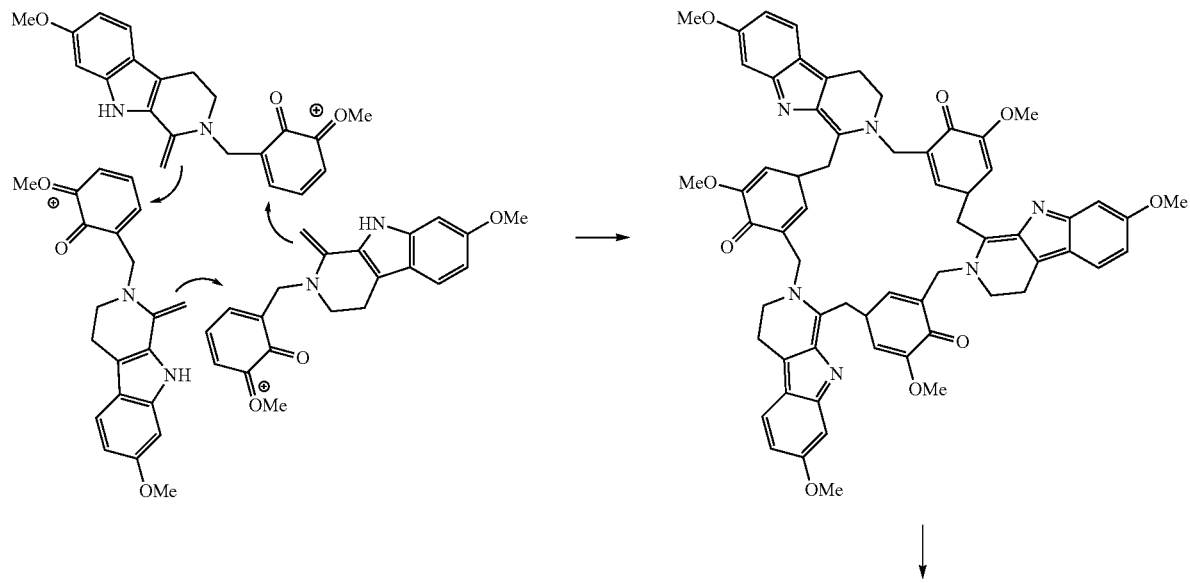
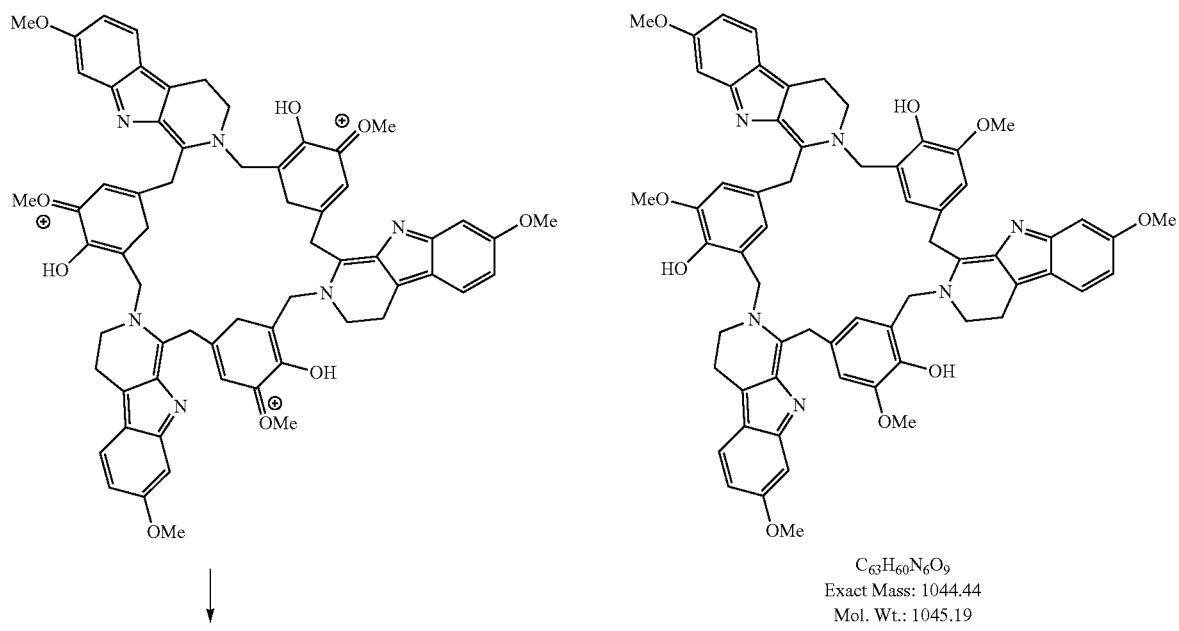
C$_{63}$H$_{60}$N$_6$O$_9$
Exact Mass: 1044.44
Mol. Wt.: 1045.19

-continued
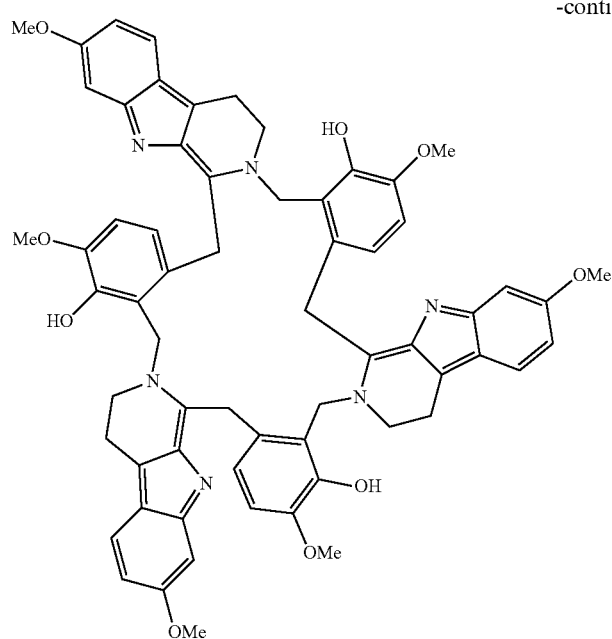
C₆₃H₆₀N₆O₉
Exact Mass: 1044.44
Mol. Wt.: 1045.19
Scheme 2 Monomers
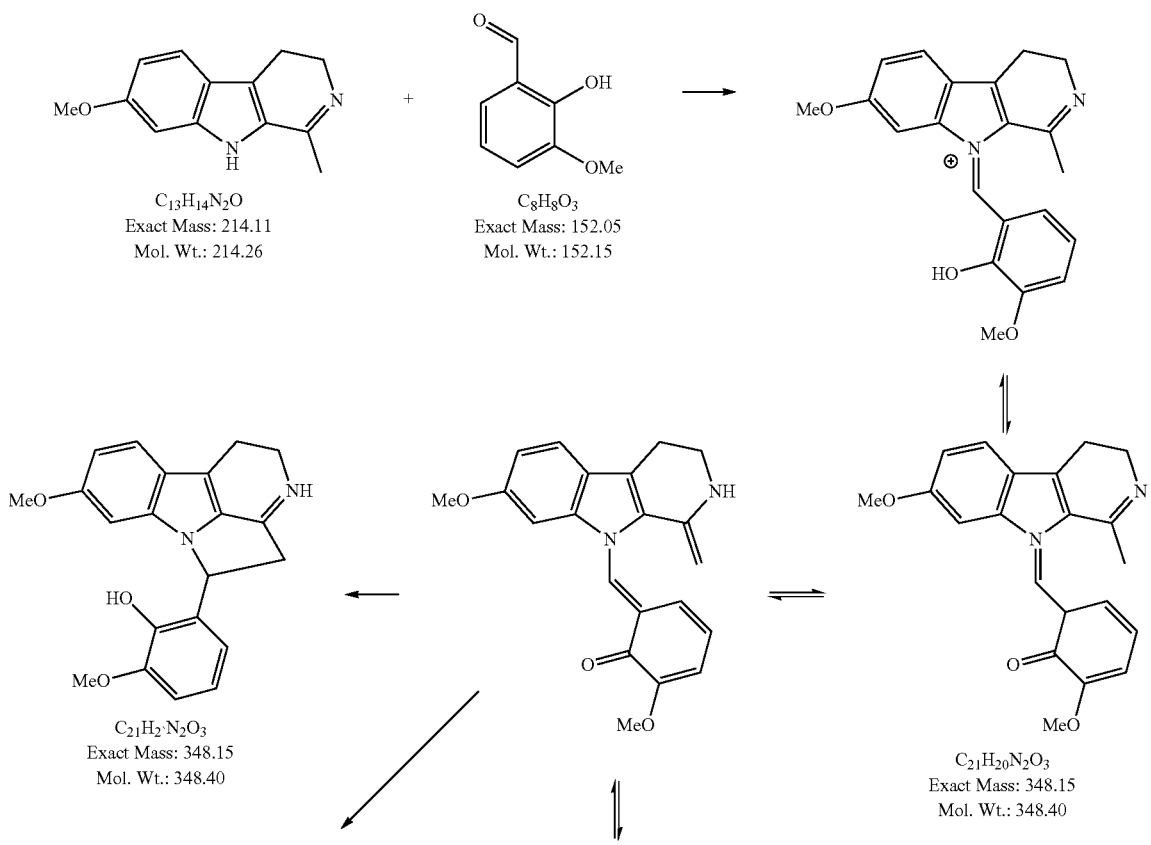

51 52
-continued
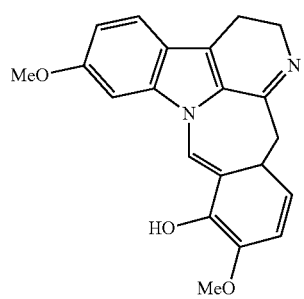 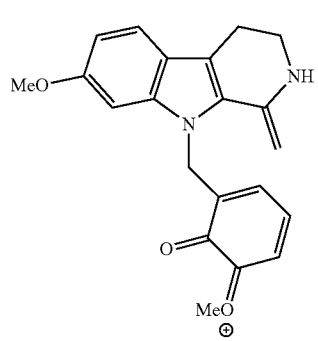 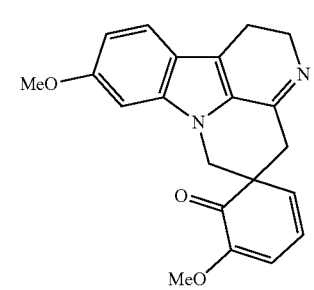
C₂₁H₂₀N₂O₃
Exact Mass: 348.15
Mol. Wt.: 348.40
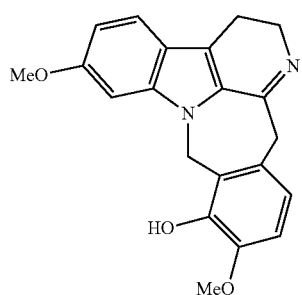
C₂₁H₂₀N₂O₃
Exact Mass: 348.15
Mol. Wt.: 348.40
Scheme 2 Dimers
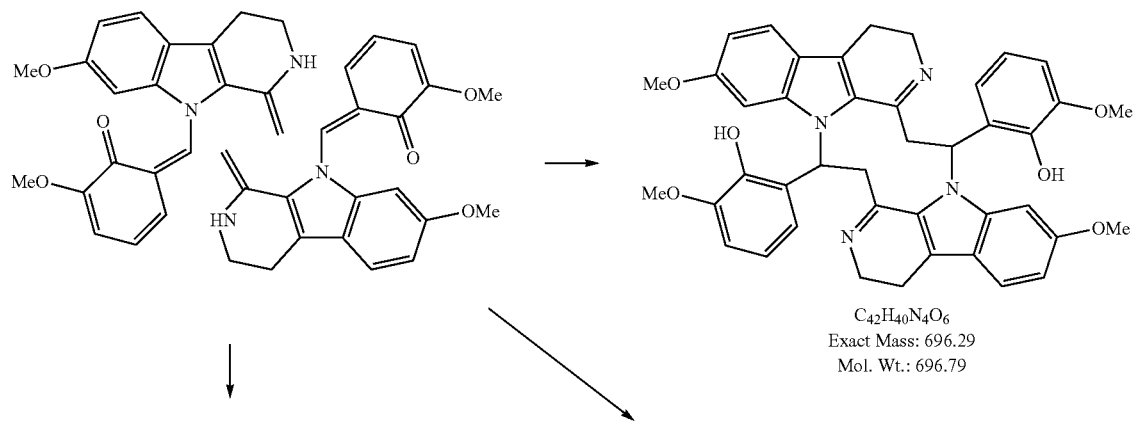
C₄₂H₄₀N₄O₆
Exact Mass: 696.29
Mol. Wt.: 696.79

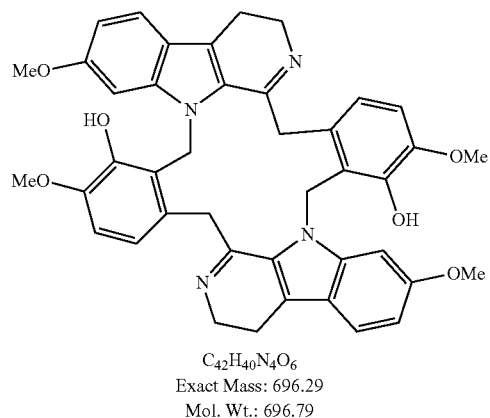
C₄₂H₄₀N₄O₆
Exact Mass: 696.29
Mol. Wt.: 696.79
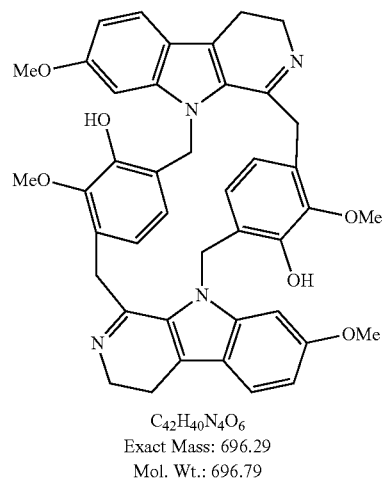
C₄₂H₄₀N₄O₆
Exact Mass: 696.29
Mol. Wt.: 696.79
Scheme 2 dimers via mixed mechanisms
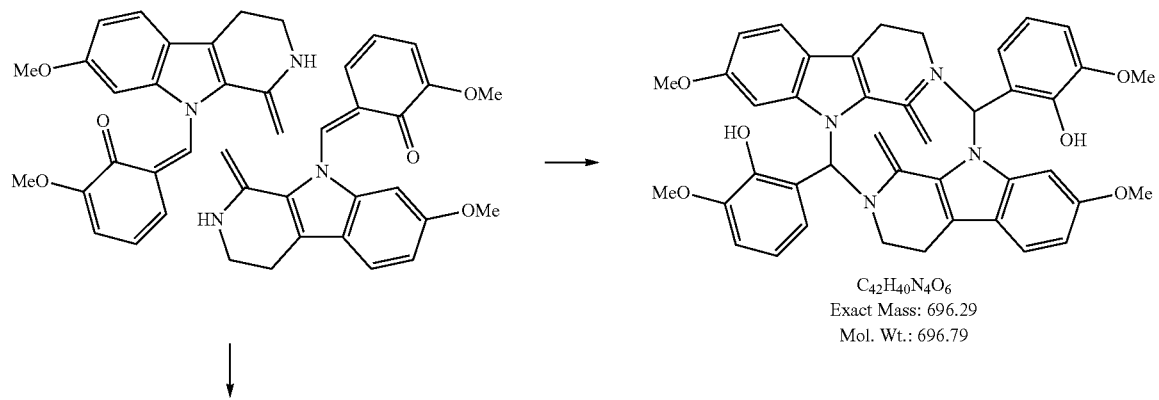
C₄₂H₄₀N₄O₆
Exact Mass: 696.29
Mol. Wt.: 696.79
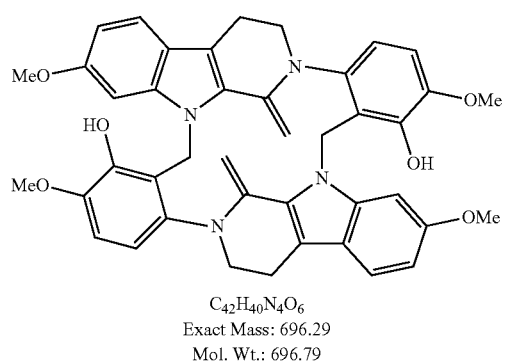
C₄₂H₄₀N₄O₆
Exact Mass: 696.29
Mol. Wt.: 696.79

Scheme 2 Trimers
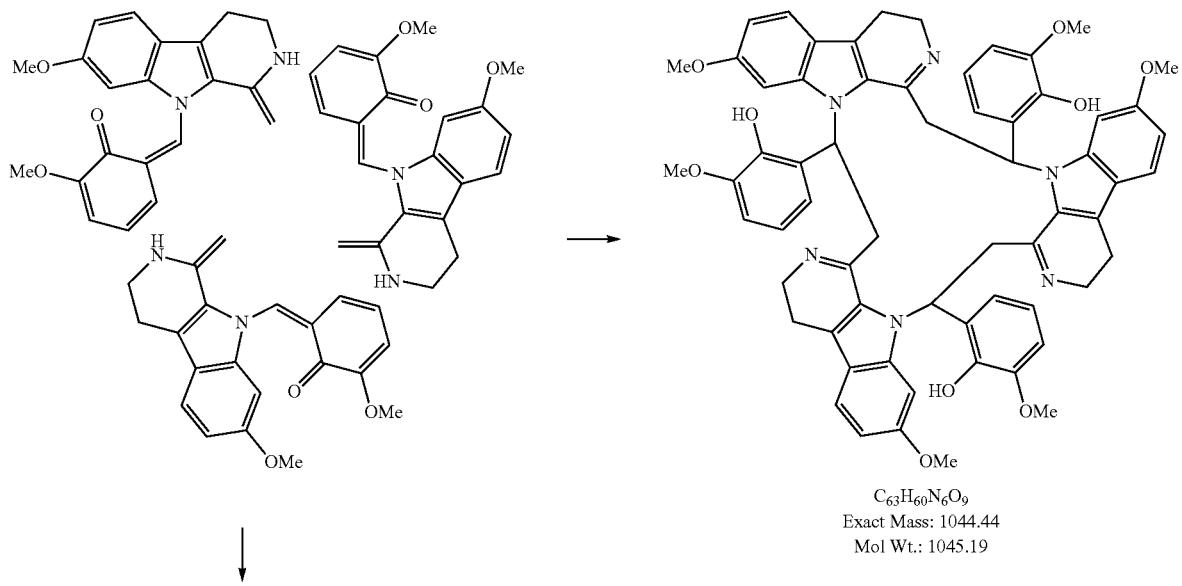
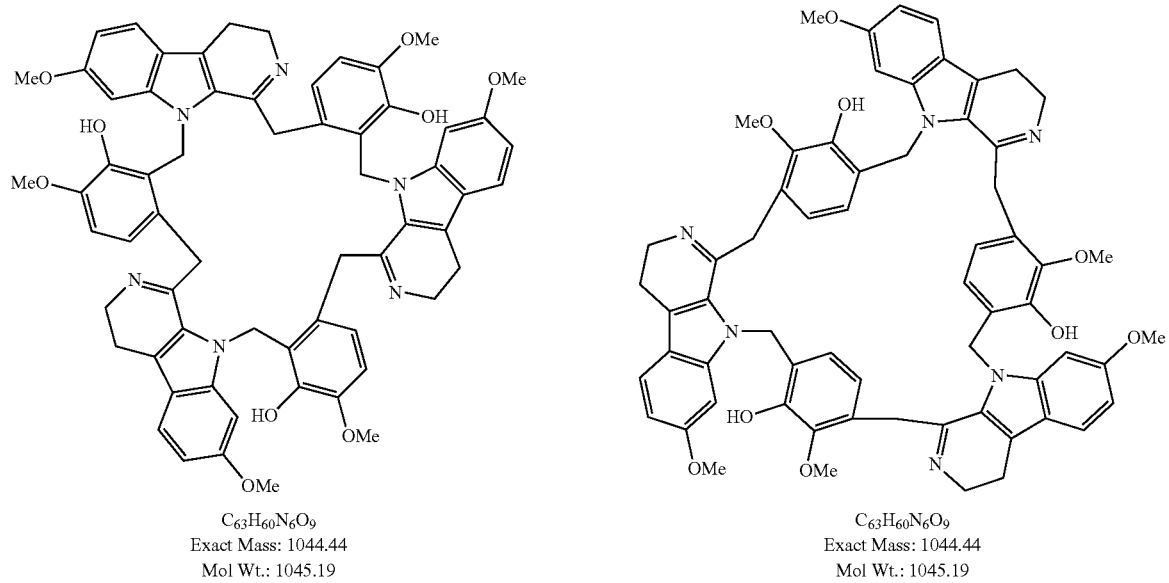

Scheme 3 Monomers
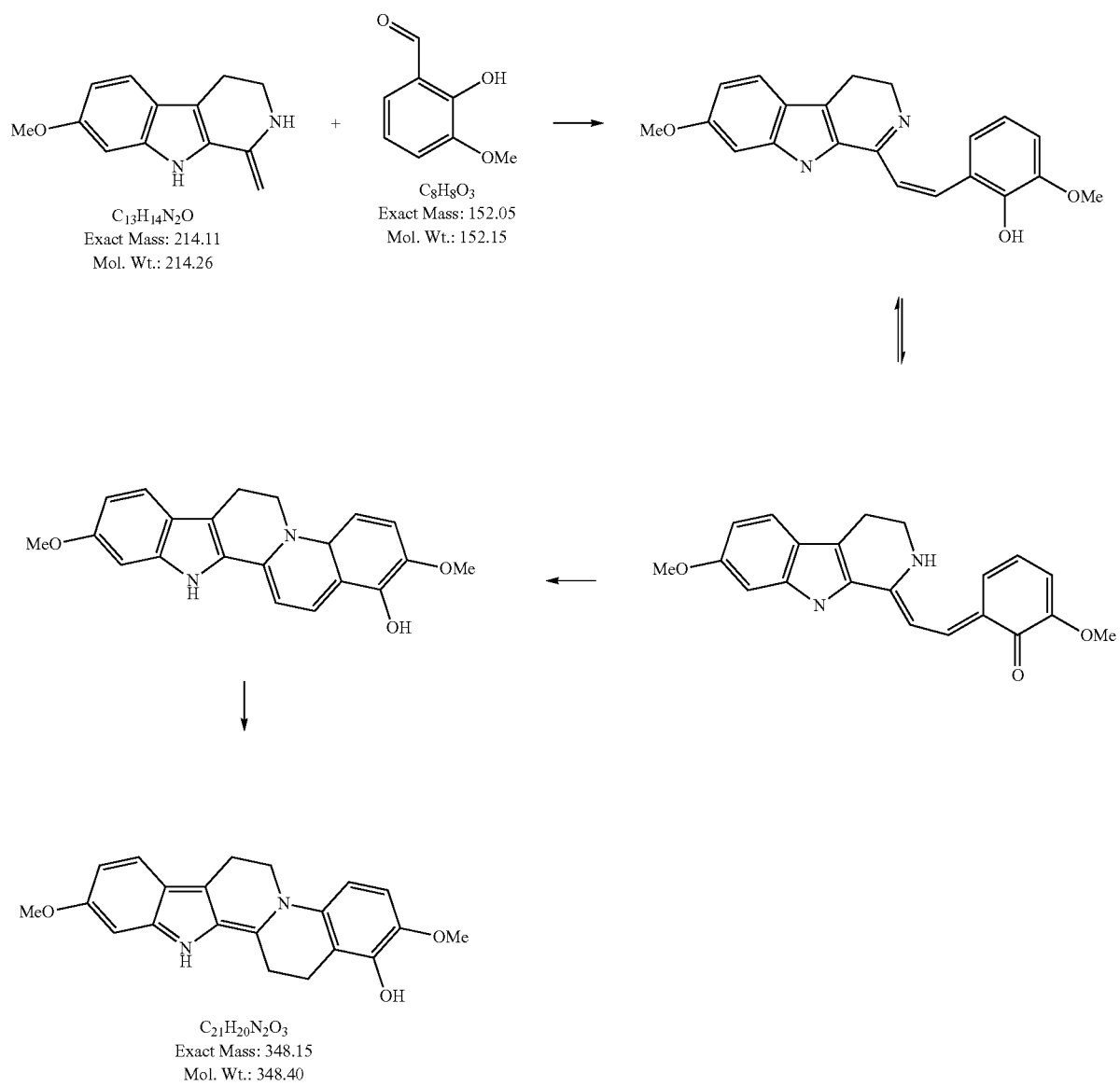
Scheme 3 Dimers
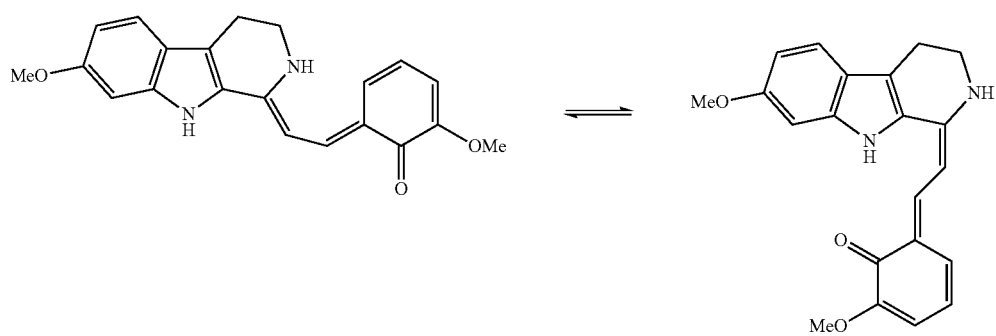

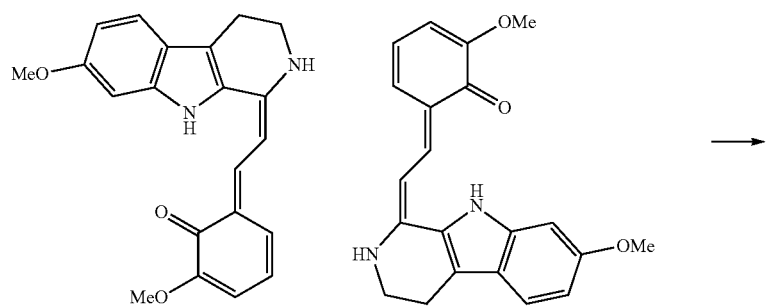
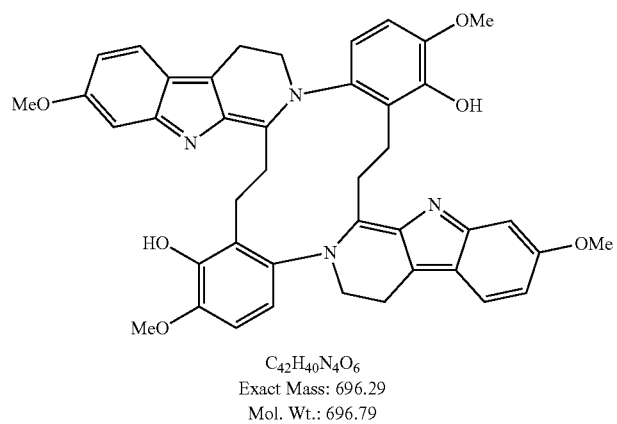
C₄₂H₄₀N₄O₆
Exact Mass: 696.29
Mol. Wt.: 696.79
Scheme 3 Trimers
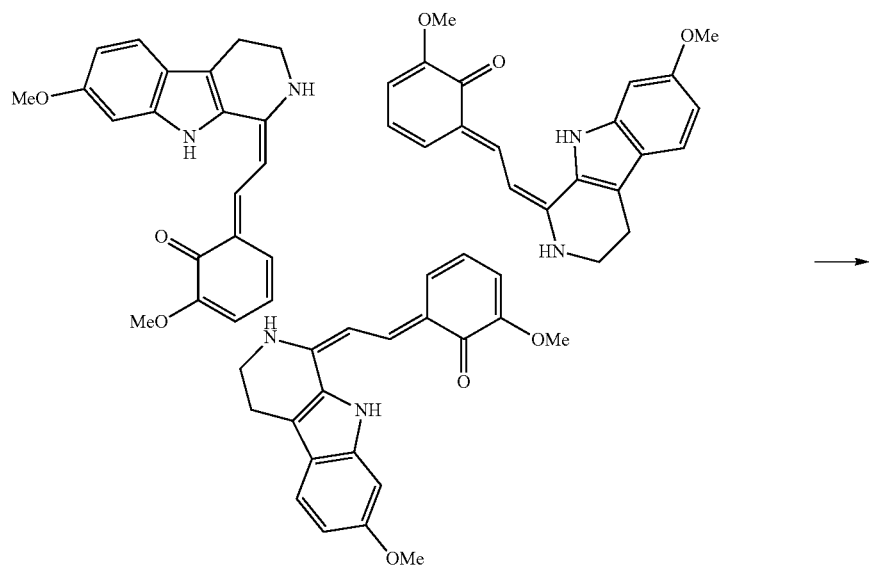

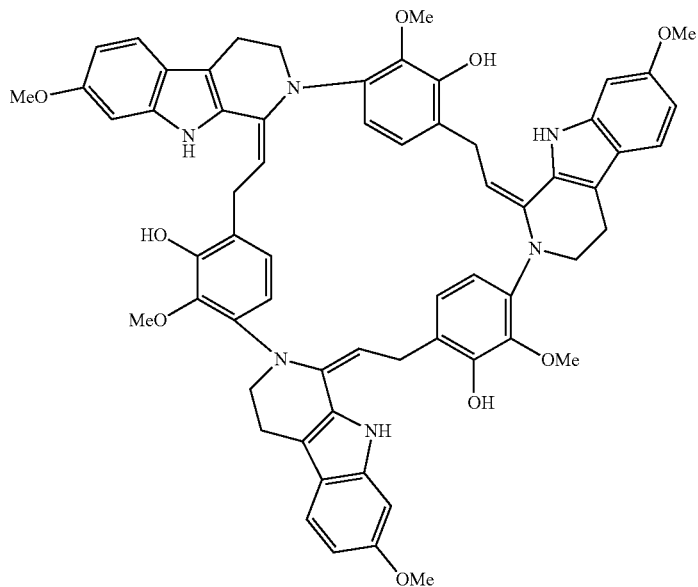
C₆₃H₆₀N₆O₉
Exact Mass: 1044.44
Mol. Wt.: 1045.19
Scheme 4
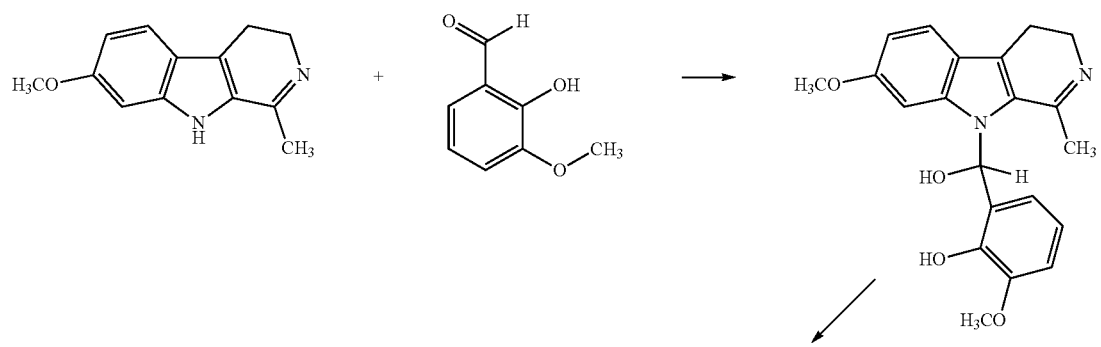
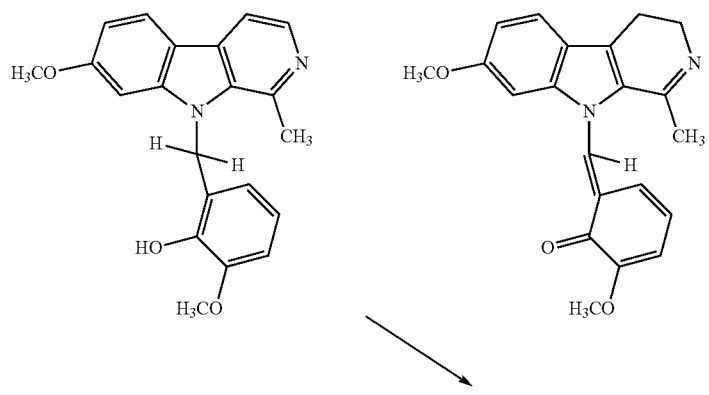

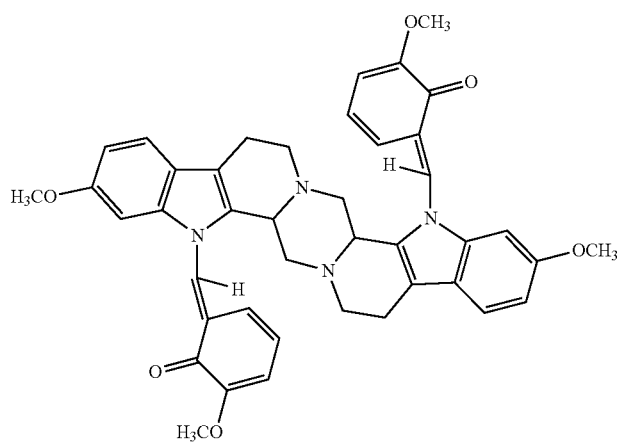
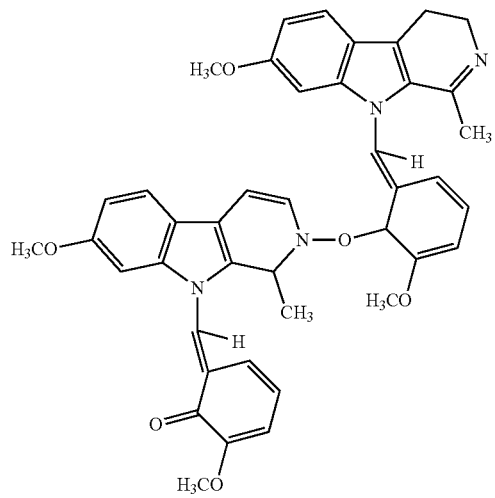
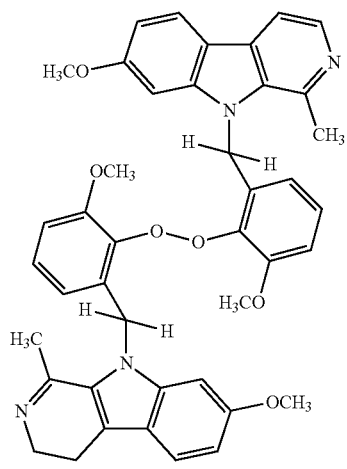
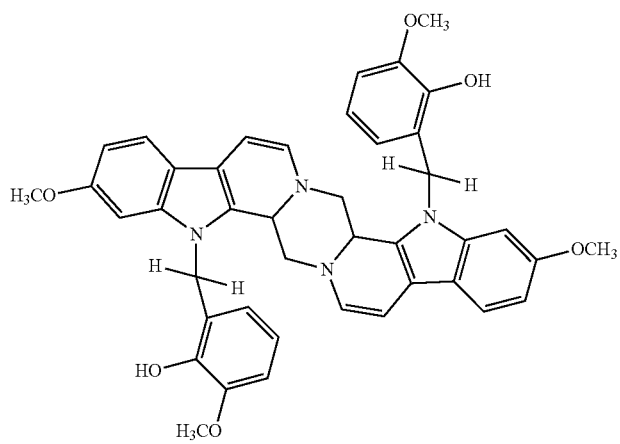
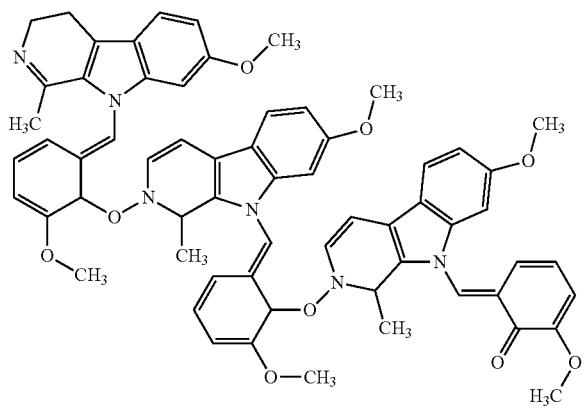 [SMILES: COC1=CC=C/C(=C\n2c3c(c4ccc(OC)cc42)C=CN(OC2C(OC)=CC=C/C2=C\n2c4c(c5ccc(OC)cc52)C=CN(OC2C(OC)=CC=C/C2=C\n2c5c(c6ccc(OC)cc62)CCN=C5C)C4C)C3C)C1=O]

It will be observed that the foregoing scheme 4 compounds involve coupling between harmaline and orthovanillin via a pyrrole nitrogen linkage, i.e., the orthovanillin moieties bond to the nitrogen atom of the pyrrole ring forming a part of harmaline.

The initial aldehyde reaction between orthovanillin and harmaline of scheme 1 may also produce the following compound having the chemical formula C21H20N2O3 and a molecular weight of 348.15. It will be observed that in this instance the initial reaction between orthovanillin and harmaline occurs at the cyclohexyl diene nitrogen atom.

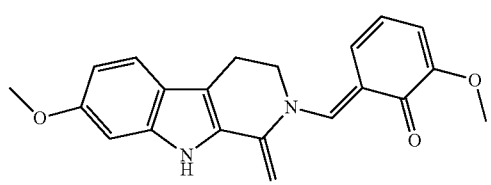

(E)-2-methoxy-6-((7-methoxy-1-methylene-3,4-dihydro-1H-pyrido[3,4-b]indol-2(9H)-yl)methylene)cyclohexa-2,4-dienone The structure of a preferred orthovanillin/diharmaline compound is set forth below:

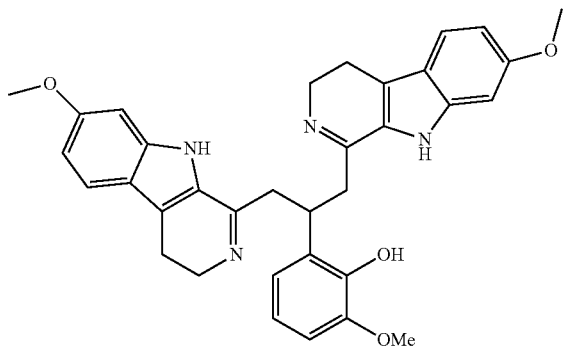

2-(1,3-bis(7-methoxy-4,9-dihydro-3H-pyrido[3,4-b]indol-1-yl)propan-2-yl)-6-methoxyphenol
Chemical Formula: C$_{34}$H$_{34}$N$_4$O$_4$
Exact Mass: 562.26

More broadly, however, preferred orthovanillin/diharmaline compounds are defined by Structure VIII below:

VIII

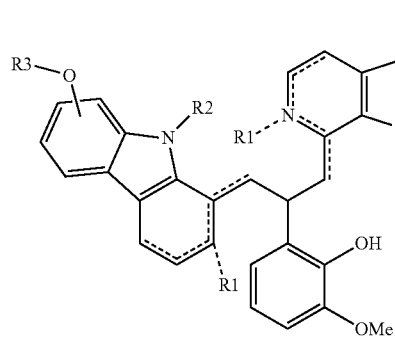

and the dimers, isomers, and tautomers thereof, where the —O—R3 groups may be independently located at any position on the terminal phenyl groups, where each R1 is independently selected from the group consisting of nothing, H, OH, and C1-C12 (preferably C1-C4) alkyl groups, each R2 is independently selected form the group consisting of H, OH, and C1-C12 (preferably C1-C4) alkyl groups, each R3 group is independently selected from the group consisting of C1-C12 (preferably C1-C4) alkyl groups, and substituted or unsubstituted phenyl groups, and wherein the designation ---- refers to the fact that there may optionally be: 1) one or two non-fused double bonds at one or two valence-permitted positions around either or both of the six-membered, N-containing rings, such as illustrations a-d below; 2) a double bond between either or both of the N-containing rings and the adjacent carbons of the central moiety, with or without an additional non-fused double bond at any valence-permitted position around the corresponding N-containing ring, such as illustrations e-g. In instances of 2) where there is a double bond between the nitrogen atom of either N-containing ring and an adjacent carbon atom thereof, R1 is nothing, such as illustrations a-c and g. However, if there is no such nitrogen double bond, the corresponding R1 is selected from the group consisting of H, OH, and C1-C12 (preferably C1-C4) alkyl groups, such as illustrations d-f; or 3) either or both of the N-containing rings are free of non-fused double bonds and each R1 is independently selected from the group consisting of H, OH, and C1-C12 (preferably C1-C4) alkyl groups.

Set forth below are illustrations depicting certain exemplary double bond configurations of either or both of the N-containing rings of structure VI.

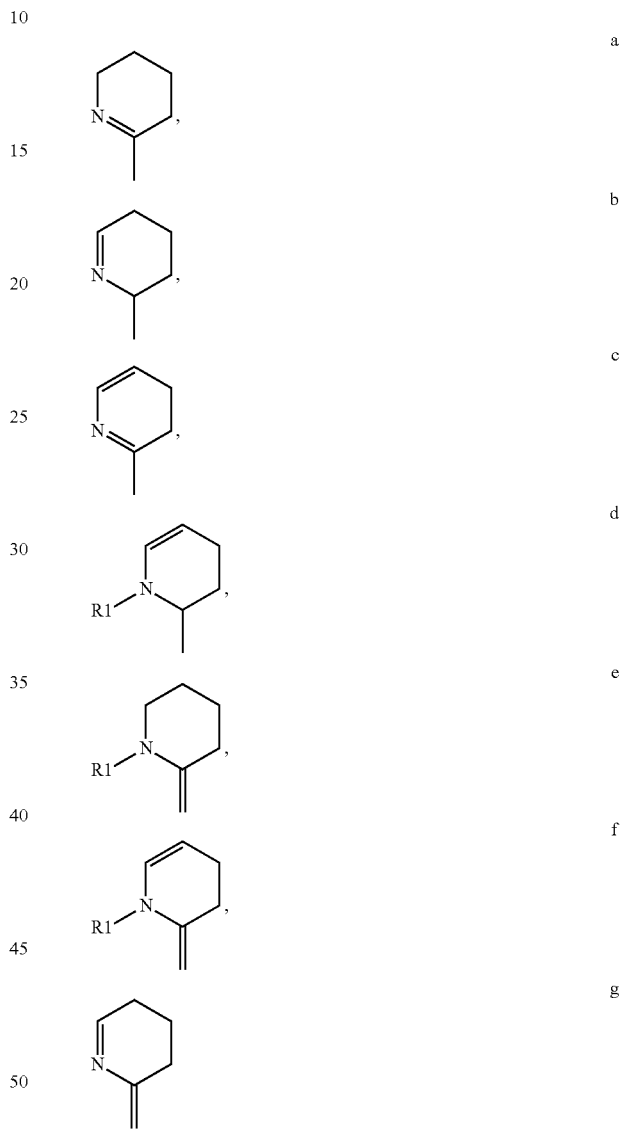

One particular aldehyde reaction for preparing orthovanillin-harmaline compounds is to mix together solid particulate orthovanillin and harmaline at a weight ratio of orthovanillin:harmaline of about 2:1, followed by adding ethanol, DMSO, or a 90% ethanol/10% DMSO mixture to the particulates. Thereupon, the dispersion is agitated and allowed to stand for 24 hours at room temperature. The specific steps are: (1) mix together 500 mg of orthovanillin and 250 mg of harmaline in a 15 mL jar; (2) gently shake the jar until a uniform powder mixture is present; (3) add 10 mL of ethanol and/or DMSO to the dry mixture; (4) agitate with a vortex mixer at 1000 rpm for 10 minutes; and (5) let the dispersion set and the reaction proceed for 24 hours at room temperature.

A similar technique involving reactions between harmaline and vanillin comprises mixing particulate harmaline and vanillin together at a weight ratio of about 2:1 (vanillin:harmaline), followed by adding ethanol to a final concentration of the reactions of from about 10-100 mg/mL. This mixture is then allowed to sit for approximately 3 days at 50° C. A bluish solid forms, which is filtered and washed with methanol, and recovered.

Phenoxy Benzaldehyde/Harmaline 594 Compounds

The aldehyde reactions between phenoxy benzaldehyde and harmaline components, carried out in the same fashion as the benzaldehyde/harmaline reaction, yield products as set forth below.

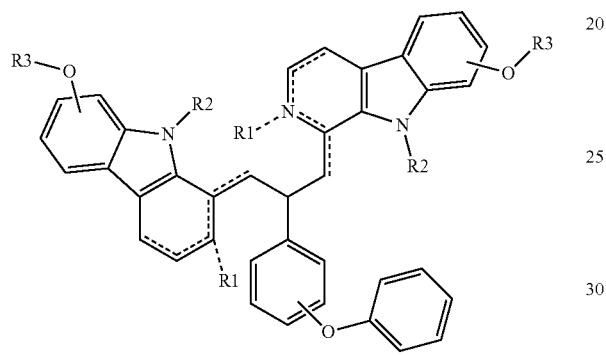

IX and the dimers, isomers, and tautomers thereof, where the —O—R3 groups may be independently located at any position on the terminal phenyl groups, where each R1 is independently selected from the group consisting of nothing, H, OH, and C1-C12 (preferably C1-C4) alkyl groups, each R2 is independently selected form the group consisting of H, OH, and C1-C12 (preferably C1-C4) alkyl groups, each R3 group is independently selected from the group consisting of C1-C12 (preferably C1-C4) alkyl groups, and substituted or unsubstituted phenyl groups, and the phenoxy group may be substituted at any position on the benzyl ring, and wherein the designation ---- refers to the fact that there may optionally be: 1) one or two non-fused double bonds at one or two valence-permitted positions around either or both of the six-membered, N-containing rings, such as illustrations a-d below; or 2) a double bond between either or both of the N-containing rings and the adjacent carbons of the central moiety, with or without an additional non-fused double bond at any valence-permitted position around the corresponding N-containing ring, such as illustrations e-g. In instances of 2) where there is a double bond between the nitrogen atom of either N-containing ring and an adjacent carbon atom thereof, R1 is nothing, such as illustrations a-c and g. However, if there is no such nitrogen double bond, the corresponding R1 is selected from the group consisting of H, OH, and C1-C12 (preferably C1-C4) alkyl groups, such as illustrations d-f; or 3) either or both of the N-containing rings are free of non-fused double bonds and each R1 is independently selected from the group consisting of H, OH, and C1-C12 (preferably C1-C4) alkyl groups.

Set forth below are illustrations depicting certain exemplary double bond configurations of either or both of the N-containing rings of structure VII.

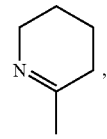

a

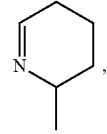

b

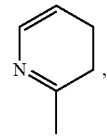

c

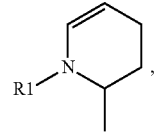

d

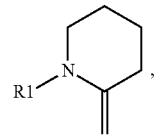

e

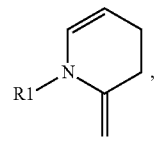

f

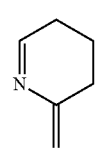

g

A particularly preferred compound of this type is set forth below and referenced in Example 24, where 3-phenoxybenzaldehyde was used.

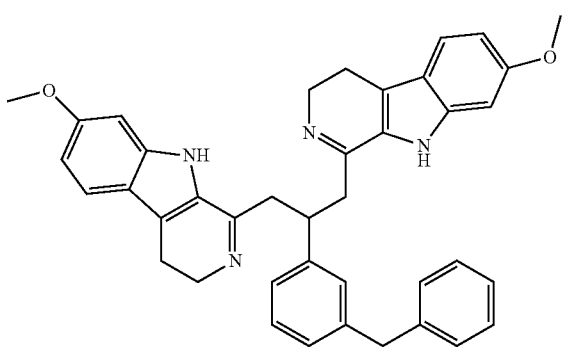

1,1'-(2-(3-phenoxyphenyl)propane-1,3-diyl)bis(7-methoxy-
4,9-dihydro-3H-pyrido[3,4-b]indole)
Chemical Formula: C$_{39}$H$_{36}$N$_4$O$_3$
Exact Mass: 608.28

Harmaline Components

Some harmaline components are tricyclic compounds of the structure

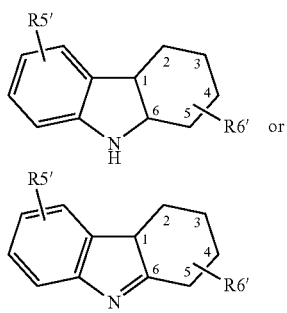

where the numbered 6-member fused ring is a N-heterocycle with a single N atom at any of the positions 2-5, and the R6 substituents may be located at any ring position; R5' is H or C1-C12 (preferably C1-C4) alkoxy; and R6' is H, a C1-C12 (preferably C1-C4) alkyl, or a C1-C12 (preferably C1-C4) carboxylic acid.

Representative compounds of this type include harmaline and the following:

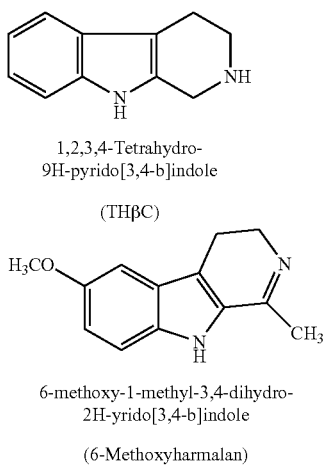

1,2,3,4-Tetrahydro-
9H-pyrido[3,4-b]indole (THβC)

6-methoxy-1-methyl-3,4-dihydro-
2H-yrido[3,4-b]indole (6-Methoxyharmalan)

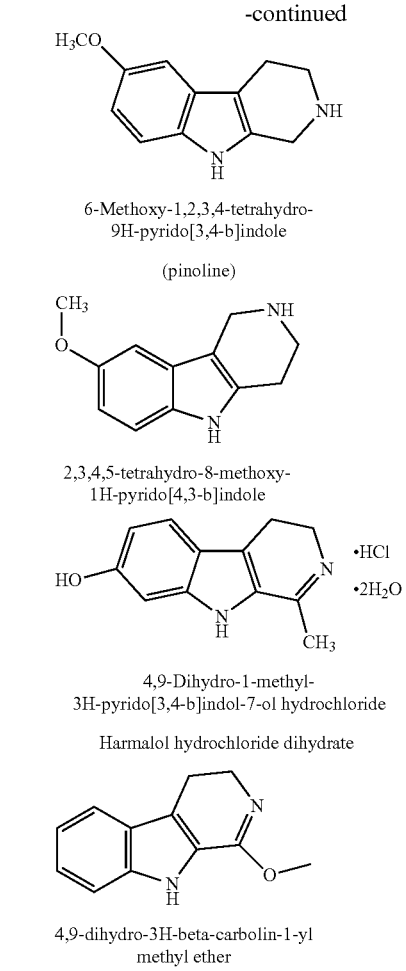

6-Methoxy-1,2,3,4-tetrahydro-
9H-pyrido[3,4-b]indole (pinoline)

2,3,4,5-tetrahydro-8-methoxy-
1H-pyrido[4,3-b]indole 4,9-Dihydro-1-methyl-
3H-pyrido[3,4-b]indol-7-ol hydrochloride Harmalol hydrochloride dihydrate 4,9-dihydro-3H-beta-carbolin-1-yl
methyl ether In the foregoing representative compounds, any methoxy substituent may be replaced by a C2-C4 alkoxy group, or by a phenoxy group.

A number of other aldehydes have been reacted with harmaline to produce compounds, apart from those described above and detailed in the following examples. In each instance, the reaction was carried out by mixing together 500 mg of aldehyde and 250 mg of harmaline in a 15 mL jar, followed by gentle shaking the jar until a uniform powder mixture is present. Thereupon, 10 mL of ethanol was added to the dry mixture, the jar was capped, and was placed in a warm water bath of about 40° C. for approximately 24 hours.

In the table below, the specific harmaline-reacted aldehydes are identified together with the compounds obtained. As to the latter, the makeup of the respective compounds is identified by reactant moieties therein less any dehydration and/or reduction by virtue of the reaction, along with the approximate molecular weights thereof. For example, a given compound recited as "H+A−H2O" refers to a product containing one moiety of harmaline and one moiety of Aldehyde, minus one water molecule, whereas 2H+A−H20-2H refers to a product containing two moieties of harmaline, one moiety of aldehyde, less one water molecule and less two hydrogen atoms.

| Aldehyde | Compound Makeup | Compound Molecular Weight |
| --- | --- | --- |
| o-anisaldehyde | H + A − H2O | 332 |
| o-anisaldehyde | 2H + A − H2O | 546 |
| o-anisaldehyde | 2H + 2A − 2H2O | 664 |
| ethyl vanillin | H + A − H2O | 362 |
| ethyl vanillin | 2H + A − H2O | 576 |
| ethyl vanillin | 2H + 2A − 2H2O | 724 |
| vanillin isobutyrate | H + A − H2O | 418 |
| vanillin isobutyrate | 2H + A − H2O | 632 |
| veratraldehyde | H + A − H2O | 362 |
| veratraldehyde | 2H + A − H2O | 576 |
| 5-nitrovanillin | H + A − H2O | 393 |
| vanillin acetate | H + A − H2O | 390 |
| vanillin acetate | 2H + A − H2O | 604 |
| vanillin acetate | 2H + 2A − 2H2O | 780 |
| 3-hydroxy-5-methoxybenzaldehyde | H + A − H2O | 348 |
| 3-hydroxy-5-methoxybenzaldehyde | 2H + A − H2O | 562 |
| 3-hydroxy-5-methoxybenzaldehyde | 2H + 2A − 2H2O | 696 |
| 2-hydroxy-4-methoxybenzaldehyde | H + A − H2O | 348 |
| 3-chloro-4-hydroxy-5-methoxybenzaldehyde | H + A − H2O | 382 |
| 3-chloro-4-hydroxy-5-methoxybenzaldehyde | 2H + A − H2O | 597 |
| 4-benzyloxy-3-methoxybenzaldehyde | H + A − H2O | 438 |
| 4-benzyloxy-3-methoxybenzaldehyde | 2H + A − H2O | 652 |
| 3,4-dimethoxy-5-hydroxybenzaldehyde | H + A − H2O | 378 |
| 3,4-dimethoxy-5-hydroxybenzaldehyde | 2H + A − H2O | 592 |
| 3,4-dimethoxy-5-hydroxybenzaldehyde | 2H + 2A − 2H2O | 756 |
| 5-bromovanillin | H + A − H2O | 427 |
| 5-bromovanillin | 2H + A − H2O | 641 |
| 2-bromo-3-hydroxy-4-methoxybenzaldehyde | H + A − H2O | 427 |
| 2-bromo-3-hydroxy-4-methoxybenzaldehyde | 2H + A − H2O | 641 |
| 3-hydroxy-2-iodo-4-methoxybenzaldehyde | H + A − H2O | 474 |
| 3-hydroxy-2-iodo-4-methoxybenzaldehyde | 2H + A − H2O | 688 |
| m-anisaldehyde | H + A − H2O | 332 |
| m-anisaldehyde | 2H + A − H2O | 546 |
| 3-phenoxybenzaldehyde | H + A − H2O | 394 |
| 3-phenoxybenzaldehyde | 2H + A − H2O | 608 |
| 4-phenoxybenzaldehyde | H + A − H2O | 394 |
| 4-phenoxybenzaldehyde | 2H + A − H2O | 608 |
| biphenyl-3-carboxaldehyde | H + A − H2O | 378 |
| biphenyl-3-carboxaldehyde | 2H + A − H2O | 592 |
| 4-fluoro-3-phenoxybenzaldehyde | H + A − H2O | 412 |
| 4-fluoro-3-phenoxybenzaldehyde | 2H + A − H2O | 626 |
| 3-fluorobenzaldehyde | H + A − H2O | 320 |
| 3-fluorobenzaldehyde | 2H + A − H2O | 534 |
| 3-fluorobenzaldehyde | 2H + 2A − 2H2O | 640 |
| 4-fluorobenzaldehyde | H + A − H2O | 320 |
| 4-fluorobenzaldehyde | 2H + A − H2O | 534 |
| 4-fluorobenzaldehyde | 2H + 2A − 2H2O | 640 |
| 3,5-fluorobenzaldehyde | H + A − H2O | 338 |
| 3,5-fluorobenzaldehyde | H + A | 356 |
| 3,5-fluorobenzaldehyde | 2H + A − H2O | 552 |
| 3,5-fluorobenzaldehyde | 2H + 2A − 2H2O | 676 |
| 2,4,5-fluorobenzaldehyde | H + A − H2O | 356 |
| 2,4,5-fluorobenzaldehyde | 2H + A − H2O | 570 |
| 2,3,4,5,6-fluorobenzaldehyde | H + A − H2O | 392 |
| 2,3,4,5,6-fluorobenzaldehyde | 2H + A − H2O | 606 |
| 2,3,4,5,6-fluorobenzaldehyde | 2H + 2A − 2H2O | 784 |
| 4-methylbenzaldehyde | H + A − H2O | 316 |
| 4-methylbenzaldehyde | H + A | 334 |
| 4-methylbenzaldehyde | 2H + A − H2O | 530 |
| teraphthalaldehyde | H + A − H2O | 330 |
| teraphthalaldehyde | 2H + A − H2O | 544 |
| teraphthalaldehyde | 2H + 2A − 2H2O | 660 |
| 4-chlorobenzaldehyde | H + A − H2O | 336 |
| 4-chlorobenzaldehyde | H + A | 354 |
| perillaldehyde | H + A − H2O | 346 |
| perillaldehyde | 2H + A − H2O | 560 |
| cuminaldehyde | H + A − H2O | 344 |
| cuminaldehyde | 2H + A − H2O | 553 |
| cuminaldehyde | 2H + A | 576 |
| cuminaldehyde | 2H + 2A − 2H20 | 688 |
| cyclohexanecarboxaldehyde | 2H + A − H2O − 2H | 520 |
| cyclohexanecarboxaldehyde | H + A | 326 |
| cyclohexanecarboxaldehyde | H + A − H20 | 308 |

The following are representative structures of some of the compounds set forth in the above table wherein two moieties of harmaline were reacted with the recited aldehydes (in some cases, the aldehydes are identified by different, equivalent names).

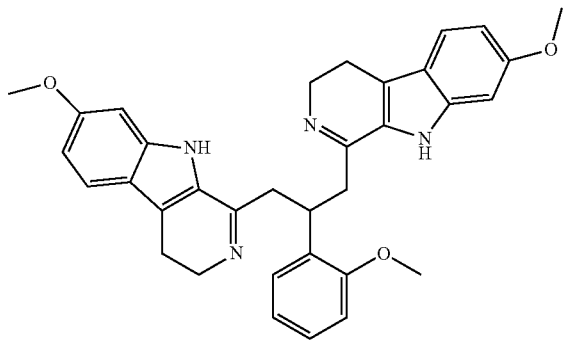

1,1'-(2-(2-methoxyphenyl)propane-1,3-diyl)bis
(7-methoxy-4,9-dihydro-3H-pyrido[3,4-b]indole)
C34H34N4O3
2-methoxybenzaldehyde, o-anisaldehyde

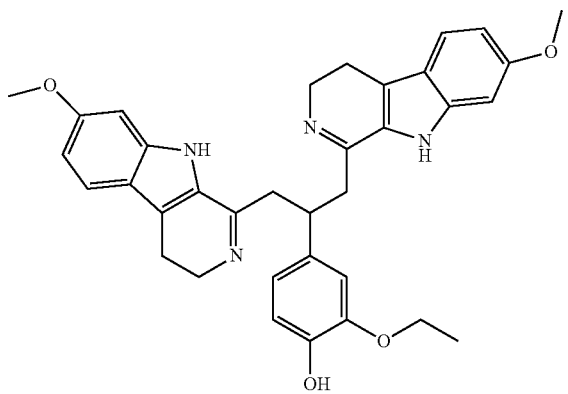

4-(1,3-bis(7-methoxy-4,9-dihydro-3H-pyrido[3,4-b]indol-1-yl)
propan-2-yl)-2-ethoxyphenol
C35H36N4O4
3-ethoxy-4-hydroxybenzaldehyde, ethyl vanillin

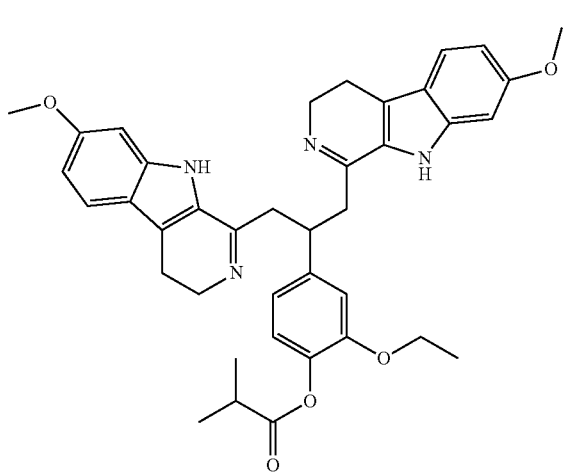

4-(1,3-bis(7-methoxy-4,9-dihydro-3H-pyrido[3,4-b]indol-1-yl)
propan-2-yl)-2-methoxyphenyl isobutyrate
C38H40N4O5
4-formyl-2-methoxyphenyl isobutyrate, vanillin isobutyrate

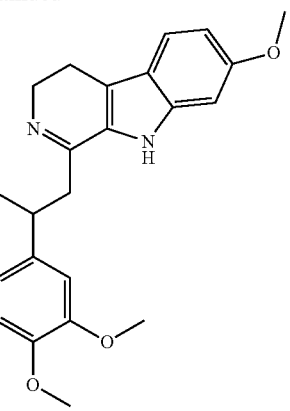

1,1'-(2-(3,4-dimethoxyphenyl)propane-1,3-diyl)bis
(7-methoxy-4,9-dihydro-3H-pyrido[3,4-b]indole)
C35H36N4O4
3,4-dimethoxybenzaldehyde, veratraldehyde

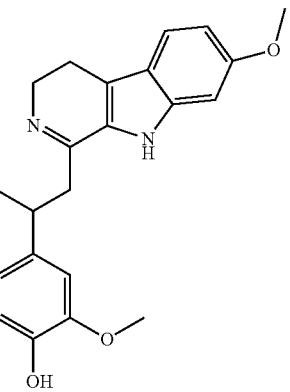

4-(1,3-bis(7-methoxy-4,9-dihydro-3H-pyrido[3,4-b]indol-1-yl)
propan-2-yl)-2-methoxy-6-nitrophenol
C34H33N5O6
4-hydroxy-3-methoxy-5-nitrobenzaldehyde, 5-nitrovanillin

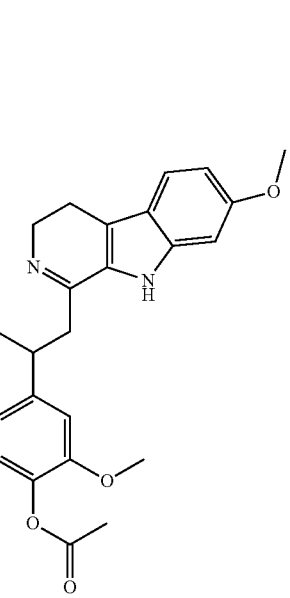

4-(1,3-bis(7-methoxy-4,9-dihydro-3H-pyrido[3,4-b]indol-1-yl)
propan-2-yl)-2-methoxyphenyl acetate
C36H36N4O5
4-formyl-2-methoxyphenyl acetate, vanillin acetate

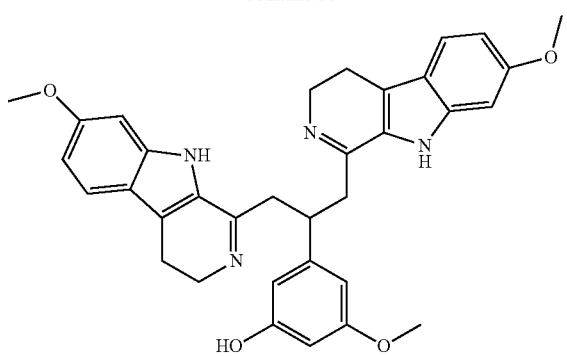

3-(1,3-bis(7-methoxy-4,9-dihydro-3H-pyrido[3,4-b]indol-1-yl)
propan-2-yl)-5-methoxyphenol
C34H34N4O4
3-hydroxy-5-methoxybenzaldehyde

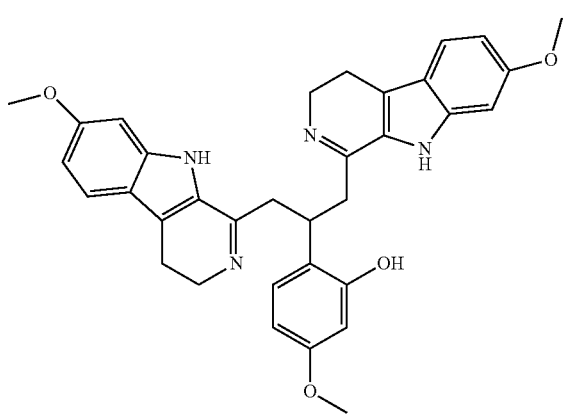

2-(1,3-bis(7-methoxy-4,9-dihydro-3H-pyrido[3,4-b]indol-1-yl)
propan-2-yl)-5-methoxyphenol
C34H34N4O4
2-hydroxy-4-methoxybenzaldehyde

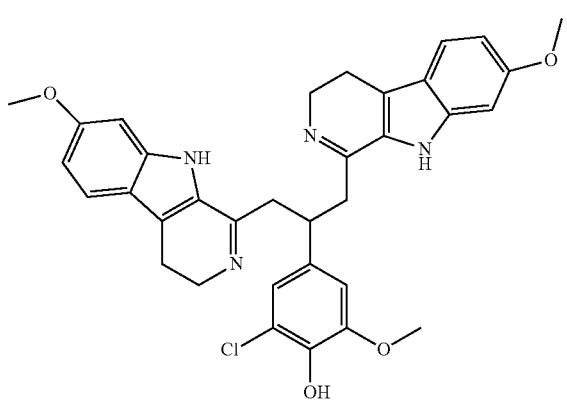

4-(1,3-bis(7-methoxy-4,9-dihydro-3H-pyrido[3,4-b]indol-1-yl)
propan-2-yl)-2-chloro-6-methoxyphenyl
C34H33ClN4O4
3-chloro-4-hydroxy-5-methoxybenzaldehyde 1,1′-(2-(benzyloxy)-3-methoxyphenyl)propane-1,3-diyl)bis
(7-methoxy-4,9-dihydro-3H-pyrido[3,4-b]indole)
C41H40N4O4
4-benzyloxy-3-methoxybenzaldehyde 5-(1,3-bis(7-methoxy-4,9-dihydro-3H-pyrido[3,4-b]indol-1-yl)
propan-2-yl)-2,3-dimethoxyphenol
C35H36N4O5
3-hydroxy-4,5-dimethoxybenzaldehyde, 3,4-dimethoxy-5-
hydroxybenzaldehyde

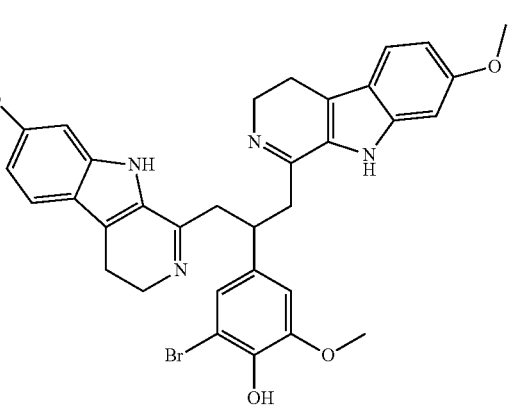

4-(1,3-bis(7-methoxy-4,9-dihydro-3H-pyrido[3,4-b]indol-1-yl)
propan-2-yl)-2-bromo-6-methoxyphenol
C34H33BrN4O4
3-bromo-4-hydroxy-5-methoxybenzaldehyde, 5-bromovanillin 77
-continued

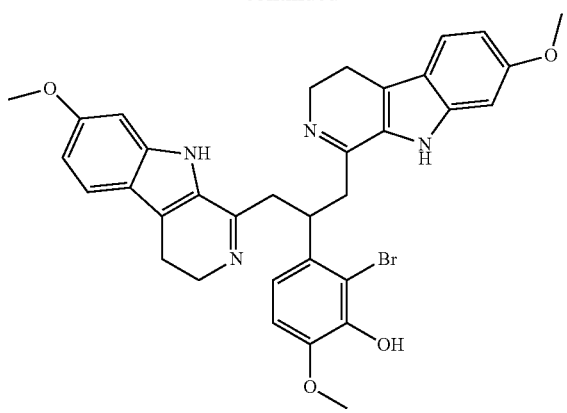

3-(1,3-bis(7-methoxy-4,9-dihydro-3H-pyrido[3,4-b]indol-1-yl)
propan-2-yl)-2-bromo-6-methoxyphenol
C34H33BrN4O4
2-bromo-3-hydroxy-4-methoxybenzaldehyde

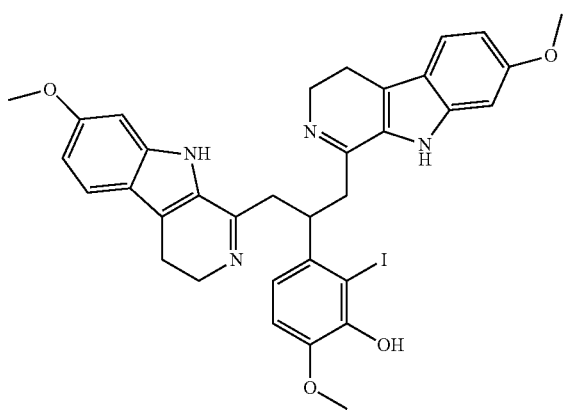

3-(1,3-bis(7-methoxy-4,9-dihydro-3H-pyrido[3,4-b]indol-1-yl)
propan-2-yl)-2-iodo-6-methoxyphenol
C34H33IN4O4
3-hydroxy-iodo-4-methoxybenzaldehyde

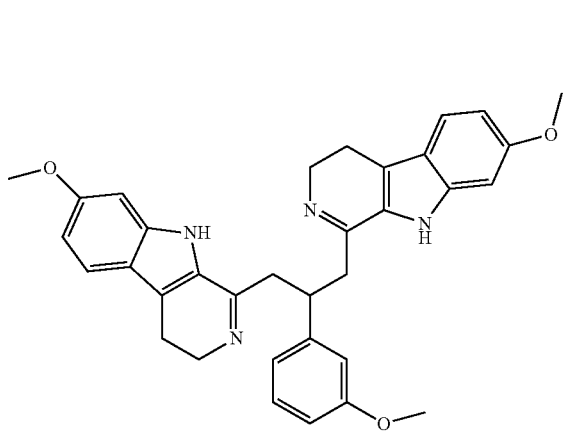

1,1'-(2-(3-methoxyphenyl)propane-1,3-diyl)bis
(7-methoxy-4,9-dihydro-3H-pyrido[3,4-b]indole)
C34H34N4O3
3-methoxybenzaldehyde, m-anisaldehyde 78
-continued

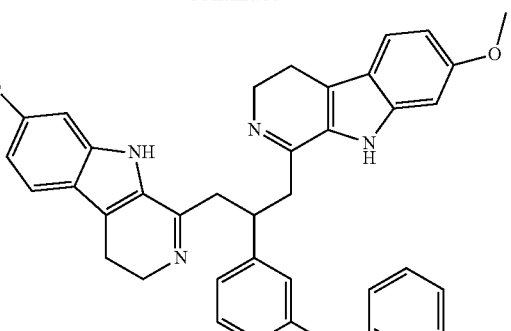

1,1'-(2-(3-methoxyphenyl)propane-1,3-diyl)bis
(7-methoxy-4,9-dihydro-3H-pyrido[3,4-b]indole)
C39H36N4O3
3-phenoxybenzaldehyde

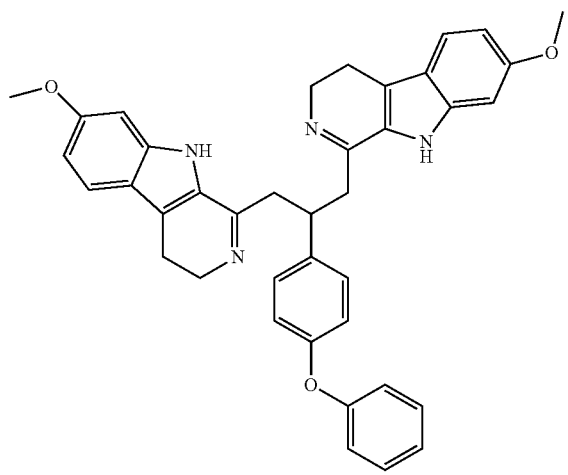

1,1'-(2-(4-phenoxyphenyl)propane-1,3-diyl)bis
(7-methoxy-4,9-dihydro-3H-pyrido[3,4-b]indole)
C39H36N4O3
4-phenoxybenzaldehyde

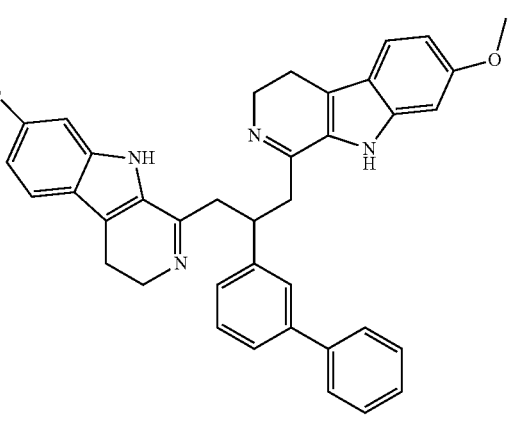

1,1'-(2-([1,1'-biphenyl]-3-yl)propane-1,3-diyl)bis
(7-methoxy-4,9-dihydro-3H-pyrido[3,4-b]indole)
C39H36N4O2
[1,1'-biphenyl]-3-carbaldehyde, biphenyl-3-carboxaldehyde

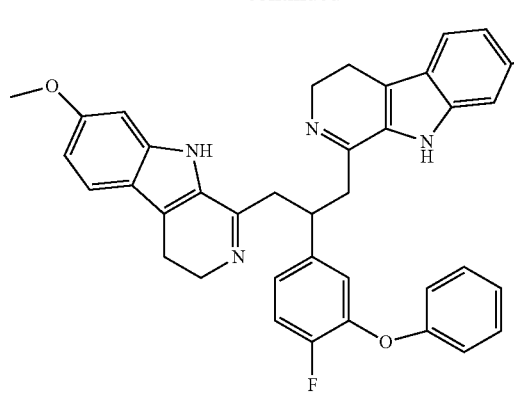

1,1′-(2-(4-fluoro-3-phenoxyphenyl)propane-1,3-diyl)bis
(7-methoxy-4,9-dihydro-3H-pyrido[3,4-b]indole)
C39H35FN4O3
4-fluoro-3-phenoxybenzaldehyde

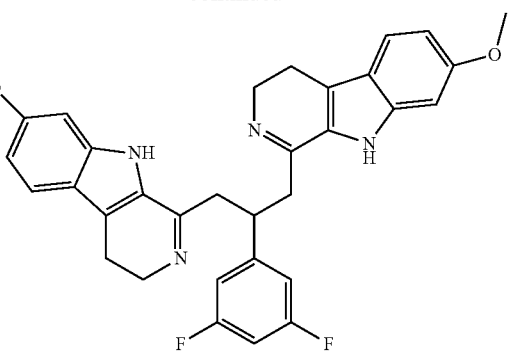

1,1′-(2-(3,5-difluorophenyl)propane-1,3-diyl)bis
(7-methoxy-4,9-dihydro-3H-pyrido[3,4-b]indole)
C33H31F2N4O2
3,5-difluorobenzaldehyde

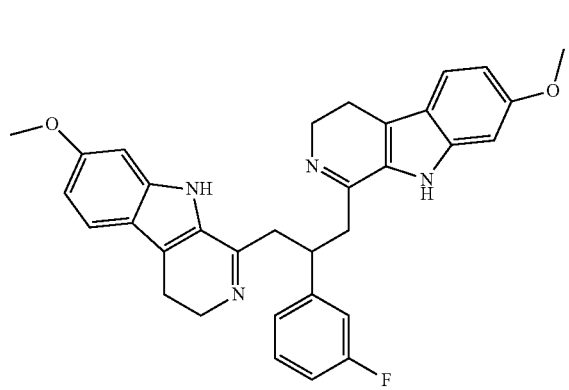

1,1′-(2-(3-fluorophenyl)propane-1,3-diyl)bis
(7-methoxy-4,9-dihydro-3H-pyrido[3,4-b]indole)
C33H31FN4O2
3-fluorobenzaldehyde

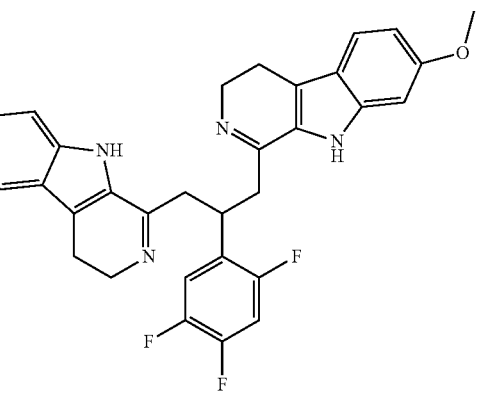

1,1′-(2-(2,4,5-trifluorophenyl)propane-1,3-diyl)bis
(7-methoxy-4,9-dihydro-3H-pyrido[3,4-b]indole)
C33H29F3N4O2
2,4,5-trifluorobenzaldehyde

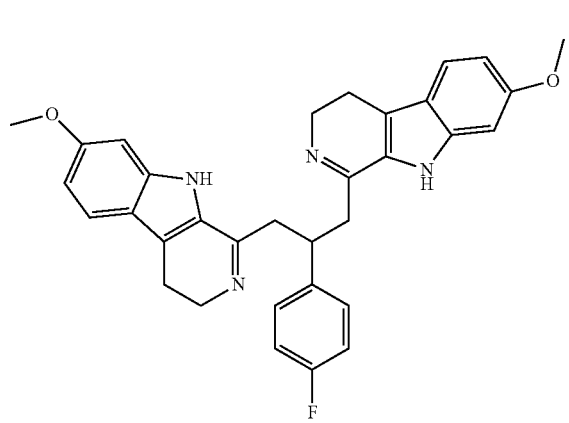

1,1′-(2-(4-fluorophenyl)propane-1,3-diyl)bis
(7-methoxy-4,9-dihydro-3H-pyrido[3,4-b]indole)
C33H31FN4O2
4-fluorobenzaldehyde

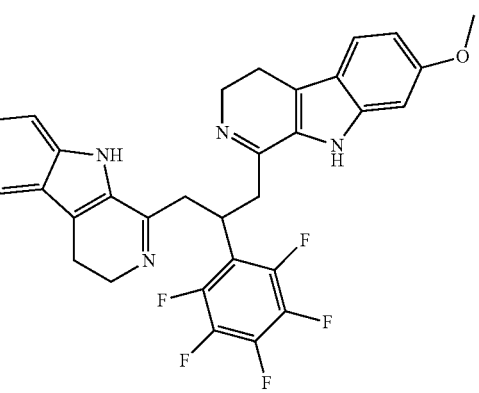

1,1′-(2-(perfluorophenyl)propane-1,3-diyl)bis
(7-methoxy-4,9-dihydro-3H-pyrido[3,4-b]indole)
C33H27F5N4O2
2,3,4,5,6-pentafluorobenzaldehyde -continued

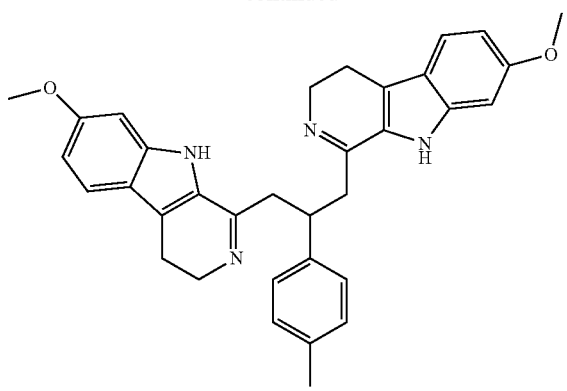

1,1′-(2-(p-tolyl)propane-1,3-diyl)bis
(7-methoxy-4,9-dihydro-3H-pyrido[3,4-b]indole)
C34H34N4O2
4-methylbenzaldehyde

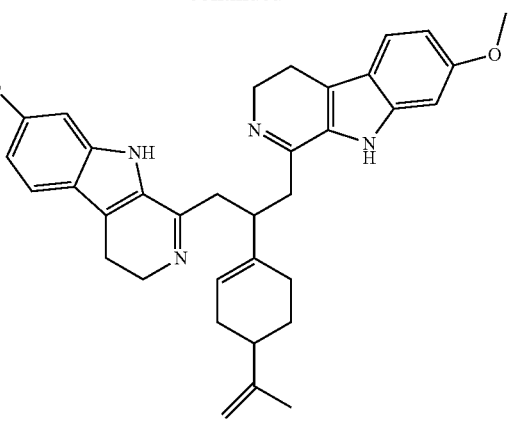

1,1′-(2-(4-(prop-1-en-2-yl)cyclohex-1-en-1-yl)propane-1,3-diyl)bis
(7-methoxy-4,9-dihydro-3H-pyrido[3,4-b]indole)
C36H40N4O2
4-(prop-1-en-2-yl)cyclohex-1-ene-1-carbaldehyde, perillaldehyde 4-(1,3-bis(7-methoxy-4,9-dihydro-3H-pyrido[3,4-b]indol-1-yl)
propan-2-yl)benzaldehyde
C34H32N4O3
Teraphthalaldehyde

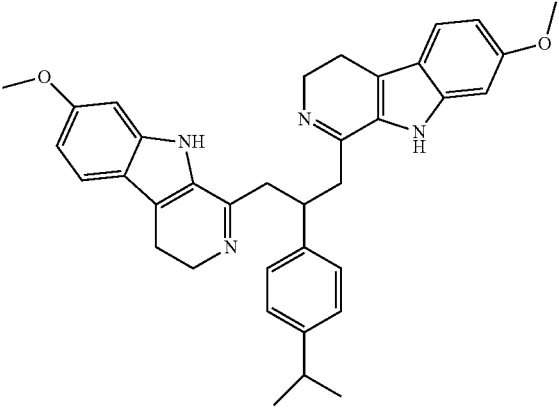

1,1′-(2-(4-isopropylphenyl)propane-1,3-diyl)bis
(7-methoxy-4,9-dihydro-3H-pyrido[3,4-b]indole)
C36H38N4O2
4-isopropylbenzaldehyde, cuminaldehyde

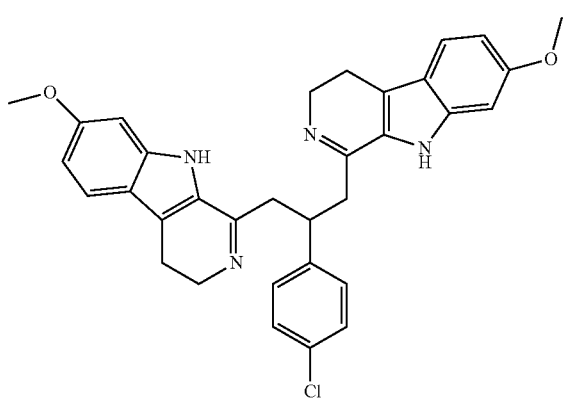

1,1′-(2-(4-chlorophenyl)propane-1,3-diyl)bis
(7-methoxy-4,9-dihydro-3H-pyrido[3,4-b]indole)
C33H31ClN4O2
4-chlorobenzaldehyde 1,1′-(2-cyclohexylpropane-1,3-diyl)bis
(7-methoxy-4,9-dihydro-3H-pyrido[3,4-b]indole)
C33H38ClN4O2
cyclohexane carboxaldehyde -continued

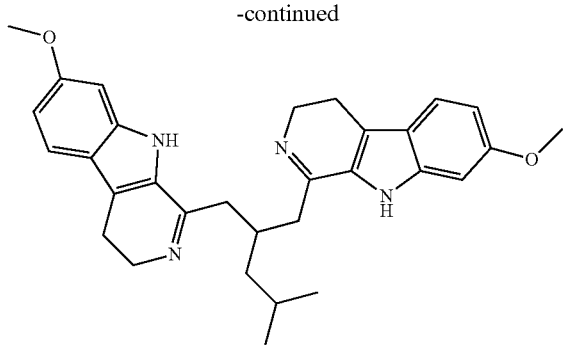

1,1'-(2-isobutylpropane-1,3-diyl)bis
(7-methoxy-4,9-dihydro-3H-pyrido[3,4-b]indole)
C31H36N4O2
Exact Mass: 496.28

Additionally, number of harmaline-like compounds were reacted with different aldehydes to produce compounds, apart from those detailed in the following examples. In each instance, the reaction was carried out by mixing together 500 mg of a selected aldehyde and 250 mg of a harmaline-like compound in a 15 mL jar, followed by gentle shaking the jar until a uniform powder mixture is present. Thereupon, 10 mL of ethanol was added to the dry mixture, the jar was capped, and was placed in a warm water bath of about 40° C. for approximately 24 hours.

In the table below, the specific harmaline-like compounds and aldehydes are identified together with the compounds obtained. As to the latter, the makeup of the respective compounds is identified by reactant moieties therein less any dehydration by virtue of the reaction, along with the approximate molecular weights thereof. For example, a given compound recited as "H+A−H2O" refers to a product containing one moiety of harmaline-like compound and one moiety of aldehyde, minus one water molecule.

| Harmaline-like Compound | Aldehyde | Compound Makeup | Compound Molecular Weight |
|---|---|---|---|
| 1 | orthovanillin | H + A − H2O | 306 |
| 1 | orthovanillin | H + 2A − H2O | 458 |
| 1 | benzaldehyde | H + 2A − H2O | 366 |
| 2 | orthovanillin | H + A | 366 |
| 2 | orthovanillin | H + A − H2O | 348 |
| 2 | orthovanillin | 2H + A − H2O | 562 |
| 2 | orthovanillin | 2H + 2A − 2H2O | 696 |
| 3 | orthovanillin | H + A | 352 |
| 4 | orthovanillin | H + A − H2O | 336 |
| 4 | orthovanillin | H + 2A − H2O | 488 |
| 5 | orthovanillin | H + A | 354 |
| 5 | orthovanillin | H + A − H2O | 336 |
| 5 | orthovanillin | 2H + A − H2O | 538 |
| 6 | benzaldehyde | H + A − H2O | 288 |

1 = 1,2,3,4-Tetrahydro-9H-pyrido[3,4-b]indole (THβC)
2 = 6-methoxy-1-methyl-3,4-dihydro-2H-yrido[3,4-b]indole (6-Methoxyharmalan)
3 = 4,9-dihydro-3H-beta-carbolin-1-yl methyl ether
4 = 6-Methoxy-1,2,3,4-tetrahydro-9H-pyrido[3,4-b]indole (pinoline)
5 = 2,3,4,5-tetrahydro-8-methoxy-IH-pyrido[4,3-b]indole
6 = 4,9-Dihydro-1-methyl-3H-pyrido[3,4-b]indol-7-ol hydrochloride (harmalol hydrochloride)

EXAMPLES

The following Examples set forth preferred therapeutic agents and methods in accordance with the invention, but it is to be understood that these examples are given by way of illustration only, and nothing therein should be taken as a limitation upon the overall scope of the invention.

Example 1

In this Example, a series of 523 compounds were prepared using the aldehyde reaction, comprising reacting respective quantities of solid synthetic orthovanillin (99% by weight purity) and synthetic harmaline (92% by weight purity). In each instance, the orthovanillin and harmaline reacted to give one or more compounds. These compositions are referred to as GZ523.001-008, and the makeup and formulation thereof are set forth below, with quantities and approximate percent-by-weight levels for these two components:

GZ523.001—294 mg orthovanillin (85.5%)+50 mg harmaline (14.5%), with 5 mL ethanol, mixed immediately;
GZ523.002—294 mg orthovanillin (85.5%)+50 mg harmaline (14.5%), with 5 mL DMSO, mixed immediately;
GZ523.003—229.3 mg orthovanillin (66.7%)+114.7 mg harmaline (33.3%) mixed together as dry ingredients and allowed to stand for 48 hours in a closed vessel, followed by the addition of 5 mL ethanol;
GZ523.004—286.7 mg orthovanillin (83.3%)+57.3 mg harmaline (16.7%) mixed together as dry ingredients and allowed to stand for 13 days, followed by the addition of 5 mL ethanol;
GZ523.005—229.3 mg orthovanillin (66.7%)+114.7 mg harmaline (33.3%), with 5 mL DMSO, mixed immediately, and allowed to stand for 24 hours;
GZ523.006—229.3 mg orthovanillin (66.7%)+114.7 mg harmaline (33.3%), with 5 mL ethanol, mixed immediately, and allowed to stand for 24 hours;
GZ523.007—172 mg orthovanillin (50%)+172 mg harmaline (50%), with 5 mL ethanol, mixed immediately, and allowed to stand for approximately 3 weeks; and
GZ523.008—229.3 mg orthovanillin (66.7%)+114.7 mg harmaline (33.3%) mixed together as dry ingredients, place in a closed vial for 45 minutes, followed by standing stand for 24 hours in a covered tray, followed by the addition of 5 mL ethanol.

Example 2

The 523 compounds of Example 1 were subjected to a series of identical in vitro assays against lymphoma (M0205) and leukemia (jurkat E6-1) cell lines, in order to determine the anti-cancer properties of the compositions, as determined by cell death. The protocol for the assays is given below.

Methods

The individual cells were grown in suspension in media (RPMI supplemented with 10% FBS), maintained at approximately 500,000 cells/mL. The cells were directly plated in 96-well plates, and each well was exposed to increasing doses of the GZ523.001-.008 compositions for 24 hours (a minimum of 4 replicates for each dosage). After a 24-hour exposure to the selected dosages of the test compositions, PrestoBlue (Life Technologies, Inc) was added to each well and fluorescence readings were taken 4-6 hours later with an excitation wavelength of 485 nm and an emission wavelength of 560 nm, using a microplate reader (Enspire Multimode, PerkinElmer). Results were averaged following background subtraction and normalized to untreated cell controls.

The results of these tests are set forth in FIGS. 1-16, where FIGS. 1-8 are the lymphoma test results and FIGS. 9-16 are the leukemia test results and, in each case, the compositions exhibited excellent anti-cancer activity at relatively low dosages. In general, dosages exceeding 10 µg/mL gave very good results, with extraordinary results above about 40 µg/mL.

Example 3

In this Example, a 523 compound was prepared containing orthovanillin and harmaline at a weight ratio of 2:1, using solid synthetic orthovanillin (99% pure) and solid synthetic harmaline (92% pure). The reactants were dispersed in ethanol to achieve a concentration 75 mg/mL, and allowed to react for a period of 24 hours. After the reaction was complete, the compound (designated as GZ523F001) was treated by HPLC to recover a high molecular weight fraction predominantly (about 70% by weight) made up of dioligomer(s) having a molecular weight of approximately 696, and unreacted harmaline. These dioligomer(s) included one or more compounds exemplified by the Scheme 1 dimers.

Figure 1:
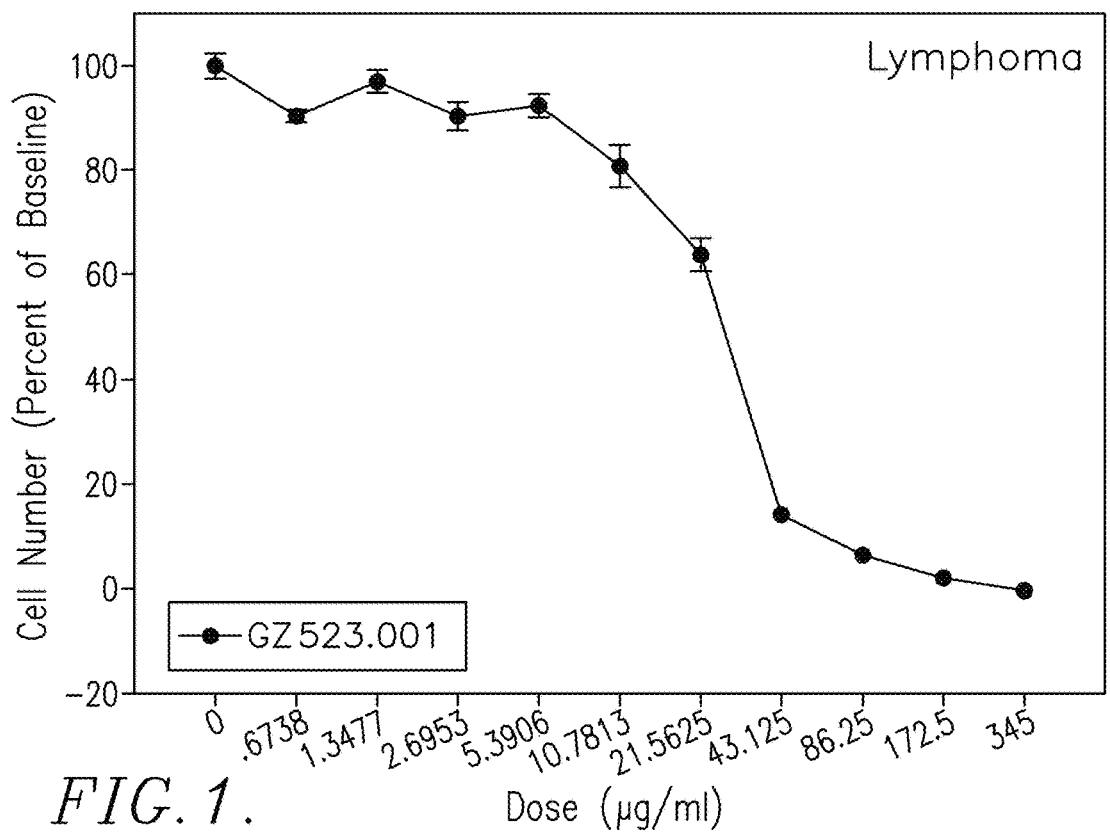
FIG. 1 is a graph of cell number versus dosage amounts of an orthovanillin/harmaline compound (GZ523.001), illustrating the effect thereof in inducing the death of lymphoma cells, as described in Example 2.
Figure 2:
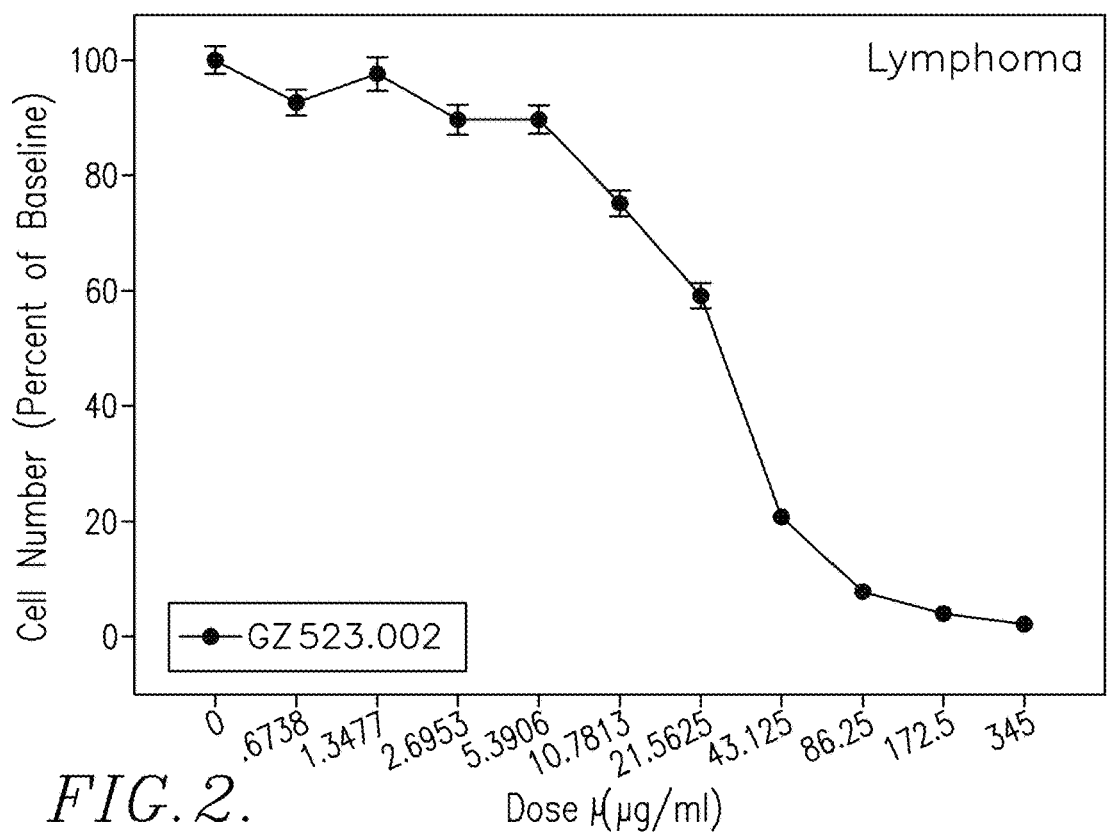
FIG. 2 is a graph of cell number versus dosage amounts of an orthovanillin/harmaline compound (GZ523.002), illustrating the effect thereof in inducing the death of lymphoma cells, as described in Example 2.
Figure 3:
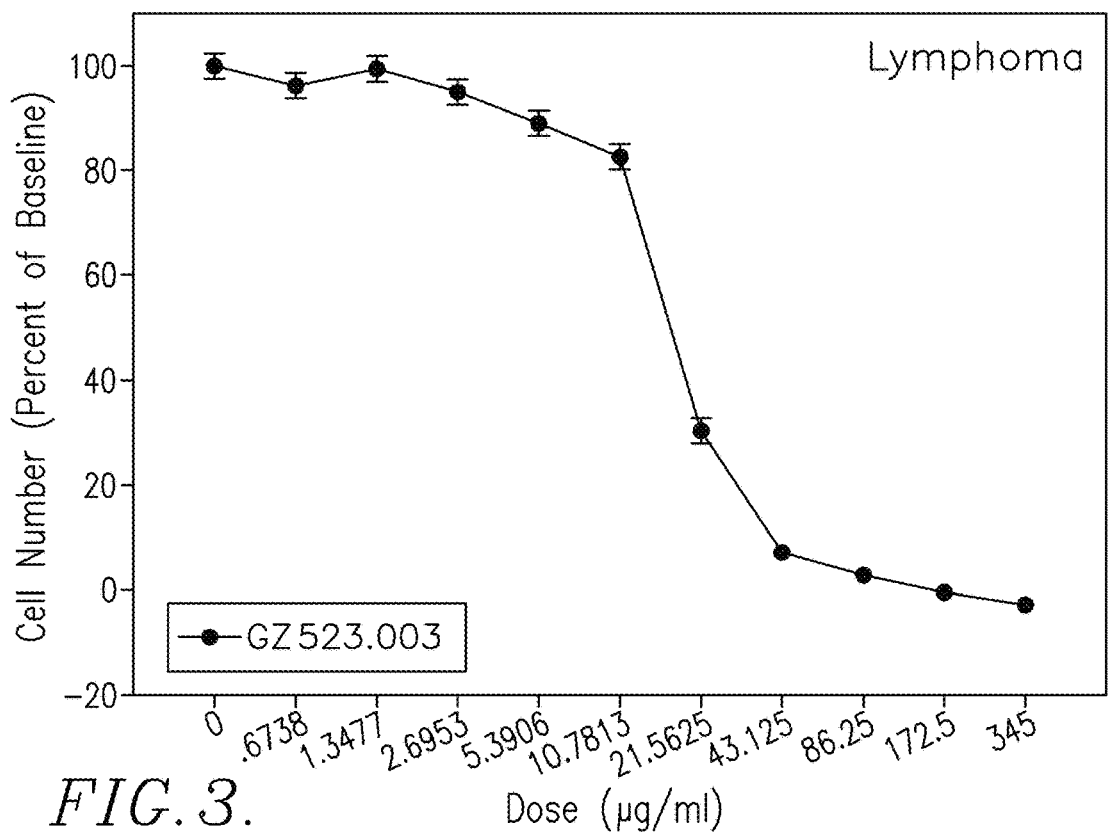
FIG. 3 is a graph of cell number versus dosage amounts of an orthovanillin/harmaline compound (GZ523.003), illustrating the effect thereof in inducing the death of lymphoma cells, as described in Example 2.
Figure 4:
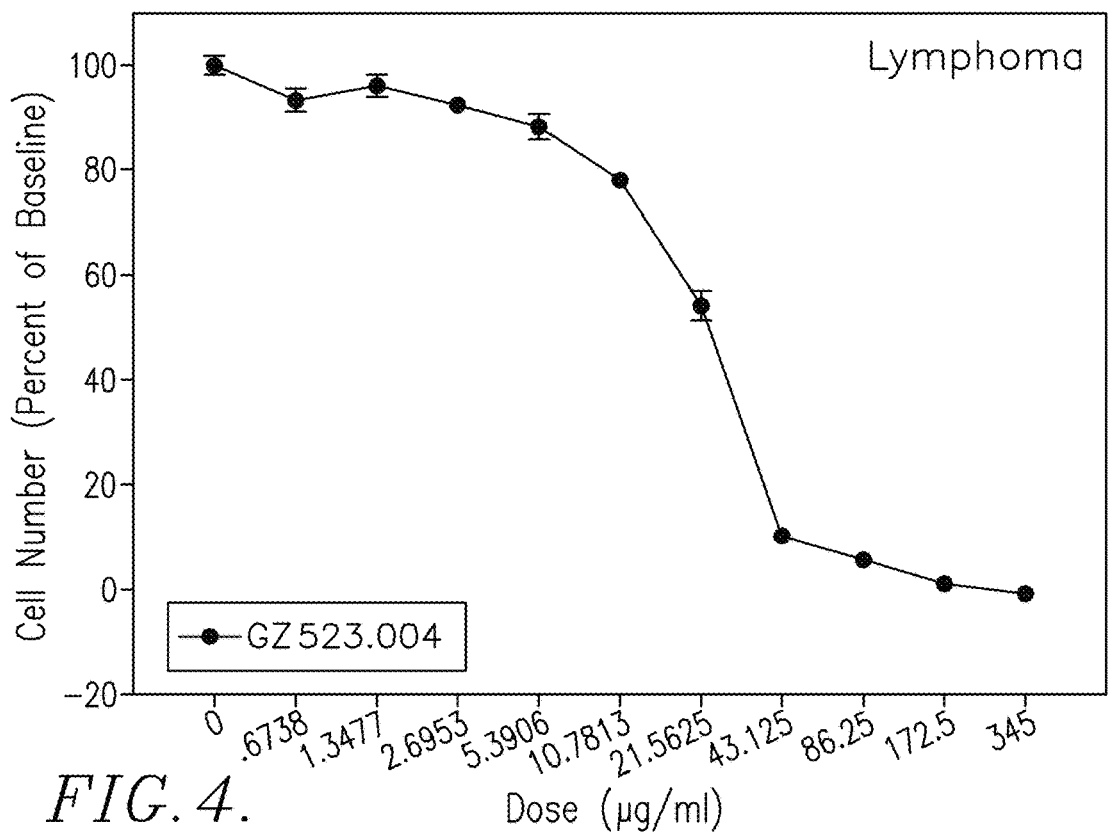
FIG. 4 is a graph of cell number versus dosage amounts of an orthovanillin/harmaline compound (GZ523.004), illustrating the effect thereof in inducing the death of lymphoma cells, as described in Example 2.
Figure 5:
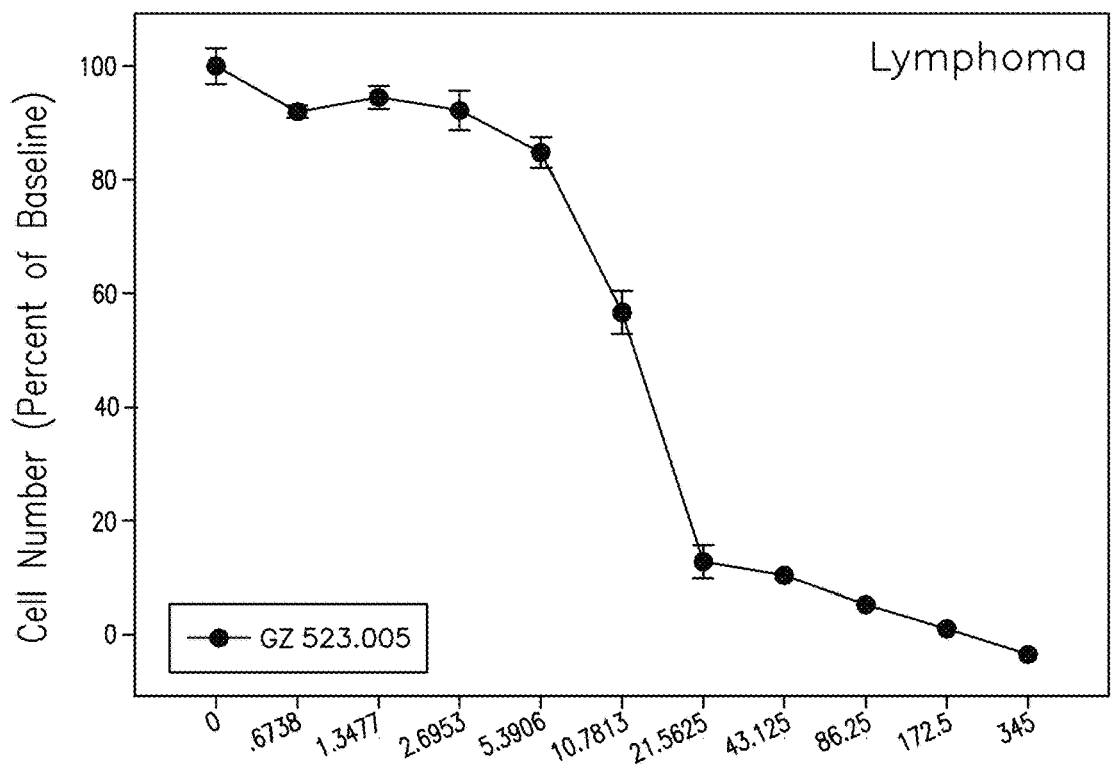
FIG. 5 is a graph of cell number versus dosage amounts of an orthovanillin/harmaline compound (GZ523.005), illustrating the effect thereof in inducing the death of lymphoma cells, as described in Example 2.
Figure 6:
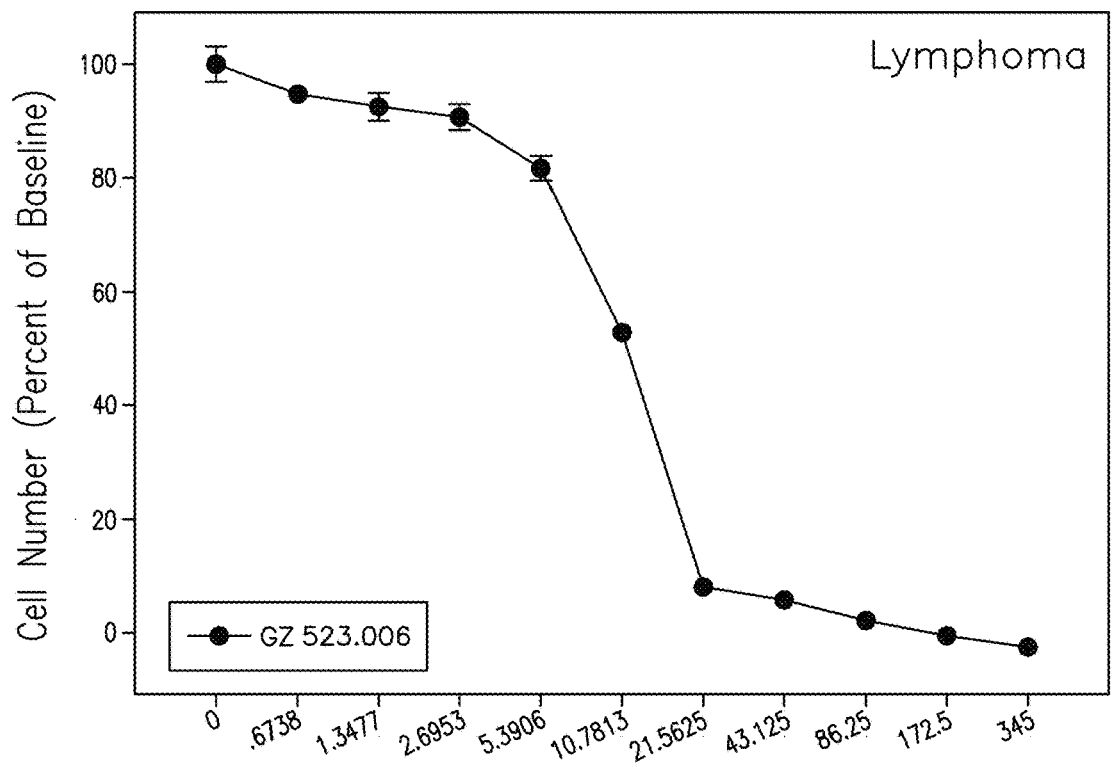
FIG. 6 is a graph of cell number versus dosage amounts of an orthovanillin/harmaline compound (GZ523.006), illustrating the effect thereof in inducing the death of lymphoma cells, as described in Example 2.
Figure 7:
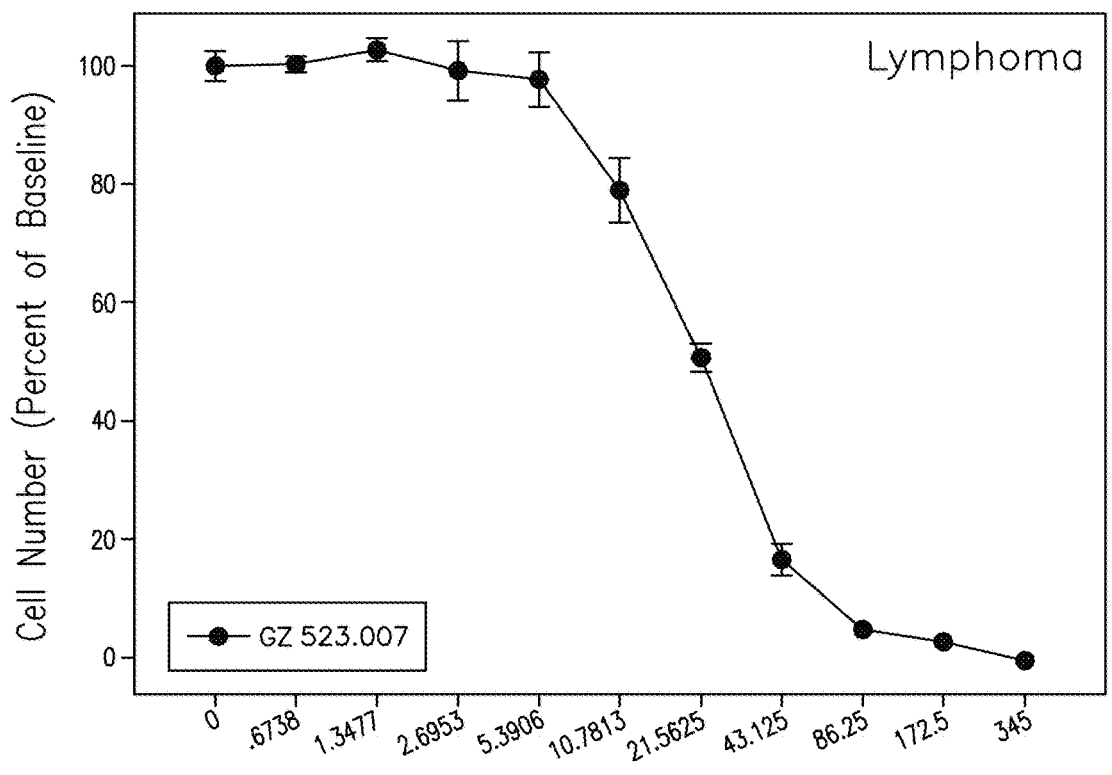
FIG. 7 is a graph of cell number versus dosage amounts of an orthovanillin/harmaline compound (GZ523.007), illustrating the effect thereof in inducing the death of lymphoma cells, as described in Example 2.
Figure 8:
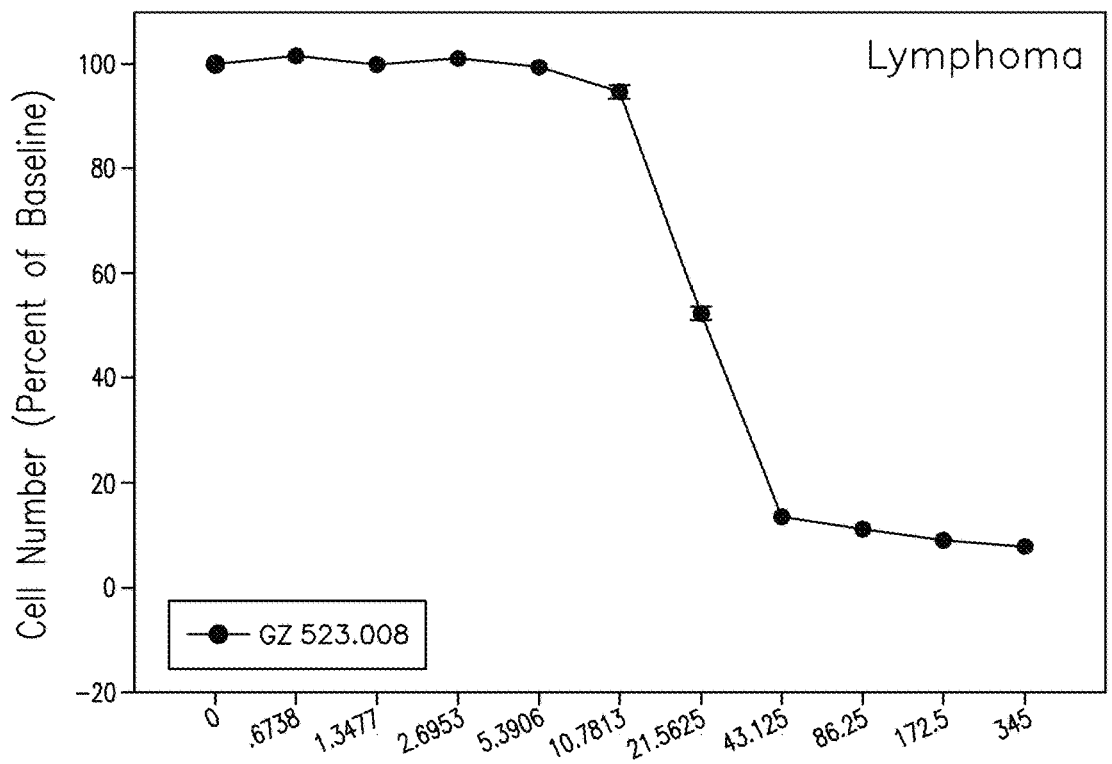
FIG. 8 is a graph of cell number versus dosage amounts of an orthovanillin/harmaline compound (GZ523.008), illustrating the effect thereof in inducing the death of lymphoma cells, as described in Example 2.
Figure 9:
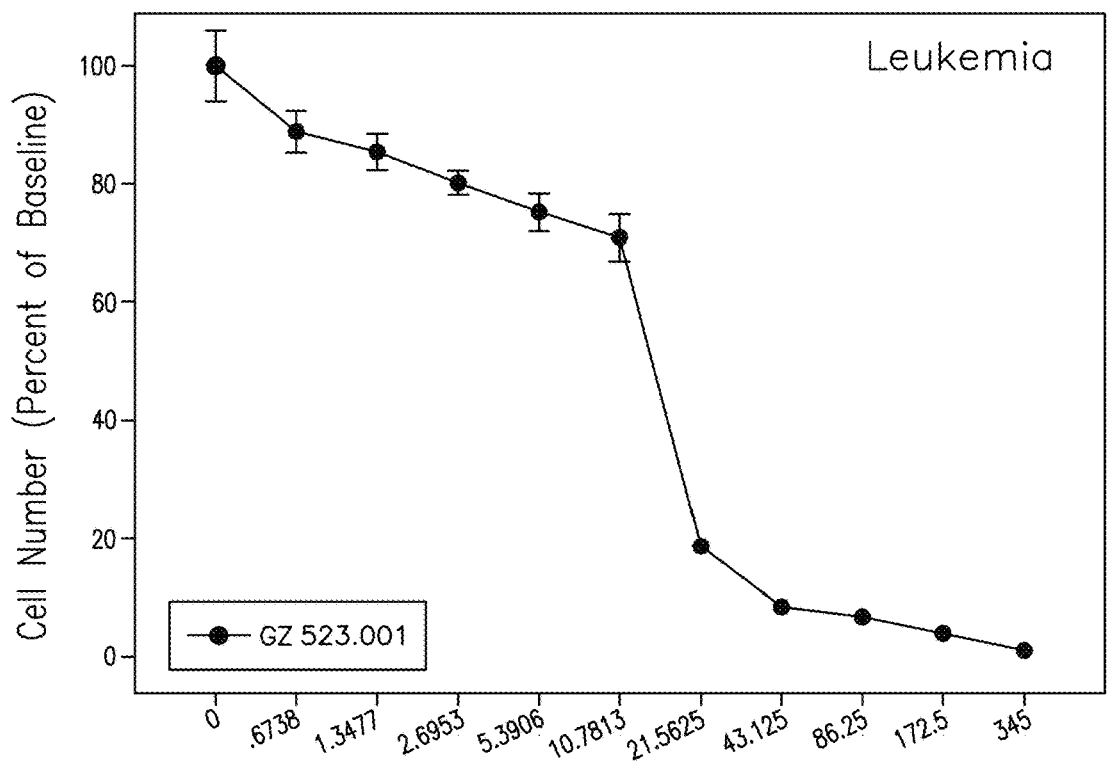
FIG. 9 is a graph of cell number versus dosage amounts of an orthovanillin/harmaline compound (GZ523.001), illustrating the effect thereof in inducing the death of leukemia cells, as described in Example 2.
Figure 10:
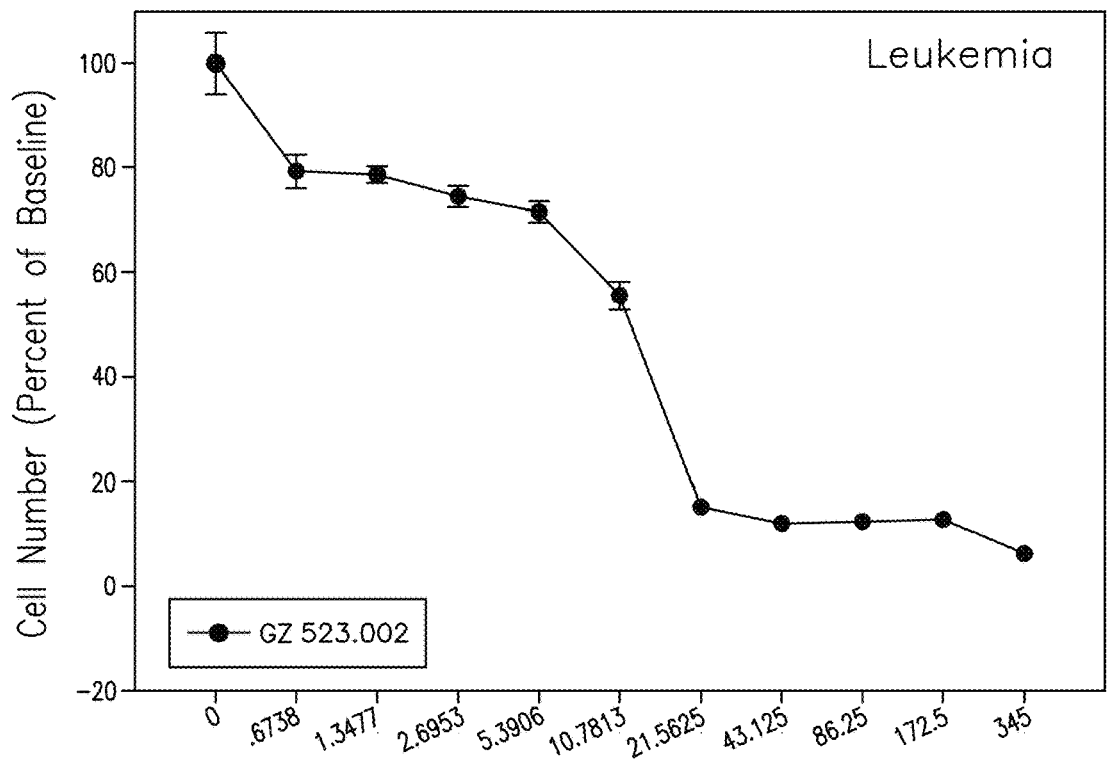
FIG. 10 is a graph of cell number versus dosage amounts of an orthovanillin/harmaline compound (GZ523.002), illustrating the effect thereof in inducing the death of leukemia cells, as described in Example 2.
Figure 11:
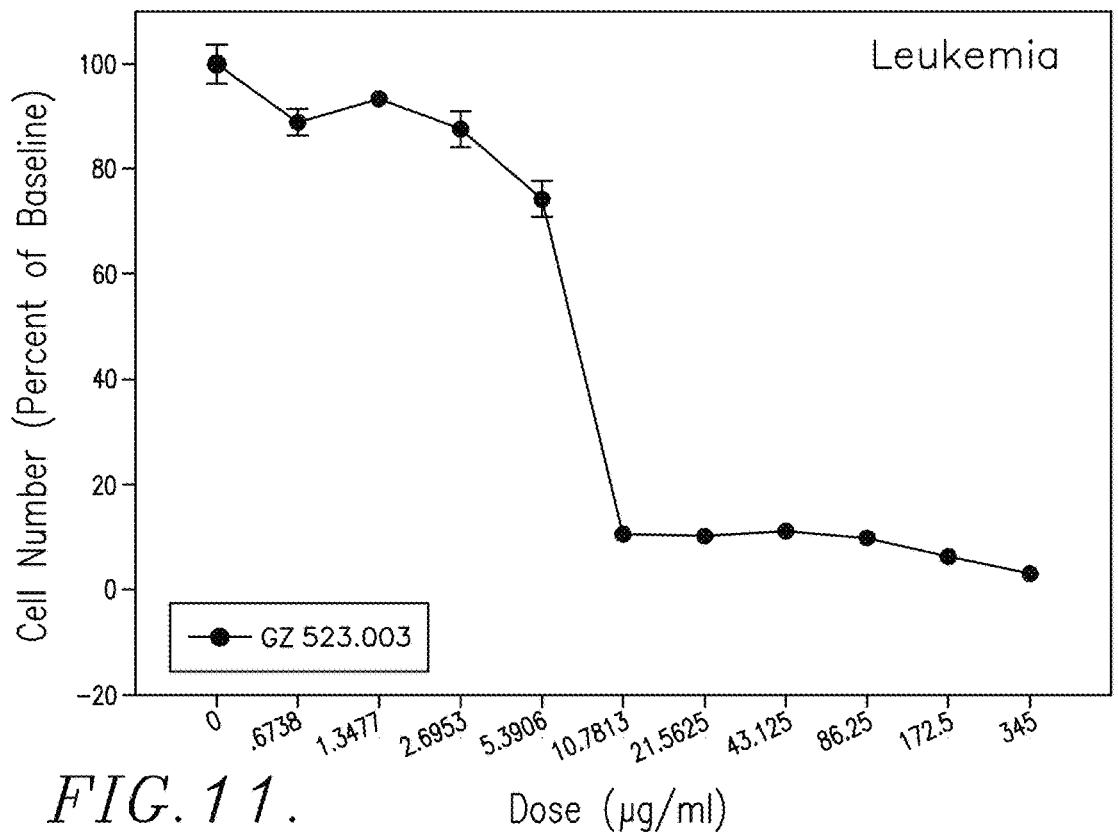
FIG. 11 is a graph of cell number versus dosage amounts of an orthovanillin/harmaline compound (GZ523.003), illustrating the effect thereof in inducing the death of leukemia cells, as described in Example 2.
Figure 12:
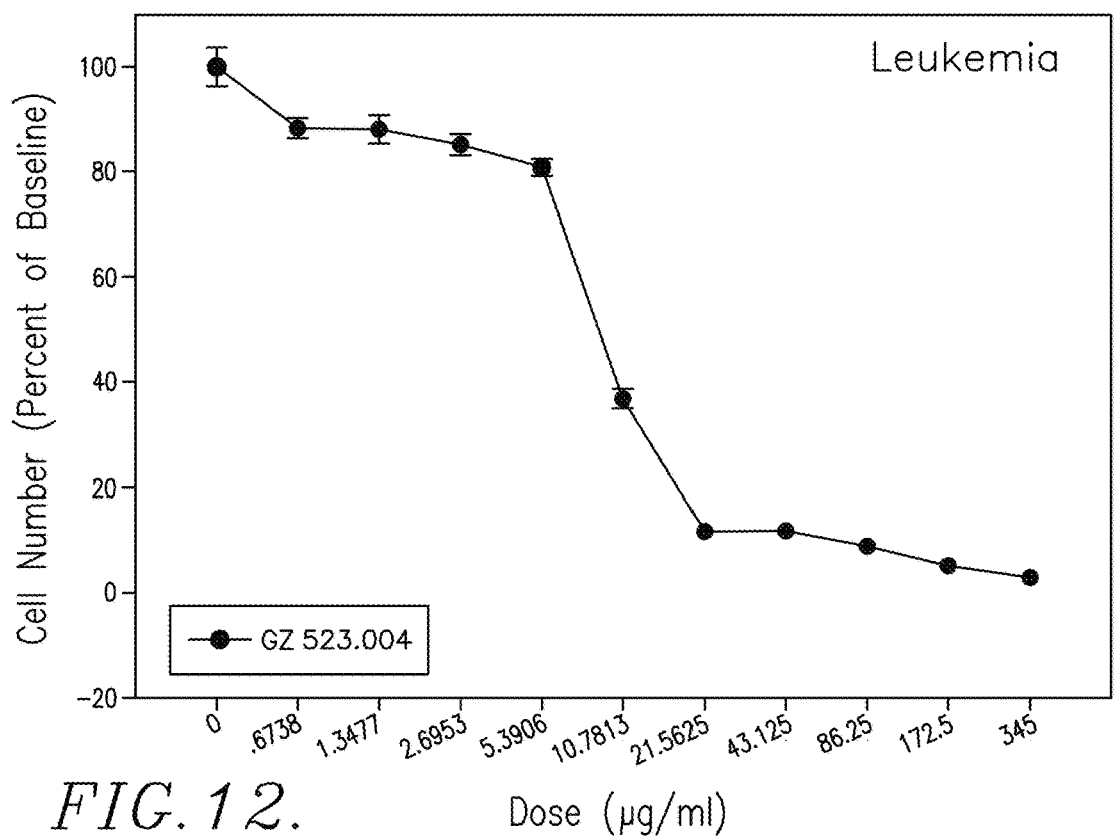
FIG. 12 is a graph of cell number versus dosage amounts of an orthovanillin/harmaline compound (GZ523.004), illustrating the effect thereof in inducing the death of leukemia cells, as described in Example 2.
Figure 13:
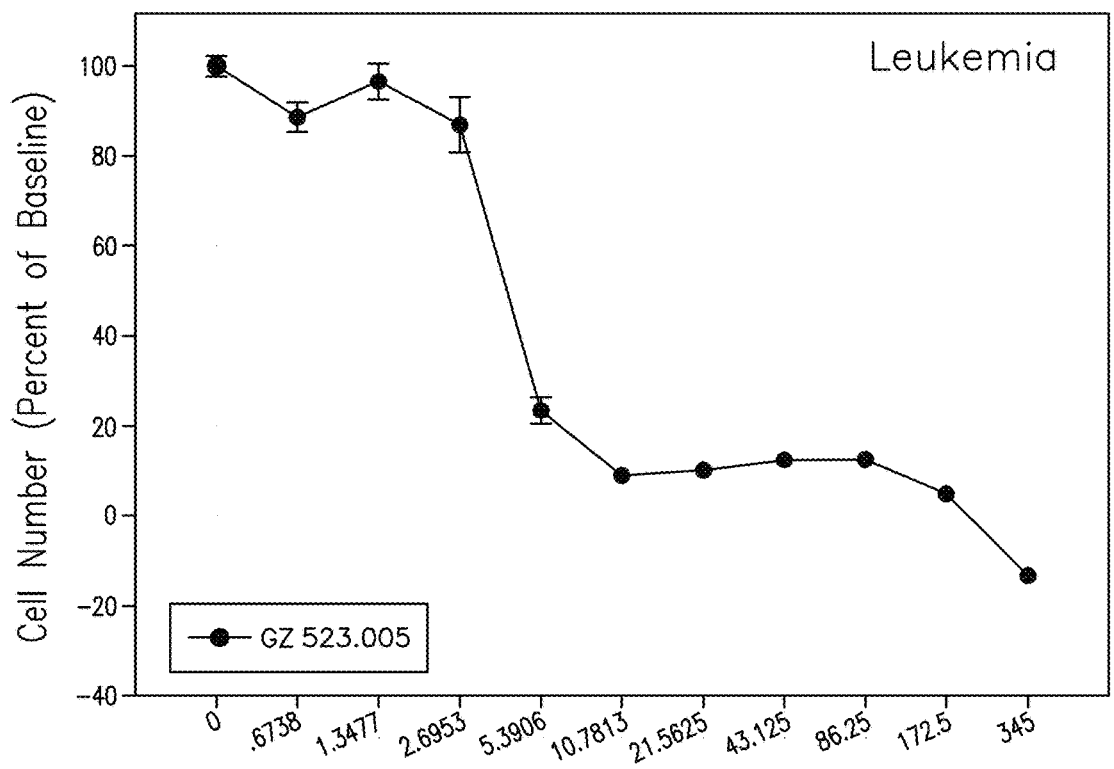
FIG. 13 is a graph of cell number versus dosage amounts of an orthovanillin/harmaline compound (GZ523.005), illustrating the effect thereof in inducing the death of leukemia cells, as described in Example 2.
Figure 14:
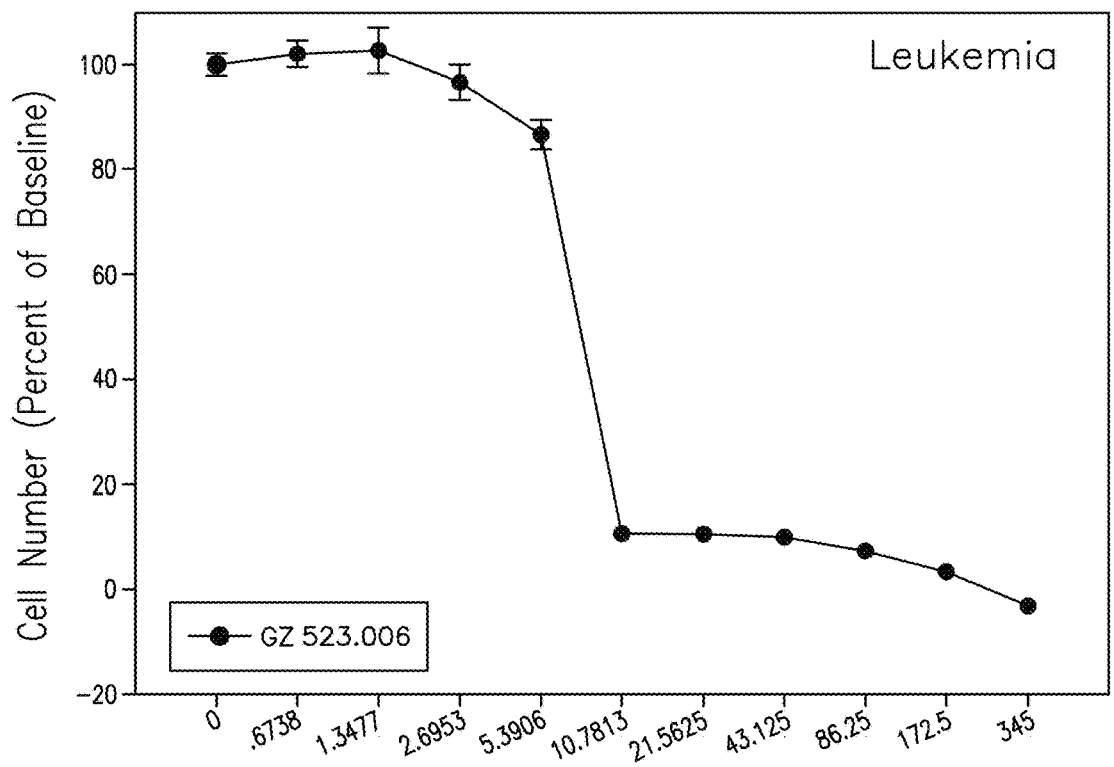
FIG. 14 is a graph of cell number versus dosage amounts of an orthovanillin/harmaline compound (GZ523.006), illustrating the effect thereof in inducing the death of leukemia cells, as described in Example 2.
Figure 15:
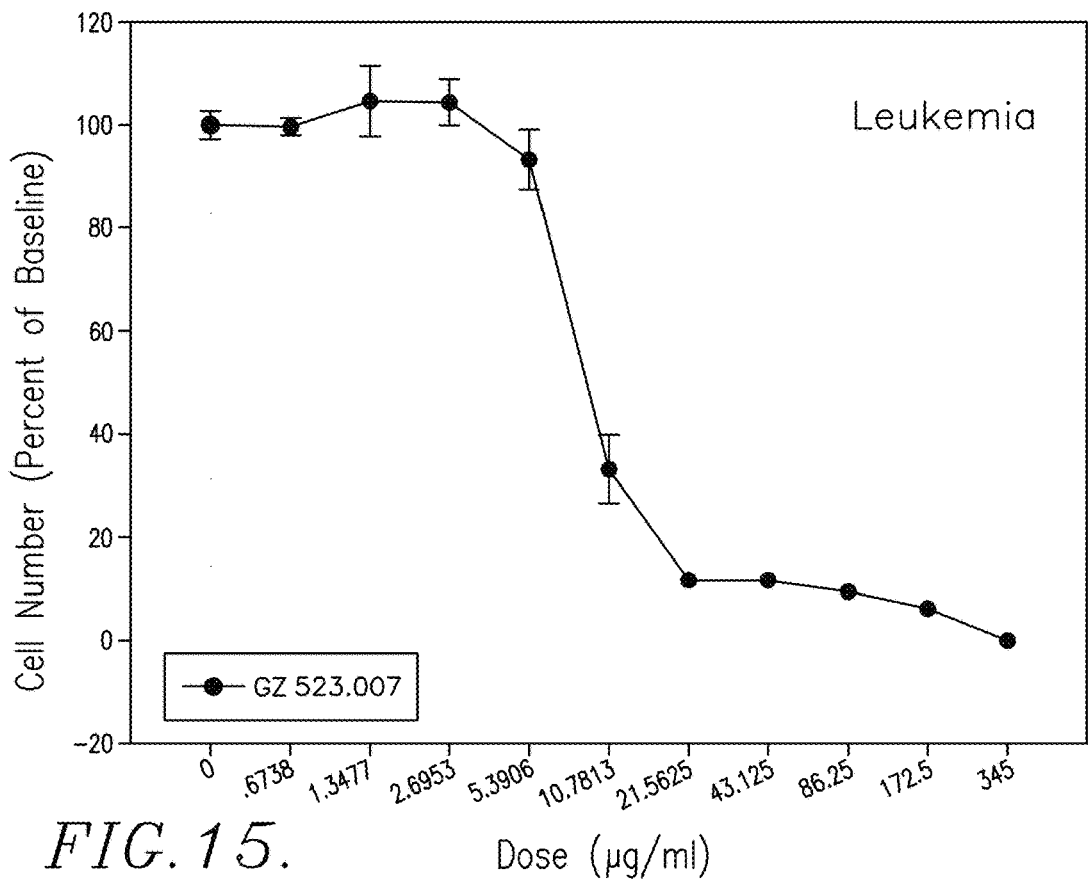
FIG. 15 is a graph of cell number versus dosage amounts of an orthovanillin/harmaline compound (GZ523.007), illustrating the effect thereof in inducing the death of leukemia cells, as described in Example 2.
Figure 16:
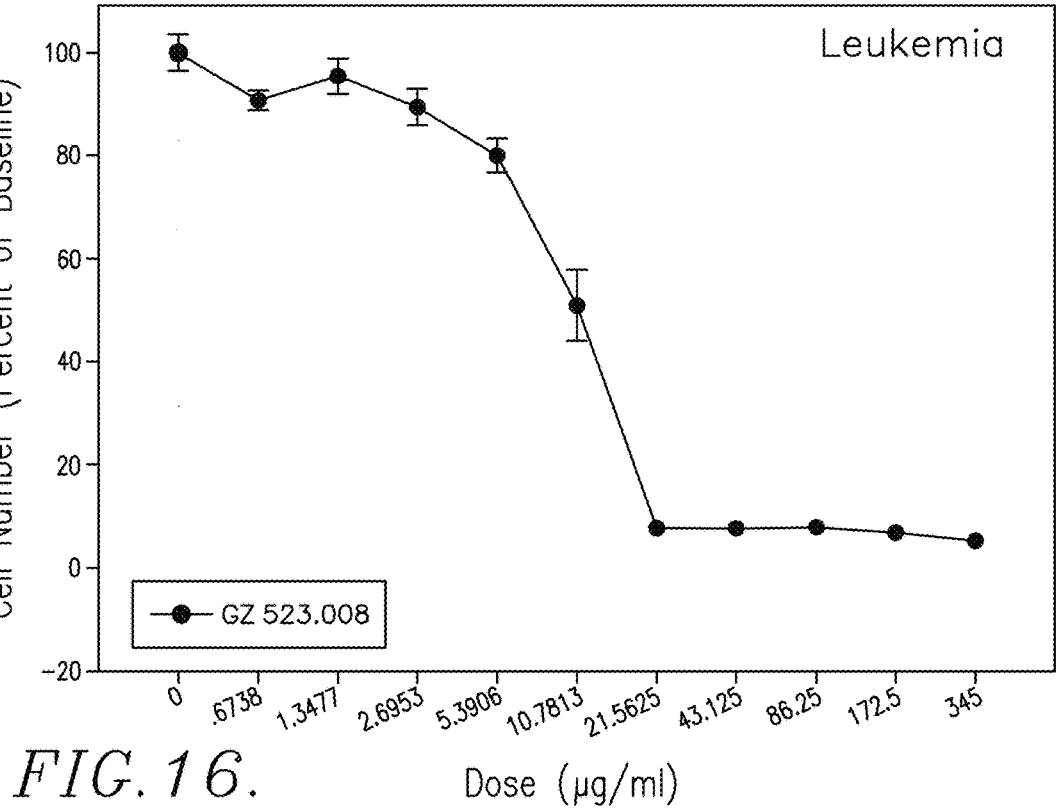
FIG. 16 is a graph of cell number versus dosage amounts of an orthovanillin/harmaline compound (GZ523.008), illustrating the effect thereof in inducing the death of leukemia cells, as described in Example 2.
Figure 17:
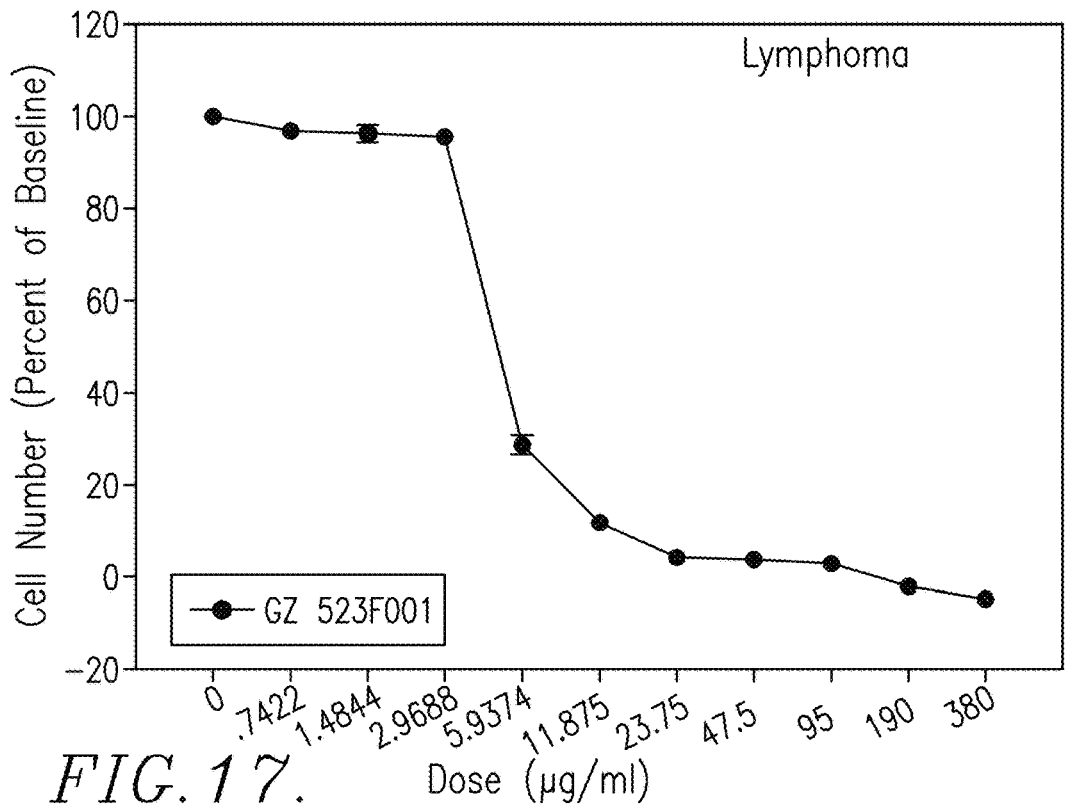
FIG. 17 is a graph of cell number versus dosage amounts of a composition containing high molecular weight dioligomer compound(s) derived from an orthovanillin/harmaline reaction, illustrating the effect thereof in inducing the death of lymphoma cells, as described in Example 3.
Figure 18:
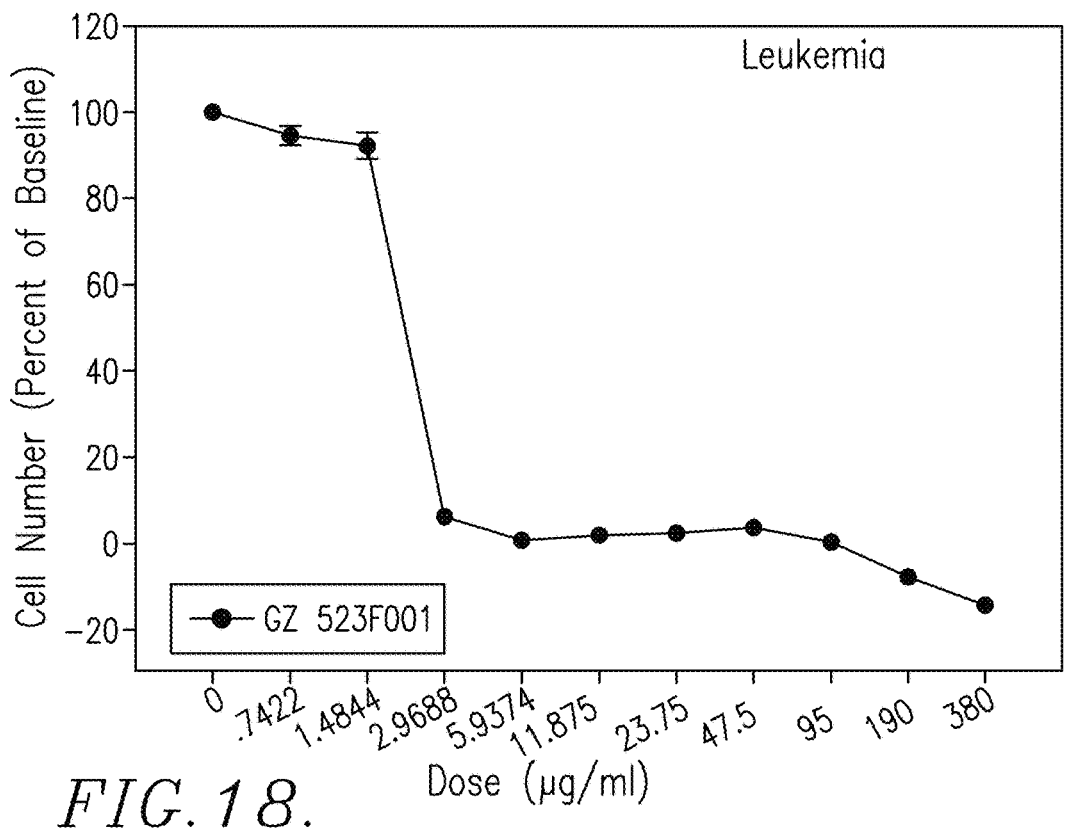
FIG. 18 is a graph of cell number versus dosage amounts of a composition containing high molecular weight dioligomer compound(s) derived from an orthovanillin/harmaline reaction, illustrating the effect thereof in inducing the death of leukemia cells, as described in Example 3.

This compound was then tested against the same lymphoma and leukemia cells as set forth in Example 2. The results of this test are set forth in FIGS. 17 and 18. These results confirm that the compounds exhibited very significant anti-cancer activities.

Example 4

In this series of tests, non-Hodgkin lymphomas were tested for their susceptibility to a preferred compound in accordance with the invention, namely GZ523.006 described in Example 1. The cell lines were grown in suspension according to the vendors' instructions and tested by the methods described in Example 2, except that there were no replications. The following Table sets forth each subtype of non-Hodgkin lymphoma tested, the cell line ID number, and the median effective dose ($EC_{50}$). The $EC_{50}$ represents the potency of the GZ523.006 composition against the cell lines, and ranged from 8-38 µg/mL, which is considered a therapeutically appropriate dosage range. The effect size of the highest concentration of GZ523.006 determines how well the composition worked to directly kill the respective cells. For all of the cell lines tested, 100% of the cancer cells were dead at a dosage of 25 µg/mL or greater.

TABLE 1

| Non-Hodgkin Lymphoma classification | Cell ID | $EC_{50}$ (µg/mL) |
|---|---|---|
| Human, B cell (mantle cell) | MO2058 | 26.12 |
| Human, B cell | DHL4 | 15.65 |
| Human, B cell (diffuse large cell mixed, and follicular) | DHL6 | 13.36 |
| Human, B cell (diffuse large cell) | DHL8 | 8.064 |
| Human, B cell (diffuse large cell) | DHL9 | 10.38 |
| Human, B cell (diffuse histiocytic) | DHL10 | 11.11 |
| Human, B cell (diffuse large cell) | DHL16 | 38.18 |
| Human, B lymphoblast | RL | 17.82 |
| Human, B cell | HBL1 | 18.95 |
| Human, lymphoblast (mantle cell) | Mino | 8.01 |
| Human, B cell (mantle cell) | Jvm13 | 14.88 |

Example 5

Figure 19:
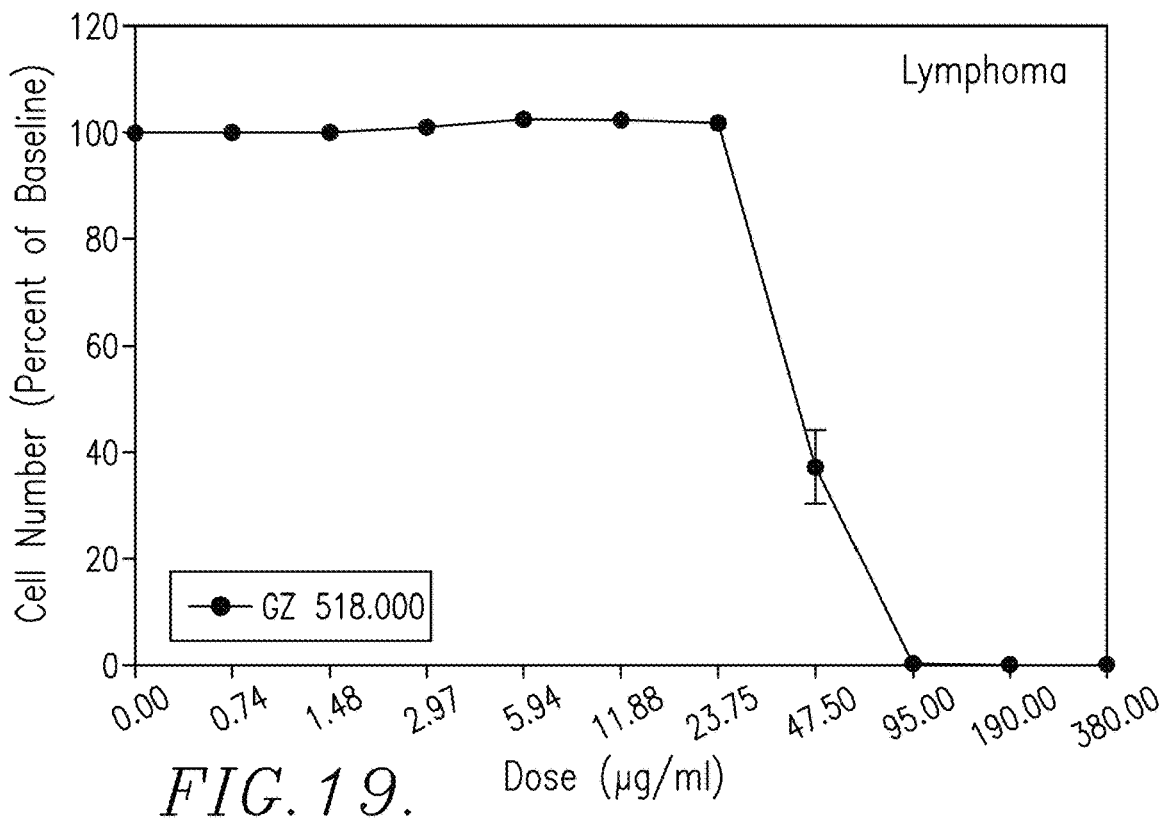
FIG. 19 is a graph of cell number versus dosage amounts of a vanillin/harmaline compound (GZ518.000), illustrating the effect thereof in inducing the death of lymphoma cells, as described in Example 5.
Figure 20:
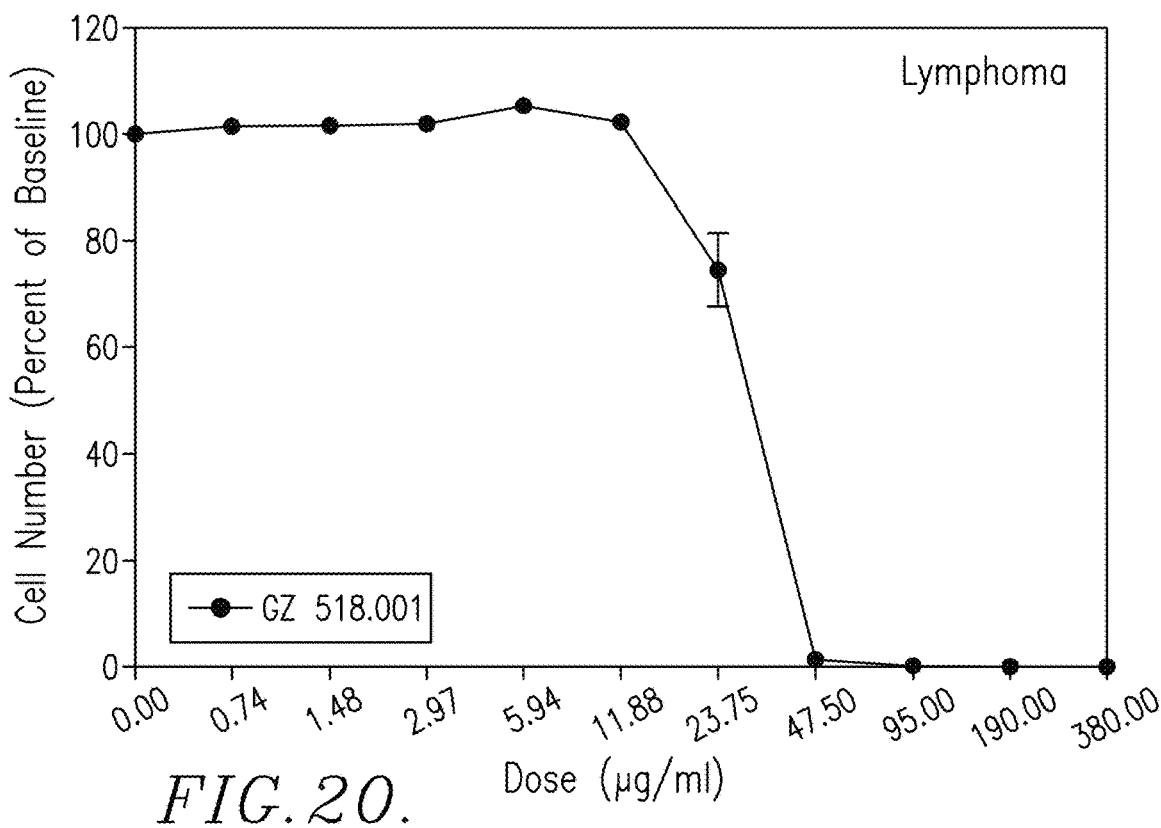
FIG. 20 is a graph of cell number versus dosage amounts of a vanillin/harmaline compound (GZ518.001), illustrating the effect thereof in inducing the death of lymphoma cells, as described in Example 5.

In this Example, a 562 compound was prepared by mixing 500 mg of vanillin powder and 250 mg of harmaline powder in a 15 mL jar. The powders were gently shaken to create a substantially uniform mixture, and 10 mL of dimethyl sulfoxide was added. The mixture was then agitated with a vortex mixer at 1000 rpm for 10 minutes to create a dispersion. In the case of one composition (GZ518.000), the dispersion compound(s) was tested immediately against lymphoma (M0205) by application to the cells, as described in Example 2. A second composition (GZ518.001) was prepared from the dispersion by allowing it to react for 24 hours at room temperature before testing against the lymphoma cells by application thereto. As set forth in FIGS. 19 and 20, both compositions and exhibited good anti-cancer properties.

Example 6

In this Example, the $EC_{50}$ values of GZ523.006 was determined for 25 different lymphoma cell lines. The experiments were performed using two-fold serial dilutions of GZ523.006 between 0.4 µg/mL and 100 µg/mL. Test wells were prepared using media and GZ523.006 controls for background subtraction. Each cell line was seeded with 10,000 cells/well, with triplicate technical replicates. After a 96-hour exposure, Alamar Blue Reagent (Life Technologies) was added to each well and incubated one hour at 37° C. Fluorescence values were recorded using a 560 nm excitation/590 nm emission filter set, and $EC_{50}$ concentrations were calculated using GraphPad Prism software. The $EC_{50}$ data for the 25 cell lines tested are set forth in FIG. 21, where: GCB-DLBCL are Germinal Center B-Cell-Diffuse Large B-Cell Lymphoma cell lines; ABC-DLBCL are Activated B-Cell-Diffuse Large B-Cell Lymphoma cell lines; MCL are Mantle Cell Lymphoma cell lines; and FL are Follicular Lymphoma cell lines. The error bars represent standard error of the mean values.

Figure 21:
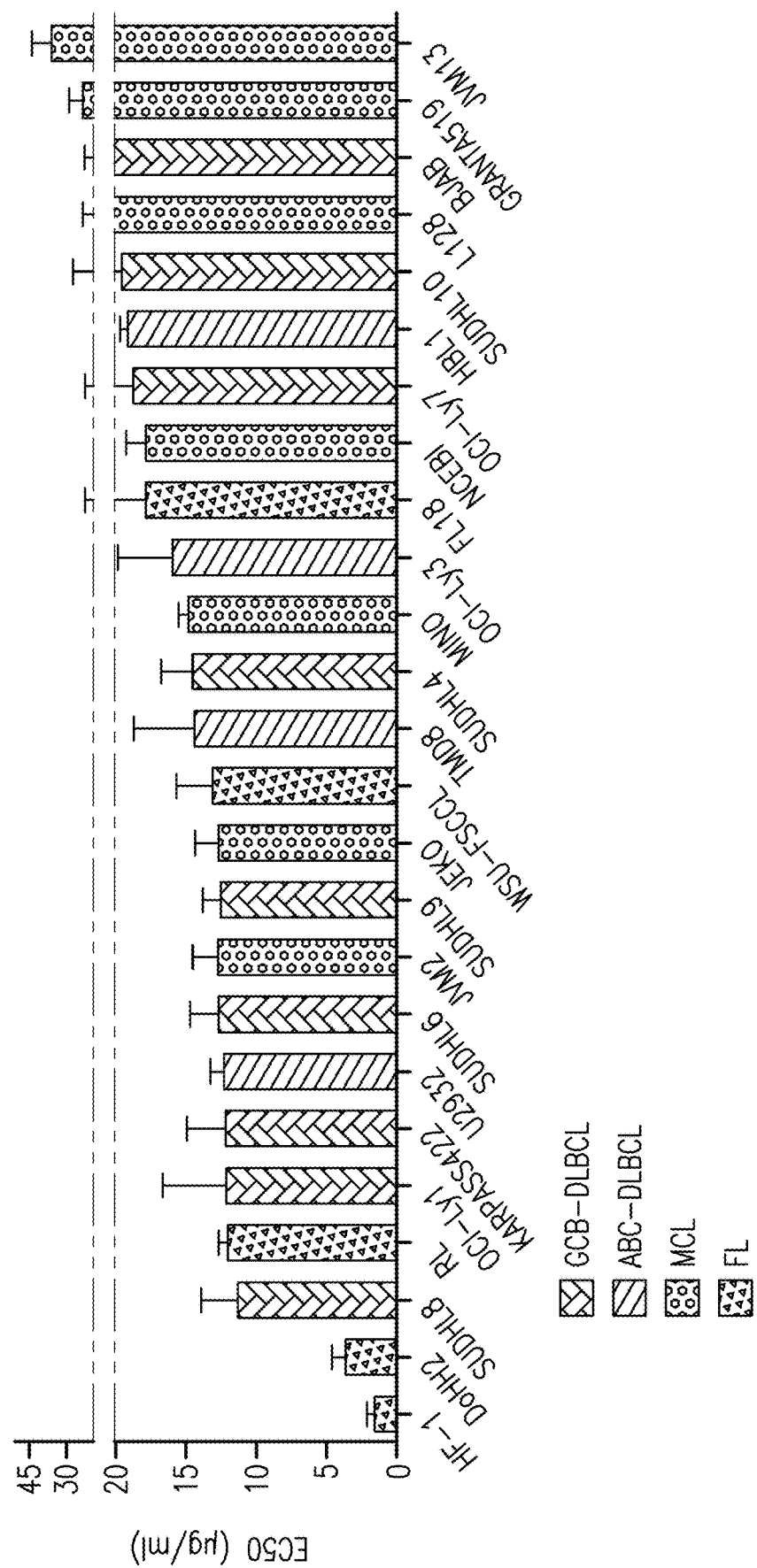
FIG. 21 is a bar graph illustrating the $EC_{50}$ values determined by treatment of a plurality of lymphoma cell lines with GZ523.006, as explained in Example 6.

Each of the cell lines of FIG. 21 were incubated with 5, 10, or 20 µg/mL for 72 hours, then incubated Hoechst 33342 dye (BD Pharmigen) for 60 minutes at 37° C. The cells were washed twice and fluorescence data was acquired using a LSRII 4-laser flow cytometer (BD Biosciences). Data was analyzed using Flojo v10 and Modfit v4.05 software to quantify the percentage of dead cells (sub-G1), senescent cells (G1 peak), and cycling cells (S-phase and G2) in each condition. The data from this series of tests is summarized in Table 2.

TABLE 2

| Cell Line | GZS23 (µg/ml) | SubG1 % | Percent of Live Cells | | |
|---|---|---|---|---|---|
| | | | G1 | G2 | S |
| SUDHL4 | 0 | 2.15 | 49.09 | 13.41 | 37.51 |
| SUDHL4 | 5 | 1.81 | 50.5 | 14.03 | 35.47 |
| SUDHL4 | 10 | 15.3 | 78.1 | 8.56 | 13.32 |
| SUDHL4 | 20 | 90.3 | N/A | N/A | N/A |
| SUDHL6 | 0 | 3.35 | 40.67 | 23.99 | 35.34 |
| SUDHL6 | 5 | 6.22 | 72.13 | 14.77 | 13.11 |
| SUDHL6 | 10 | 44.6 | 86.25 | 9.58 | 4.17 |
| SUDHL6 | 20 | 92.3 | N/A | N/A | N/A |
| SUDHL8 | 0 | 2.28 | 32.71 | 8.81 | 58.48 |
| SUDHL8 | 5 | 1.66 | 35.59 | 9.49 | 54.92 |
| SUDHL8 | 10 | 6.48 | 32.41 | 18.01 | 49.58 |
| SUDHL8 | 20 | 88.1 | N/A | N/A | N/A |
| SUDHL9 | 0 | 2.42 | 29.2 | 22.39 | 48.41 |
| SUDHL9 | 5 | 9.52 | 28.84 | 35.61 | 35.56 |
| SUDHL9 | 10 | 57.9 | 27.43 | 0 | 72.57 |
| SUDHL9 | 20 | 79.3 | 42.45 | 0 | 57.55 |
| SUDHL10 | 0 | 6.05 | 30.76 | 16.38 | 52.86 |
| SUDHL10 | 5 | 4.23 | 30.03 | 10.54 | 59.43 |

TABLE 2-continued

| Cell Line | GZS23 (μg/ml) | SubG1 % | Percent of Live Cells | | |
|---|---|---|---|---|---|
| | | | G1 | G2 | S |
| SUDHL10 | 10 | 8.14 | 31.86 | 11.11 | 57.03 |
| SUDHL10 | 20 | 91.5 | 30.9 | 12.23 | 56.87 |
| KARPASS422 | 0 | 7.92 | 42.06 | 14.98 | 42.96 |
| KARPASS422 | 5 | 34.7 | 47.02 | 16.22 | 36.76 |
| KARPASS422 | 10 | 77.3 | N/A | N/A | N/A |
| KARPASS422 | 20 | 96.2 | N/A | N/A | N/A |
| BJAB | 0 | 3.79 | 27.53 | 27.45 | 45.01 |
| BJAB | 5 | 4.94 | 32.33 | 23.68 | 44 |
| BJAB | 10 | 20 | 29.11 | 22.23 | 48.66 |
| BJAB | 20 | 35.2 | 54.49 | 13.32 | 32.2 |
| OCI-Ly1 | 0 | 3.37 | 53.29 | 11.19 | 35.52 |
| OCI-Ly1 | 5 | 6.04 | 52.93 | 14.28 | 32.79 |
| OCI-Ly1 | 10 | 6.64 | 52.06 | 14.21 | 33.73 |
| OCI-Ly1 | 20 | 32.7 | 37.08 | 14.73 | 48.19 |
| OCI-Ly7 | 0 | 10.4 | 29.77 | 17.25 | 52.99 |
| OCI-Ly7 | 5 | 7.85 | 31.08 | 12.21 | 56.72 |
| OCI-Ly7 | 10 | 12.7 | 33.42 | 11.94 | 54.64 |
| OCI-Ly7 | 20 | 86.1 | N/A | N/A | N/A |
| OCI-Ly3 | 0 | 7.94 | 43.31 | 15.37 | 41.32 |
| OCI-Ly3 | 5 | 15.9 | 62.11 | 7.34 | 30.54 |
| OCI-Ly3 | 10 | 12.8 | 59.85 | 9.14 | 31.01 |
| OCI-Ly3 | 20 | 60 | 53.31 | 10.82 | 35.87 |
| U2932 | 0 | 2.01 | 59.86 | 19.61 | 20.53 |
| U2932 | 5 | 4.61 | 66.42 | 16.48 | 17.09 |
| U2932 | 10 | 9.61 | 69.8 | 16.14 | 14.06 |
| U2932 | 20 | 28.5 | 51.28 | 23.97 | 24.76 |
| HBL1 | 0 | 10.7 | 36.34 | 19.16 | 44.5 |
| HBL1 | 5 | 16.3 | 70.39 | 14.87 | 14.73 |
| HBL1 | 10 | 25.4 | 73.47 | 9.55 | 16.98 |
| HBL1 | 20 | 85.1 | N/A | N/A | N/A |
| RL | 0 | 3.49 | 31.15 | 25.23 | 43.62 |
| RL | 5 | 23.4 | 40.26 | 16.07 | 43.67 |
| RL | 10 | 30.2 | 44.22 | 15.17 | 40.61 |
| RL | 20 | 30.2 | 50.11 | 23.31 | 26.57 |
| DoHH2 | 0 | 2.71 | 37.26 | 15.73 | 47.01 |
| DoHH2 | 5 | 9.45 | 71.44 | 9.12 | 19.44 |
| DoHH2 | 10 | 67.6 | 55.75 | 11.86 | 32.39 |
| DoHH2 | 20 | 84.1 | 41.51 | 19.14 | 39.34 |
| FL18 | 0 | 5.5 | 34.8 | 16.47 | 48.73 |
| FL18 | 5 | 3.13 | 30.55 | 20.78 | 48.67 |
| FL18 | 10 | 14.1 | 34.08 | 20.46 | 45.45 |
| FL18 | 20 | 90.4 | N/A | N/A | N/A |
| WSU-FSCCL | 0 | 2.12 | 42.98 | 14.12 | 42.89 |
| WSU-FSCCL | 5 | 3.38 | 45.67 | 15.31 | 39.02 |
| WSU-FSCCL | 10 | N/A | N/A | N/A | N/A |
| WSU-FSCCL | 20 | 49.7 | N/A | N/A | N/A |
| JVM13 | 0 | 5.2 | 53.26 | 10.27 | 36.47 |
| JVM13 | 5 | 6.18 | 56.27 | 12.25 | 31.48 |
| JVM13 | 10 | 7.99 | 59.61 | 11.5 | 28.88 |
| JVM13 | 20 | 47.5 | 71.02 | 6.26 | 22.72 |
| JEKO | 0 | 10.6 | 54.04 | 4.86 | 41.1 |
| JEKO | 5 | 9.89 | 46.76 | 7.02 | 46.22 |
| JEKO | 10 | 73.3 | 21.36 | 14.55 | 64.09 |
| JEKO | 20 | 96.9 | N/A | N/A | N/A |
| L128 | 0 | 2.97 | 43.38 | 4.74 | 51.88 |
| L128 | 5 | 4.26 | 59.46 | 6.3 | 34.24 |
| L128 | 10 | 8.35 | 70.13 | 6.99 | 22.87 |
| L128 | 20 | 72.7 | N/A | N/A | N/A |
| MINO | 0 | 2.2 | 44.64 | 5.38 | 49.98 |
| MINO | 5 | 2.79 | 59.12 | 7.81 | 33.07 |
| MINO | 10 | 3.74 | 65.18 | 7.96 | 26.86 |
| MINO | 20 | 70 | 64.83 | 6 | 29.18 |
| NCEBI | 0 | 2.99 | 41.89 | 16.51 | 41.59 |
| NCEBI | 5 | 6.52 | 41.1 | 15.94 | 42.96 |
| NCEBI | 10 | 12.8 | 48.57 | 11.19 | 40.24 |
| NCEBI | 20 | 45.8 | 32.41 | 10.59 | 57 |
| GRANTA519 | 0 | 8.23 | 41.15 | 14.66 | 44.18 |
| GRANTA519 | 5 | 10.1 | 41.57 | 14.49 | 43.93 |
| GRANTA519 | 10 | 10.7 | 41.57 | 11.54 | 46.89 |
| GRANTA519 | 20 | 33.3 | N/A | N/A | N/A |
| JVM2 | 0 | 9.04 | 55.42 | 24.5 | 20.08 |
| JVM2 | 5 | 6.68 | 57.93 | 26.86 | 15.21 |
| JVM2 | 10 | 9.05 | 59.39 | 26.53 | 14.07 |
| JVM2 | 20 | 36.9 | 65.19 | 18.18 | 16.63 |

The mechanism of GZ523.0006 cell death was interrogated using Annexin V and 7-AAD staining, with the BD Apoptosis Detection Kit (BD Pharmigen). Four cell lines were selected that showed high sensitivity to GZ523.006. The cell lines were incubated with 5, 10, or 20 μg/mL of GZ523.006 for 72 hours, washed, re-suspended in 1× Annexin V Binding Buffer, and stained with PE-Annexin V and 7-AAD for 15 minutes at room temperature in the dark. The cells were then suspended in additional binding buffer and analyzed using an LSRII 4-layer flow cytometer (BD Biosciences). Data were analyzed using Flojo v10, by gating on untreated cells. The summary of results of this experiment are set forth on Table 3.

TABLE 3

| Cell line | GZ523 (μg/ml} | Annexin-V negative 7AAD positive | Annexin-V positive 7 AAD positive | Annexin-V positive 7AAD negative | Annexin-V negative 7 AAD negative |
|---|---|---|---|---|---|
| DoHH2 | 0 | 0.74 | 1.96 | 2.38 | 94.9 |
| DoHH2 | 5 | 63.6 | 20.9 | 5.58 | 9.86 |
| DoHH2 | 10 | 48.2 | 44.9 | 5.26 | 1.55 |
| DoHH2 | 20 | 51 | 48.2 | 0.071 | 0.71 |
| SUDHL4 | 0 | 0.77 | 0.47 | 1.99 | 96.8 |
| SUDHL4 | 5 | 1.7 | 0.82 | 1.44 | 96 |
| SUDHL4 | 10 | 11.7 | 2.09 | 2.08 | 84.2 |
| SUDHL4 | 20 | 2.59 | 82.2 | 11.7 | 3.45 |
| KARPAS422 | 0 | 0.73 | 2.31 | 4.13 | 92.8 |
| KARPAS422 | 5 | 8.3 | 17.5 | 11.9 | 62.3 |
| KARPAS422 | 10 | 14.5 | 12.9 | 7.92 | 64.7 |
| KARPAS422 | 20 | 41.3 | 45.4 | 8.28 | 5.06 |
| RL | 0 | 1.49 | 0.68 | 2.24 | 95.6 |
| RL | 5 | 9.93 | 2.88 | 2.62 | 84.6 |
| RL | 10 | 21.4 | 3.56 | 1.7 | 73.3 |
| RL | 20 | 24.4 | 69.1 | 3.2 | 3.31 |

Figure 22:
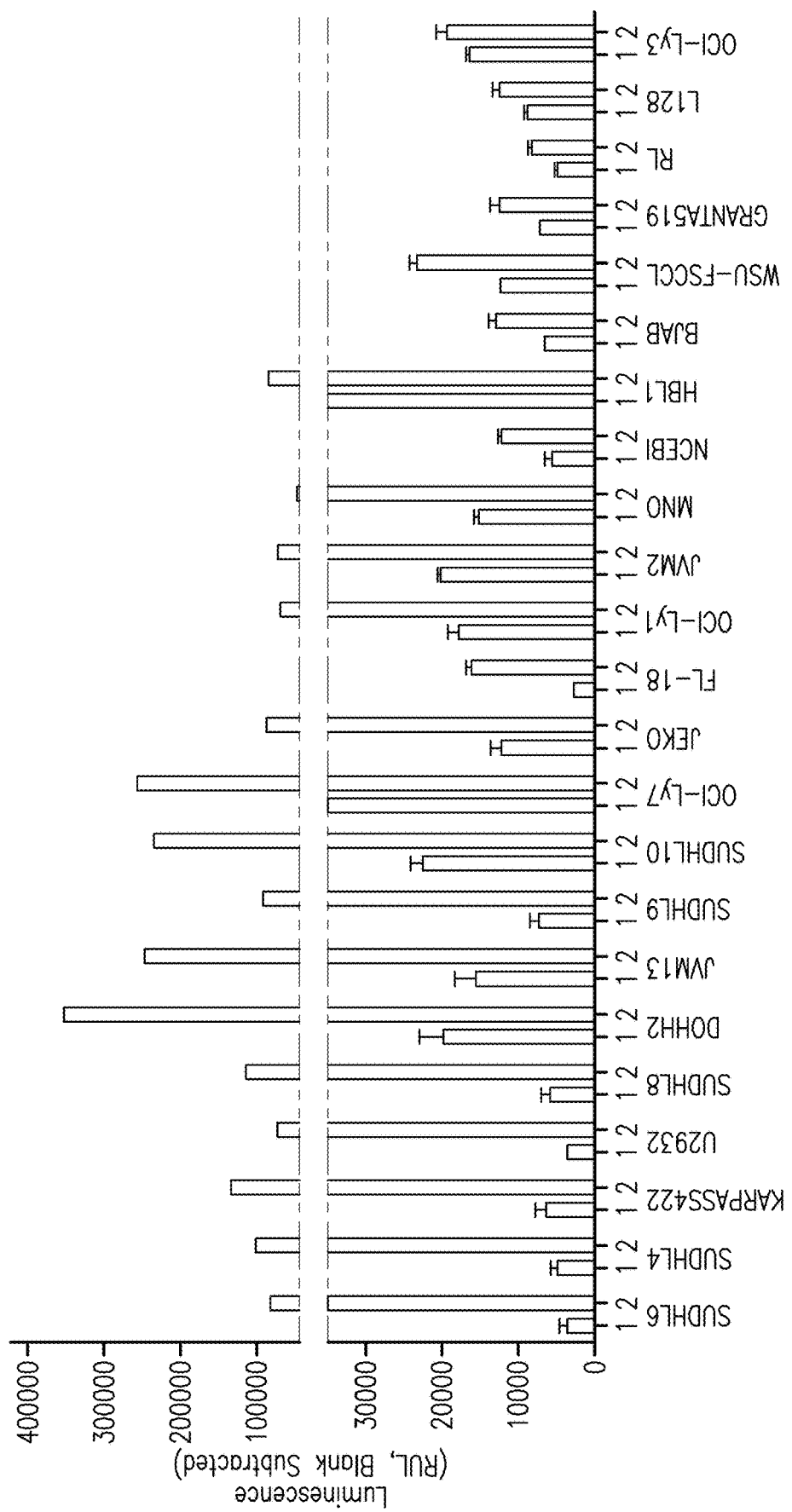
FIG. 22 is a bar graph depicting the results of comparative Caspase 3/7 assays using GZ523.006 against a number of lymphoma cell lines, confirming the cytotoxic properties of GZ523.006 through induction of apoptosis.
Figure 23:
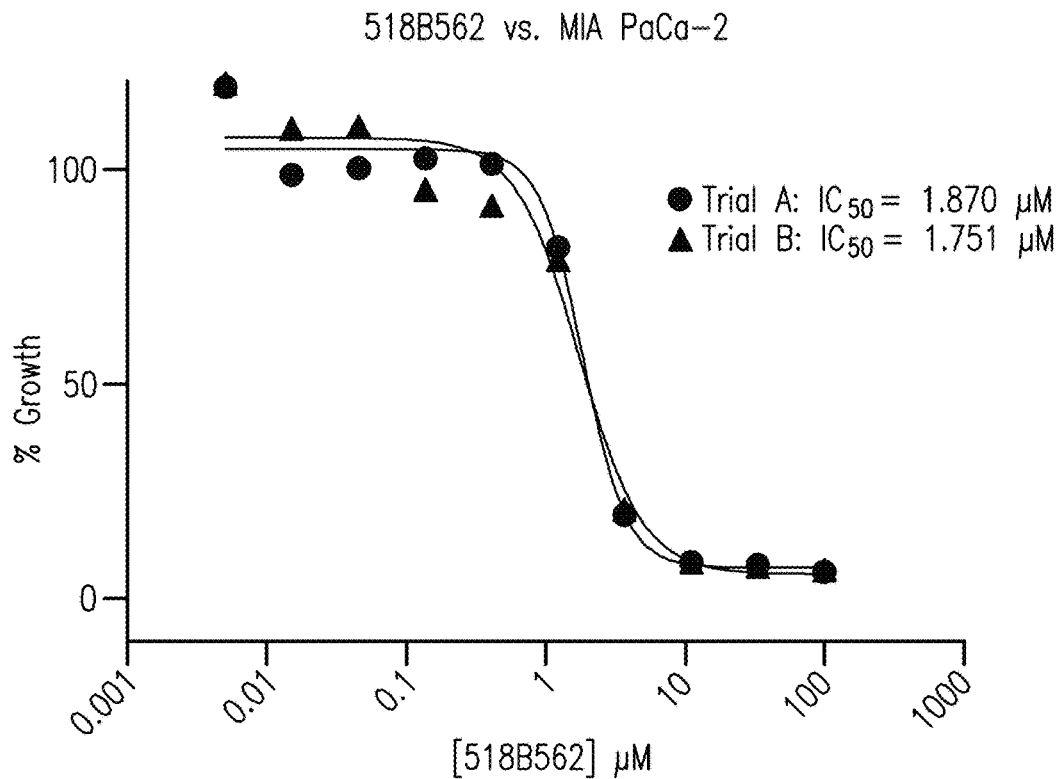
FIG. 23 is a graph illustrating cell growth as a function of the concentration of the 518B562 compound, in the MIA PaCa-2 cell proliferation assay described in Example 8.
Figure 24:
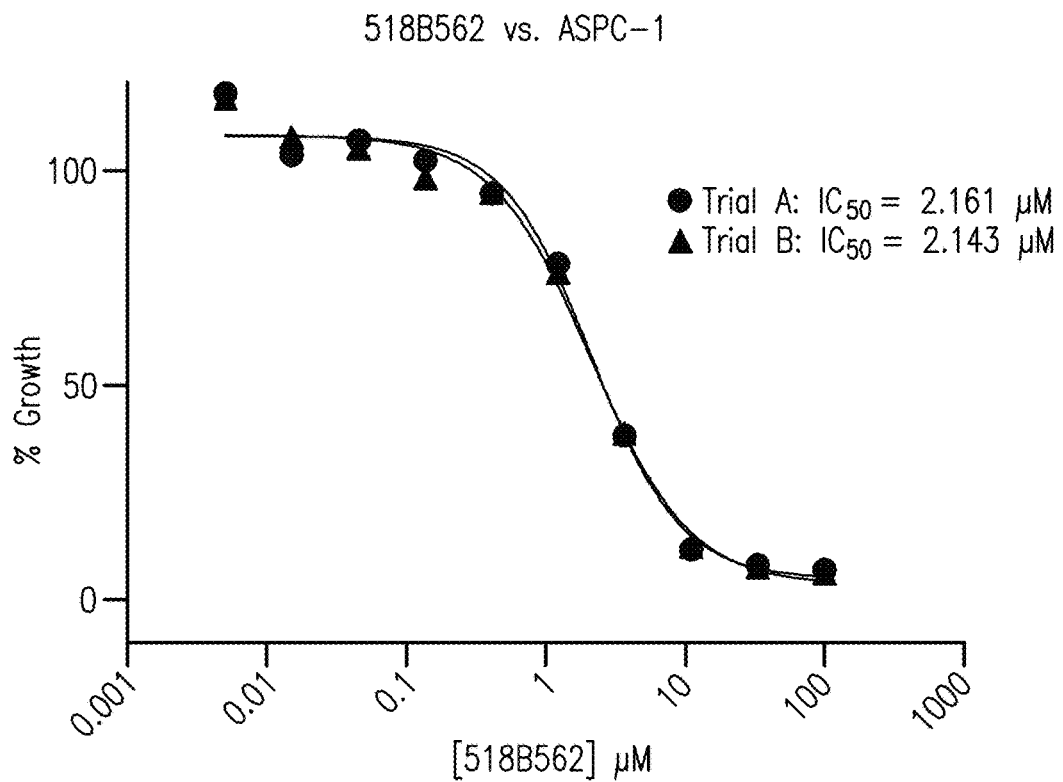
FIG. 24 is a graph illustrating cell growth as a function of the concentration of the 518B562 compound, in the ASPC-1 cell proliferation assay described in Example 8.
Figure 25:
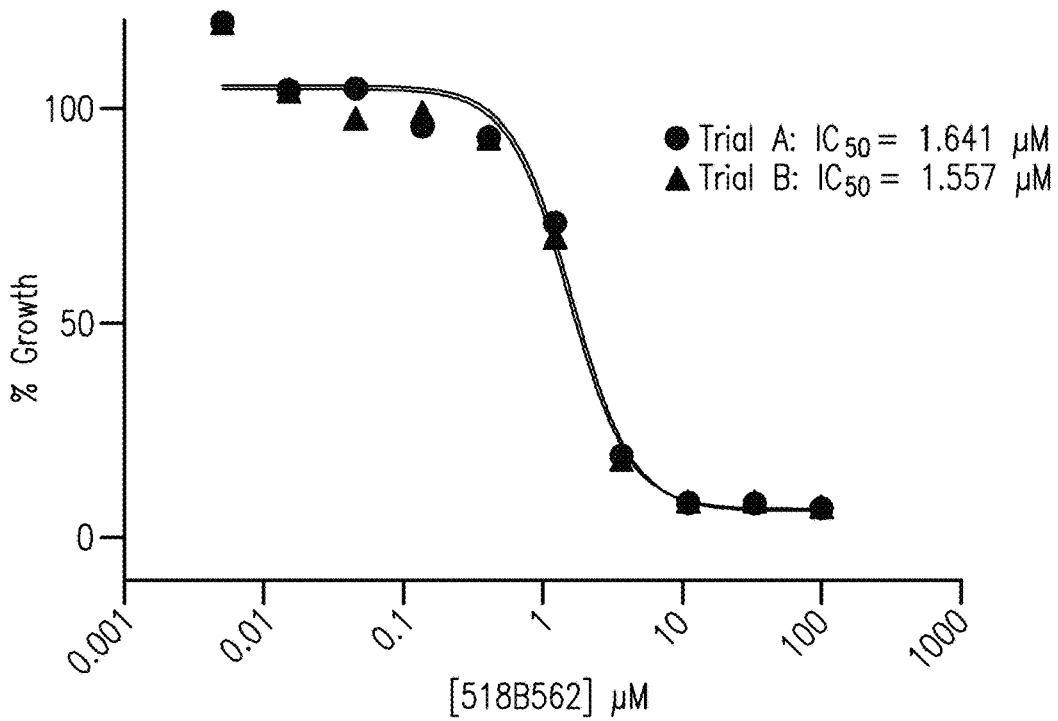
FIG. 25 is a graph illustrating cell growth as a function of the concentration of the 518B562 compound, in the BxPC-3 cell proliferation assay described in Example 8.
Figure 26:
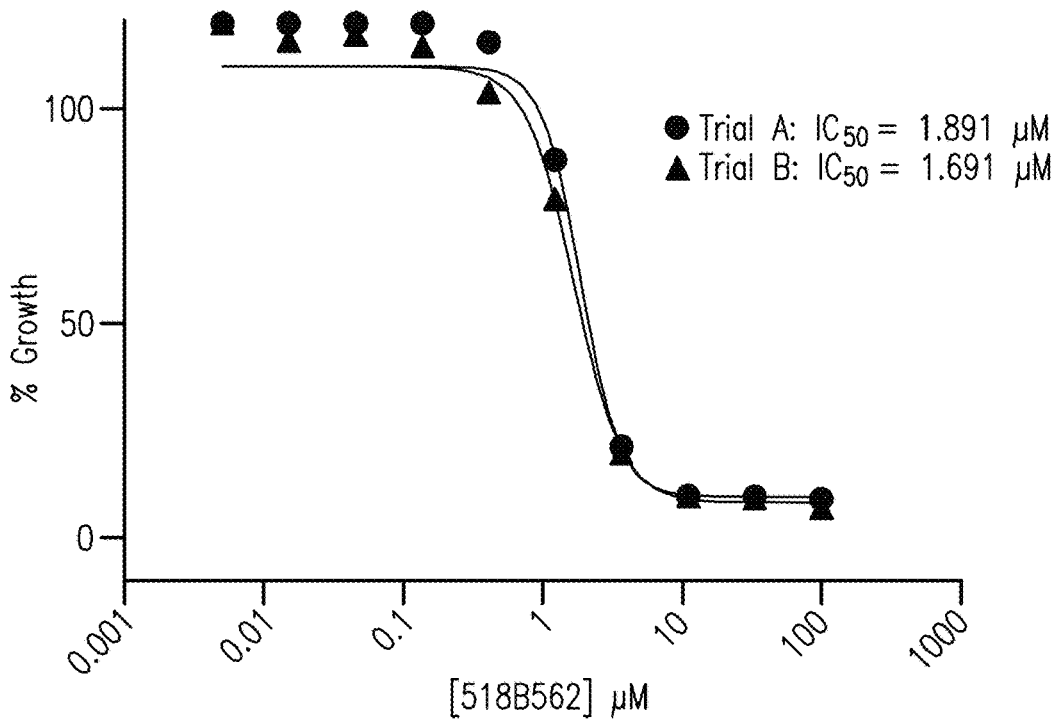
FIG. 26 is a graph illustrating cell growth as a function of the concentration of the 518B562 compound, in the AN3CA cell proliferation assay described in Example 8.
Figure 27:
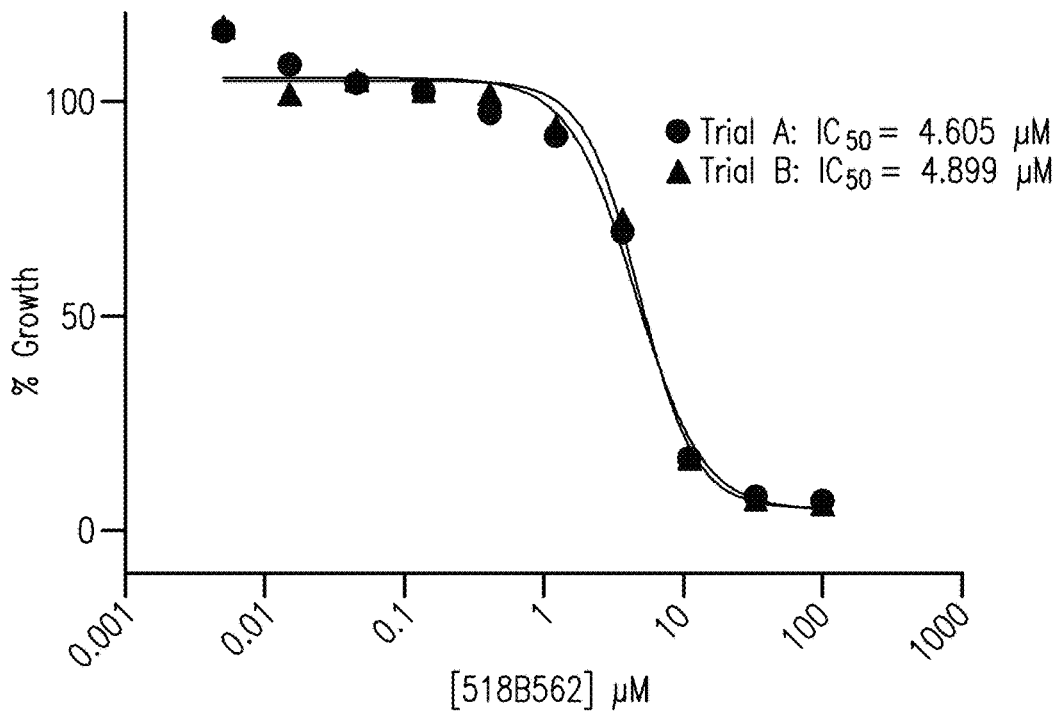
FIG. 27 is a graph illustrating cell growth as a function of the concentration of the 518B562 compound, in the HEC-1a cell proliferation assay described in Example 8.
Figure 28:
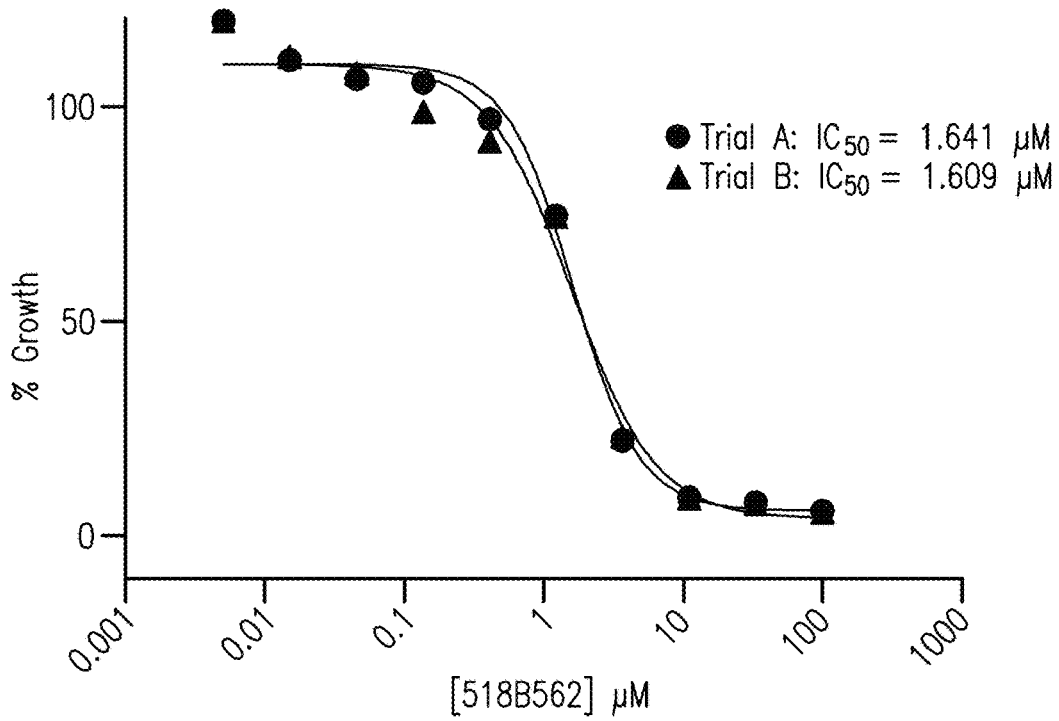
FIG. 28 is a graph illustrating cell growth as a function of the concentration of the 518B562 compound, in the MDA-MB-231 cell proliferation assay described in Example 8.
Figure 29:
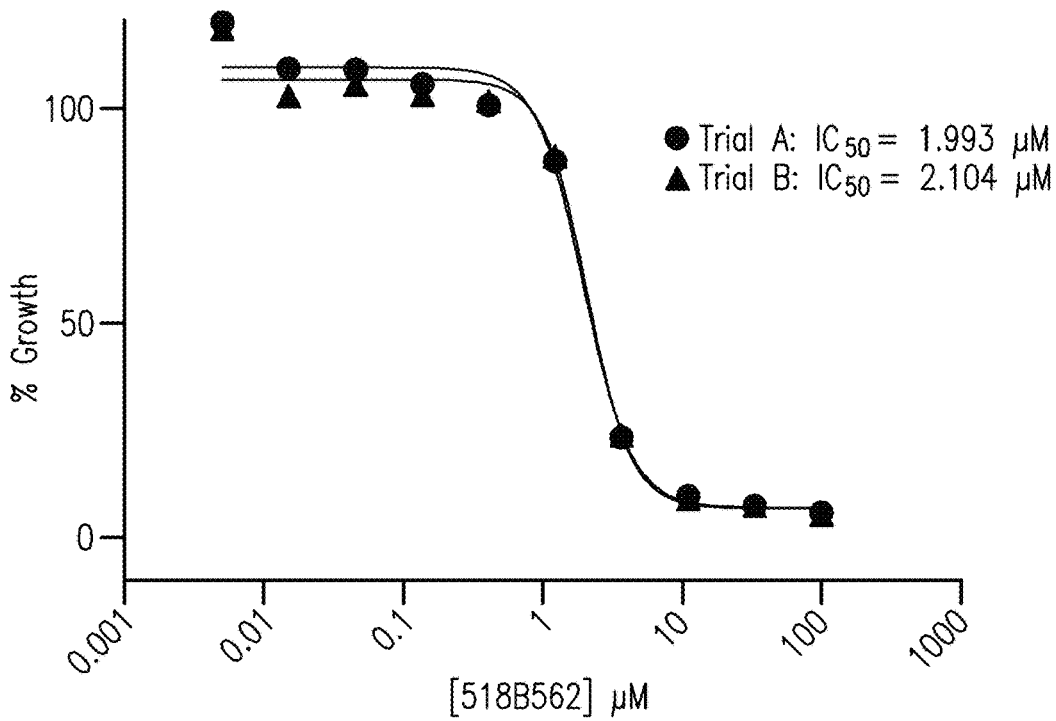
FIG. 29 is a graph illustrating cell growth as a function of the concentration of the 518B562 compound, in the MDA-MB-468 cell proliferation assay described in Example 8.
Figure 30:
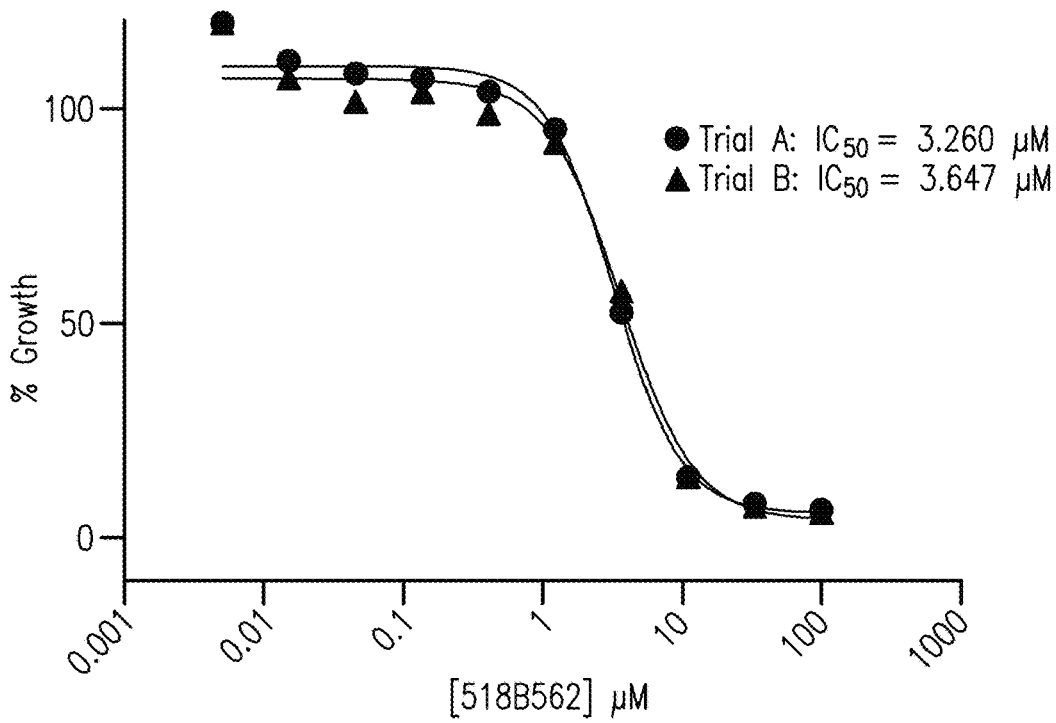
FIG. 30 is a graph illustrating cell growth as a function of the concentration of the 518B562 compound, in the HCC70 cell proliferation assay described in Example 8.
Figure 31:
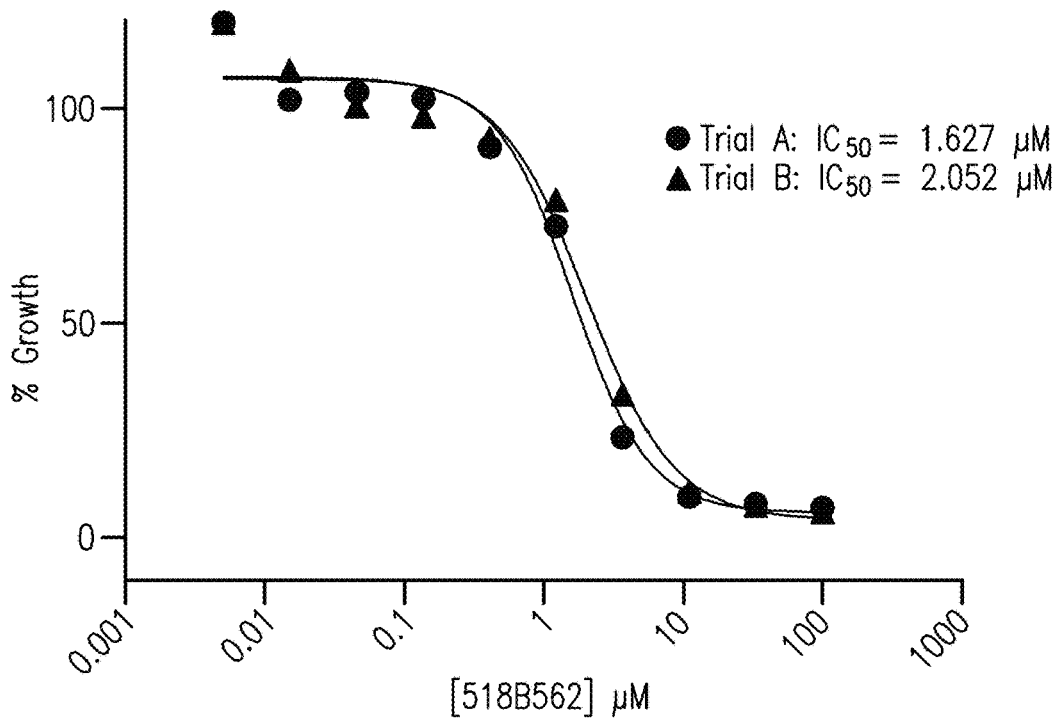
FIG. 31 is a graph illustrating cell growth as a function of the concentration of the 518B562 compound, in the H1975 cell proliferation assay described in Example 8.
Figure 32:
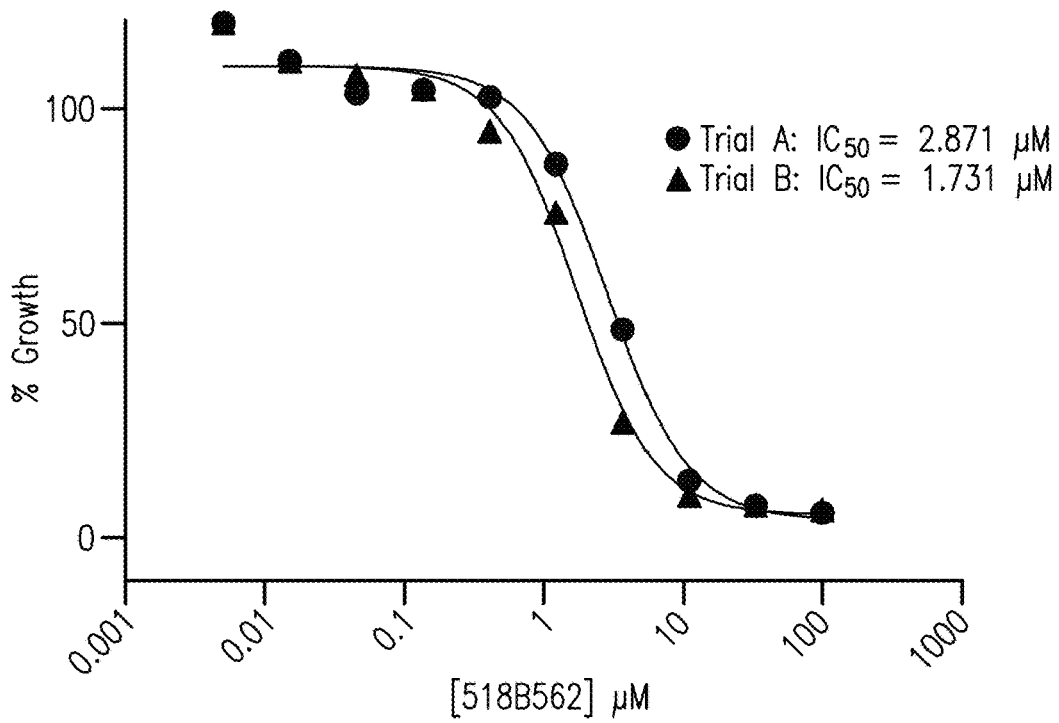
FIG. 32 is a graph illustrating cell growth as a function of the concentration of the 518B562 compound, in the H1650 cell proliferation assay described in Example 8.
Figure 33:
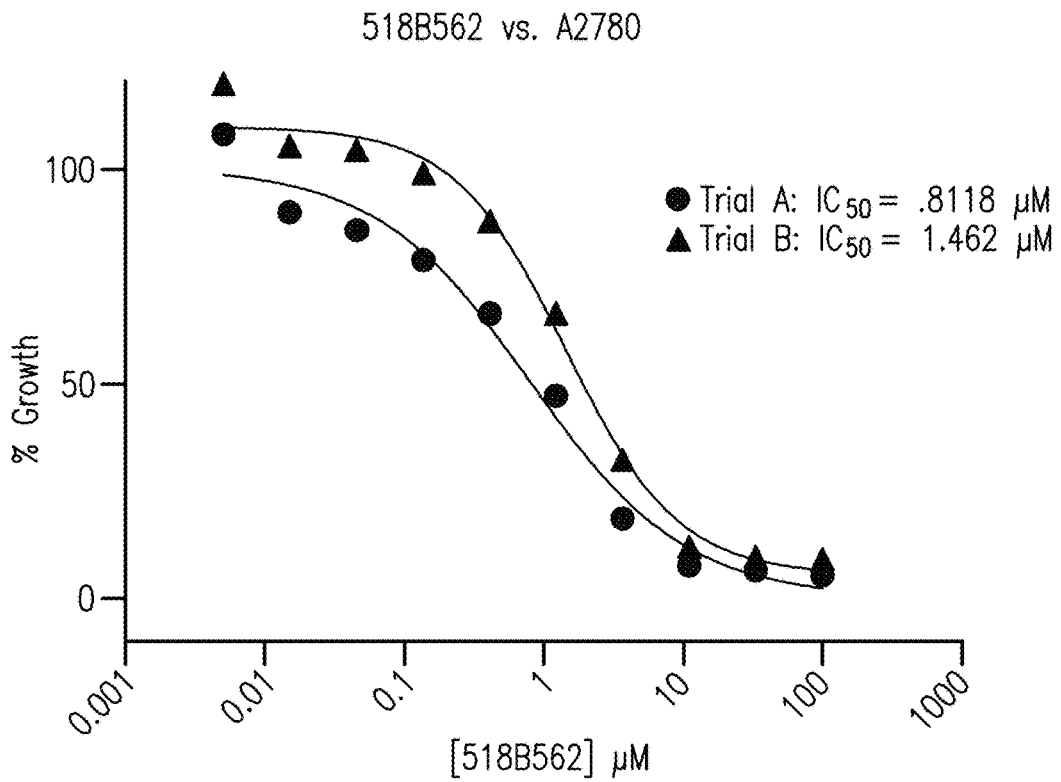
FIG. 33 is a graph illustrating cell growth as a function of the concentration of the 518B562 compound, in the A2780 cell proliferation assay described in Example 8.
Figure 34:
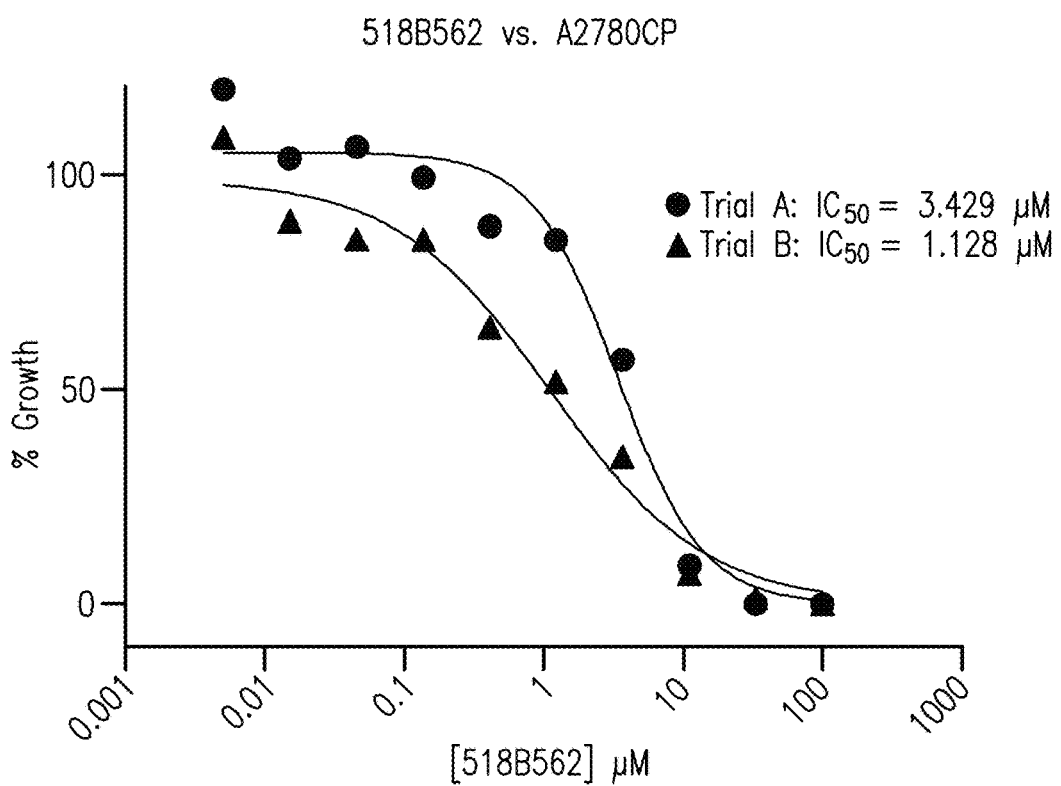
FIG. 34 is a graph illustrating cell growth as a function of the concentration of the 518B562 compound, in the A2780CP cell proliferation assay described in Example 8.
Figure 35:
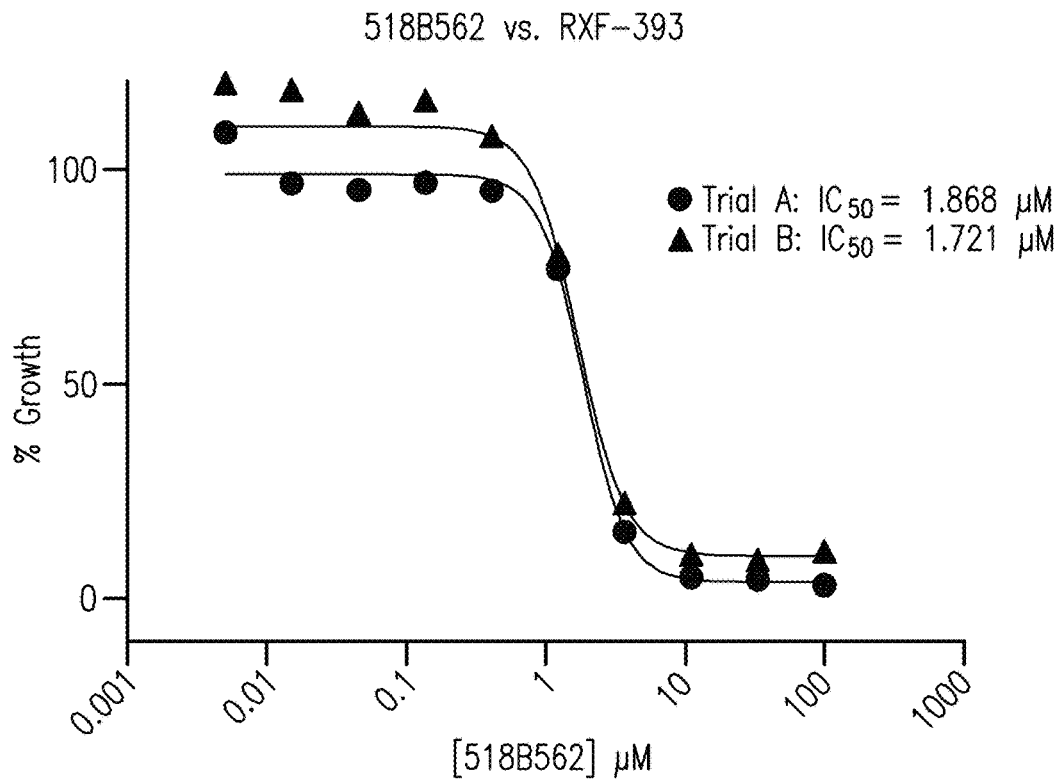
FIG. 35 is a graph illustrating cell growth as a function of the concentration of the 518B562 compound, in the RXF-393 cell proliferation assay described in Example 8.
Figure 36:
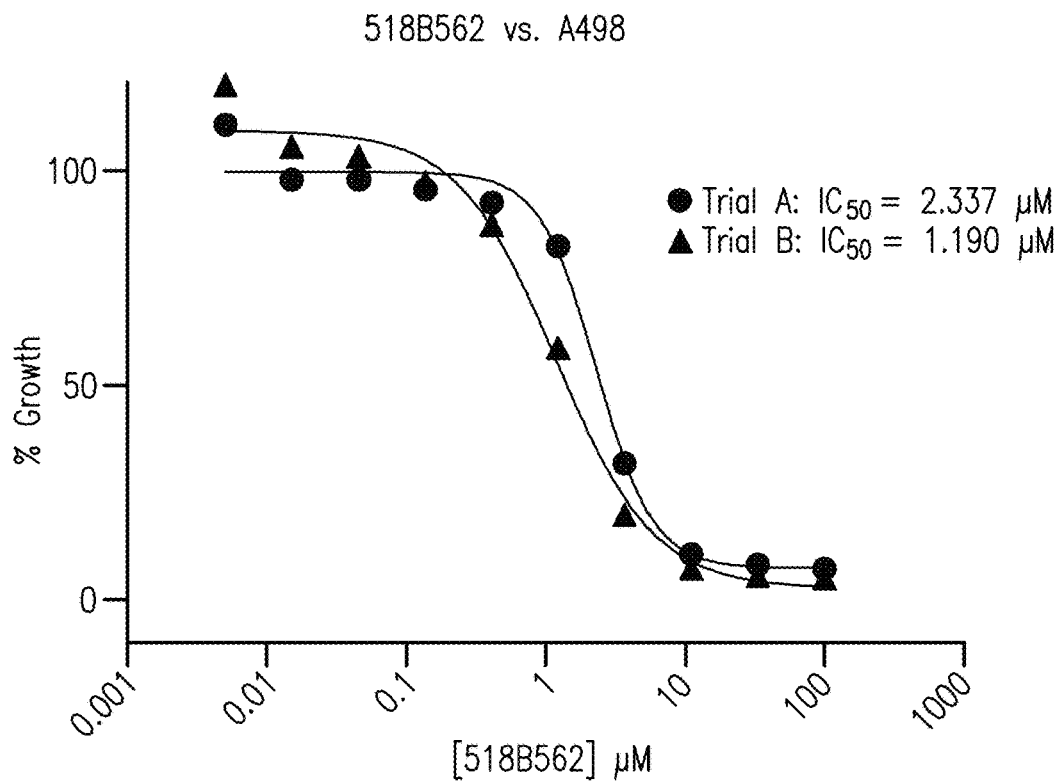
FIG. 36 is a graph illustrating cell growth as a function of the concentration of the 518B562 compound, in the A498 cell proliferation assay described in Example 8.
Figure 37:
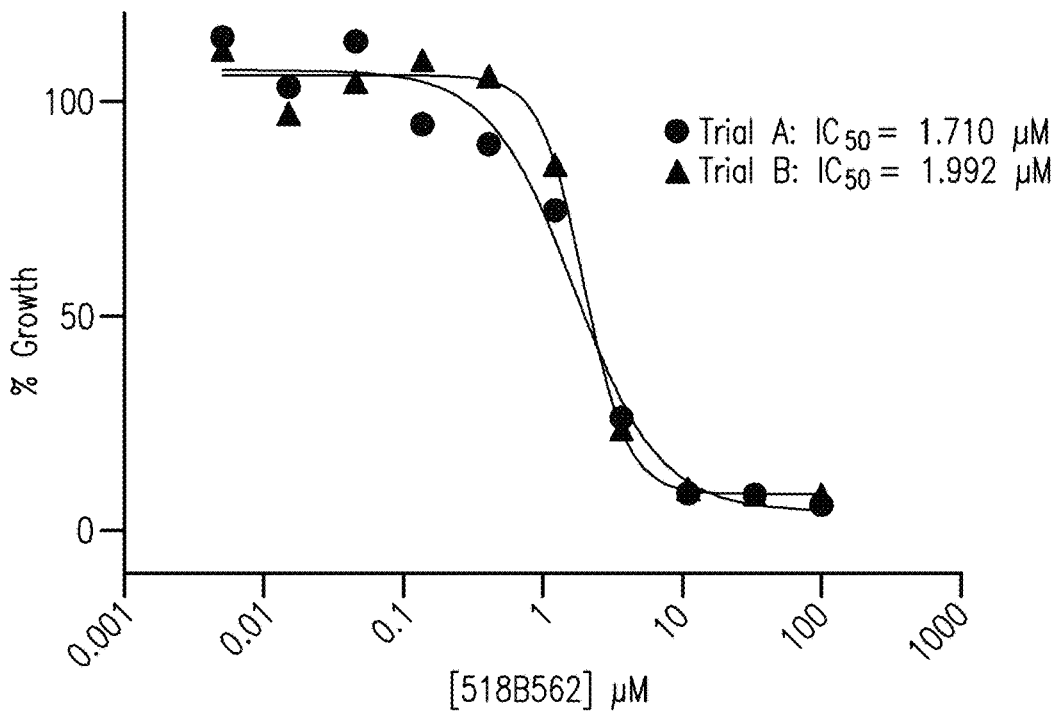
FIG. 37 is a graph illustrating cell growth as a function of the concentration of the 518B562 compound, in the N87 cell proliferation assay described in Example 8.
Figure 38:
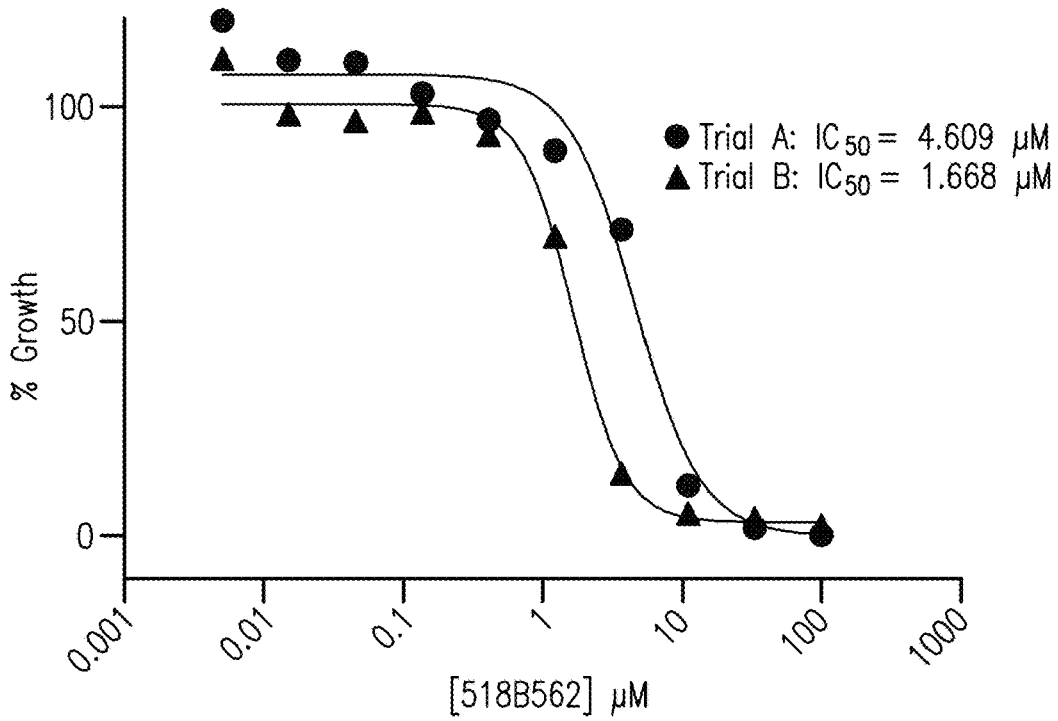
FIG. 38 is a graph illustrating cell growth as a function of the concentration of the 518B562 compound, in the SiHA cell proliferation assay described in Example 8.
Figure 39:
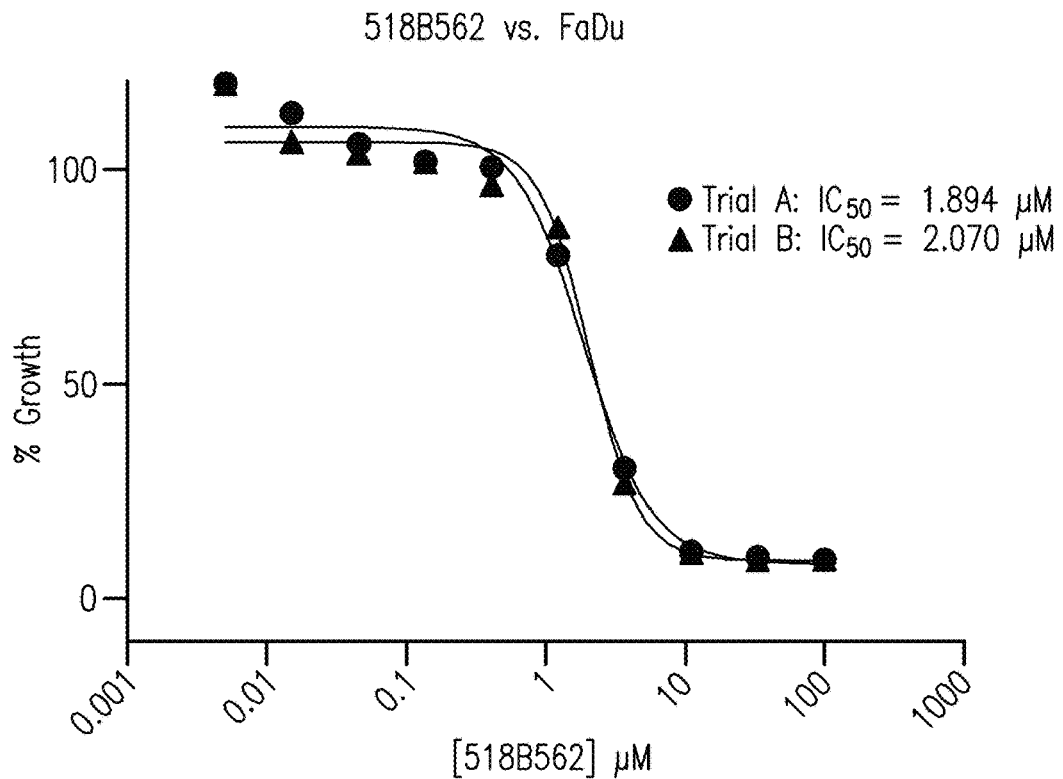
FIG. 39 is a graph illustrating cell growth as a function of the concentration of the 518B562 compound, in the FaDu cell proliferation assay described in Example 8.
Figure 40:
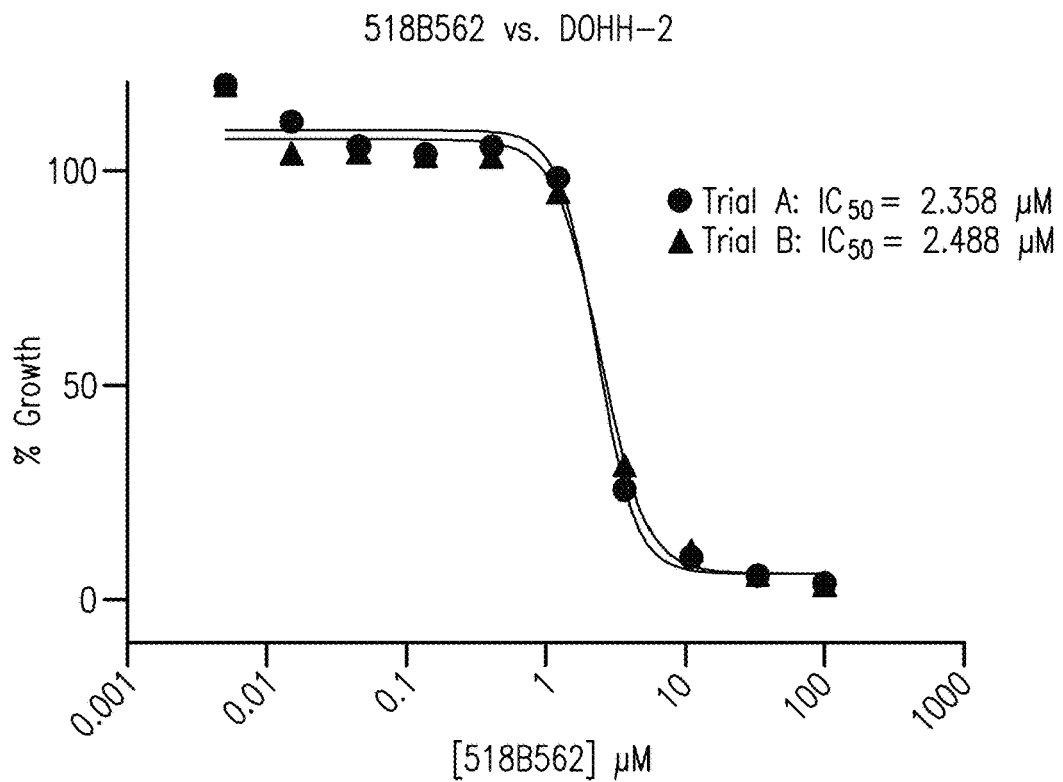
FIG. 40 is a graph illustrating cell growth as a function of the concentration of the 518B562 compound, in the DOHH-2 cell proliferation assay described in Example 8.
Figure 41:
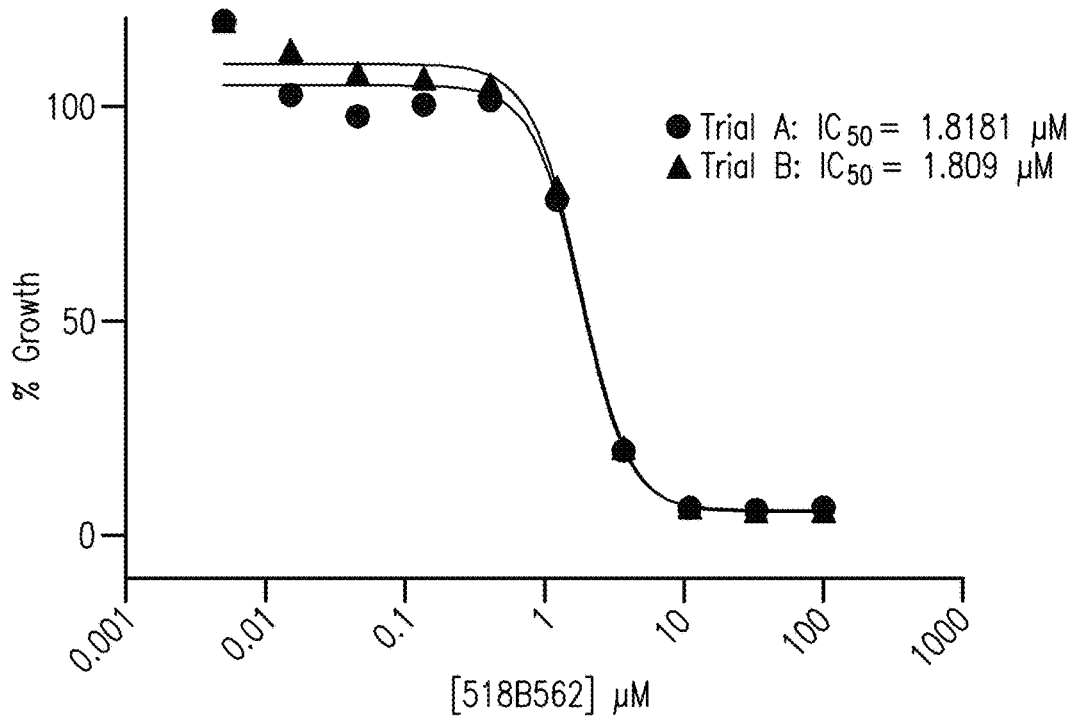
FIG. 41 is a graph illustrating cell growth as a function of the concentration of the 518B562 compound, in the SU-DHL-4 cell proliferation assay described in Example 8.
Figure 42:
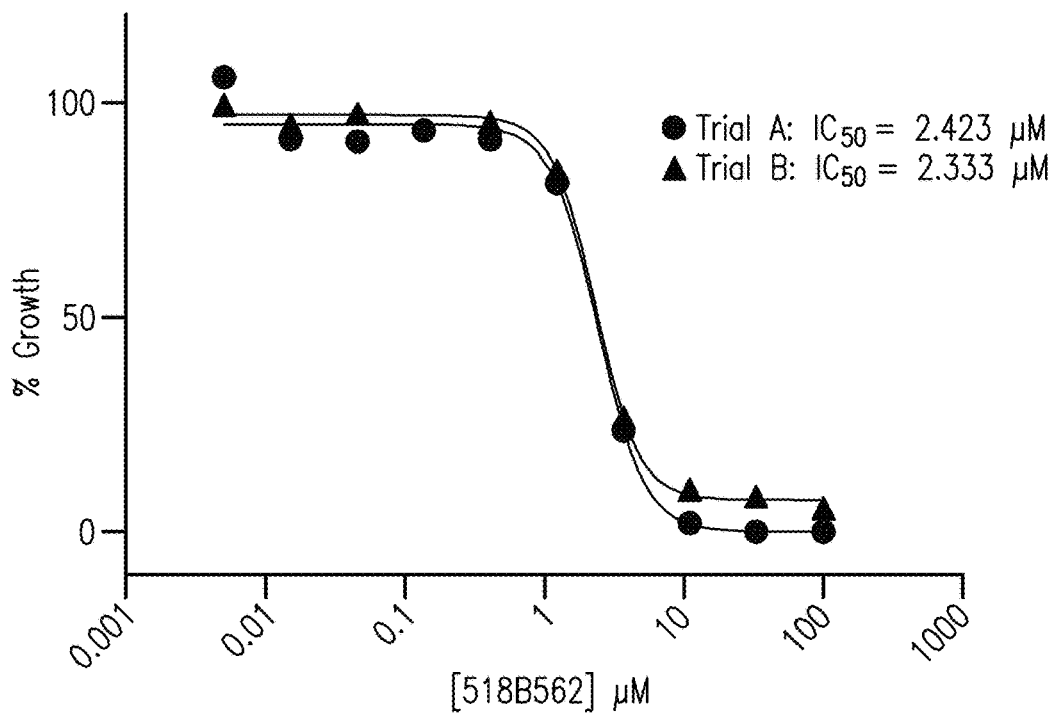
FIG. 42 is a graph illustrating cell growth as a function of the concentration of the 518B562 compound, in the OCI-LY3 cell proliferation assay described in Example 8.
Figure 43:
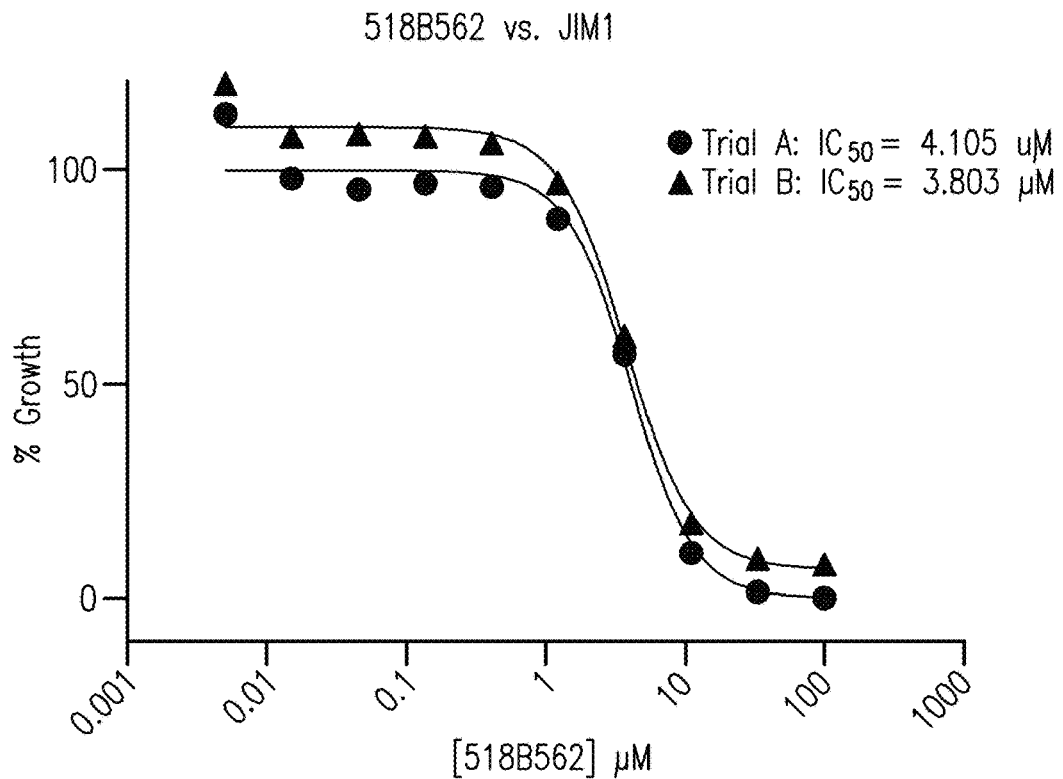
FIG. 43 is a graph illustrating cell growth as a function of the concentration of the 518B562 compound, in the JIM1 cell proliferation assay described in Example 8.
Figure 44:
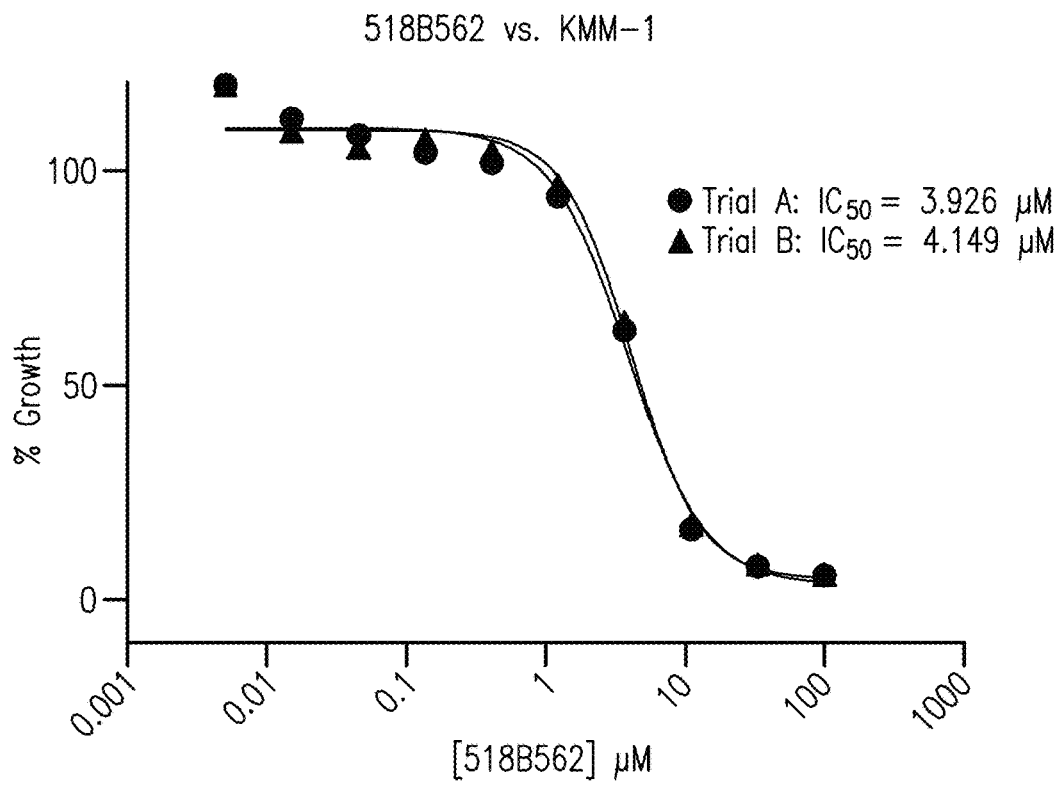
FIG. 44 is a graph illustrating cell growth as a function of the concentration of the 518B562 compound, in the KMM-1 cell proliferation assay described in Example 8.
Figure 45:
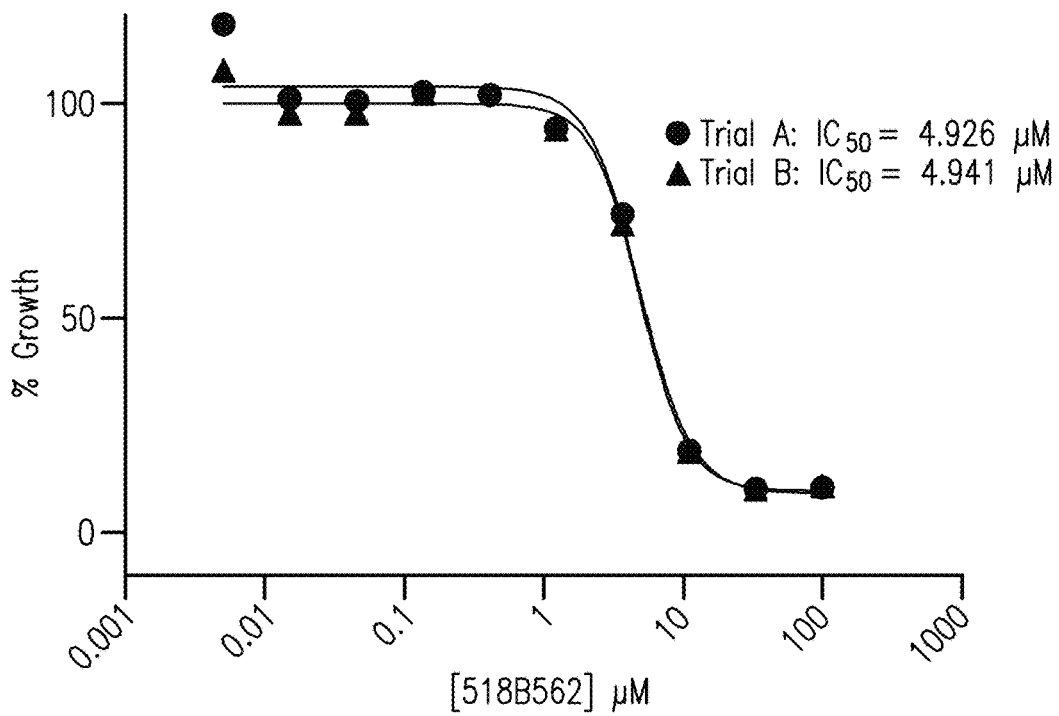
FIG. 45 is a graph illustrating cell growth as a function of the concentration of the 518B562 compound, in the KMS-11 cell proliferation assay described in Example 8.
Figure 46:
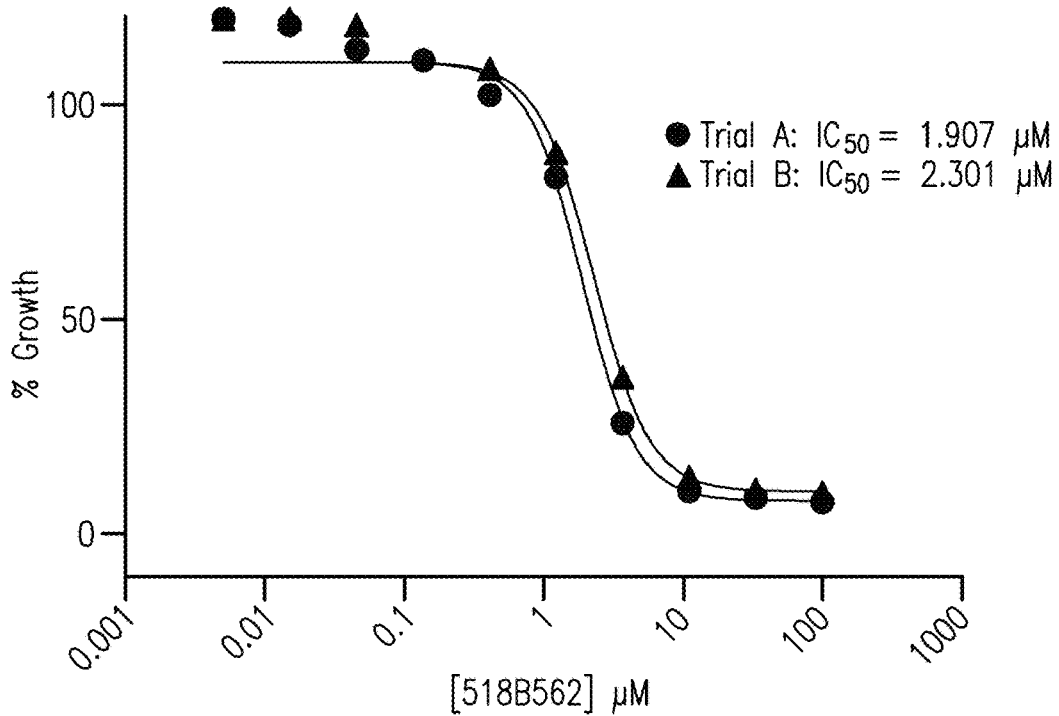
FIG. 46 is a graph illustrating cell growth as a function of the concentration of the 518B562 compound, in the KMS-27 cell proliferation assay described in Example 8.
Figure 47:
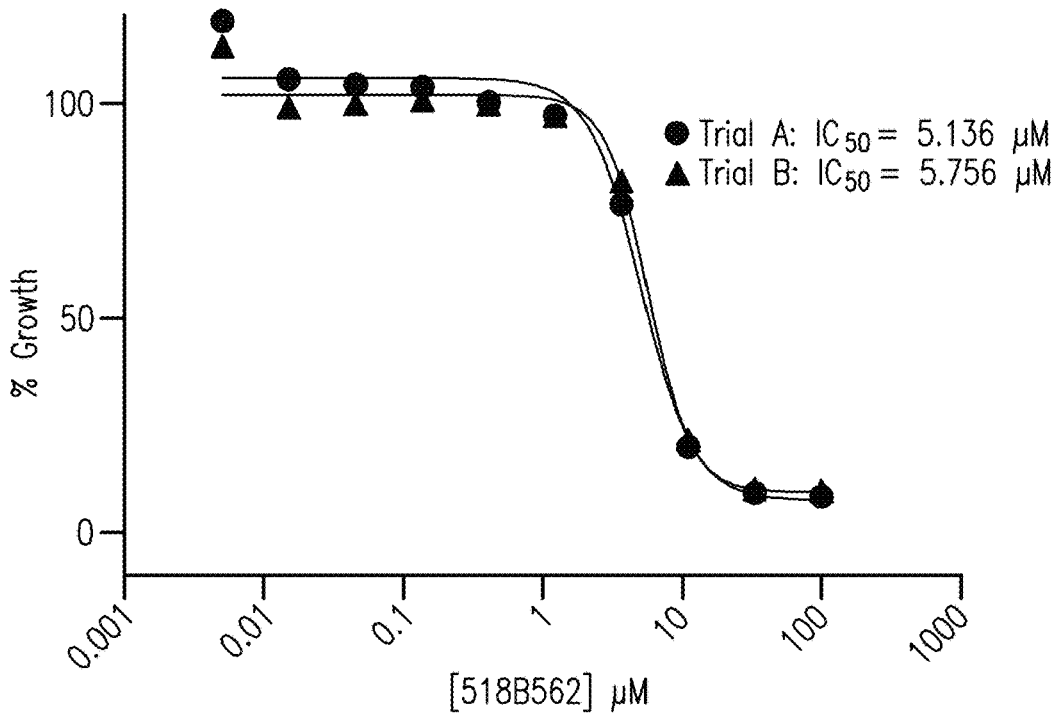
FIG. 47 is a graph illustrating cell growth as a function of the concentration of the 518B562 compound, in the KMS-34 cell proliferation assay described in Example 8.
Figure 48:
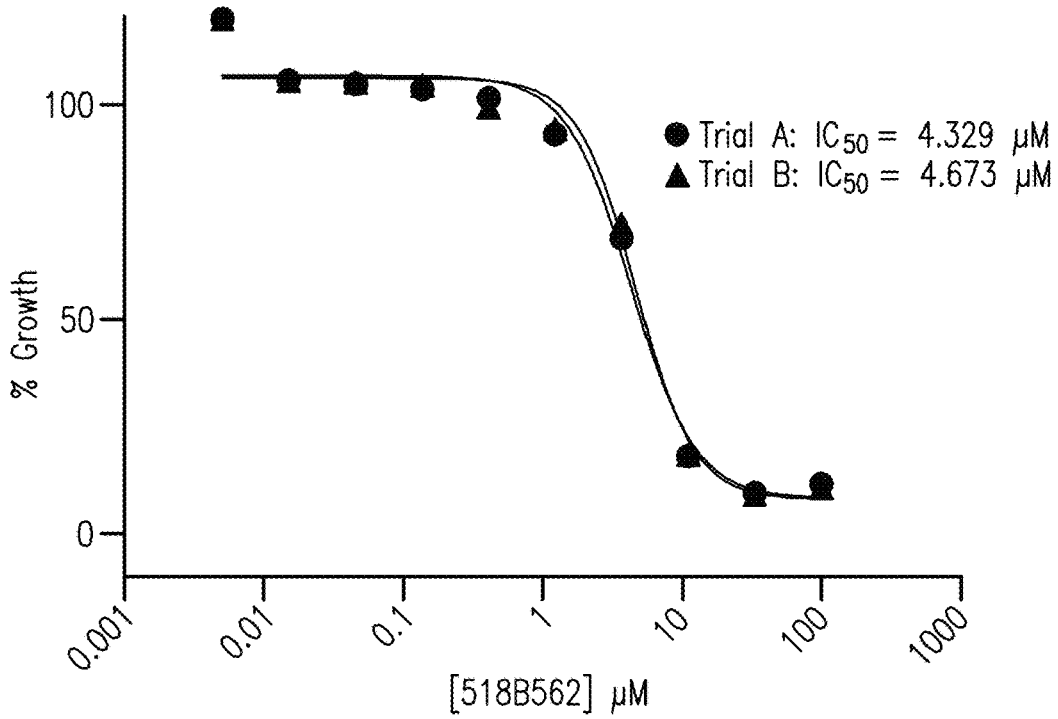
FIG. 48 is a graph illustrating cell growth as a function of the concentration of the 518B562 compound, in the H929 cell proliferation assay described in Example 8.
Figure 49:
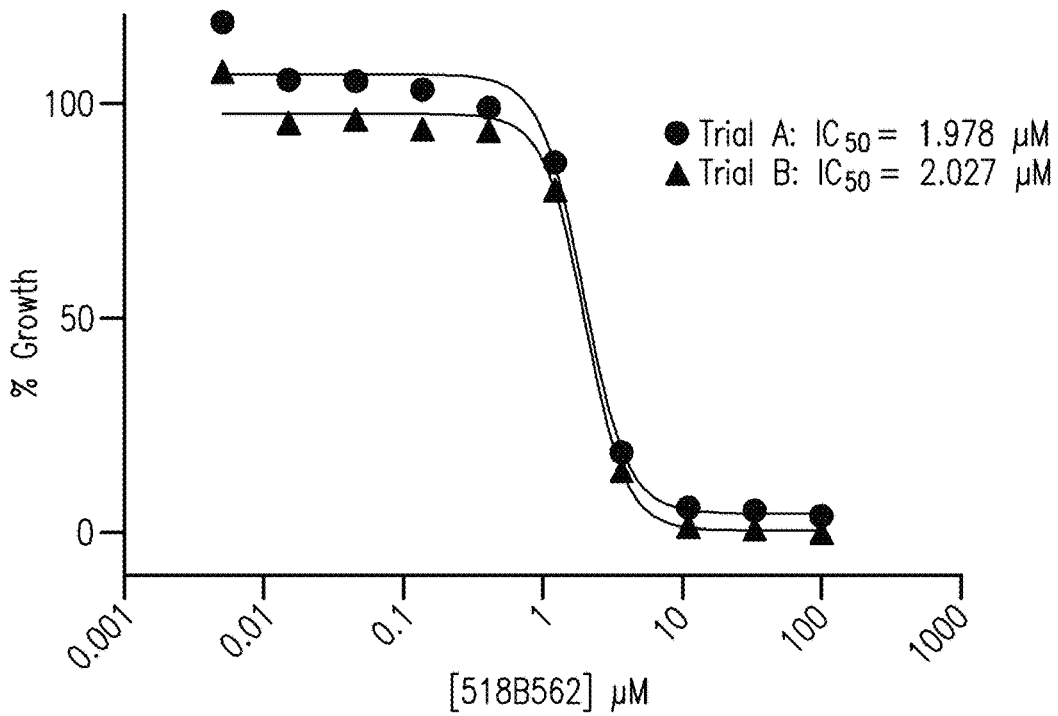
FIG. 49 is a graph illustrating cell growth as a function of the concentration of the 518B562 compound, in the L363 cell proliferation assay described in Example 8.
Figure 50:
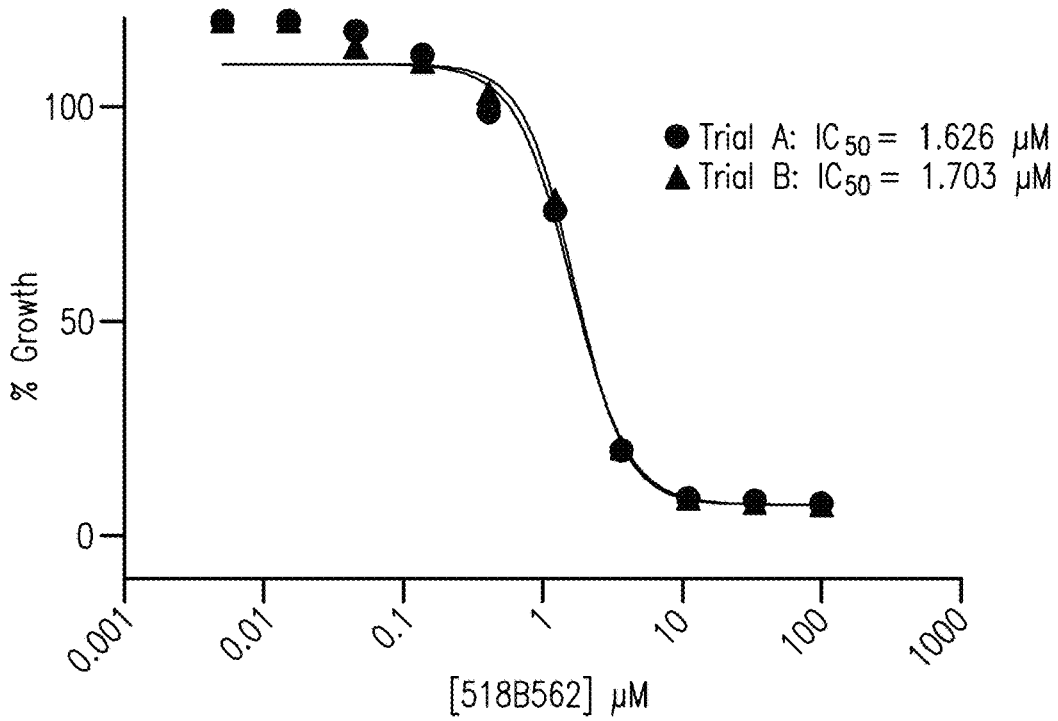
FIG. 50 is a graph illustrating cell growth as a function of the concentration of the 518B562 compound, in the MM.1s cell proliferation assay described in Example 8.
Figure 51:
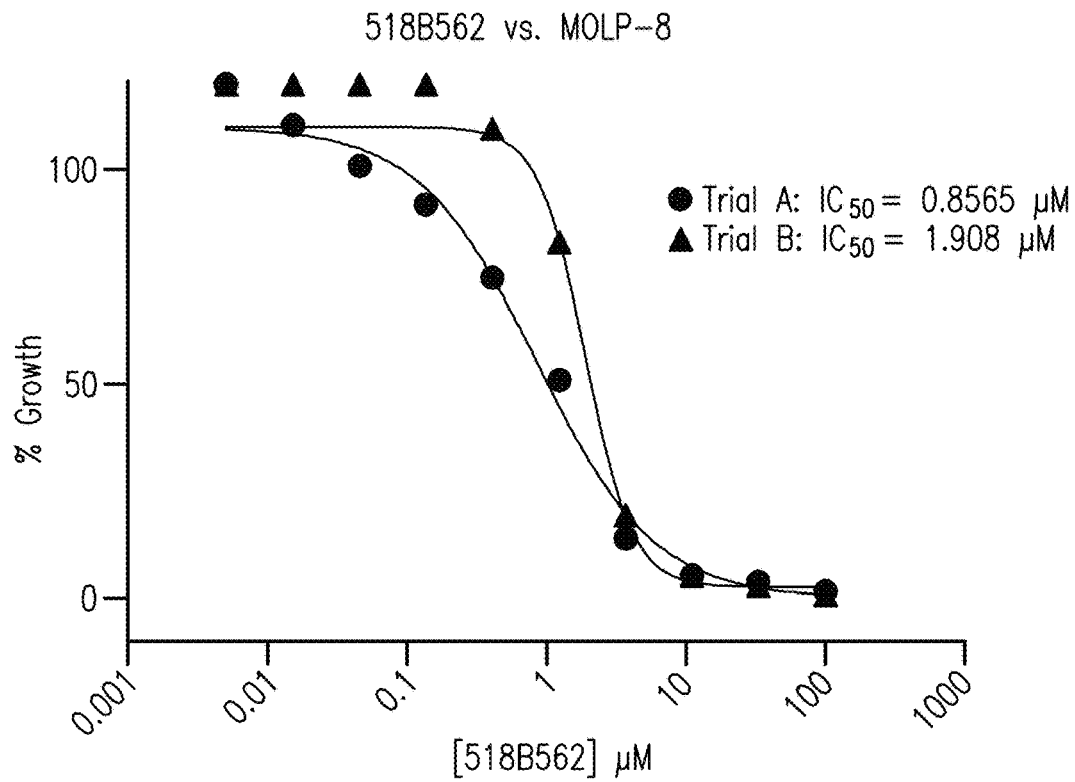
FIG. 51 is a graph illustrating cell growth as a function of the concentration of the 518B562 compound, in the MOLP-8 cell proliferation assay described in Example 8.
Figure 52:
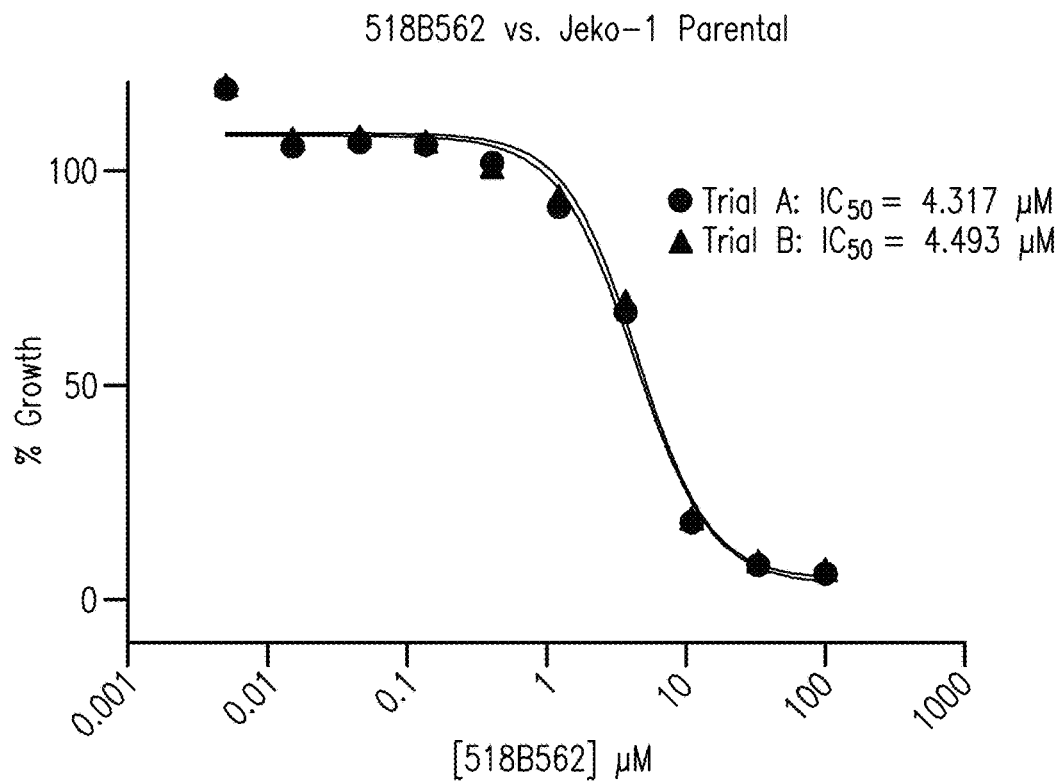
FIG. 52 is a graph illustrating cell growth as a function of the concentration of the 518B562 compound, in the Jeko-1 Parental cell proliferation assay described in Example 8.
Figure 53:
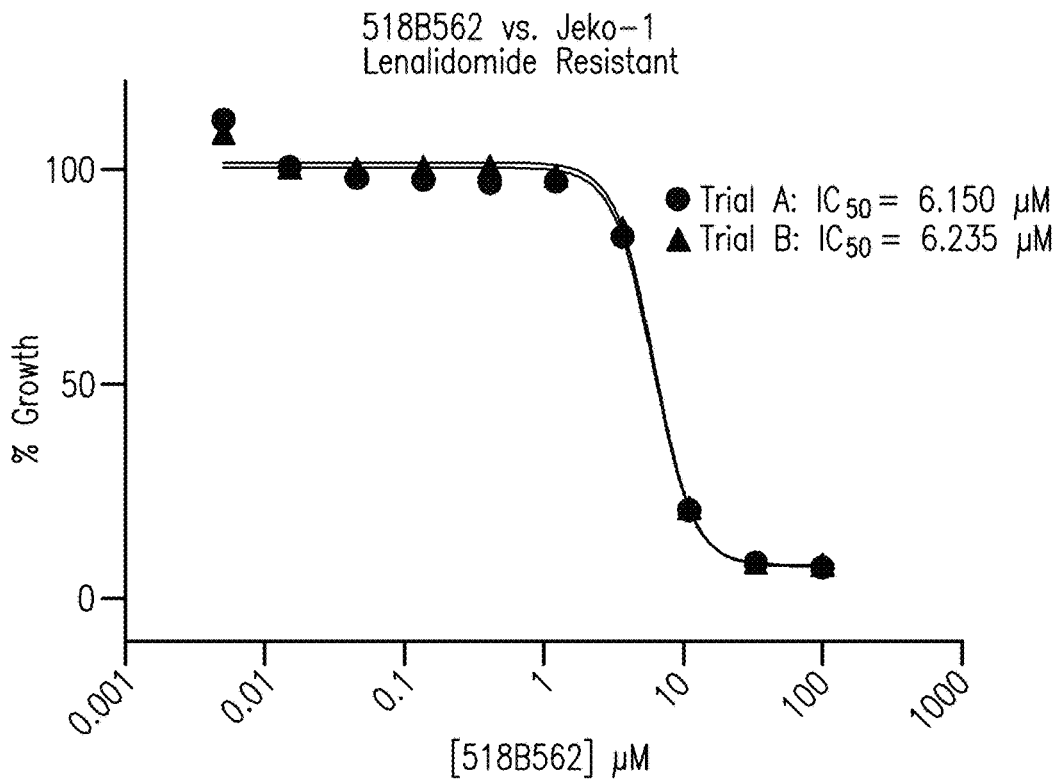
FIG. 53 is a graph illustrating cell growth as a function of the concentration of the 518B562 compound, in the Jeko-1 Lenalidomine Resistant cell proliferation assay described in Example 8.
Figure 54:
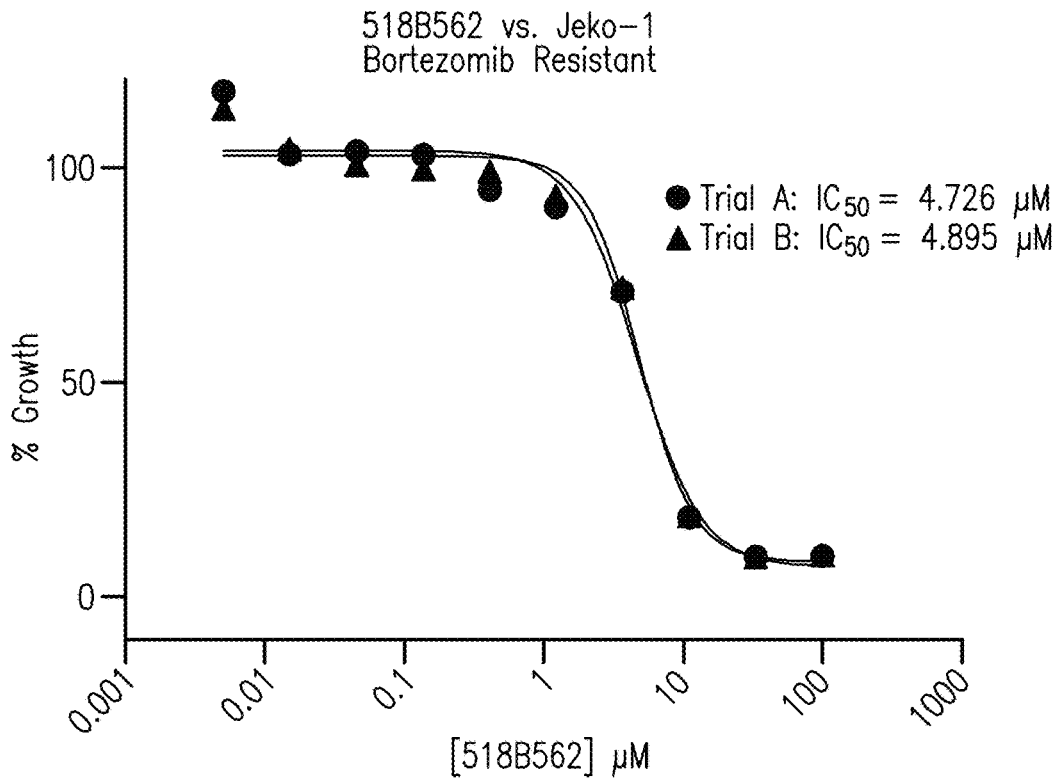
FIG. 54 is a graph illustrating cell growth as a function of the concentration of the 518B562 compound, in the Jeko-1 Bortezomib Resistant cell proliferation assay described in Example 8.
Figure 55:
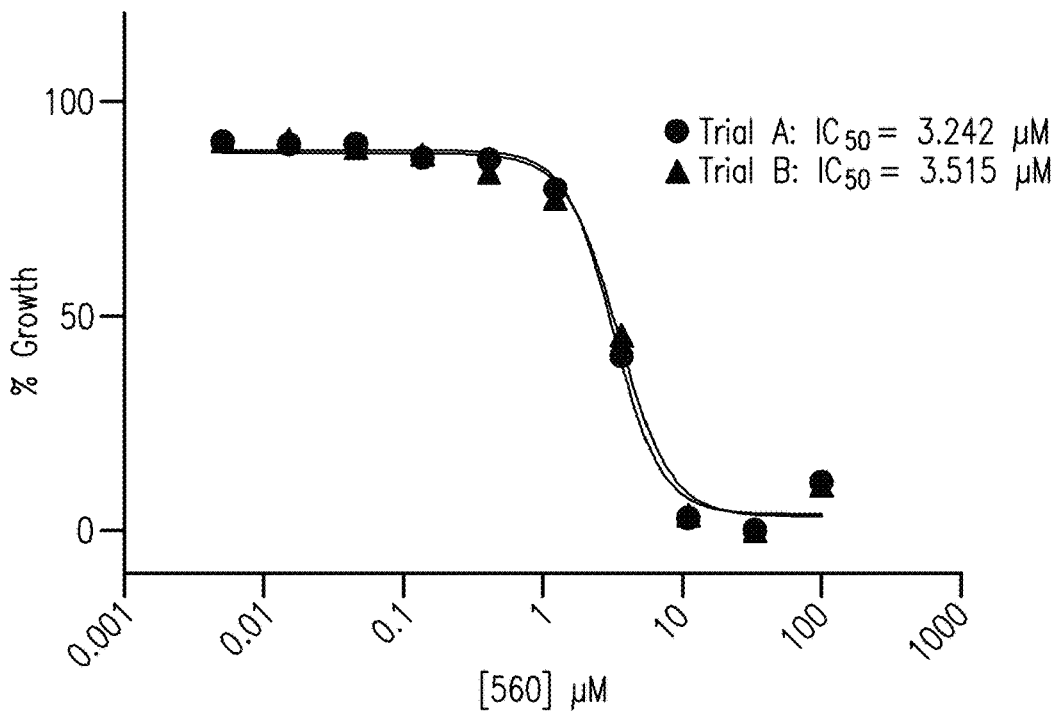
FIG. 55 is a graph illustrating cell growth as a function of the concentration of the 560 compound, in the MIA PaCa-2 cell proliferation assay described in Example 8.
Figure 56:
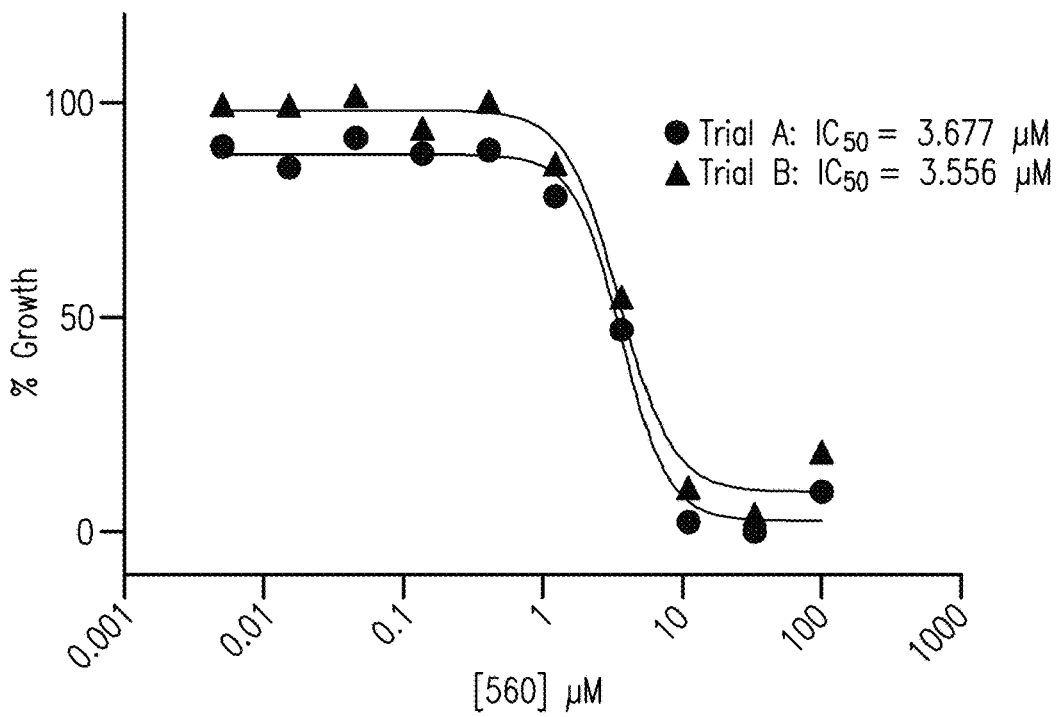
FIG. 56 is a graph illustrating cell growth as a function of the concentration of the 560 compound, in the ASPC-1 cell proliferation assay described in Example 8.
Figure 57:
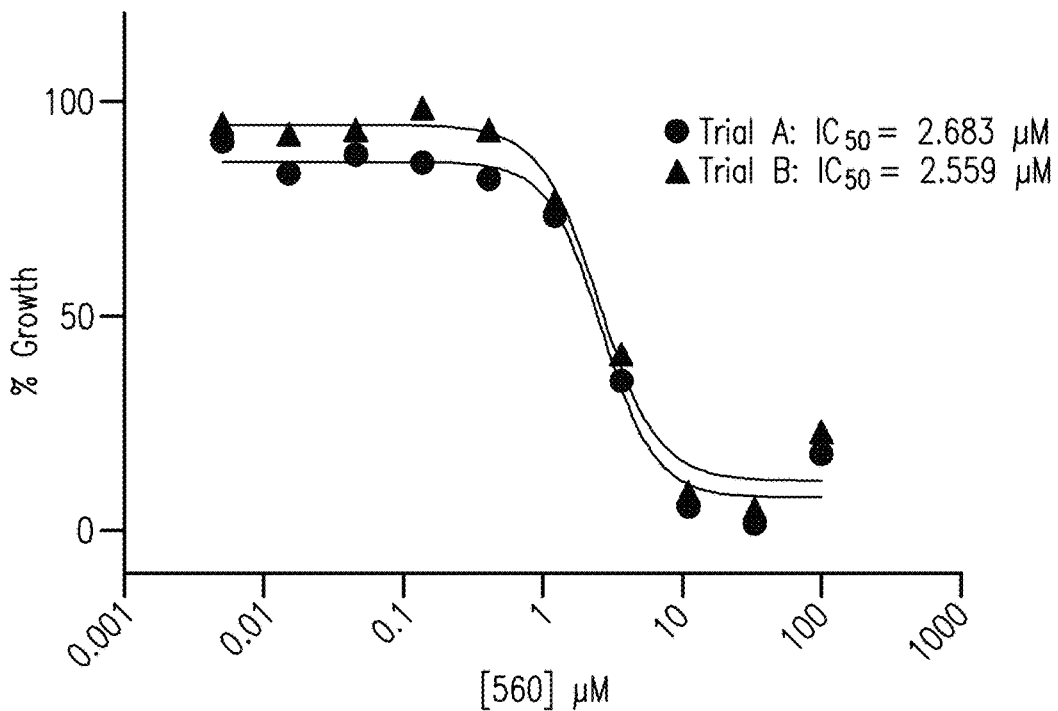
FIG. 57 is a graph illustrating cell growth as a function of the concentration of the 560 compound, in the BxPC-3 cell proliferation assay described in Example 8.
Figure 58:
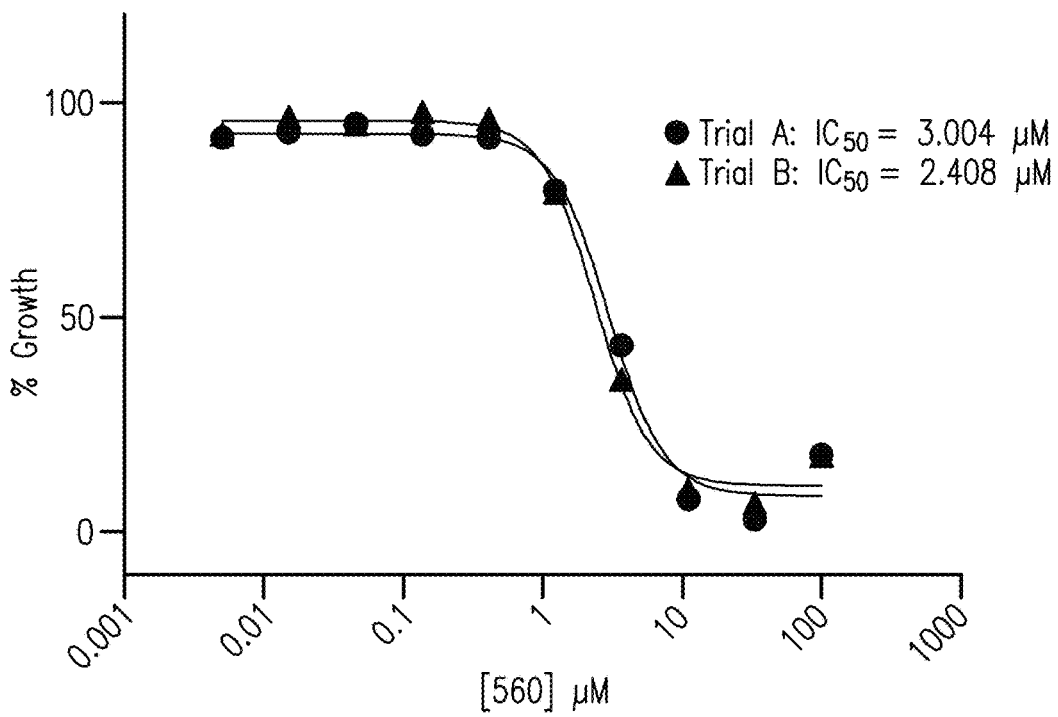
FIG. 58 is a graph illustrating cell growth as a function of the concentration of the 560 compound, in the AN3CA cell proliferation assay described in Example 8.
Figure 59:
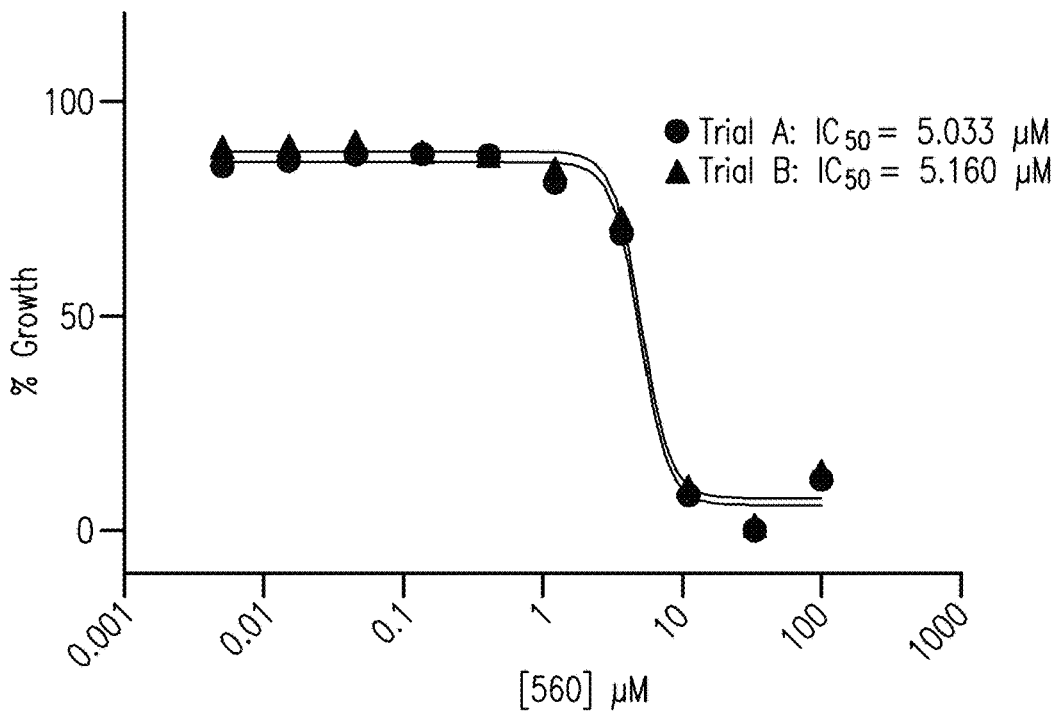
FIG. 59 is a graph illustrating cell growth as a function of the concentration of the 560 compound, in the HEC-1a cell proliferation assay described in Example 8.
Figure 60:
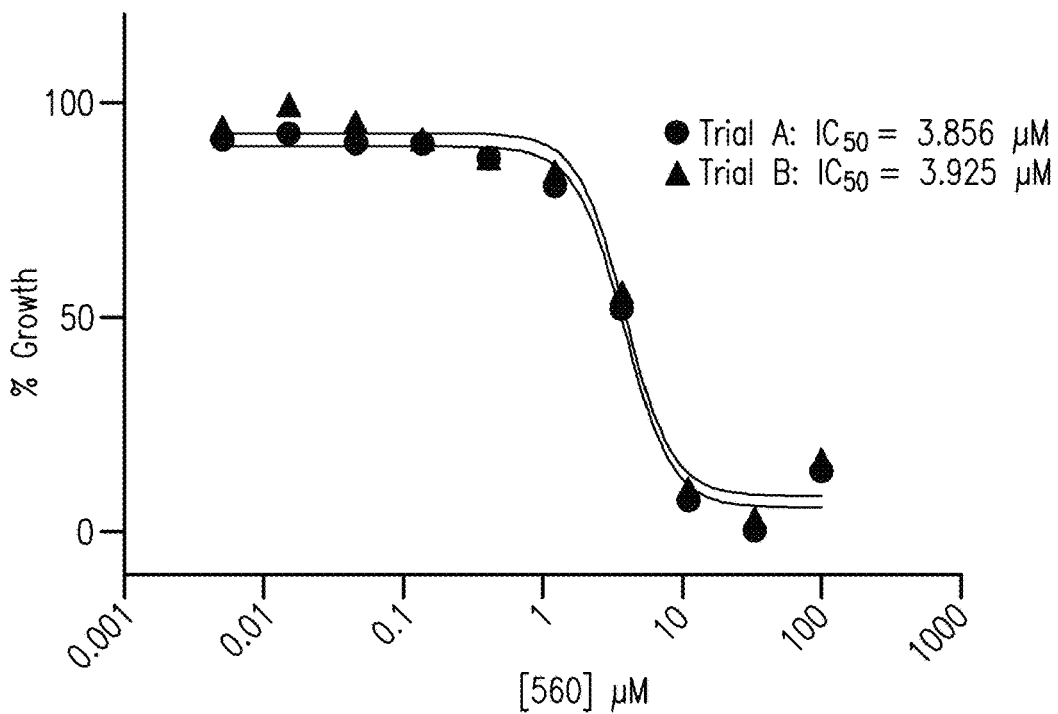
FIG. 60 is a graph illustrating cell growth as a function of the concentration of the 560 compound, in the MDA-MB-231 cell proliferation assay described in Example 8.
Figure 61:
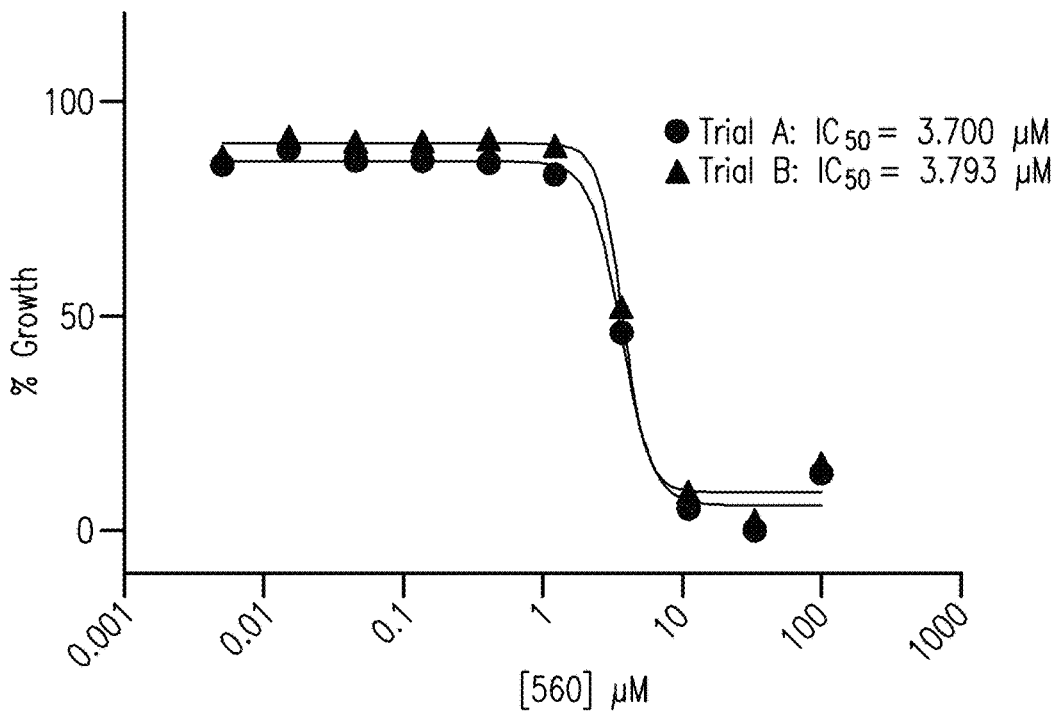
FIG. 61 is a graph illustrating cell growth as a function of the concentration of the 560 compound, in the MDA-MB-468 cell proliferation assay described in Example 8.
Figure 62:
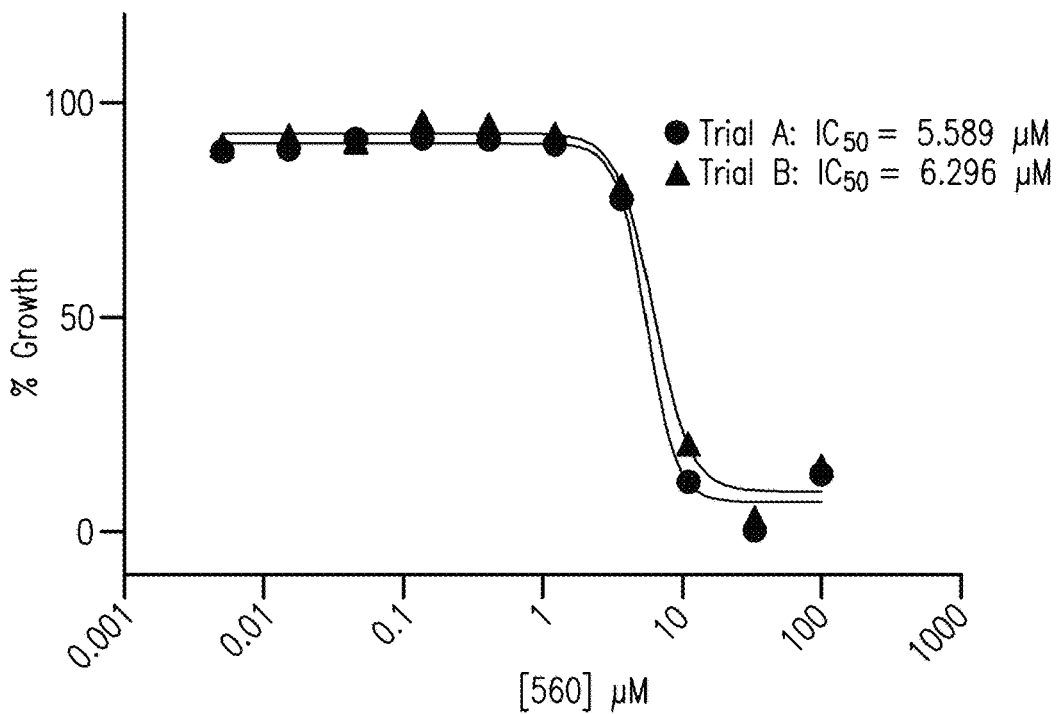
FIG. 62 is a graph illustrating cell growth as a function of the concentration of the 560 compound, in the HCC70 cell proliferation assay described in Example 8.
Figure 63:
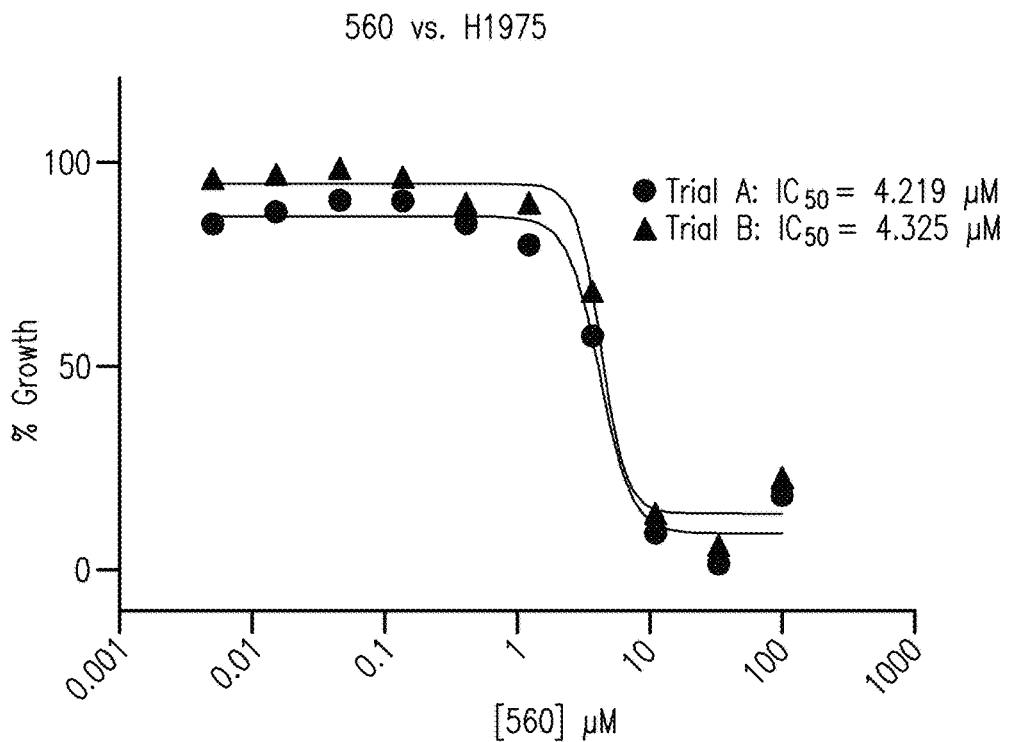
FIG. 63 is a graph illustrating cell growth as a function of the concentration of the 560 compound, in the H1975 cell proliferation assay described in Example 8.
Figure 64:
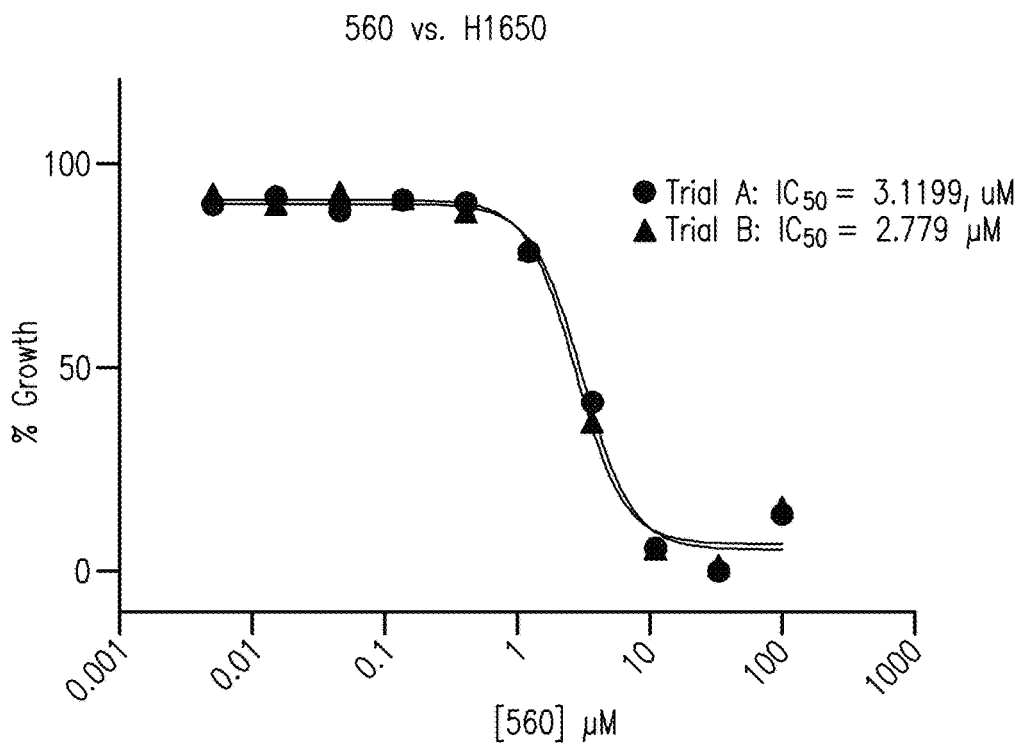
FIG. 64 is a graph illustrating cell growth as a function of the concentration of the 560 compound, in the H1650 cell proliferation assay described in Example 8.
Figure 65:
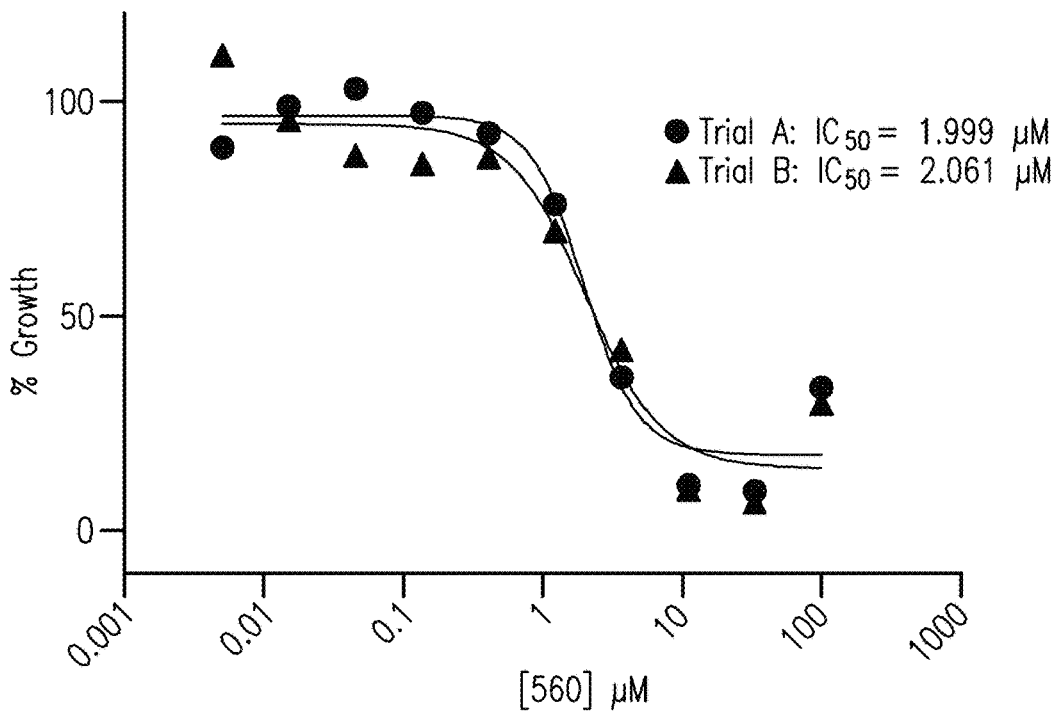
FIG. 65 is a graph illustrating cell growth as a function of the concentration of the 560 compound, in the A2780 cell proliferation assay described in Example 8.
Figure 66:
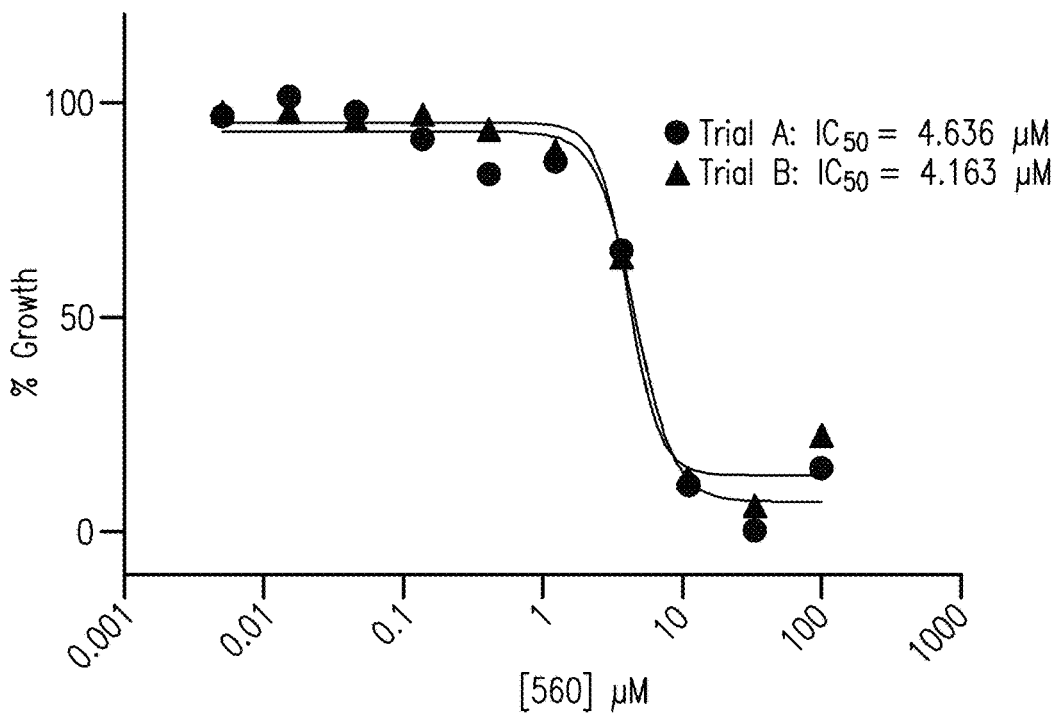
FIG. 66 is a graph illustrating cell growth as a function of the concentration of the 560 compound, in the A2780CP cell proliferation assay described in Example 8.
Figure 67:
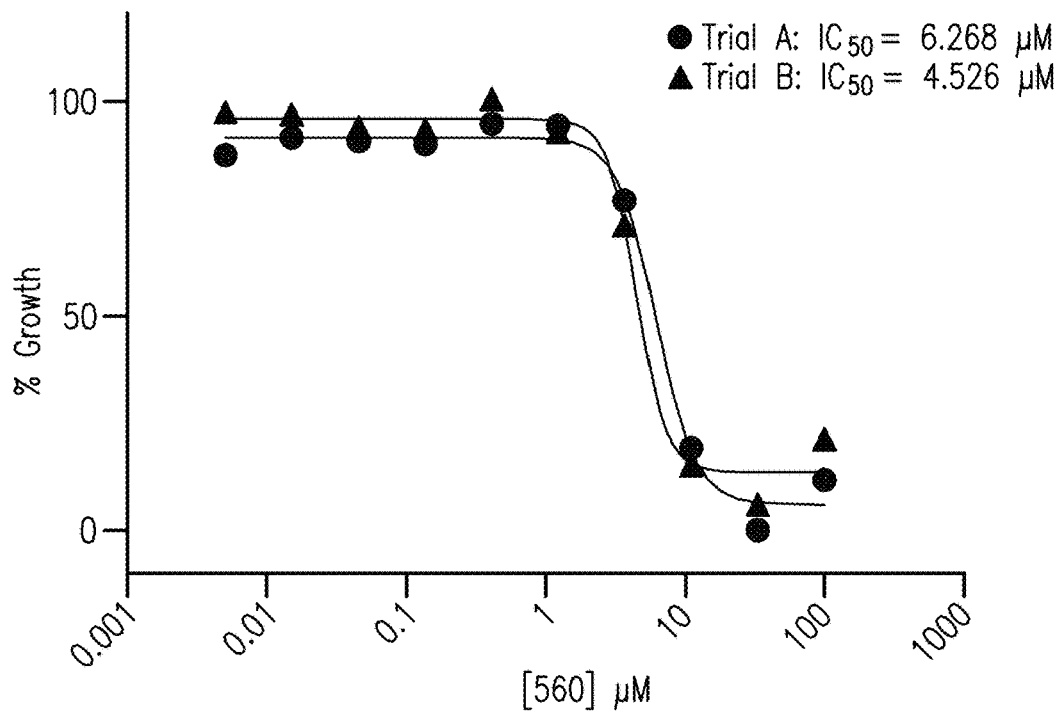
FIG. 67 is a graph illustrating cell growth as a function of the concentration of the 560 compound, in the RXF-393 cell proliferation assay described in Example 8.
Figure 68:
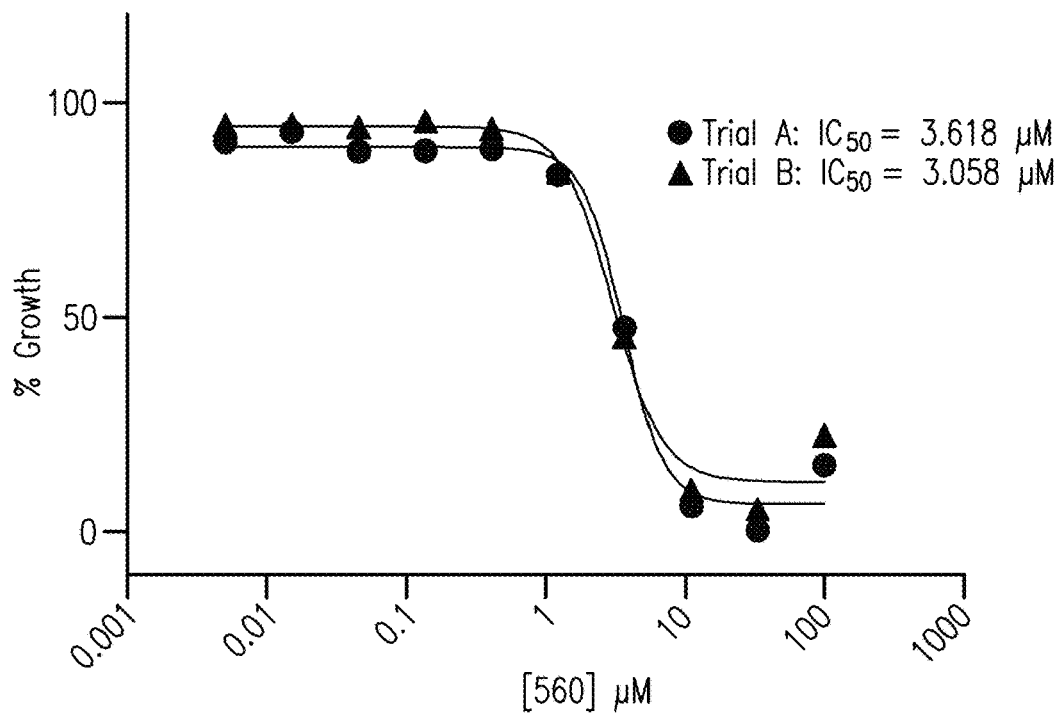
FIG. 68 is a graph illustrating cell growth as a function of the concentration of the 560 compound, in the A498 cell proliferation assay described in Example 8.
Figure 69:
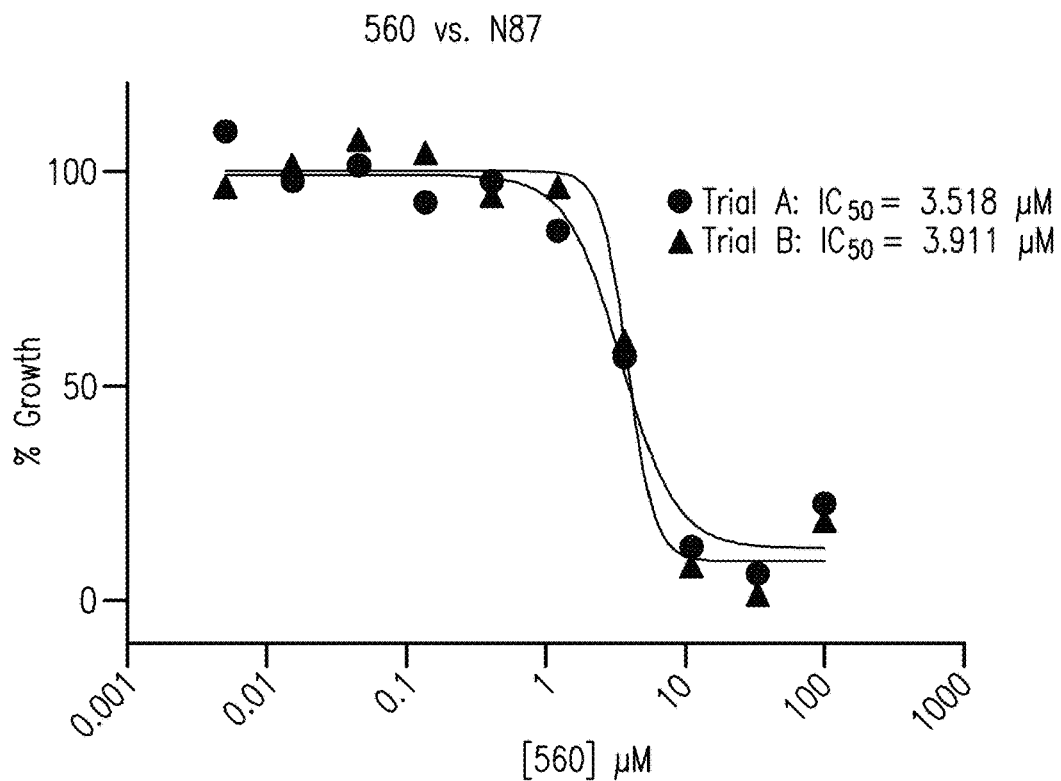
FIG. 69 is a graph illustrating cell growth as a function of the concentration of the 560 compound, in the N87 cell proliferation assay described in Example 8.
Figure 70:
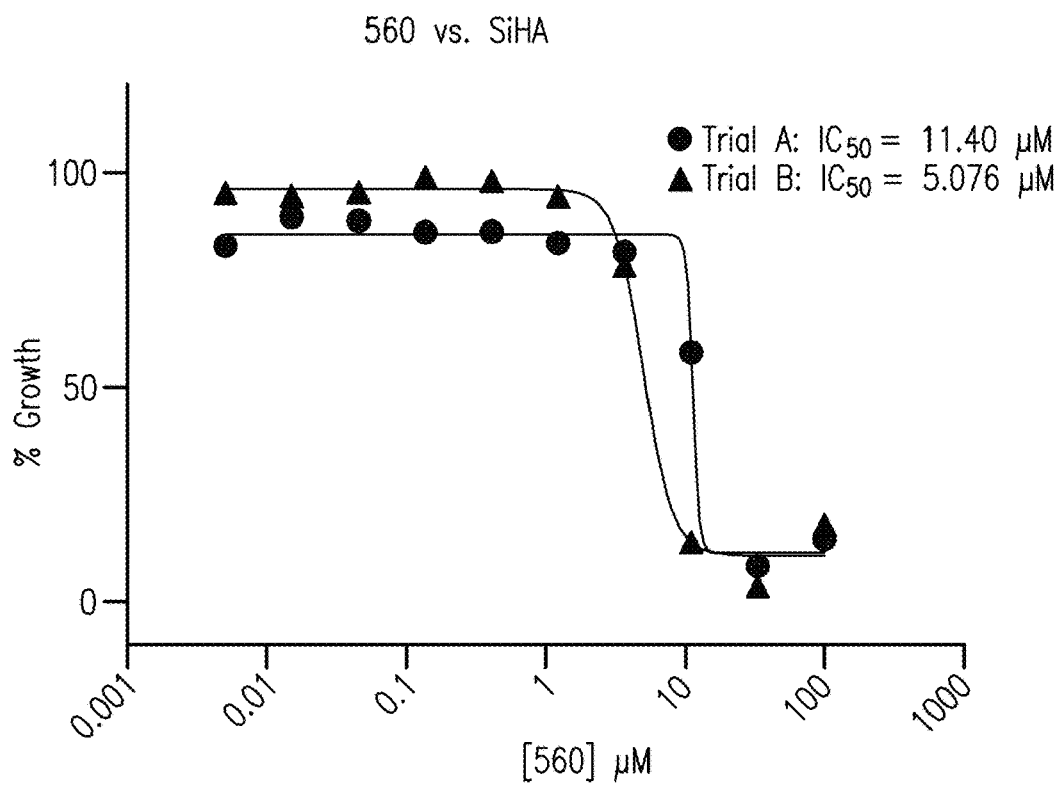
FIG. 70 is a graph illustrating cell growth as a function of the concentration of the 560 compound, in the SiHA cell proliferation assay described in Example 8.
Figure 71:
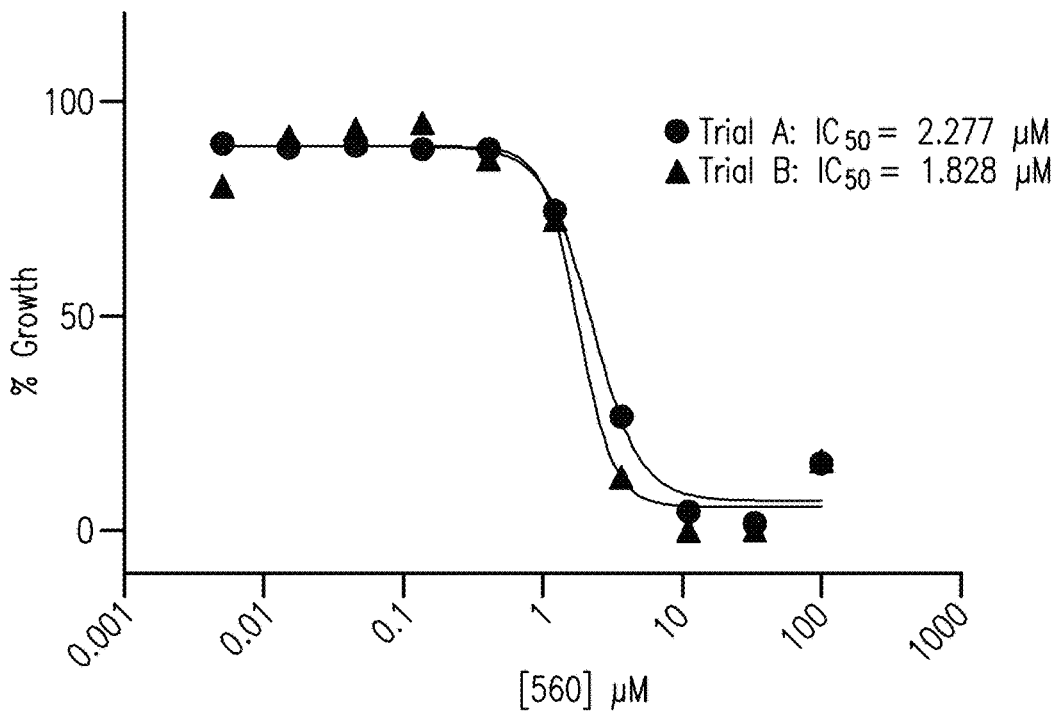
FIG. 71 is a graph illustrating cell growth as a function of the concentration of the 560 compound, in the FaDu cell proliferation assay described in Example 8.
Figure 72:
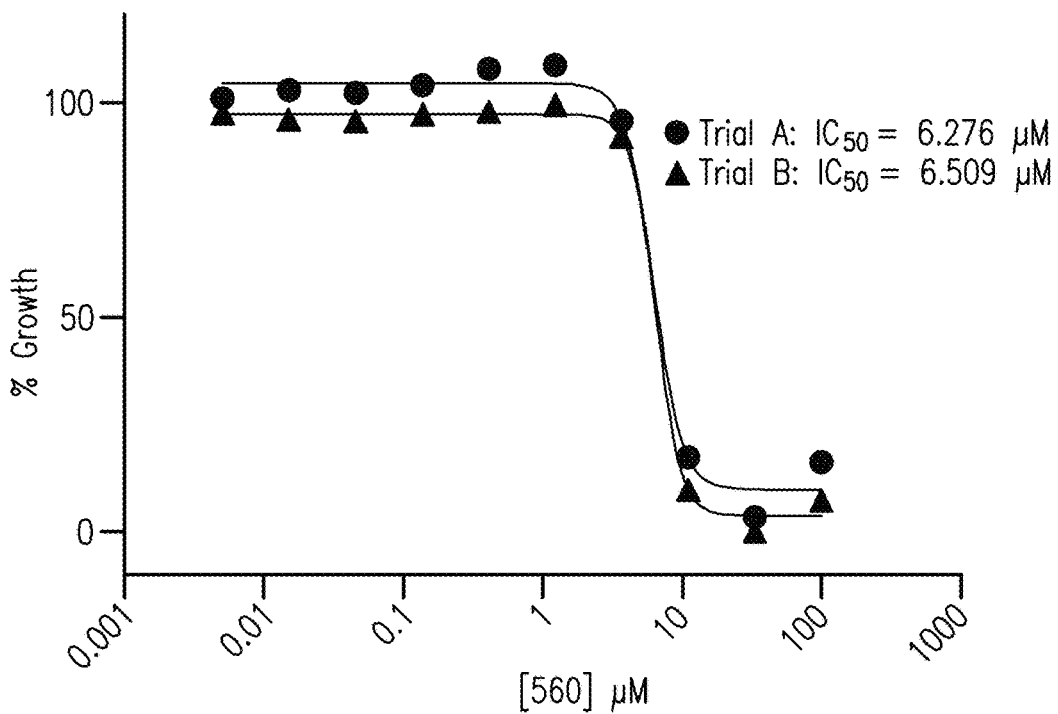
FIG. 72 is a graph illustrating cell growth as a function of the concentration of the 560 compound, in the DOHH-2 cell proliferation assay described in Example 8.
Figure 73:
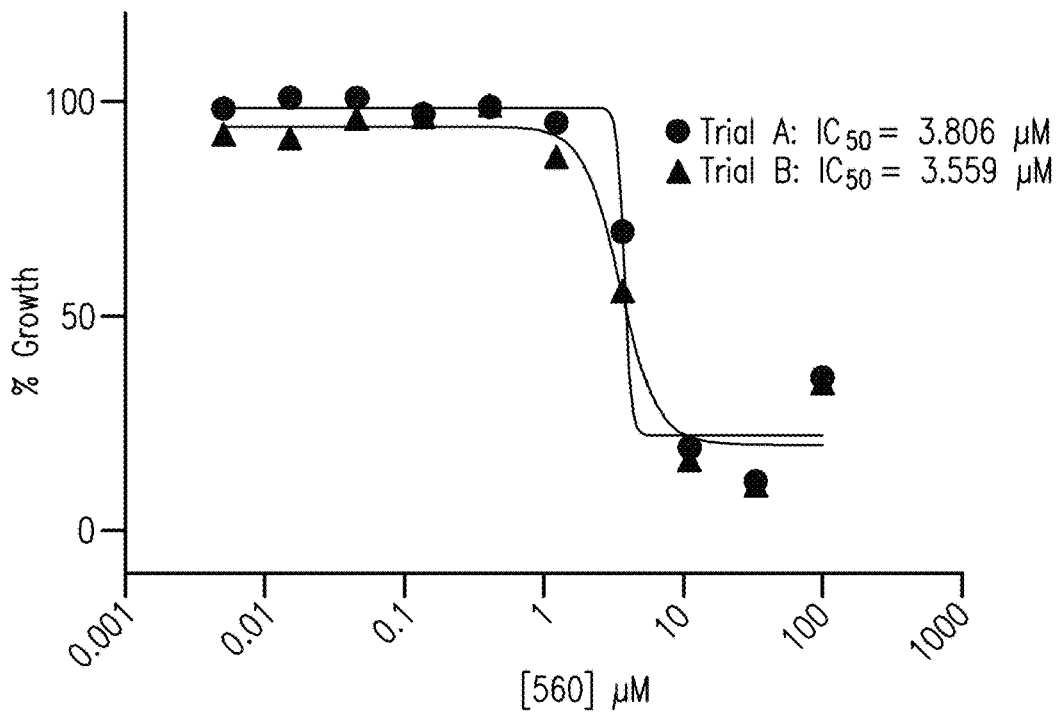
FIG. 73 is a graph illustrating cell growth as a function of the concentration of the 560 compound, in the SU-DHL-4 cell proliferation assay described in Example 8.
Figure 74:
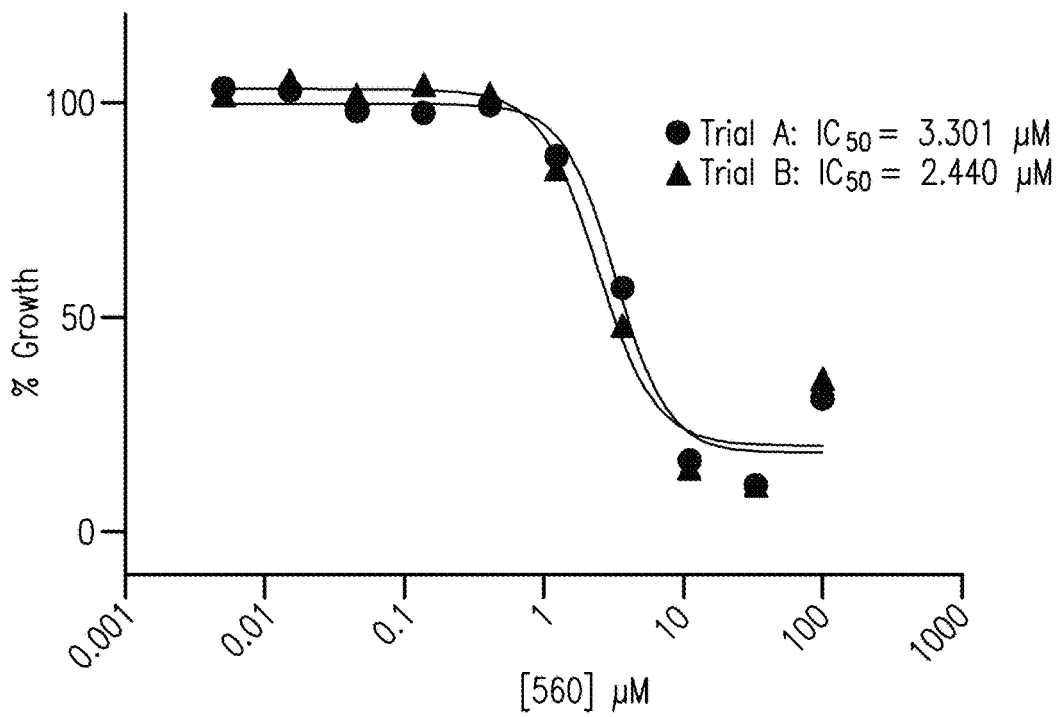
FIG. 74 is a graph illustrating cell growth as a function of the concentration of the 560 compound, in the OCI-LY3 cell proliferation assay described in Example 8.
Figure 75:
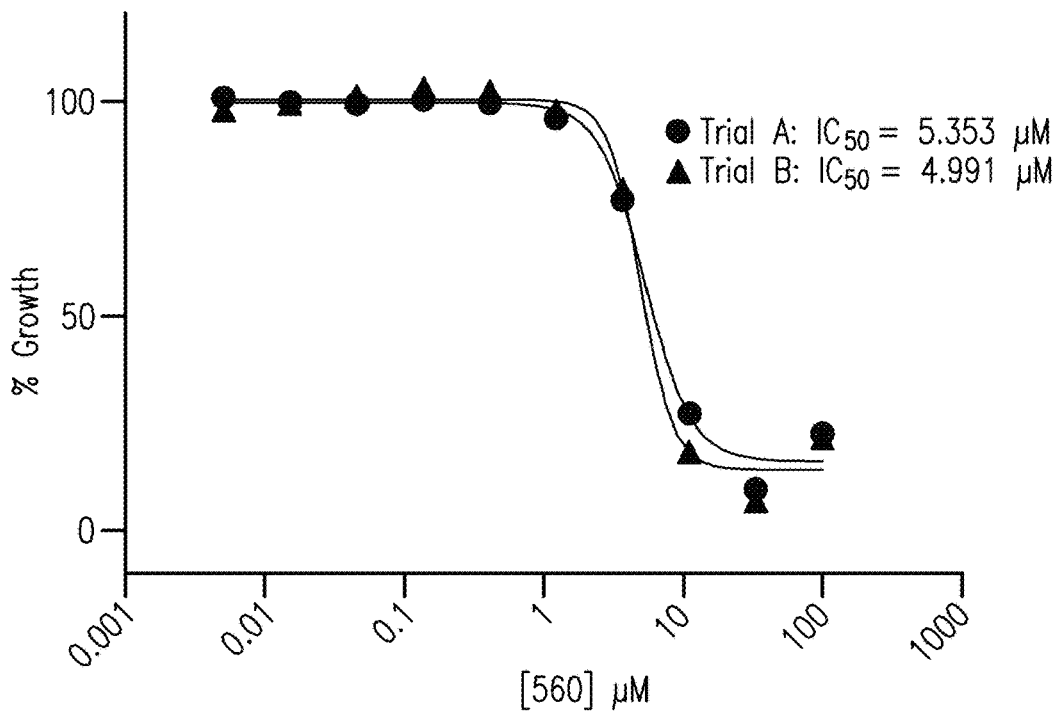
FIG. 75 is a graph illustrating cell growth as a function of the concentration of the 560 compound, in the JIM1 cell proliferation assay described in Example 8.
Figure 76:
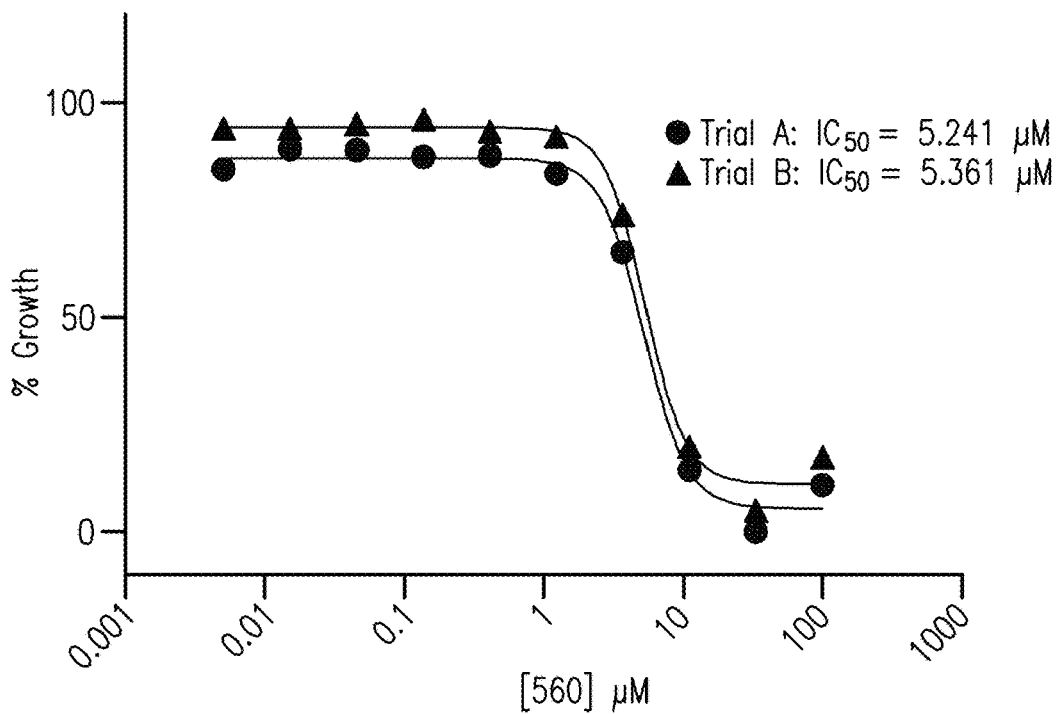
FIG. 76 is a graph illustrating cell growth as a function of the concentration of the 560 compound, in the KMM-1 cell proliferation assay described in Example 8.
Figure 77:
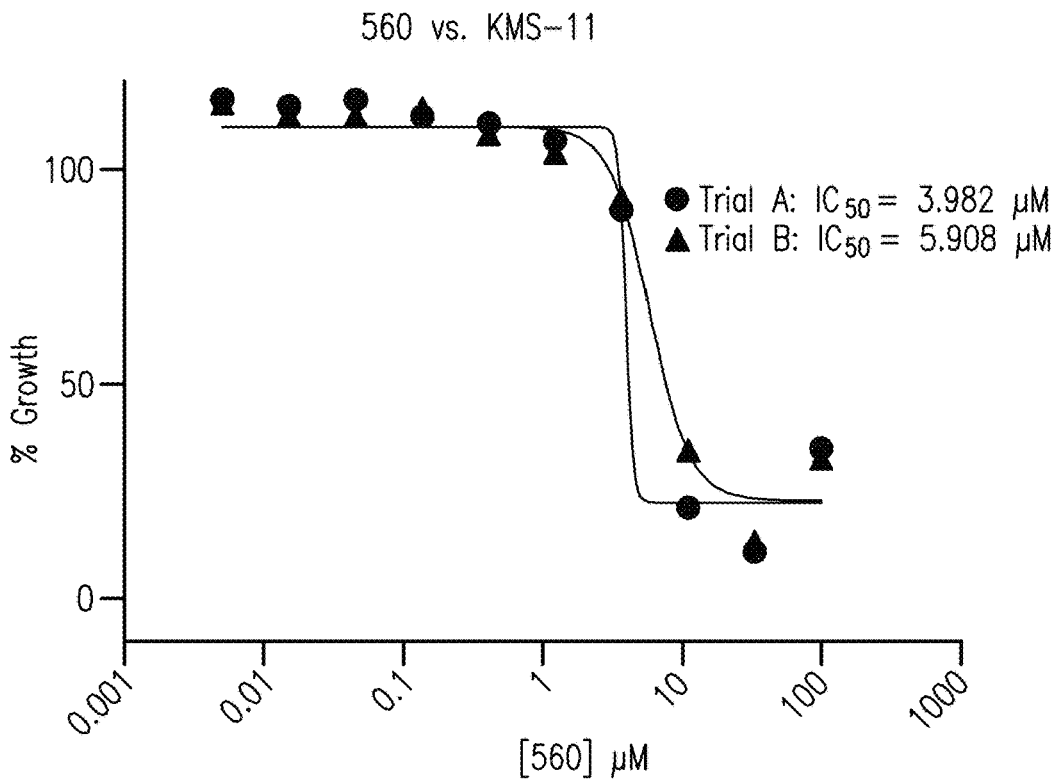
FIG. 77 is a graph illustrating cell growth as a function of the concentration of the 560 compound, in the KMS-11 cell proliferation assay described in Example 8.
Figure 78:
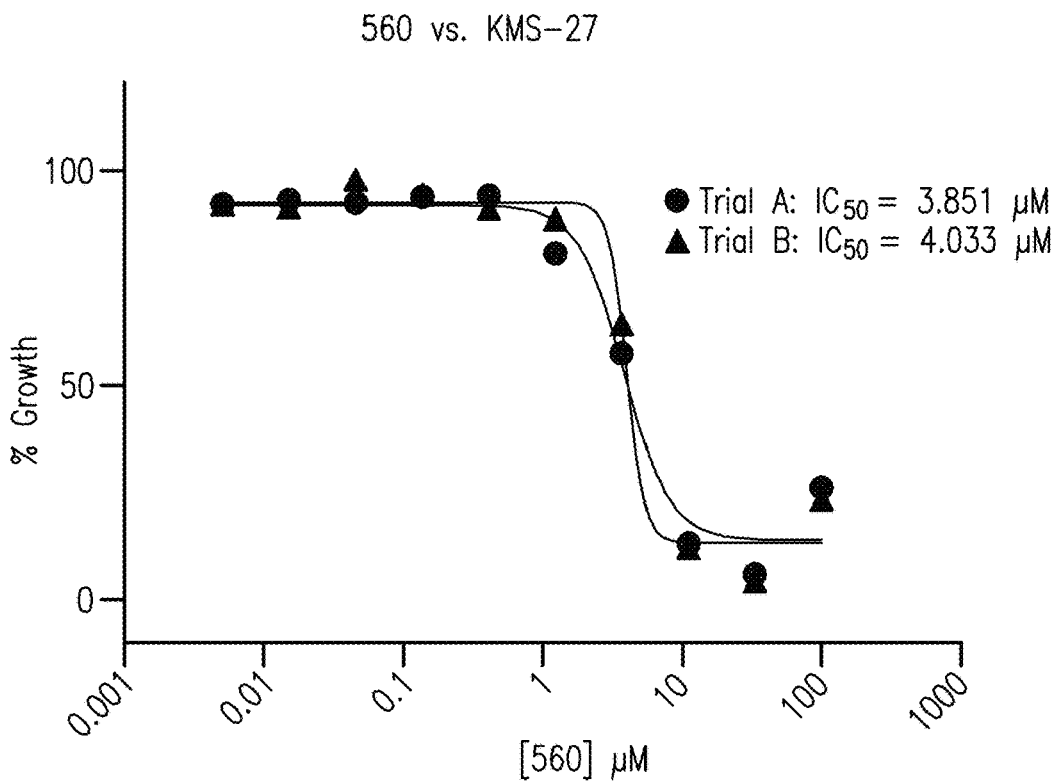
FIG. 78 is a graph illustrating cell growth as a function of the concentration of the 560 compound, in the KMS-27 cell proliferation assay described in Example 8.
Figure 79:
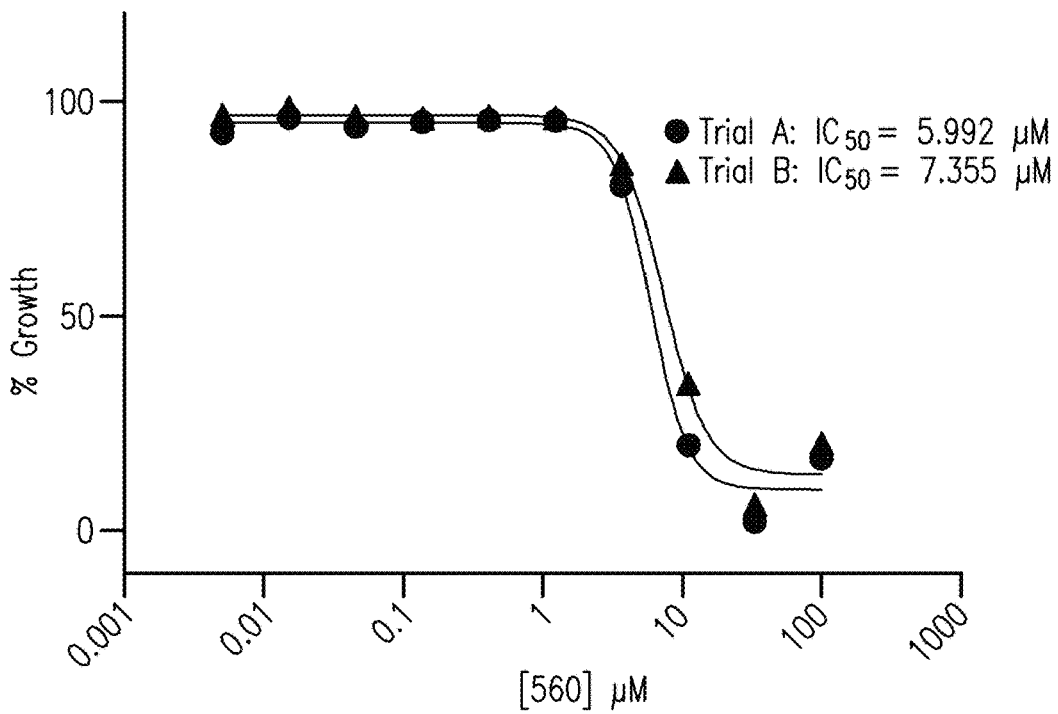
FIG. 79 is a graph illustrating cell growth as a function of the concentration of the 560 compound, in the KMS-34 cell proliferation assay described in Example 8.
Figure 80:
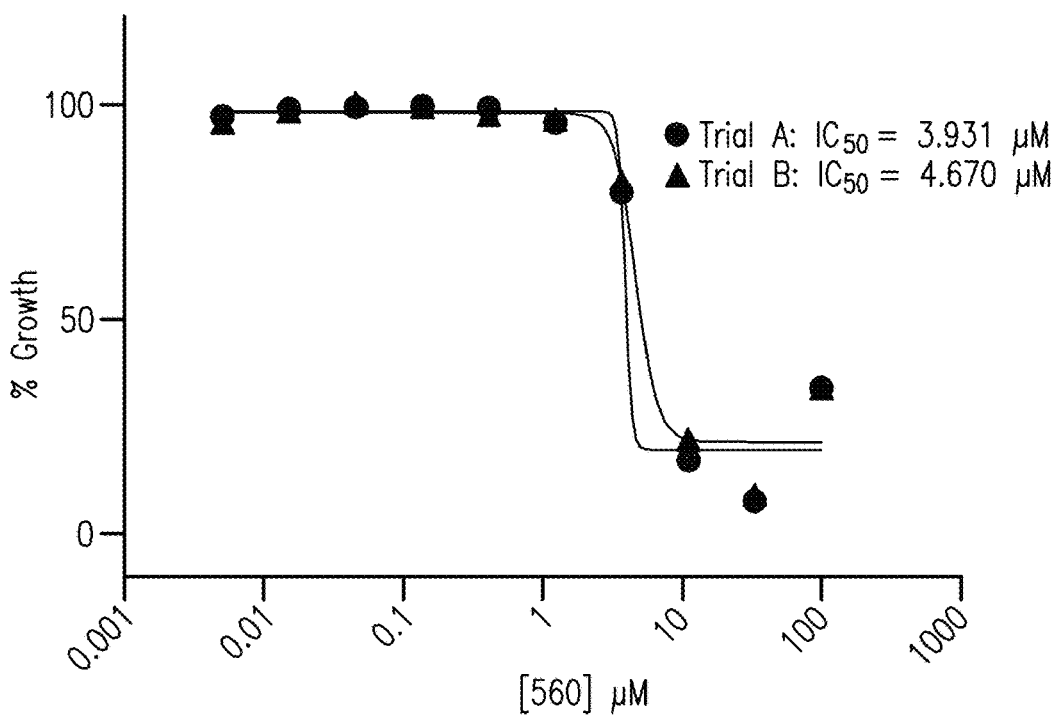
FIG. 80 is a graph illustrating cell growth as a function of the concentration of the 560 compound, in the H929 cell proliferation assay described in Example 8.
Figure 81:
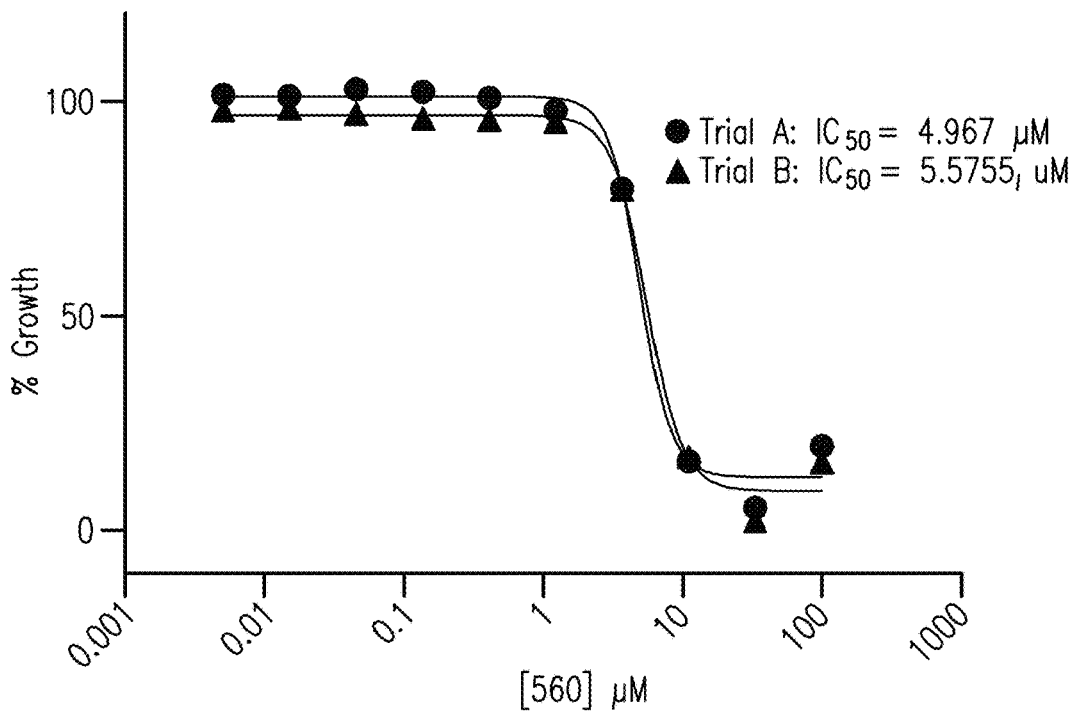
FIG. 81 is a graph illustrating cell growth as a function of the concentration of the 560 compound, in the L363 cell proliferation assay described in Example 8.
Figure 82:
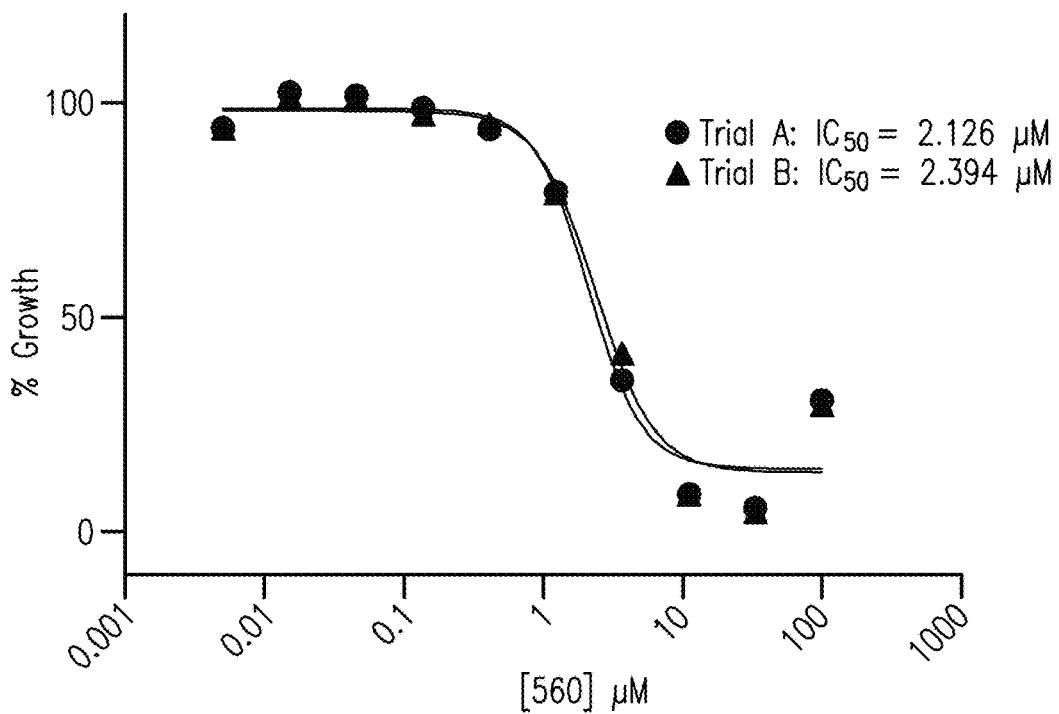
FIG. 82 is a graph illustrating cell growth as a function of the concentration of the 560 compound, in the MM.1s cell proliferation assay described in Example 8.
Figure 83:
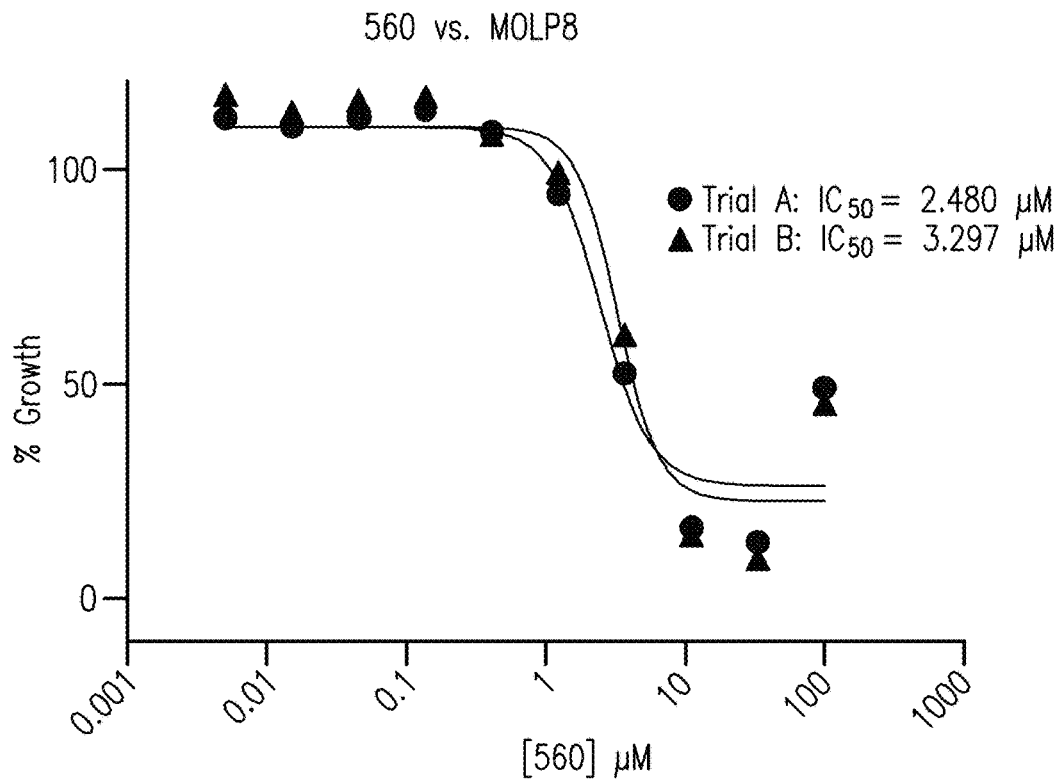
FIG. 83 is a graph illustrating cell growth as a function of the concentration of the 560 compound, in the MOLP-8 cell proliferation assay described in Example 8.
Figure 84:
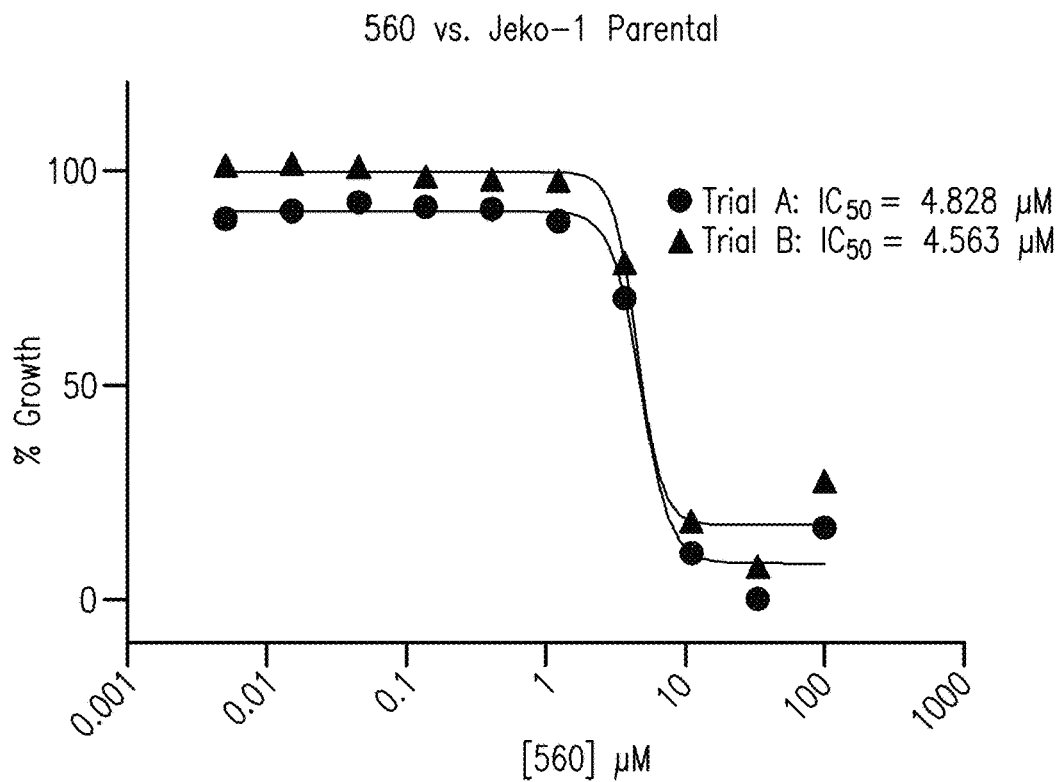
FIG. 84 is a graph illustrating cell growth as a function of the concentration of the 560 compound, in the Jeko-1 Parental cell proliferation assay described in Example 8.
Figure 85:
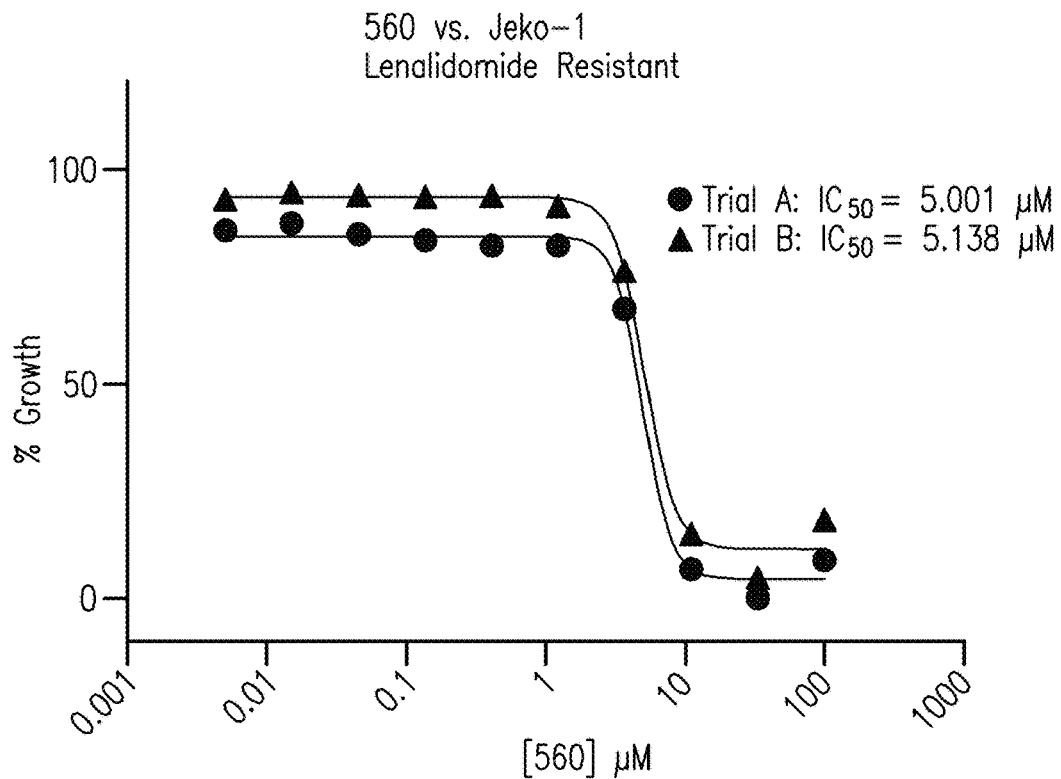
FIG. 85 is a graph illustrating cell growth as a function of the concentration of the 560 compound, in the Jeko-1 Lenalidomine Resistant cell proliferation assay described in Example 8.
Figure 86:
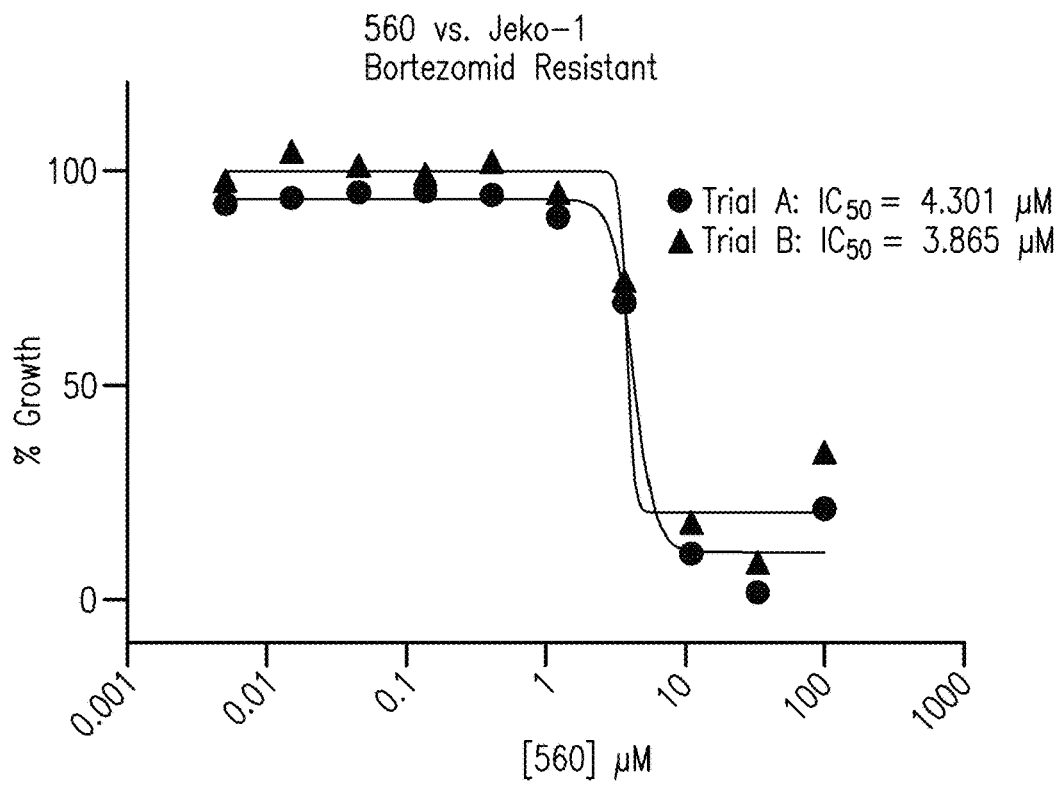
FIG. 86 is a graph illustrating cell growth as a function of the concentration of the 560 compound, in the Jeko-1 Bortezomib Resistant cell proliferation assay described in Example 8.
Figure 87:
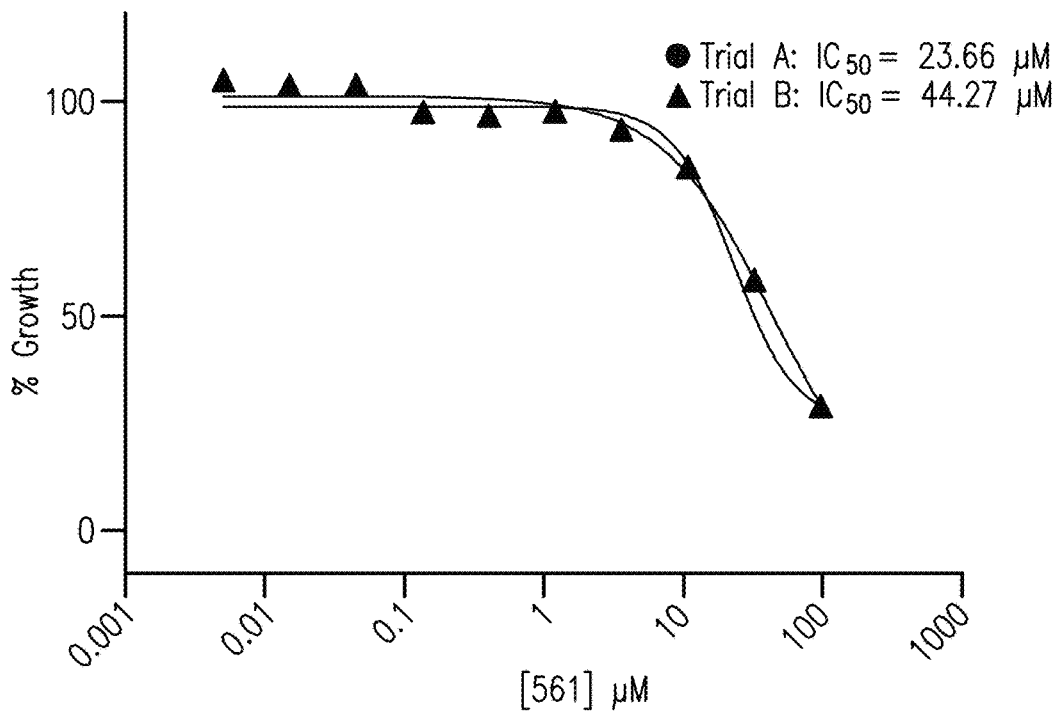
FIG. 87 is a graph illustrating cell growth as a function of the concentration of the 561 compound, in the MIA PaCa-2 cell proliferation assay described in Example 8.
Figure 88:
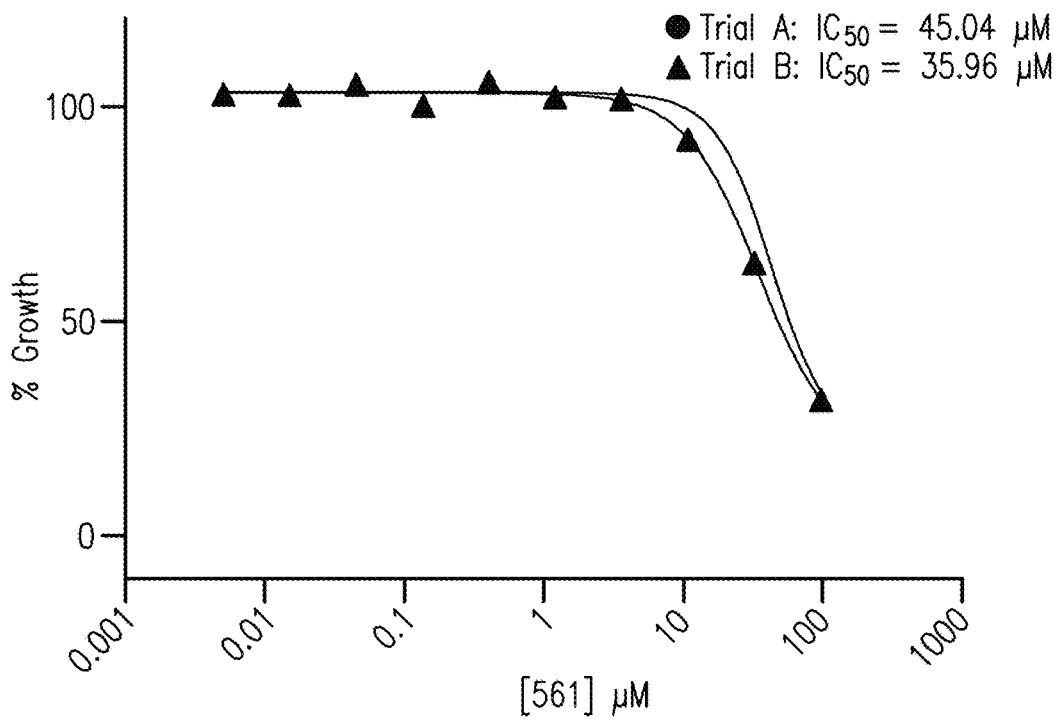
FIG. 88 is a graph illustrating cell growth as a function of the concentration of the 561 compound, in the ASPC-1 cell proliferation assay described in Example 8.
Figure 89:
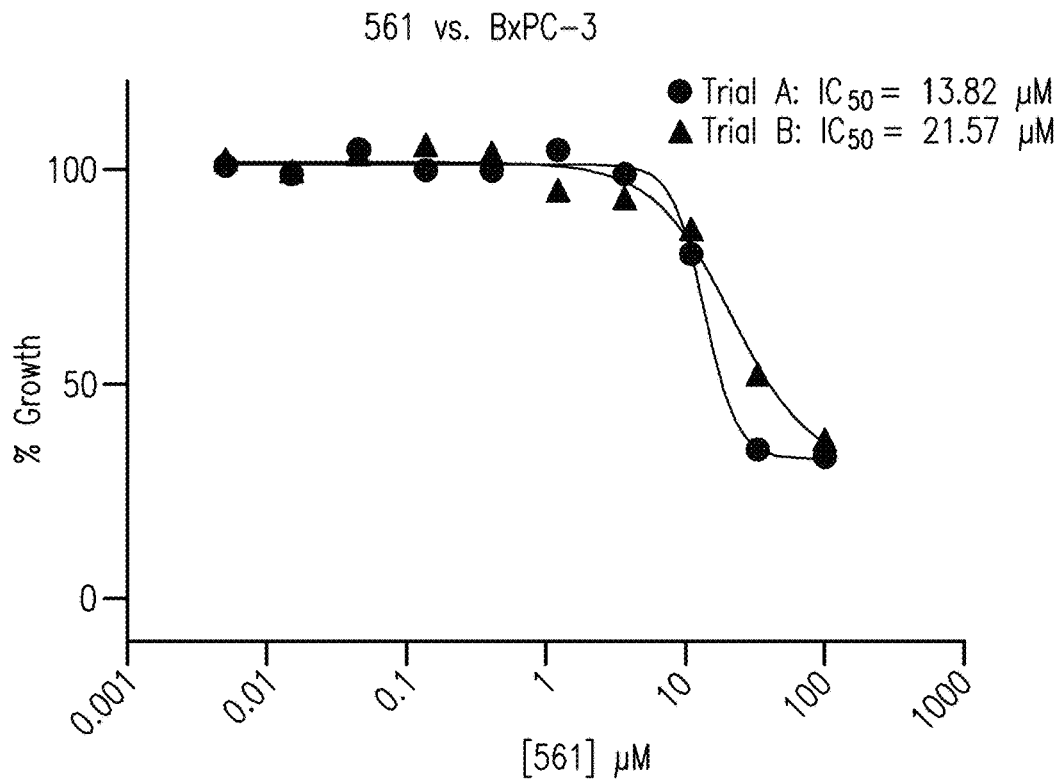
FIG. 89 is a graph illustrating cell growth as a function of the concentration of the 561 compound, in the BxPC-3 cell proliferation assay described in Example 8.
Figure 90:
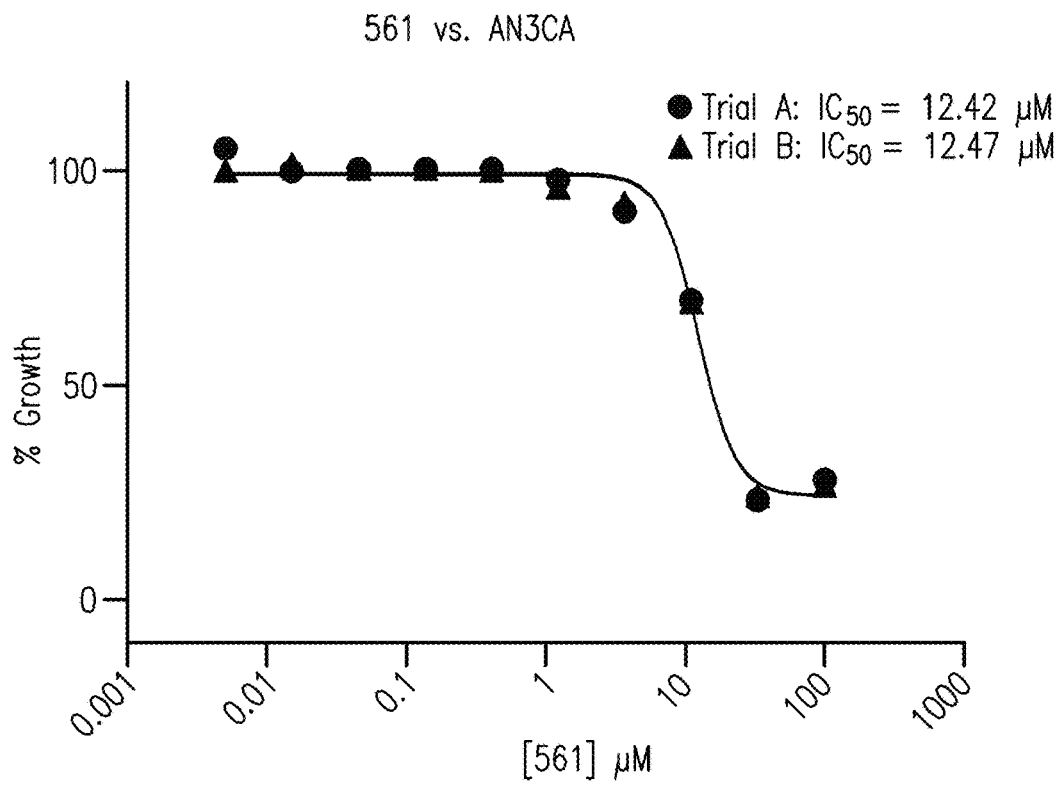
FIG. 90 is a graph illustrating cell growth as a function of the concentration of the 561 compound, in the AN3CA cell proliferation assay described in Example 8.
Figure 91:
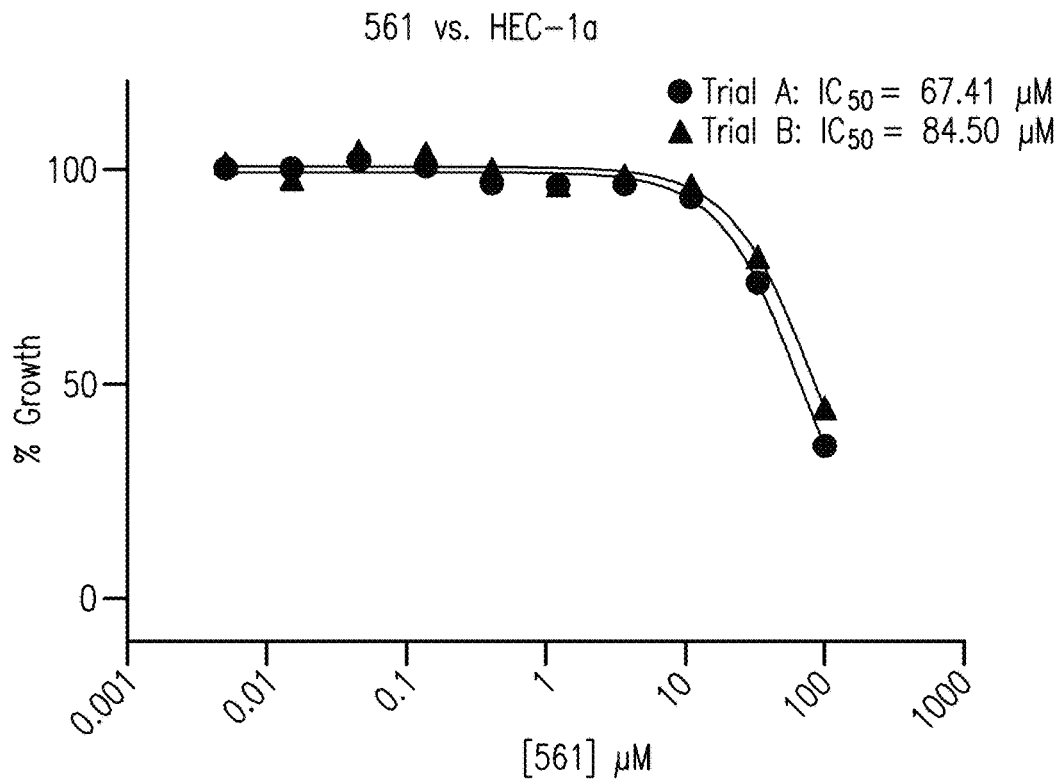
FIG. 91 is a graph illustrating cell growth as a function of the concentration of the 561 compound, in the HEC-1a cell proliferation assay described in Example 8.
Figure 92:
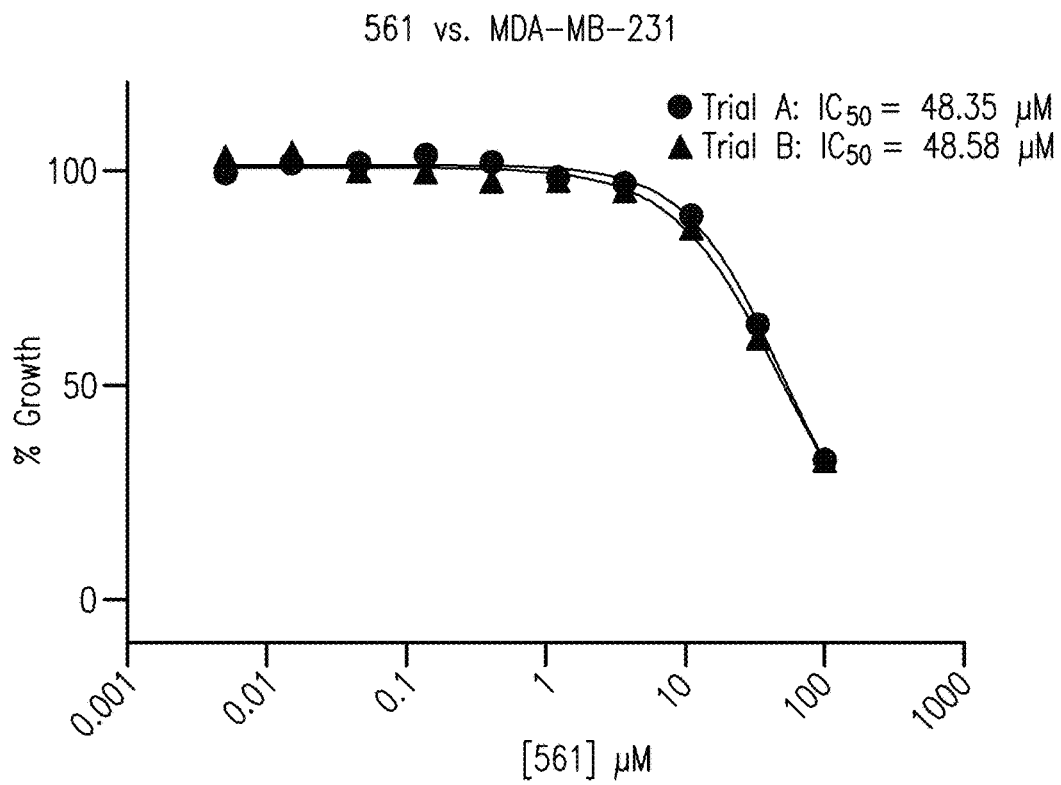
FIG. 92 is a graph illustrating cell growth as a function of the concentration of the 561 compound, in the MDA-MB-231 cell proliferation assay described in Example 8.
Figure 93:
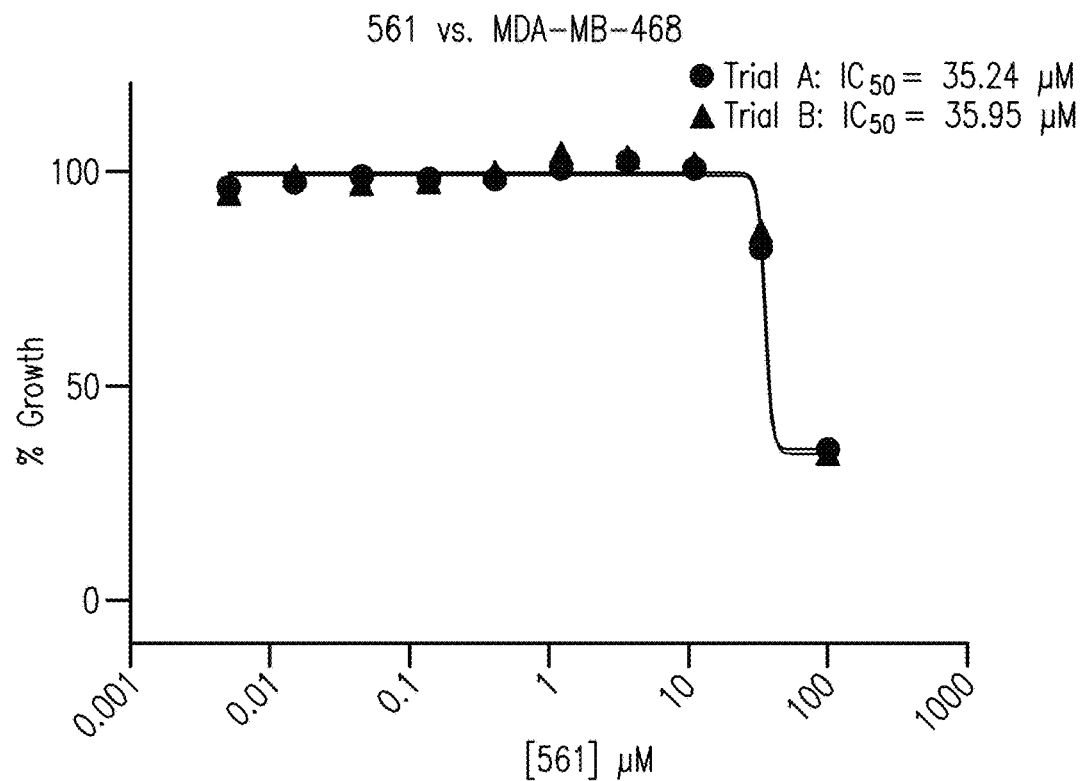
FIG. 93 is a graph illustrating cell growth as a function of the concentration of the 561 compound, in the MDA-MB-468 cell proliferation assay described in Example 8.
Figure 94:
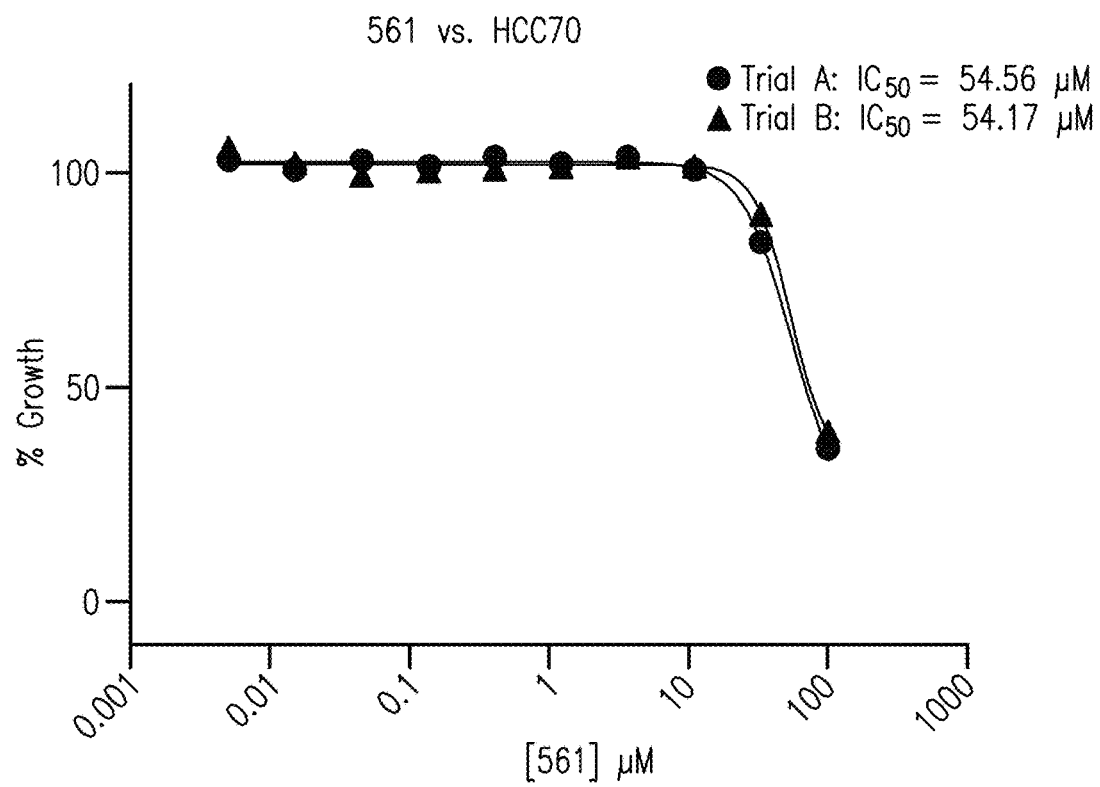
FIG. 94 is a graph illustrating cell growth as a function of the concentration of the 561 compound, in the HCC70 cell proliferation assay described in Example 8.
Figure 95:
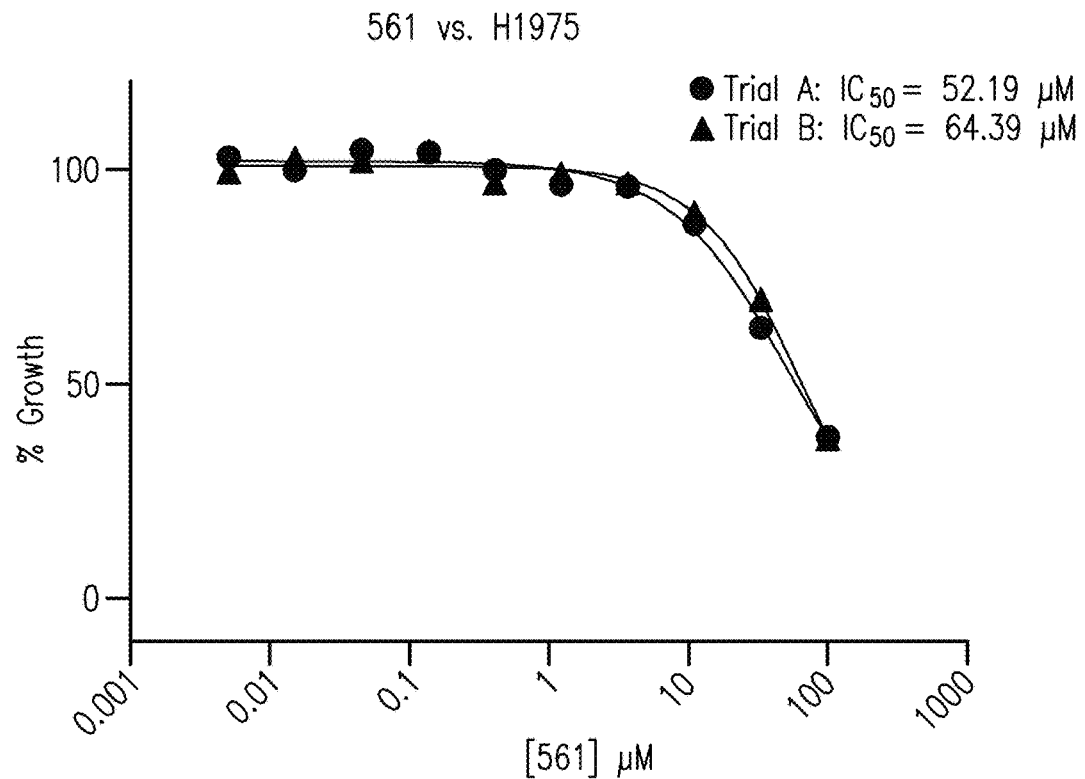
FIG. 95 is a graph illustrating cell growth as a function of the concentration of the 561 compound, in the H1975 cell proliferation assay described in Example 8.
Figure 96:
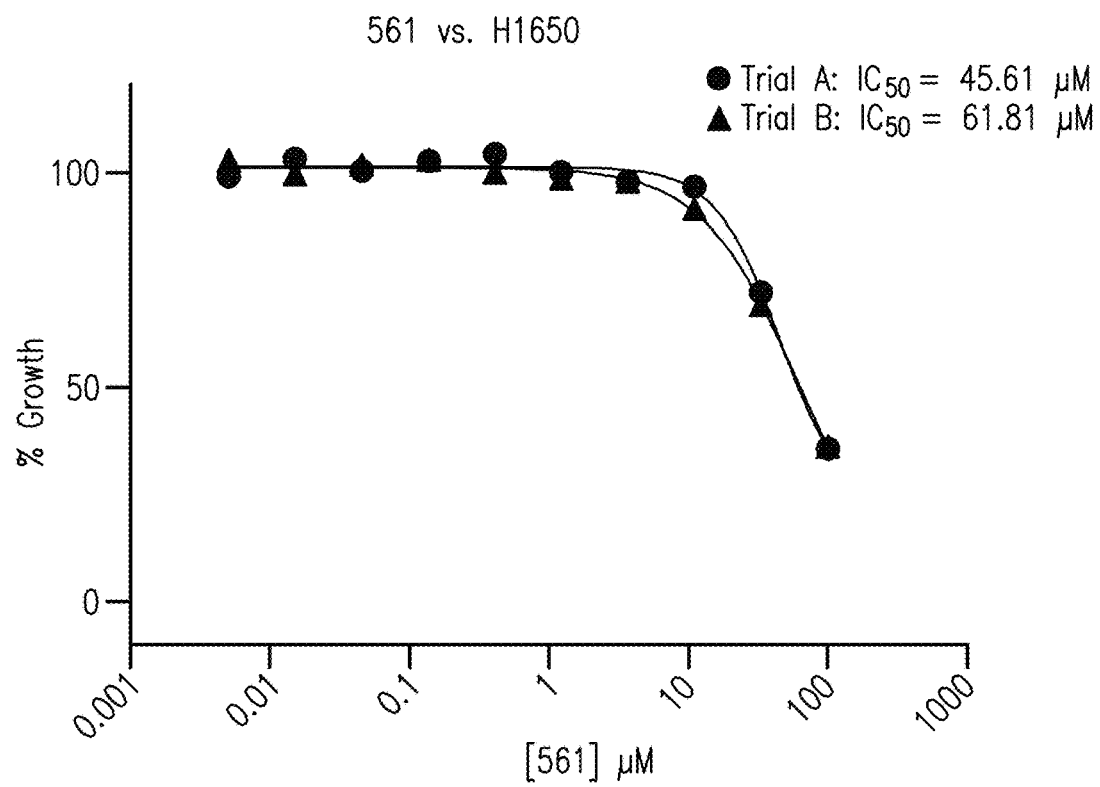
FIG. 96 is a graph illustrating cell growth as a function of the concentration of the 561 compound, in the H1650 cell proliferation assay described in Example 8.
Figure 97:
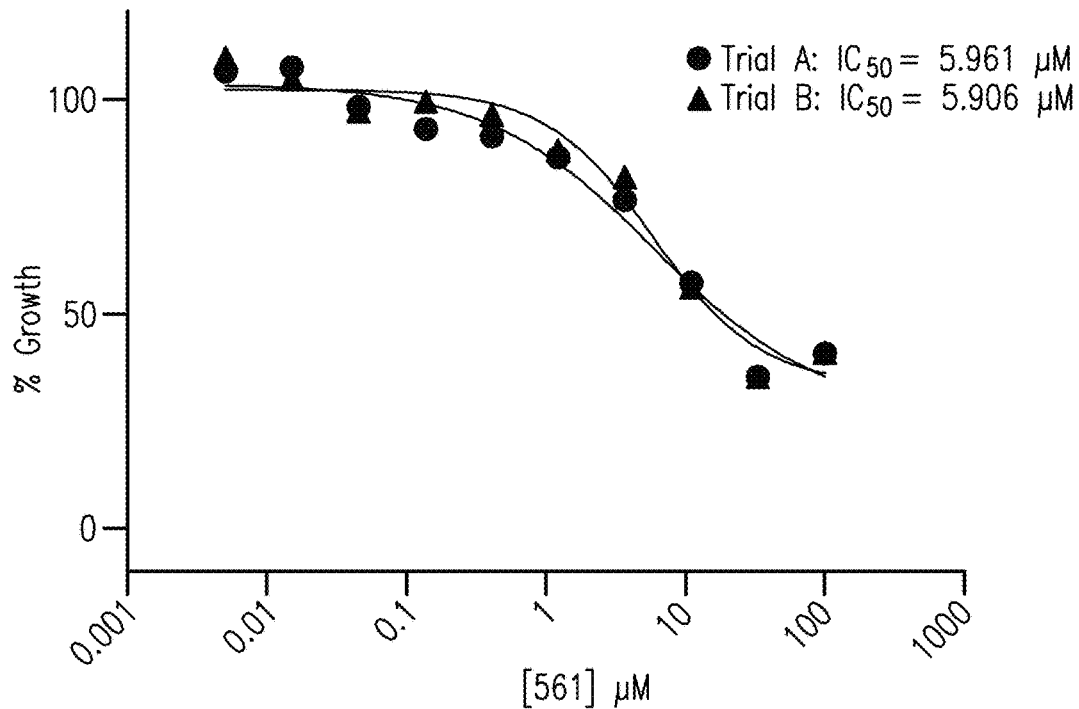
FIG. 97 is a graph illustrating cell growth as a function of the concentration of the 561 compound, in the A2780 cell proliferation assay described in Example 8.
Figure 98:
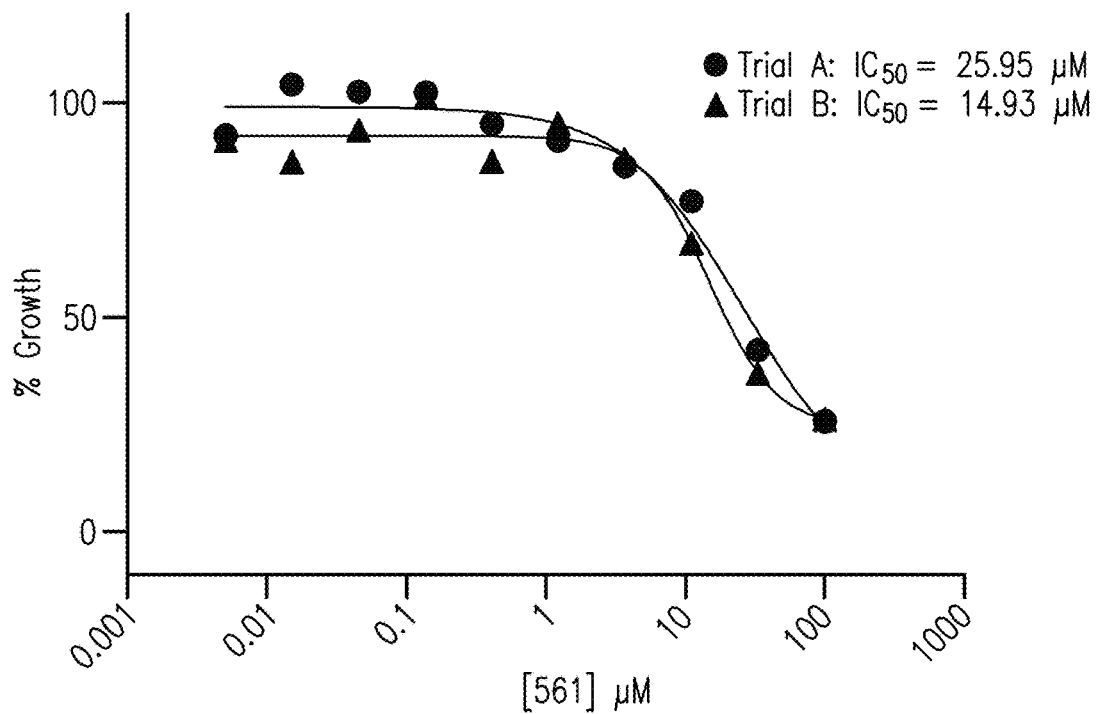
FIG. 98 is a graph illustrating cell growth as a function of the concentration of the 561 compound, in the A2780CP cell proliferation assay described in Example 8.
Figure 99:
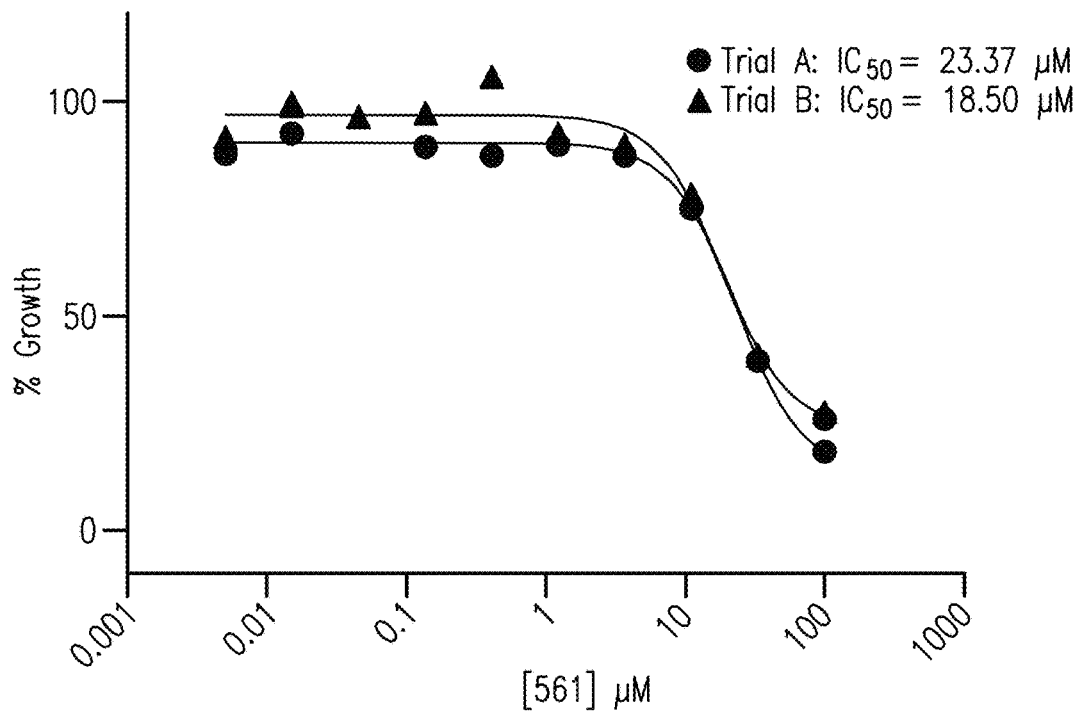
FIG. 99 is a graph illustrating cell growth as a function of the concentration of the 561 compound, in the RXF-393 cell proliferation assay described in Example 8.
Figure 100:
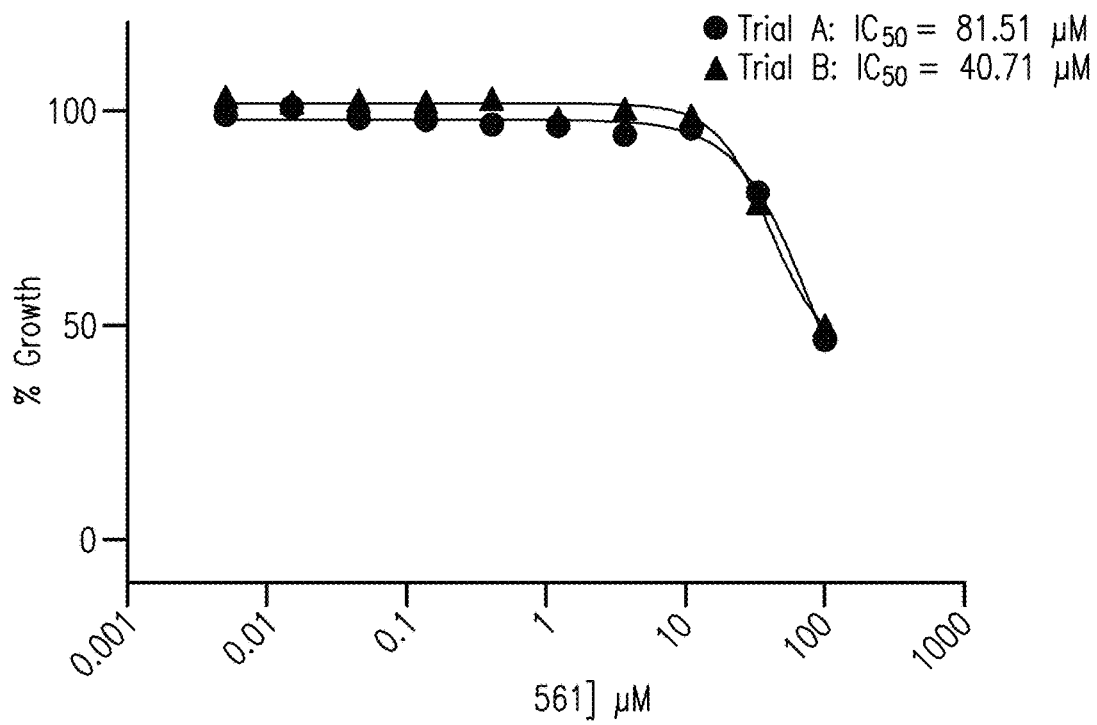
FIG. 100 is a graph illustrating cell growth as a function of the concentration of the 561 compound, in the A498 cell proliferation assay described in Example 8.
Figure 101:
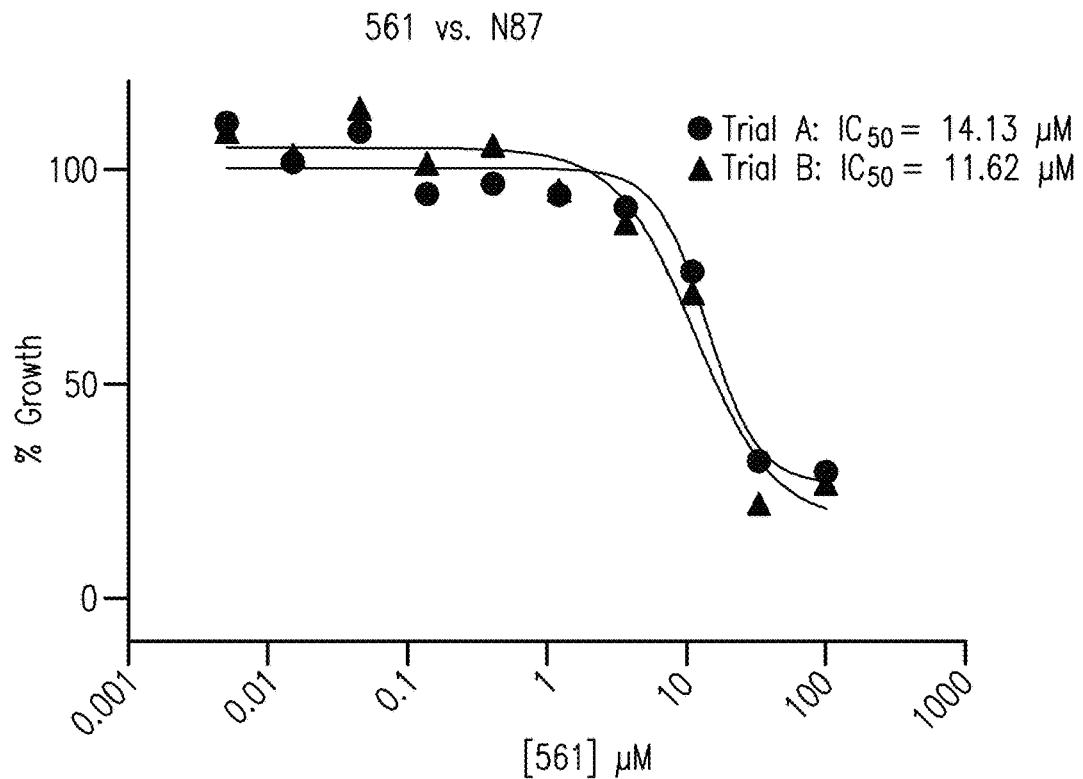
FIG. 101 is a graph illustrating cell growth as a function of the concentration of the 561 compound, in the N87 cell proliferation assay described in Example 8.
Figure 102:
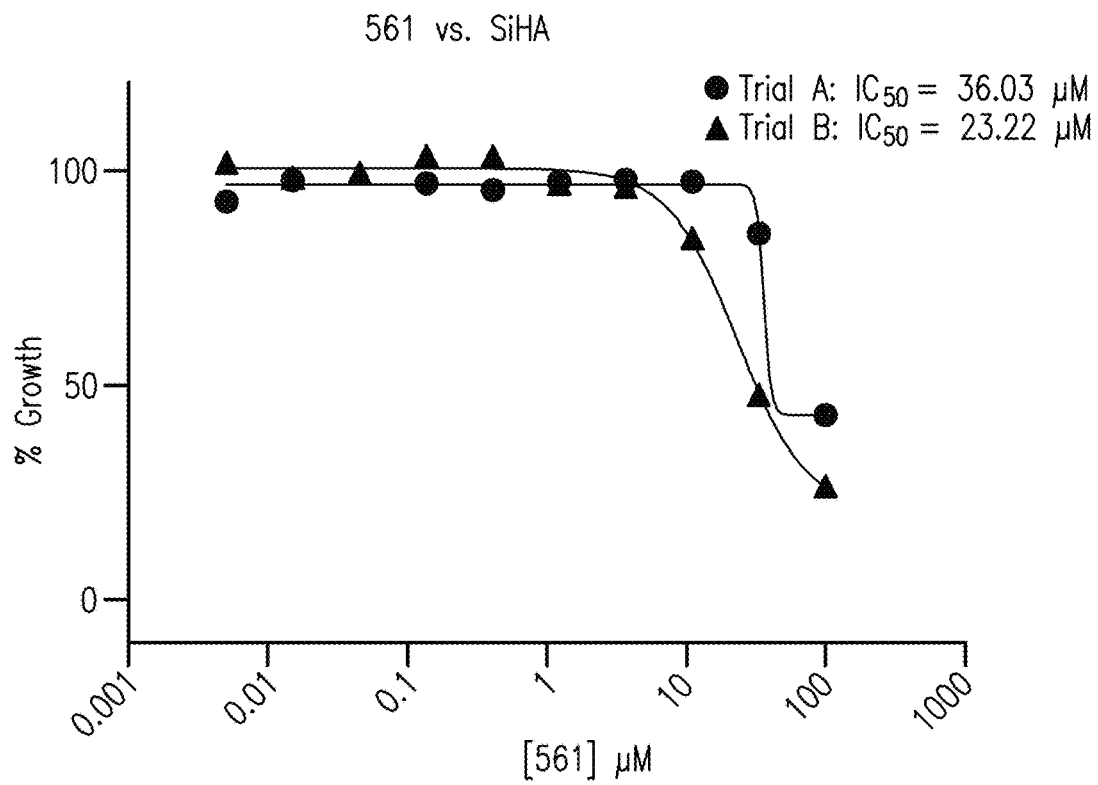
FIG. 102 is a graph illustrating cell growth as a function of the concentration of the 561 compound, in the SiHA cell proliferation assay described in Example 8.
Figure 103:
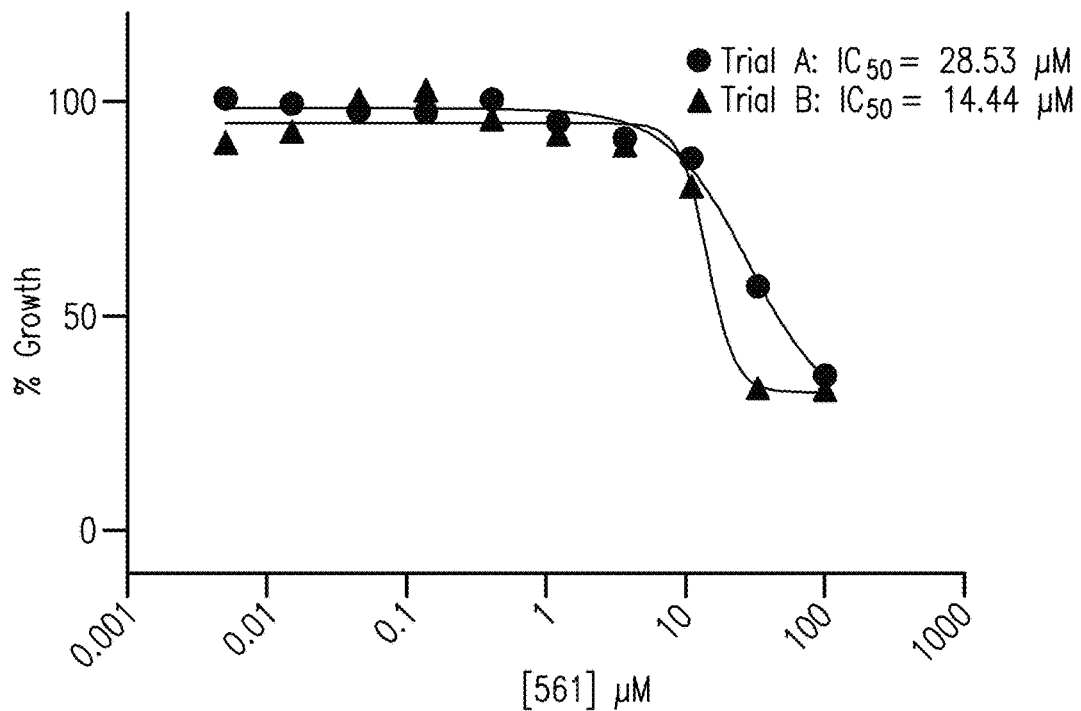
FIG. 103 is a graph illustrating cell growth as a function of the concentration of the 561 compound, in the FaDu cell proliferation assay described in Example 8.
Figure 104:
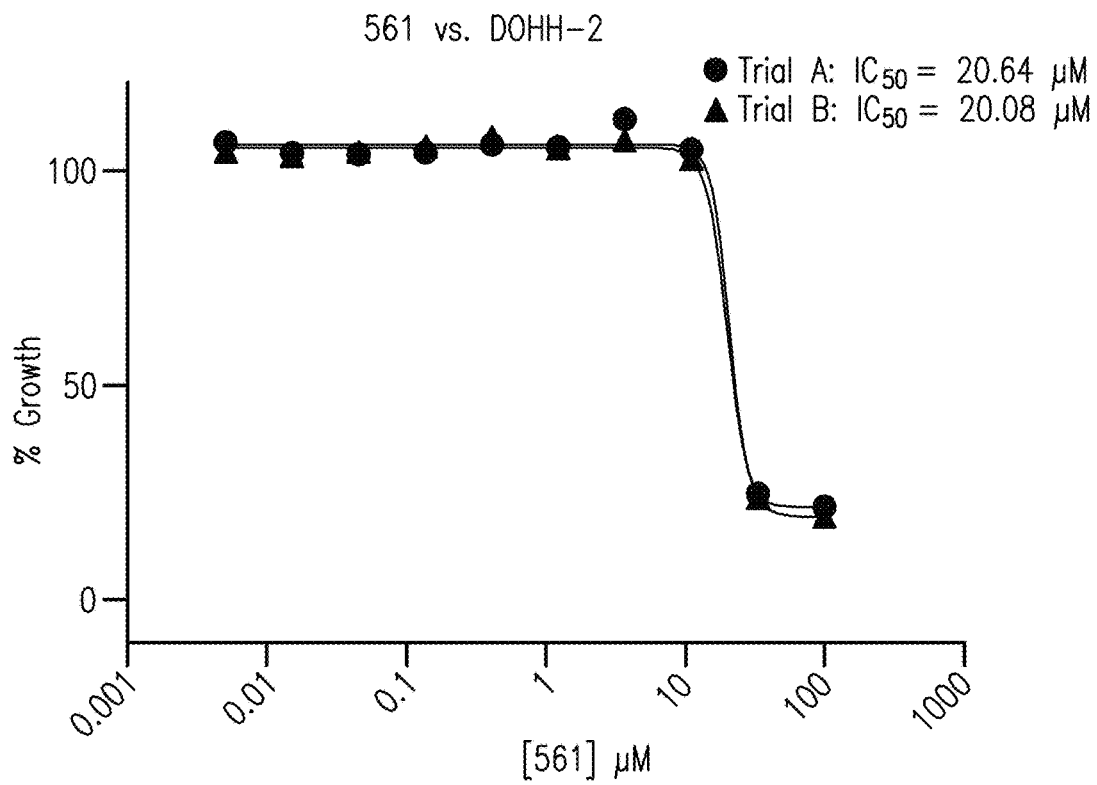
FIG. 104 is a graph illustrating cell growth as a function of the concentration of the 561 compound, in the DOHH-2 cell proliferation assay described in Example 8.
Figure 105:
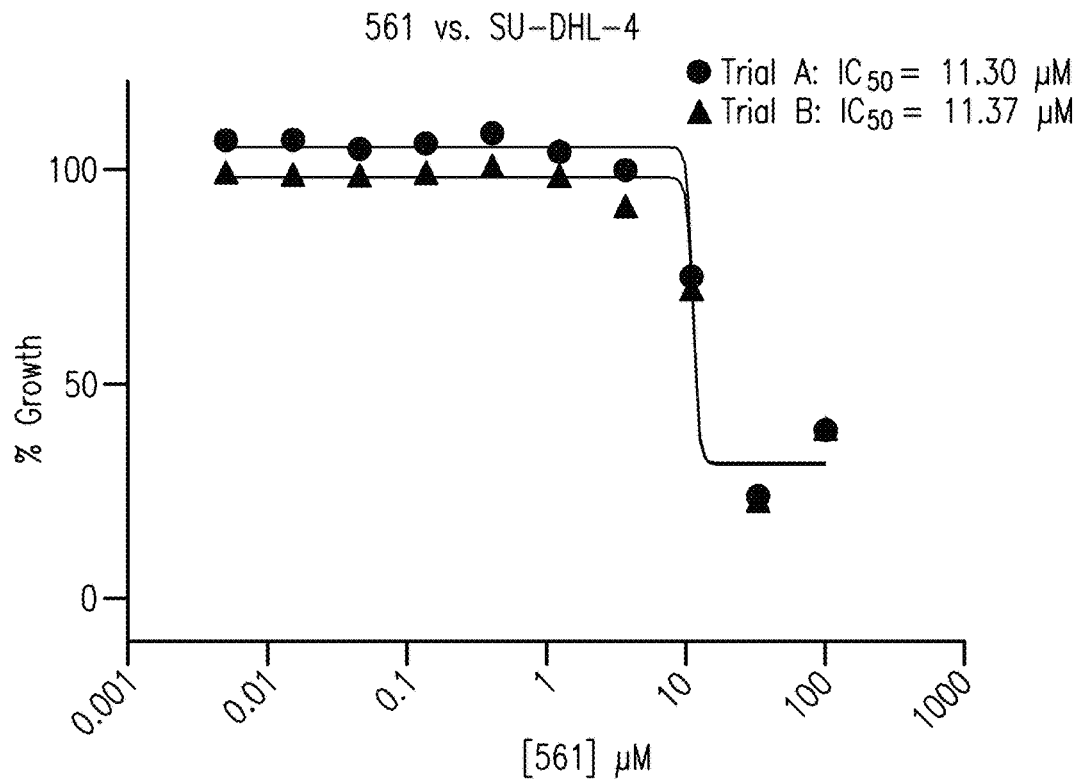
FIG. 105 is a graph illustrating cell growth as a function of the concentration of the 561 compound, in the SU-DHL-4 cell proliferation assay described in Example 8.
Figure 106:
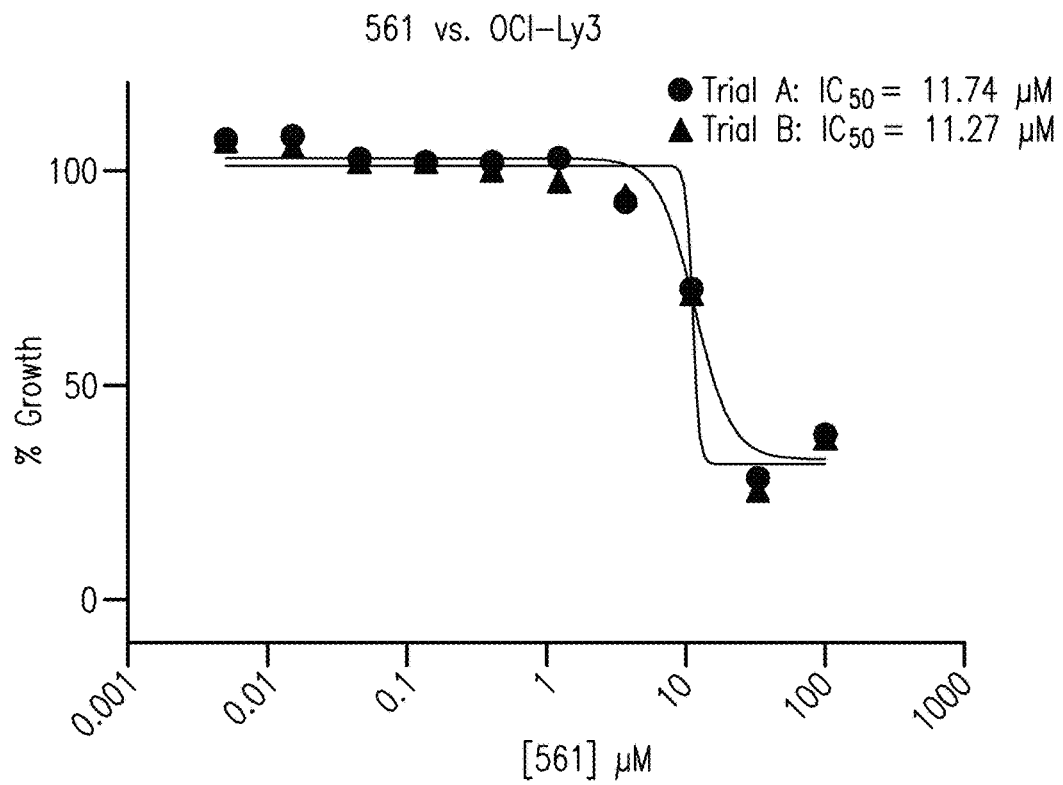
FIG. 106 is a graph illustrating cell growth as a function of the concentration of the 561 compound, in the OCI-LY3 cell proliferation assay described in Example 8.
Figure 107:
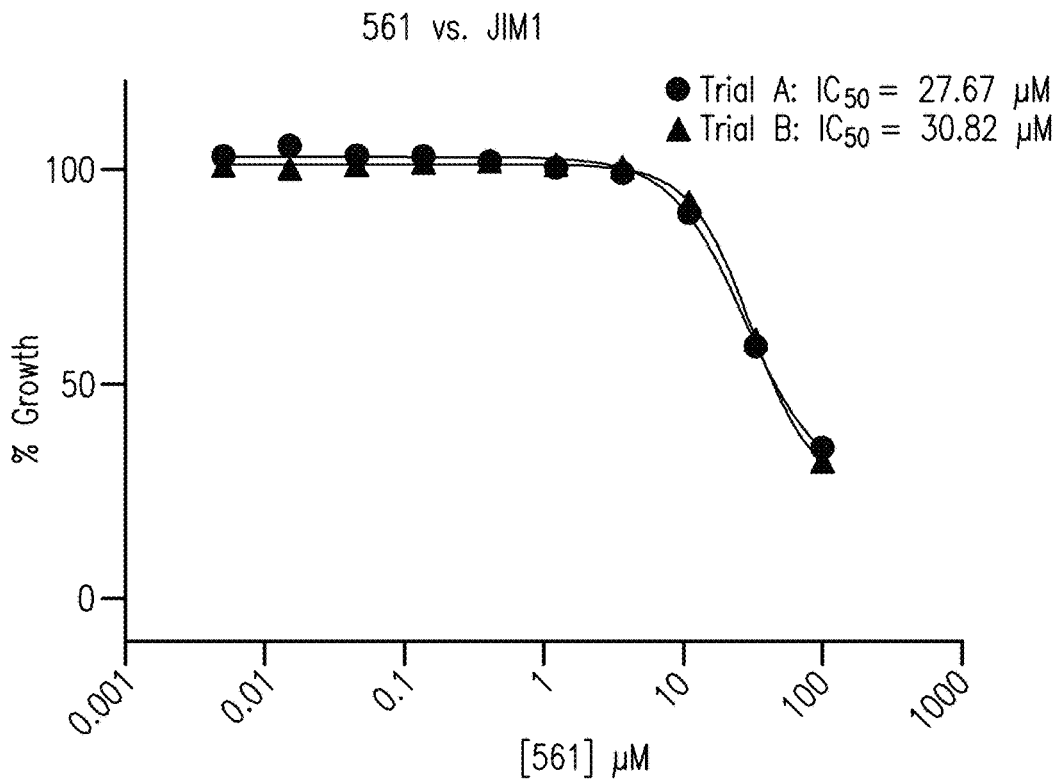
FIG. 107 is a graph illustrating cell growth as a function of the concentration of the 561 compound, in the JIM1 cell proliferation assay described in Example 8.
Figure 108:
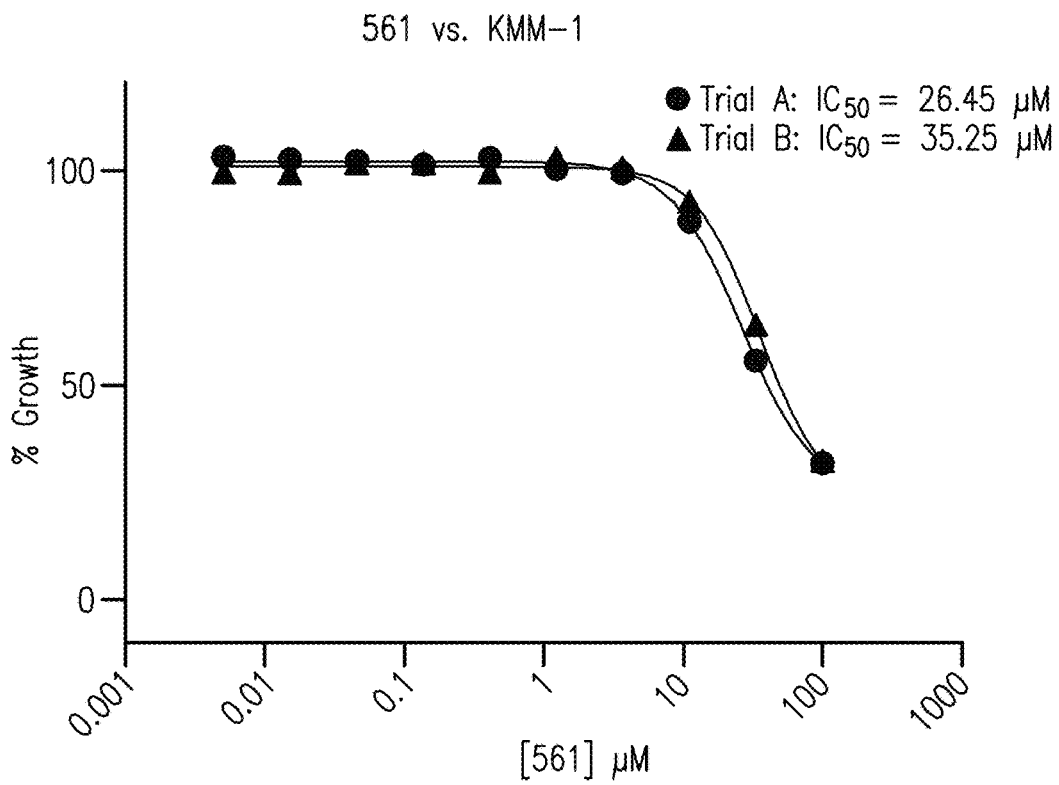
FIG. 108 is a graph illustrating cell growth as a function of the concentration of the 561 compound, in the KMM-1 cell proliferation assay described in Example 8.
Figure 109:
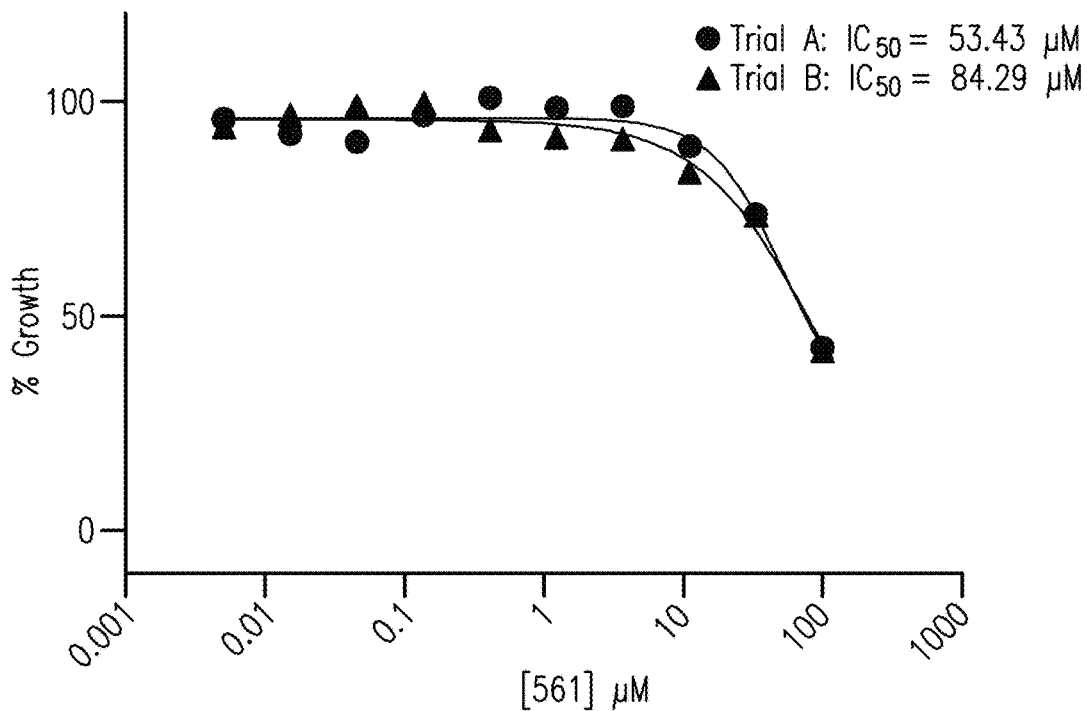
FIG. 109 is a graph illustrating cell growth as a function of the concentration of the 561 compound, in the KMS-11 cell proliferation assay described in Example 8.
Figure 110:
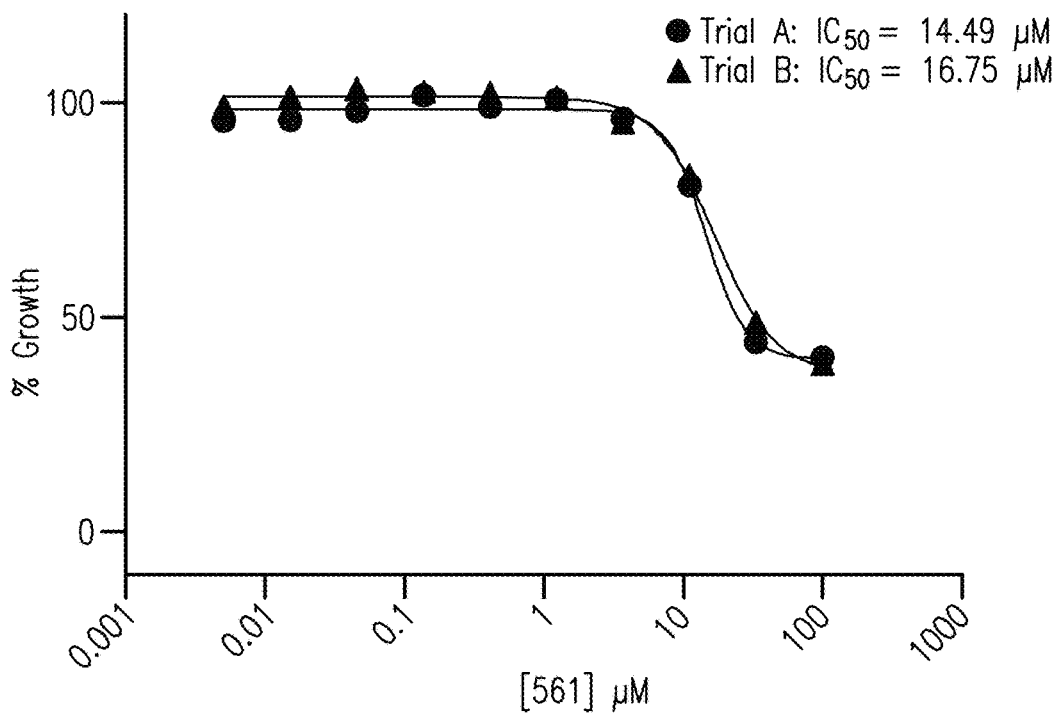
FIG. 110 is a graph illustrating cell growth as a function of the concentration of the 561 compound, in the KMS-27 cell proliferation assay described in Example 8.
Figure 111:
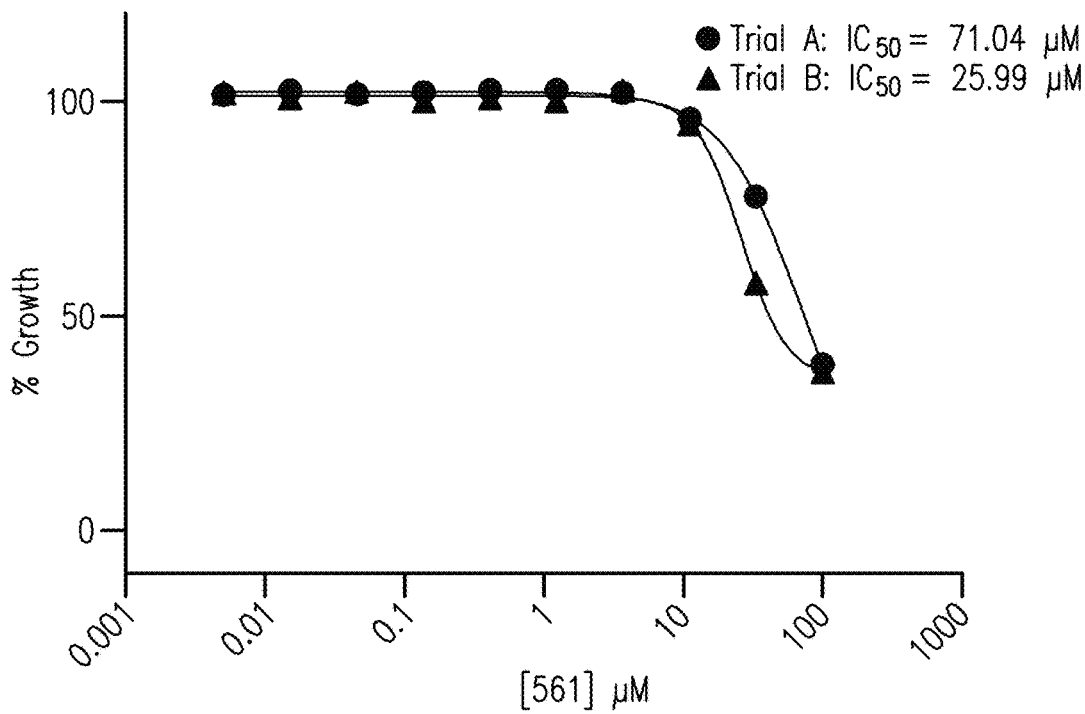
FIG. 111 is a graph illustrating cell growth as a function of the concentration of the 561 compound, in the KMS-34 cell proliferation assay described in Example 8.
Figure 112:
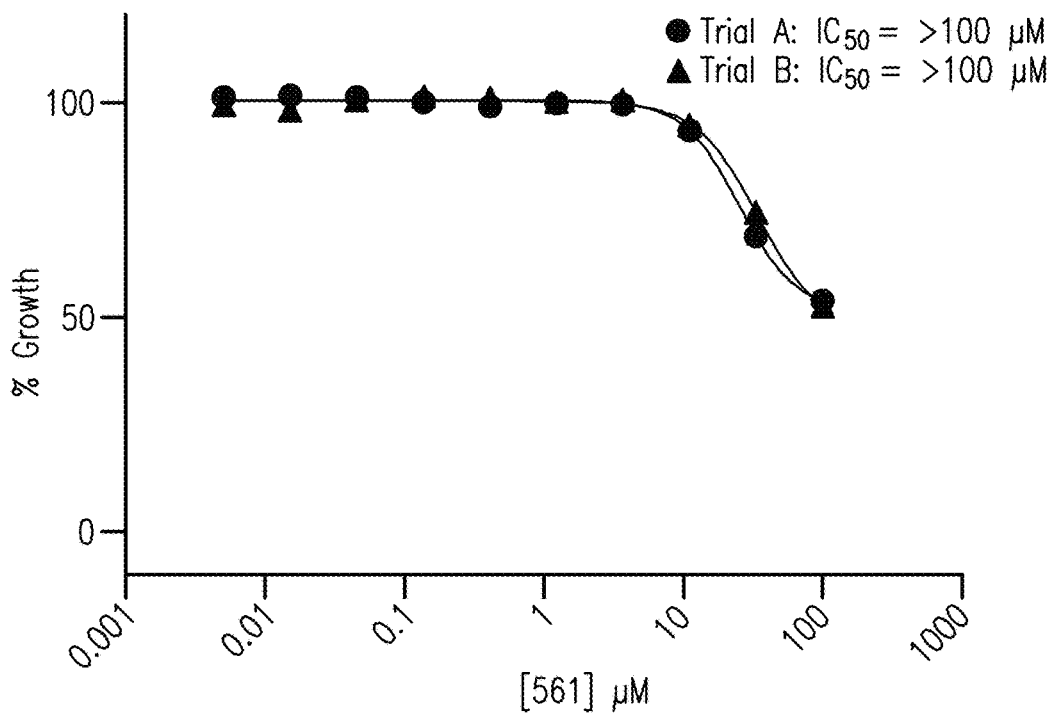
FIG. 112 is a graph illustrating cell growth as a function of the concentration of the 561 compound, in the H929 cell proliferation assay described in Example 8.
Figure 113:
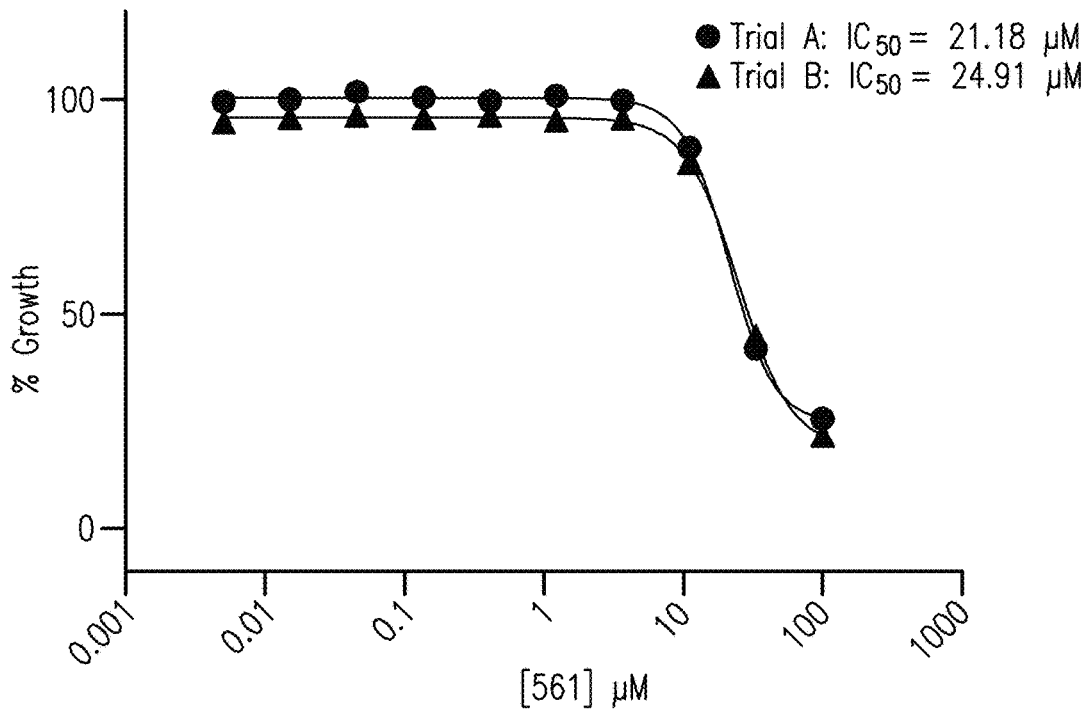
FIG. 113 is a graph illustrating cell growth as a function of the concentration of the 561 compound, in the L363 cell proliferation assay described in Example 8.
Figure 114:
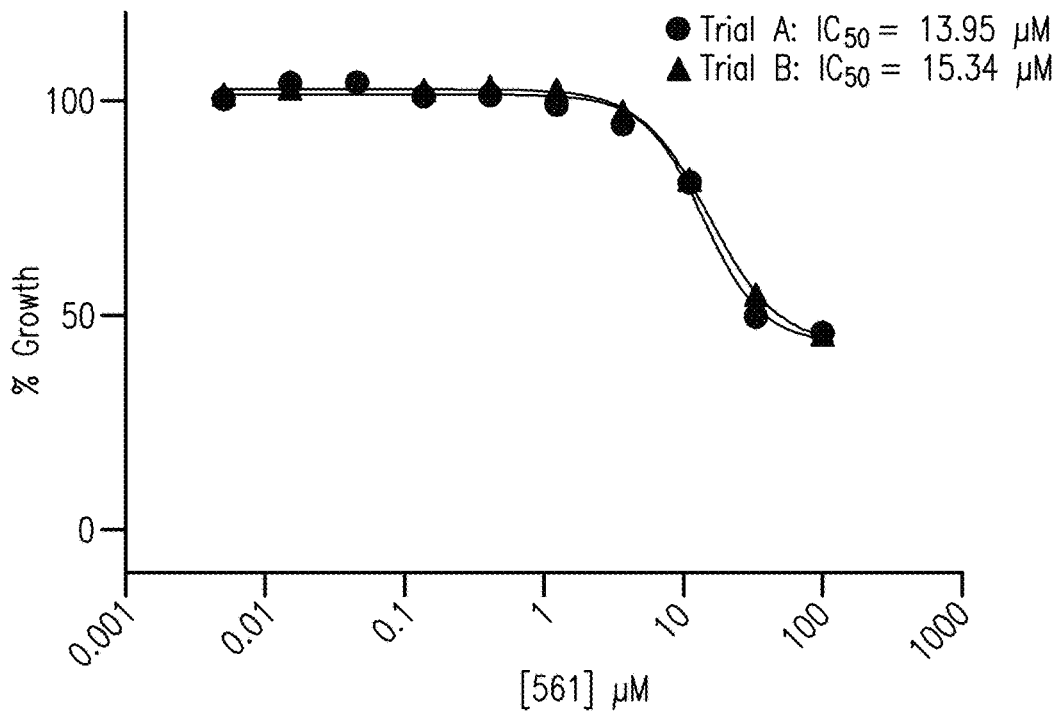
FIG. 114 is a graph illustrating cell growth as a function of the concentration of the 561 compound, in the MM.1s cell proliferation assay described in Example 8.
Figure 115:
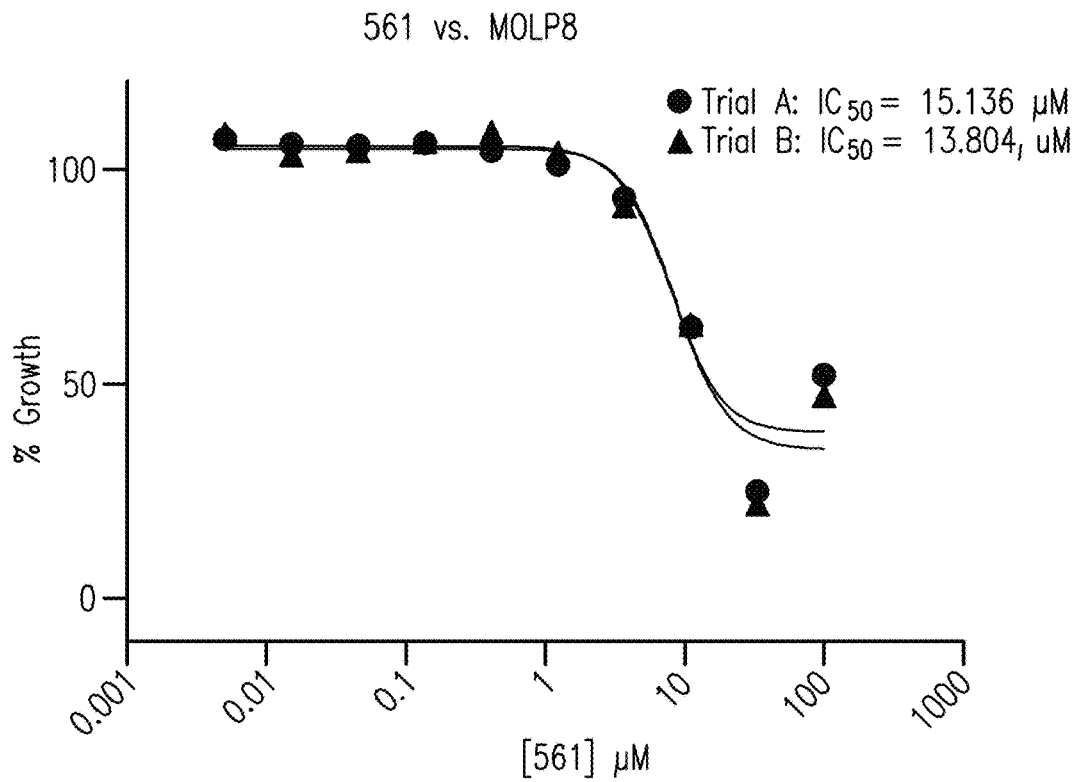
FIG. 115 is a graph illustrating cell growth as a function of the concentration of the 561 compound, in the MOLP-8 cell proliferation assay described in Example 8.
Figure 116:
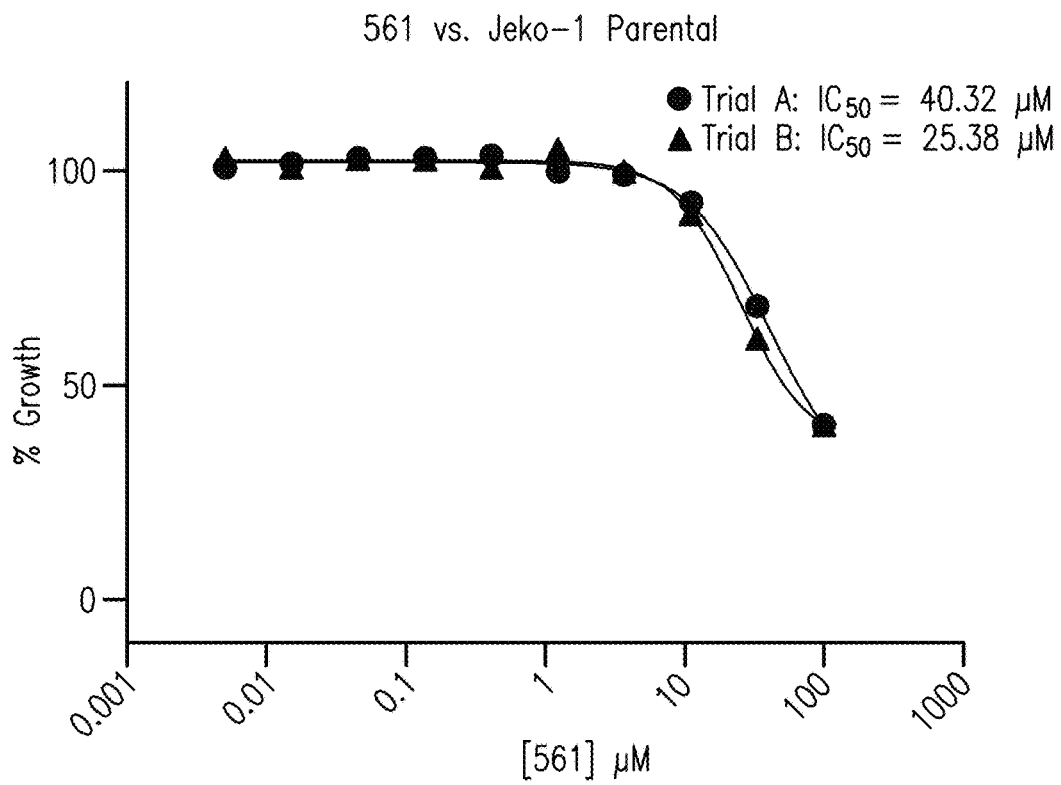
FIG. 116 is a graph illustrating cell growth as a function of the concentration of the 561 compound, in the Jeko-1 Parental cell proliferation assay described in Example 8.
Figure 117:
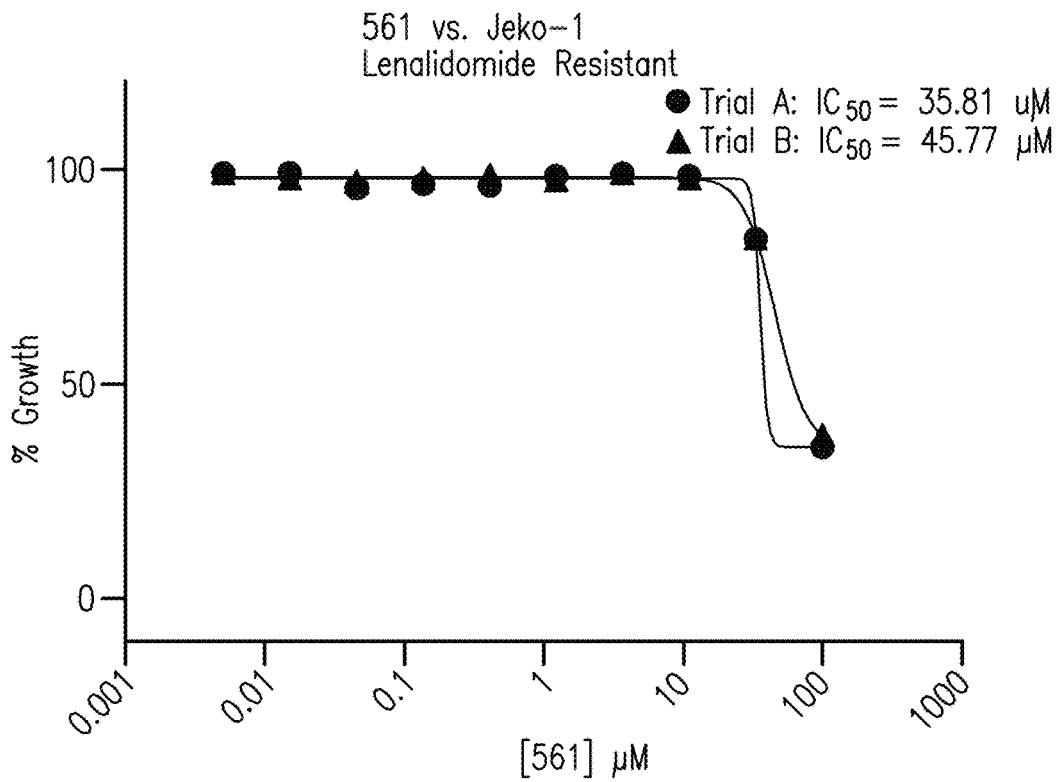
FIG. 117 is a graph illustrating cell growth as a function of the concentration of the 561 compound, in the Jeko-1 Lenalidomine Resistant cell proliferation assay described in Example 8.
Figure 118:
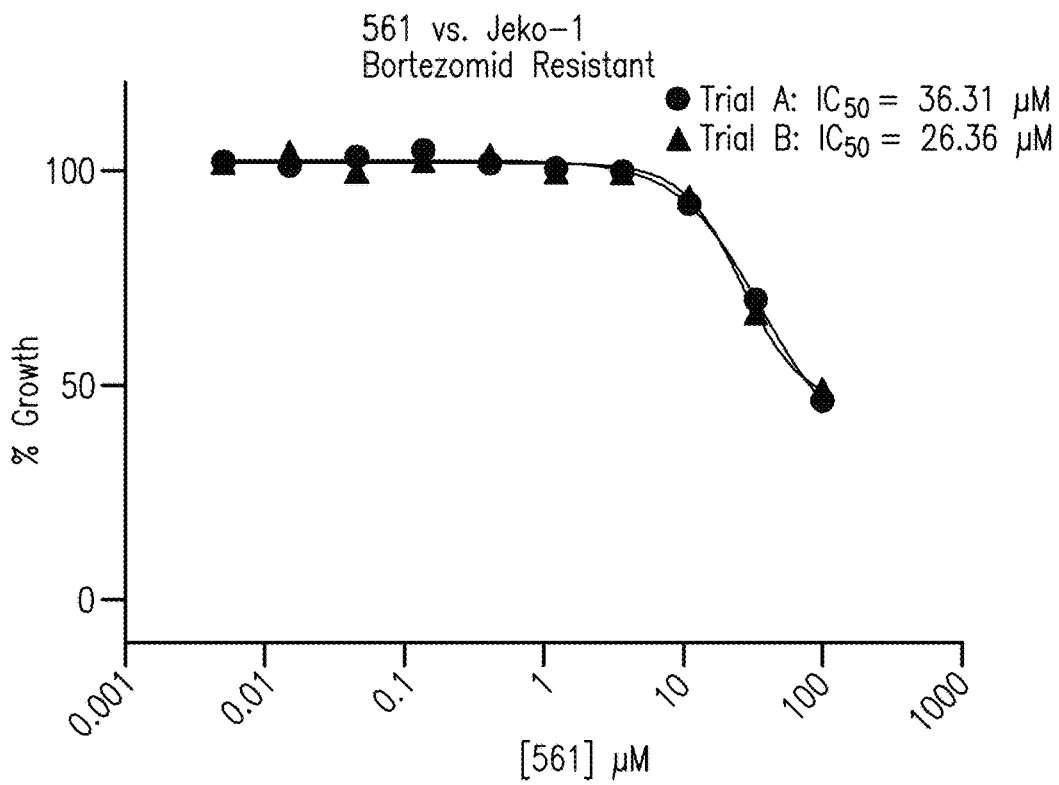
FIG. 118 is a graph illustrating cell growth as a function of the concentration of the 561 compound, in the Jeko-1 Bortezomib Resistant cell proliferation assay described in Example 8.

A Caspace 3/7 assay was performed by induction of apoptosis using a luminescence-based Caspace cleavage assay. Cells were plated at 10,000 cells per well and exposed to 20 µg/mL of GZ523.006 for 48 hours. Caspace activation was measured using the Caspace-Glo 3/7 assay (Promega), and compared with vehicle control exposures. Caspace activation was measured with triplicate technical replicates and duplicate experimental replicates using a luminescence plate reader. These test results are summarized in FIG. 22, where Bar 1 is the control and Bar 2 is treated cells. The error bars represent standard error of the mean values. These tests confirm that GZ523.006 exhibits cytotoxic properties against lymphoma cell lines to the induction of apoptosis. Mantle cell lymphoma cell lines exhibited the highest resistance, while Diffuse Large B-Cell Lymphomas of the Germinal Center B-Cell-like subtype exhibited the greatest sensitivity.

Example 7

1 Objective

The objective of this study was to determine the maximum tolerated dose and potential toxicity of GZ523.010 following 7 days of daily oral administration in CD1 mice. GZ523.010 was prepared by mixing 2433 mg orthovanillin, 1217 mg harmaline, and 5 mL of ethanol. This mixture was then sonicated at 35° C. for one hour to assure complete mixing, and was then allowed to stand for 24 hours at room temperature.

2 Study Overview

There were four dose groups consisting of a vehicle control group and 3 dose groups for 7 days of repeated oral gavage dosing with 10 mice/sex/group. Animals were dosed once daily with GZ523.010 and euthanized on study Day 8. All animals were observed daily for any clinical signs after dose administration. Gross necropsy was conducted for each animal and clinical pathology was performed for all available samples at termination. The first day of dosing was defined as study Day 1. The study design and variables evaluated are presented in Table 4 and Table 5.

TABLE 4

Study Design

| Group | No. of Animals | Test Article | Dose Level (mg/kg) | Dose Volume (mL/kg) | Dose Route/Frequency |
|---|---|---|---|---|---|
| 1 (Control) | 10/sex | Vehicle | 0 | 20 | Oral Gavage/Once daily for 7 days |
| 2 (Low) | 10/sex | GZ523.010 | 50 | 20 | |
| 3 (Mid) | 10/sex | GZ523.010 | 100 | 20 | |
| 4 (High) | 10/sex | GZ523.010 | 300 | 20 | |

TABLE 5

Variables Evaluated and Intervals

| Parameters | Intervals |
|---|---|
| Mortality Observation | Twice daily |
| Physical Examination | Once during acclimation |
| Body Weight | Daily |
| Food Consumption | Daily (group average) |
| Clinical Observations | Twice daily |
| Clinical pathology | Hematology, coagulation & serum chemistry for three available animals from each gender per group |
| Gross necropsy | All animals with full list of tissues reserved for future analysis |

3 Materials and Methods 3.1 GZ523.010

| Test/Control Article Name: | GZ523.010 | Distilled Water |
|---|---|---|
| Lot/Batch No: | 20160530.1500 | S1277 |
| Storage Condition: | 4-8° C. | Room temperature |
| Manufacturer: | NA (sponsor provided) | Southern Beverage Packers |
| Components: | 730 mg/mL GZ523.010 in ethanol | water |

3.2 Test System 3.2.1 Animals, Housing, and Environmental Conditions

| Species/Strain: | *Mus Musculus*, CD-1 mice |
|---|---|
| Source: | Charles River |
| Number and Gender: | 40 male and 40 female |
| Age: | 7.6 weeks at dose initiation |
| Weight Range (Day −1): | 21.1-33.6 g at dose initiation |
| Identification: | Ear notch and cage card |
| Acclimation: | 8 days |
| Caging: | polycarbonate shoebox cages |
| Number Per Cage: | 2-3 |
| Environmental Conditions: | Temperature: 20-28° C. (68-82.4° F.) |
| Photoperiod: | 12 hours light/12 hours dark |
| Medication: | No additional medication |
| Randomization: | Randomized per body weight within gender |

3.2.2 Diet and Water

| Diet: | Type | Rodent pellet diet |
|---|---|---|
| | Name | Harlan rodent diet certified, lot#: 012816MA |
| | Availability | ad libitum |
| Water: | Sources | Standard facility deep well |
| | Availability | ad libitum via Lixit |
| | Analysis for Contaminants | No coliform bacteria, *E. coli*, or heavy metals reported |
| Comments | | No contaminants were detected in the water at levels that would be expected to interfere with study results. |

3.3 Dose Procedure

All animals were dosed via oral gavage once daily for 7 days according to Table 4. The dose volume was calculated based on the most recent body weights. Food and water were provided during the entire study period.

3.4 Mortality/Moribundity

General in-cage observations for mortality/moribundity were made twice daily.

3.5 Physical Examinations

All study animals were given physical examinations by qualified personnel once during acclimation to determine study eligibility, and again prior to termination. Examinations included, but were not limited to, examination of the skin and external ears, eyes, abdomen, neurological, behavior, and general body condition.

3.6 Clinical Observations

Detailed clinical observations were performed twice daily. The animals were observed for any signs of illness or reaction to treatment. Records of appearance, change, or disappearance of clinical signs were maintained on clinical observation sheets for each individual observation time point.

3.7 Body Weights and Food Consumption

All study animals were weighed daily during Day −1 through termination on Day 8. Group average food consumption was recorded daily from Day −1 through Day 7.

3.8 Termination and Necropsy

All animals were euthanized with CO2 at termination. Necropsy was performed on each animal and all designated issues/organs were collected for future potential analysis. The following tissues (when present), except testes and eyes, were preserved in 10% neutral-buffered formalin. Testes were fixed in modified Davidson's solution and eyes in Davidson's solution. Collected tissues were preserved for further evaluation.

| | |
|---|---|
| adrenal (2) | ovary (2) |
| aorta | pancreas |
| bone (femur & sternum with marrow) | pituitary gland |
| brain (cerebellum, cerebrum, pons) | prostate |
| cecum | rectum |
| colon | salivary gland [mandibular (2)] |
| duodenum | sciatic nerve |
| epididymis (2) | seminal vesicles |
| esophagus | skeletal muscle (quadriceps femoris) |
| eyes, (including optic nerve) | skin on abdominal region |
| heart | spinal cord (cervical, thoracic, lumbar) |
| ileum | spleen |
| jejunum | Sternum with bone marrow |
| kidney (2) | stomach |
| lesions* | testes (2) |
| liver | thymus |
| lung with main stem bronchi | thyroid (2) (parathyroid) |
| lymph nodes (mandibular) | trachea |
| lymph node (cover dose site) | urinary bladder |
| mammary gland (females) | uterus (+cervix + oviducts) & vagina |

*Gross lesions were collected at the discretion of the personnel conducting the necropsy.

3.9 Clinical Pathology

Clinical pathology was performed at termination. The clinical pathology analysis was performed on all designated animals that were euthanized on schedule. Animals were food fast overnight.

Serum Chemistry: Blood samples when available (~0.5 mL) were collected from three study animals per gender from each group, and allowed to clot for 15 minutes in room temperature. No anticoagulant was used. Serum samples were prepared by centrifuging at 3000 RPM for ~15 minutes. The serum chemistry includes with priority (√). When a sample was insufficient for analysis, several samples from same group were pooled together:

| | |
|---|---|
| Alanine aminotransferase (ALT) √ | Creatinine √ |
| | Creatine Kinase √ |
| Albumin √ | Globulin |
| Alkaline Phosphatase (ALP) √ | Glucose |
| Aspartate Aminotransferase (AST) √ | Inorganic Phosphorus |
| Gamma Glutamyltransferase (GGT) | Potassium √ |
| Blood Urea Nitrogen (BUN) √ | Sodium √ |
| Calcium | Total Bilirubin |
| Chloride | Total Protein |
| Cholesterol | Triglycerides |

Coagulation: Blood samples (~0.4 mL/animal) when available were collected from three study animals per gender from each group. Sodium citrate (3.2%) was used as the anticoagulant. Plasma was prepared by centrifuging for approximately 15 minutes at 3000 rpm at 4° C. The blood coagulation analysis included, but was not limited to:

| | |
|---|---|
| Activated Partial Thromboplastin Time (APTT) | Prothrombin Time (PT) |

Hematology Analysis: Blood samples when available (~0.4 mL) were collected from three study animals per gender from each group. K3-EDTA was used as anticoagulant. The hematology analysis includes (with priority (l)):

| | |
|---|---|
| White Blood Cell Count √ | Differential White Blood Cell Count |
| Red Blood Cell Count √ | Neutrophils (% and absolute) |
| RDW (Red Cell Distribution Width) √ | Eosinophils (% and absolute) |
| Hemoglobin√ | |
| Hematocrit√ | Basophils (% and absolute) |
| Mean Cell Volume √ | Lymphocytes (% and absolute) √ |
| Mean Cell Hemoglobin √ | Monocytes (% and absolute) √ |
| Mean Cell Hemoglobin Concentration √ | Platelet Count √ |
| | MPV (mean platelet volume) √ |

4 Results

4.1 Dose Administration

The dose administrations are summarized in Table 6. All study animals were successfully administered with the target amount of vehicle or test article formulation. All dose formulations were prepared prior to dose administration. Before preparing the dose formulation, it was observed that the stock test article (730 mg/mL) was not a uniform consistency. Therefore, a dose concentration of 100 mg/mL was not able to be formulated due to large amount of precipitates. The protocol was amended to decrease the dose concentration. The stock formulation was warmed to room temperature and rigorously agitated with sonication to reach a uniform (mud like) consistency. This was then diluted to 73 mg/mL with ethanol (secondary stock). The secondary stock was used to prepare each final dose formulation. The final consistency of dose formulation appeared to be a suspension and was mixed thoroughly before dosing.

TABLE 6

Summary Dose Administration-Actual Dose Level

| | Male | | | | Female | | | |
|---|---|---|---|---|---|---|---|---|
| Group | 1 | 2 | 3 | 4 | 1 | 2 | 3 | 4 |
| Dose Level (mg/kg/day) | 0 (Vehicle) | 50 (Low) | 100 (Mid) | 300 (High) | 0 (Vehicle) | 50 (Low) | 100 (Mid) | 300 (High) |
| N | 10 | 11 | 10 | 10 | 10/9[a] | 9[b] | 10 | 10 |
| Day 1 | 0 | 50.0 | 99.5 | 291.6 | 0 | 50.0 | 100.8 | 298.9 |
| Day 2 | 0 | 51.5 | 122.5 | 311.4 | 0 | 38.9 | 94.6 | 241.8 |
| Day 3 | 0 | 49.9 | 99.6 | 300.4 | 0 | 50.4 | 101.0 | 293.2 |
| Day 4 | 0 | 50.9 | 98.9 | 304.3 | 0 | 50.9 | 99.8 | 289.9 |
| Day 5 | 0 | 50.2 | 101.6 | 296.9 | 0 | 50.6 | 100.0 | 298.1 |
| Day 6 | 0 | 49.5 | 100.7 | 294.3 | 0 | 50.4 | 99.8 | 292.7 |
| Day 7 | 0 | 49.4 | 100.4 | 293.2 | 0 | 51.3 | 98.9 | 298.9 |
| Mean | 0 | 50.2 | 103.3 | 298.9 | 0 | 48.9 | 99.3 | 287.6 |

[a] One mouse (1F17:12-0) was euthanized prior to dose on day 6 due to tail injury;
[b] One mouse was identified to be male at termination (suspected to be misidentified at shipping).

4.2 Mortality/Moribundity

There were no observed instances of mortality or significant moribundity during the study period.

4.3 Physical Examinations

All study animals underwent physical examinations by a veterinarian once during acclimation and again prior to termination. All animals were generally healthy and deemed suitable for study inclusion.

4.4 Clinical Observations

Clinical observation findings are listed in Table 7. There were no test article-related findings during the exposure period following daily oral gavage dose administration.

TABLE 7

Group Summary Clinical Observation Findings

| Study ID | Animal ID | Study Day | AM/PM | Clinical Observations |
|---|---|---|---|---|
| 1F17 | 12-0 | 6 | AM & PM | Animal found with slough tail, ~0.5 inch of tail was de-gloved; animal was euthanized |
| 3M6 | 37-1 | 7 | PM | Small laceration, tail tip |
| 4M10 | 40-1 | 4 | PM | Bottom right tooth broken |
| 4M10 | 40-1 | 5 | AM & PM | Broken right bottom incisor |

4.5 Body Weights

Group summary body weight and weight change results are presented in Tables 8 and 9. Over the course of the study, most study animals generally gained weight, especially for males. The weights of females retained or slightly decreased and there were no remarkable differences among groups.

TABLE 8

Group Summary Body Weight Results (g)

| | | | Male | | | | Female | | | |
|---|---|---|---|---|---|---|---|---|---|---|
| | | Group | 1 | 2 | 3 | 4 | 1 | 2 | 3 | 4 |
| | | Dose Level (mg/kg/day) | 0 (Veh) | 50 (Low) | 100 (Mid) | 300 (High) | 0 (Veh) | 50 (Low) | 100 (Mid) | 300 (High) |
| | | N | 10 | 11 | 10 | 10 | 10/9 | 9 | 10 | 10 |
| Day (−1) | Mean | | 30.5 | 30.0 | 29.1 | 28.8 | 25.9 | 25.1 | 25.8 | 25.0 |
| | SD | | 1.8 | 1.9 | 2.1 | 2.2 | 1.0 | 1.2 | 1.5 | 2.3 |
| Day 1 | Mean | | 24.0 | 29.2 | 23.7 | 27.9 | 25.9 | 32.2 | 26.4 | 31.0 |
| | SD | | 0.6 | 1.2 | 1.2 | 0.9 | 0.7 | 0.9 | 0.7 | 1.3 |

TABLE 8-continued

Group Summary Body Weight Results (g)

| | | Male | | | | Female | | | |
|---|---|---|---|---|---|---|---|---|---|
| | | Group | | | | | | | |
| | | 1 | 2 | 3 | 4 | 1 | 2 | 3 | 4 |
| | | Dose Level (mg/kg/day) | | | | | | | |
| | | 0 (Veh) | 50 (Low) | 100 (Mid) | 300 (High) | 0 (Veh) | 50 (Low) | 100 (Mid) | 300 (High) |
| | | N | | | | | | | |
| | | 10 | 11 | 10 | 10 | 10/9 | 9 | 10 | 10 |
| Day 2 | Mean | 31.3 | 30.0 | 29.1 | 29.5 | 25.7 | 24.3 | 25.3 | 25.1 |
| | SD | 2.0 | 2.3 | 2.2 | 2.3 | 1.4 | 1.2 | 1.7 | 2.4 |
| Day 3 | Mean | 30.9 | 31.0 | 29.8 | 29.6 | 25.5 | 24.7 | 25.6 | 24.9 |
| | SD | 2.1 | 2.5 | 2.0 | 2.6 | 1.3 | 1.2 | 1.5 | 2.2 |
| Day 4 | Mean | 31.1 | 31.4 | 30.0 | 29.4 | 25.6 | 24.8 | 25.5 | 25.1 |
| | SD | 2.0 | 2.3 | 2.3 | 2.5 | 1.1 | 1.4 | 1.6 | 2.4 |
| Day 5 | Mean | 31.5 | 31.9 | 30.3 | 29.6 | 25.9 | 24.8 | 26.1 | 25.1 |
| | SD | 2.0 | 2.6 | 2.3 | 2.7 | 1.1 | 1.2 | 1.8 | 2.4 |
| Day 6 | Mean | 31.4 | 31.8 | 30.4 | 29.7 | 25.7 | 24.5 | 25.8 | 25.1 |
| | SD | 2.3 | 2.6 | 2.2 | 2.7 | 1.4 | 1.3 | 1.5 | 2.2 |
| Day 7 | Mean | 31.7 | 32.0 | 30.6 | 29.6 | 25.7 | 24.8 | 25.7 | 25.1 |
| | SD | 2.1 | 2.4 | 2.1 | 2.9 | 1.4 | 1.4 | 1.3 | 2.2 |
| Day 8[b] | Mean | 28.5 | 28.4 | 27.3 | 27.2 | 23.4 | 22.1 | 23.3 | 23.1 |
| | SD | 1.0 | 2.3 | 2.3 | 2.4 | 1.4 | 1.2 | 1.3 | 2.0 |

[a] One mouse (1F17:12-0) was euthanized prior to dose on day 6 due to tail injury.
[b] Animals were fasted overnight.

TABLE 9

Group Summary Body Weight Change Results (g/day)

| | | Male | | | | Female | | | |
|---|---|---|---|---|---|---|---|---|---|
| | | Group | | | | | | | |
| | | 1 | 2 | 3 | 4 | 1 | 2 | 3 | 4 |
| | | Dose Level (mg/kg/day) | | | | | | | |
| | | 0 (Veh) | 50 (Low) | 100 (Mid) | 300 (High) | 0 (Veh) | 50 (Low) | 100 (Mid) | 300 (High) |
| | | N | | | | | | | |
| | | 10 | 11 | 10 | 10 | 10/9 | 9a | 10 | 10 |
| Day (−1 to 1) | Mean | −6.56 | −0.85 | −5.32 | −0.87 | 0.01 | 7.07 | 0.61 | 5.98 |
| | SD | 2.01 | 2.35 | 2.56 | 2.25 | 1.36 | 1.48 | 1.59 | 2.58 |
| Day 1 to 2 | Mean | 7.31 | 0.86 | 5.37 | 1.52 | −0.20 | −7.91 | −1.16 | −5.94 |
| | SD | 2.21 | 2.69 | 2.45 | 2.42 | 1.42 | 1.68 | 1.80 | 2.68 |
| Day 2 to 3 | Mean | −0.41 | 0.93 | 0.70 | 0.10 | −0.23 | 0.44 | 0.31 | −0.22 |
| | SD | 0.60 | 0.72 | 0.80 | 0.58 | 0.54 | 0.67 | 0.44 | 0.64 |
| Day 3 to 4 | Mean | 0.22 | 0.40 | 0.19 | −0.20 | 0.15 | 0.10 | −0.04 | 0.24 |
| | SD | 0.41 | 0.57 | 0.41 | 0.45 | 0.62 | 0.45 | 0.55 | 0.58 |
| Day 4 to 5 | Mean | 0.38 | 0.57 | 0.27 | 0.28 | 0.25 | 0.02 | 0.56 | 0.03 |
| | SD | 0.33 | 0.49 | 0.27 | 0.34 | 0.60 | 0.44 | 0.56 | 0.48 |
| Day 5 to 6 | Mean | −0.08 | −0.10 | 0.11 | 0.04 | −0.18 | −0.37 | −0.27 | 0.02 |
| | SD | 0.38 | 0.39 | 0.27 | 0.41 | 0.55 | 1.01 | 0.88 | 0.72 |
| Day 6 to 7 | Mean | 0.34 | 0.19 | 0.19 | −0.07 | 0.07 | 0.31 | −0.18 | −0.07 |
| | SD | 0.31 | 0.35 | 1.45 | 0.31 | 0.41 | 0.58 | 0.64 | 0.53 |
| Day 7 to 8 | Mean | −3.22 | −3.64 | −3.23 | −2.43 | −2.33 | −2.68 | −2.36 | −1.98 |
| | SD | 0.34 | 0.49 | 1.29 | 0.47 | 0.43 | 0.54 | 0.45 | 0.46 |
| Day (−1 to 8)[b] | Mean | −0.25 | −0.21 | −0.22 | −0.21 | −0.31 | −0.38 | −0.32 | −0.24 |
| | SD | 0.09 | 0.12 | 0.11 | 0.11 | 0.13 | 0.15 | 0.10 | 0.09 |

[a] One mouse (1F17:12-0) was euthanized prior to dose on day 6 due to tail injury.
[b] Animals were fasted overnight.

4.6 Food Consumption

Group food consumption summary results are presented in Table 10. Over the course of the study, study animals generally had similar food consumption. Overall, there were no remarkable differences among groups.

TABLE 10

| | | Group Summary Food Consumption (g/day) | | | | | | | |
|---|---|---|---|---|---|---|---|---|---|
| | | Gender | | | | | | | |
| | | Male | | | | Female | | | |
| | | Group | | | | | | | |
| | | 1 | 2 | 3 | 4 | 1 | 2 | 3 | 4 |
| | | Dose Level (mg/kg/day) | | | | | | | |
| | | 0 (Veh) | 50 (Low) | 100 (Mid) | 300 (High) | 0 (Veh) | 50 (Low) | 100 (Mid) | 300 (High) |
| | | N | | | | | | | |
| | | 10 | 11 | 10 | 10 | 10/9 | 9 | 10 | 10 |
| Day 1 | Mean | 5.5 | 5.2 | 9.2 | 10.6 | 4.0 | 4.1 | 6.6 | 9.3 |
| | SD | 0.5 | 0.6 | 1.6 | 1.5 | 0.5 | 0.6 | 2.7 | 1.1 |
| Day 2 | Mean | 4.5 | 5.1 | 4.6 | 5.6 | 4.0 | 3.6 | 3.7 | 4.3 |
| | SD | 0.3 | 0.9 | 1.0 | 2.3 | 0.7 | 0.8 | 0.7 | 0.7 |
| Day 3 | Mean | 5.0 | 4.4 | 4.3 | 12.7 | 3.2 | 3.4 | 3.5 | 3.1 |
| | SD | 0.5 | 0.6 | 0.5 | 14.4 | 0.6 | 0.8 | 0.9 | 1.0 |
| Day 4 | Mean | 4.4 | 5.3 | 4.8 | 4.4 | 4.4 | 4.0 | 4.5 | 4.0 |
| | SD | 0.5 | 0.8 | 0.6 | 0.8 | 0.8 | 1.1 | 0.4 | 0.5 |
| Day 5 | Mean | 6.4 | 5.0 | 4.5 | 4.6 | 4.1 | 3.6 | 8.4 | 3.7 |
| | SD | 4.2 | 0.5 | 0.1 | 1.7 | 1.3 | 0.5 | 8.7 | 0.6 |
| Day 6 | Mean | 4.0 | 5.1 | 4.7 | 4.5 | 3.6 | 3.5 | 7.3 | 3.8 |
| | SD | 2.2 | 0.3 | 0.5 | 1.3 | 0.7 | 0.9 | 7.2 | 0.8 |
| Day 7 | Mean | 4.7 | 5.8 | 4.4 | 3.5 | 6.6 | 3.8 | 7.5 | 7.3 |
| | SD | 1.0 | 3.3 | 0.2 | 0.4 | 2.8 | 0.5 | 5.2 | 3.3 |
| Day 8[a] | Mean | 1.1 | 1.0 | 0.7 | 0.6 | 1.8 | 0.4 | 5.4 | 2.1 |
| | SD | 0.9 | 1.6 | 0.5 | 0.1 | 4.3 | 0.2 | 10.3 | 0.9 |

[a]Food consumed before fasting.

4.7 Clinical Pathology

Blood samples were collected from euthanized mice for hematology and serum chemistry analysis. Some blood samples (serum) did not have sufficient volume to complete all target parameter analyses.

Hematology and coagulation data are summarized in Table 11. When compared to the control group (Group 1), none of the hematology or coagulation parameters appeared to be affected in the mice that were treated with test article at different dose levels.

Serum chemistry data are summarized in Table 12. All serum chemistry results appeared within normal ranges. When compared to the control group (Group 1), none of the serum chemistry parameters appeared to be affected in the mice that were treated with test article formulation at different dose levels.

TABLE 11

| | | Group Mean Hematology and Coagulation at Termination | | | | | | | |
|---|---|---|---|---|---|---|---|---|---|
| | | Gender | | | | | | | |
| | | Male | | | | Female | | | |
| | | Group | | | | | | | |
| | | 1 | 2 | 3 | 4 | 1 | 2 | 3 | 4 |
| | | Dose Level (mg/kg/day) | | | | | | | |
| | | 0 (Veh) | 50 (Low) | 100 (Mid) | 300 (High) | 0 (Veh) | 50 (Low) | 100 (Mid) | 300 (High) |
| | | N | | | | | | | |
| | | 4 | 3 | 3 | 3 | 3 | 3 | 3 | 3 |
| | | Red Blood Cells | | | | | | | |
| RBC | $10^6/\mu L$ | 10.15 | 9.80 | 10.68 | 10.56 | 10.37 | 10.53 | 9.76 | 10.07 |
| HCT | % | 60.6 | 57.9 | 61.7 | 60.4 | 60.8 | 59.7 | 57.5 | 60.1 |
| HGB | g/dL | 17.1 | 16.5 | 17.2 | 17.2 | 17.7 | 18.4 | 16.9 | 17.5 |
| MCV | fL | 59.8 | 59.2 | 57.8 | 57.3 | 58.6 | 56.6 | 58.9 | 59.8 |

TABLE 11-continued

Group Mean Hematology and Coagulation at Termination

| | | Gender | | | | | | | |
|---|---|---|---|---|---|---|---|---|---|
| | | Male | | | | Female | | | |
| | | Group | | | | | | | |
| | | 1 | 2 | 3 | 4 | 1 | 2 | 3 | 4 |
| | | Dose Level (mg/kg/day) | | | | | | | |
| | | 0 (Veh) | 50 (Low) | 100 (Mid) | 300 (High) | 0 (Veh) | 50 (Low) | 100 (Mid) | 300 (High) |
| | | N | | | | | | | |
| | | 4 | 3 | 3 | 3 | 3 | 3 | 3 | 3 |
| MCH | pg | 16.8 | 16.8 | 16.1 | 16.3 | 17.1 | 17.6 | 17.3 | 17.4 |
| MCHC | g/dL | 28.2 | 28.5 | 27.9 | 28.5 | 29.2 | 31.2 | 29.4 | 29.2 |
| | | White Blood Cells | | | | | | | |
| WBC | 10/μL | 7.49 | 6.07 | 8.67 | 6.00 | 7.23 | 10.03 | 6.73 | 6.01 |
| Neutrophils | 10/μL | 1.06 | 0.93 | 1.62 | 0.82 | 1.46 | 1.25 | 0.74 | 0.86 |
| | % | 14.3 | 15.8 | 18.4 | 13.4 | 20.2 | 11.8 | 10.8 | 14.4 |
| Lymphocytes | 10/μL | 4.98 | 3.84 | 5.75 | 3.83 | 4.13 | 7.03 | 4.70 | 3.48 |
| | % | 68.4 | 61.9 | 66.8 | 62.2 | 57.3 | 71.8 | 69.6 | 56.3 |
| Monocytes | 10/μL | 0.09 | 0.09 | 0.08 | 0.06 | 0.07 | 0.08 | 0.06 | 0.04 |
| | % | 1.2 | 1.5 | 0.9 | 1.0 | 0.9 | 0.7 | 0.9 | 0.8 |
| Eosinophils | 10/μL | 1.32 | 1.10 | 0.94 | 1.23 | 1.44 | 1.51 | 0.99 | 1.42 |
| | % | 15.3 | 19.1 | 10.8 | 20.6 | 19.8 | 13.8 | 15.5 | 25.3 |
| Basophils | 10/μL | 0.03 | 0.01 | 0.05 | 0.02 | 0.04 | 0.07 | 0.03 | 0.03 |
| | % | 0.4 | 0.2 | 0.6 | 0.3 | 0.5 | 0.8 | 0.5 | 0.6 |
| LUC | 10/μL | 0.07 | 0.10 | 0.22 | 0.04 | 0.10 | 0.09 | 0.20 | 0.16 |
| | % | 0.9 | 1.5 | 2.6 | 0.7 | 1.3 | 1.0 | 2.8 | 2.6 |
| | | Clotting Potential | | | | | | | |
| Platelets | 10/μL | 1323 | 1103 | 1365 | 1357 | 658 | 1197 | 784 | 884 |
| | | Coagulation | | | | | | | |
| N | | 3 | 5 | 4 | 3 | 3 | 2 | 3 | 3 |
| PT | sec | 11.3 | 14.1 | 11.0 | 10.0 | 10.7 | 11.7 | 10.5 | 10.8 |
| APTT | sec | 29.6 | 33.2 | 35.6 | 27.4 | 29.9 | 39.4 | 28.8 | 27.6 |

TABLE 12

Group Mean Serum Chemistry at Termination

| | | Gender | | | | | | | |
|---|---|---|---|---|---|---|---|---|---|
| | | Male | | | | Female | | | |
| | | Group | | | | | | | |
| | | 1 | 2 | 3 | 4 | 1 | 2 | 3 | 4 |
| | | Dose Level (mg/kg/day) | | | | | | | |
| | | 0 (Veh) | 50 (Low) | 100 (Mid) | 300 (High) | 0 (Veh) | 50 (Low) | 100 (Mid) | 300 (High) |
| | | N | | | | | | | |
| Electrolyte | Balance | 6 | 4 | 4 | 6 | 6 | 4 | 4 | 6 |
| Sodium | mEq/L | 153 | 152 | 155 | 155 | 152 | 153 | 155 | 156 |
| Potassium | mEq/L | 7.7 | 9.3 | 9.7 | 9.5 | 9.0 | 8.6 | 9.8 | 9.1 |
| Chloride | mEq/L | 106 | 106 | 111 | 111 | 109 | 104 | 110 | 110 |
| Calcium | mg/dL | 10.6 | 10.7 | 10.7 | 10.9 | 10.5 | 11.0 | 11.0 | 10.9 |
| Phosphorus | mg/dL | . | 9.9 | 11.5 | 10.4 | 9.9 | 10.1 | 11.1 | . |
| | | Carbohydrate Metabolism | | | | | | | |
| Glucose | mg/dL | 133 | 112 | 145 | 136 | 92 | 125 | 102 | 113 |
| | | Liver Function a) Hepatocellular | | | | | | | |
| ALT | U/L | 23 | 25 | 39 | 42 | 64 | 40 | 30 | 33 |
| AST | U/L | 100 | 97 | 269 | 218 | 223 | 199 | 119 | 203 |

TABLE 12-continued

Group Mean Serum Chemistry at Termination

| | | Gender | | | | | | | |
|---|---|---|---|---|---|---|---|---|---|
| | | Male | | | | Female | | | |
| | | Group | | | | | | | |
| | | 1 | 2 | 3 | 4 | 1 | 2 | 3 | 4 |
| | | Dose Level (mg/kg/day) | | | | | | | |
| | | 0 (Veh) | 50 (Low) | 100 (Mid) | 300 (High) | 0 (Veh) | 50 (Low) | 100 (Mid) | 300 (High) |
| | | N | | | | | | | |
| Electrolyte | Balance | 6 | 4 | 4 | 6 | 6 | 4 | 4 | 6 |
| Liver Function b) Hepatobiliary | | | | | | | | | |
| ALP | U/L | 134 | 150 | 124 | 139 | 111 | 153 | 119 | 156 |
| T. Bilirubin | mg/dL | 0.2 | 0.5 | 0.2 | 0.3 | 0.3 | 0.3 | 0.2 | 0.2 |
| Kidney Function | | | | | | | | | |
| Creatinine | mg/dL | 0.2 | 0.2 | 0.2 | 0.2 | 0.2 | 0.2 | 0.2 | 0.2 |
| BUN | mg/dL | 21 | 19 | 26 | 25 | 19 | . | 18 | 16 |
| Others | | | | | | | | | |
| T. Protein | g/dL | 5.0 | 5.7 | 5.5 | 5.6 | 5.8 | 5.8 | 5.7 | 5.6 |
| Albumin | g/dL | 3.3 | 3.4 | 3.2 | 3.4 | 3.5 | 3.5 | 3.5 | 3.5 |
| Globulin | g/dL | 1.7 | 2.4 | 2.2 | 2.3 | 2.3 | 2.3 | 2.2 | 2.2 |
| A/G | ratio | 2.4 | 1.5 | 1.5 | 1.5 | 1.6 | 1.5 | 1.7 | 1.6 |
| Cholesterol | mg/dL | 212 | 277 | 174 | 219 | 126 | . | 122 | . |
| Triglycerides | mg/dL | 94 | 155 | 95 | 163 | 135 | 106 | 73 | 130 |
| GGT | U/L | 3 | 5 | 3 | 3 | 3 | 3 | 3 | 3 |

"." indicates an insufficient sample volume 4.8 Necropsy and Tissue Collection

A complete necropsy was conducted on all study animals. Necropsy included examination of the external surface, all orifices, and cranial, thoracic, abdominal, and pelvic cavities including contents. Macroscopic findings are summarized in Table 13. All findings were considered to be incidental, and unrelated to the test article administration. All tissues were collected, including the entire remaining carcasses, and fixed for future potential evaluation.

TABLE 13

Individual Animal Necropsy Findings

| Study ID | Animal ID | Study Day | Findings |
|---|---|---|---|
| 3F12 | 3-1 | 8 | ~3 mm cyst left ovary filled with serosanguineous fluid |
| 3F17 | 15-0 | 8 | Right ovary very small, no follicle seen |
| 4F15 | 14-0 | 8 | Both ovaries surrounded by thin walled cyst containing clear fluid |

5 Summary and Conclusions

The study was conducted to determine the maximum tolerated dose and potential toxicity of the test article following 7 days of daily oral administration in CD1 mice. There were four dose groups consisting of a vehicle control group and 3 dose groups. Treatments were administered for 7 days as repeated oral gavage doses, with 10 mice/sex/group. All animals were successfully dosed once daily as proposed and euthanized on study Day 8. All animals were observed daily for any clinical signs following dose administration. Gross necropsy was conducted for each animal and clinical pathology was performed for all available samples at the termination.

There were no unscheduled deaths and no significant observations of moribundity during the study period. In general, all animals had normal food consumption and gained weight as expected over the course of the study. There were no test article-related clinical findings. Clinical pathology analysis and necropsy at termination showed that all study animals were in normal conditions.

In conclusion, animals tolerated the doses of GZ523.010 up to 300 mg/kg/day via oral administration daily for 7 days. Under the conditions of this study, the No-Observed Adverse Effect Level (NOAEL) was determined to be 300 mg/kg/day.

Example 8

In this Example, in vitro cell proliferation assays were performed using: (1) Human Myeloma tumor cell lines; (2) Human Lymphoma tumor cell lines; (3) Solid Human tumor cell lines; and (4) Parental, Lenalidomide resistant and Bortezomib resistant Jeko-1 Mantle cell Lymphoma tumor cell lines. The compounds tested were three diharmaline compounds, namely the 518B562 (or simply 562), 560, and 561 compounds. In addition, a monoharmaline product designated as 518F014 was also tested. This monoharmaline product had the following structure:

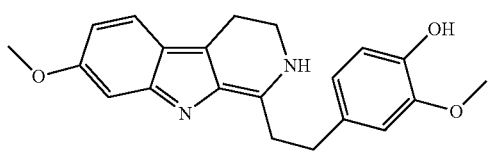

2-methoxy-4-(2-(7-methoxy-3,4-dihydro-2H-
pyrido[3,4-b]indol-1-yl)ethyl)phenol
Chemical Formula: $C_{21}H_{22}N_2O_3$
Exact Mass: 350.16

The 518B562 compound was prepared by mixing together particulate harmaline and vanillin at a weight ratio of about 2:1 (vanillin:harmaline), followed by adding ethanol to a final concentration of the reactions of from about 10-100 mg/mL. This mixture is then allowed to sit for approximately 3 days at 50° C. A bluish solid forms, which is filtered and washed with methanol, and recovered. It was found that addition of an acid such as hydrochloric acid to reduce the pH of the product, increased the solubility thereof.

The 560 compound was prepared by mixing together 500 mg of benzaldehyde and 250 mg of harmaline in a 15 mL jar followed by shaking. 10 mL of DSMO was then added to the mixture, followed by agitation using a vortex mixer at 1000 rpm for 10 minutes. The vortexed mixture was then allowed to set for 24 hours at room temperature. The resultant product was an orange liquid containing 10.6 mM compound, and was stored at 4° C. until use.

The 561 compound was prepared by mixing together 500 mg of cinnamaldehyde and 250 mg of harmaline in a 15 mL jar followed by shaking. 10 mL of DSMO was then added to the mixture, followed by agitation using a vortex mixer at 1000 rpm for 10 minutes. The vortexed mixture was then allowed to set for 24 hours at room temperature. The resultant product was an orange solid dispersed in liquid containing 10 mM compound, and was stored at 4° C. until use.

Each proliferation assay was carried out as follows. The test cells were plated in growth media using a 384-well microtiter plate at 50 μL volume. The cells were incubated for 24 hours at 37° C. in a humidified incubator. After 24 hours of incubation, the test compounds were added to the test wells in DSMO solvent, at concentrations ranging from 0.0075-100 μM. Control wells received equal volumes of DSMO, without compound. Following drugging, the cells were incubated for 72 hours at 37° C. in a humidified incubator. After this exposure, 100 μL of a 1:1 mixture of sterile water and CellTiter-Glo® reagent (Promega) was added to each well. The plates were then incubated for 60 minutes at room temperature, followed by recording the luminescence value of each well using a luminometer as a measure of cell proliferation.

The following Table 14 sets forth the cell lines tested using the respective compounds, a summary of the $IC_{50}$ Results, and an identification of the corresponding graphical Figure for each assay.

TABLE 14

In Vitro Cell Proliferation Assays Using 518B562, 560, and 561 Compounds with Summary of $IC_{50}$ Results

| Cell Line | Tissue Type | Mean $IC_{50}$ (μM) 518F014 | Mean $IC_{50}$ (μM) 518B562 | FIG. No. | Mean $IC_{50}$ (μM) 560 | FIG. No. | Mean $IC_{50}$ (μM) 561 | FIG. No. |
|---|---|---|---|---|---|---|---|---|
| MIA PaCa-2 | Pancreatic | >100 | 1.811 | 23 | 3.379 | 55 | 33.97 | 87 |
| ASPC-1 | | 87.13* | 2.152 | 24 | 3.617 | 56 | 40.50 | 88 |
| BxPC-3 | | 98.65* | 1.599 | 25 | 2.621 | 57 | 17.70 | 89 |
| AN3CA | Endometrial | 88.10* | 1.791 | 26 | 2.706 | 58 | 12.45 | 90 |
| HEC-1a | | >100 | 4.752 | 27 | 5.097 | 59 | 75.96 | 91 |
| MDA-MB-231 | Triple | 78.23* | 1.625 | 28 | 3.891 | 60 | 48.47 | 92 |
| MDA-MB-468 | Negative | >100 | 2.049 | 29 | 3.747 | 61 | 35.60 | 93 |
| HCC70 | Breast | >100 | 3.454 | 30 | 5.943 | 62 | 54.37 | 94 |
| H1975 (EGFR mut) | Non Small | 79.71* | 1.840 | 31 | 4.272 | 63 | 58.29 | 95 |
| H1650 (EGFR mut) | Cell Lung | >100 | 2.301 | 32 | 2.950 | 64 | 53.71 | 96 |
| A2780 | Ovarian | 70.90* | 1.137 | 33 | 2.030 | 65 | 5.934 | 97 |
| A2780CP | | >100 | 2.279 | 34 | 4.400 | 66 | 20.44 | 98 |
| RXF-393 | Renal | 96.52* | 1.795 | 35 | 5.397 | 67 | 20.94 | 99 |
| A498 | | >100 | 1.764 | 36 | 3.338 | 68 | 61.11 | 100 |
| N87 | Gastric | 40.62 | 1.851 | 37 | 3.715 | 69 | 12.88 | 101 |
| SiHA | Squamous | >100* | 5.133 | 38 | 11.61 | 70 | >100* | 102 |
| FaDu | | >100 | 1.982 | 39 | 2.053 | 71 | 21.49 | 103 |
| DOHH-2 | Diffuse Large B-Cell Lymphoma | >100 | 2.423 | 40 | 6.393 | 72 | 20.36 | 104 |
| SU-DHL-4 | | 91.30* | 1.814 | 41 | 3.683 | 73 | 11.34 | 105 |
| SU-DHL-6 | | 50.00* | 0.8188 | — | 3.517 | — | 10.68 | — |
| OCI-LY3 | | >100* | 2.378 | 42 | 2.871 | 74 | 11.51 | 106 |
| JIM1 | | 85.16 | 3.954 | 43 | 5.172 | 75 | 29.25 | 107 |
| KHM-1B | Human | 94.08* | 3.365 | — | 7.575 | — | 100 | — |
| KMM-1 | Myeloma | 82.16* | 4.038 | 44 | 5.301 | 76 | 30.85 | 108 |
| KMS-11 | | >100 | 4.934 | 45 | 4.945 | 77 | 68.36 | 109 |
| KMS-27 | | 91.16* | 2.104 | 46 | 3.942 | 78 | 15.62 | 110 |
| KMS-34 | | >100 | 5.446 | 47 | 6.674 | 79 | 48.52 | 111 |
| H929 | | 80.31 | 4.501 | 48 | 4.301 | 80 | >100 | 112 |
| L363 | | 99.13* | 2.003 | 49 | 5.271 | 81 | 23.05 | 113 |
| MM.IS | | >100 | 1.665 | 50 | 2.260 | 82 | 14.65 | 114 |
| MOLP-8 | | 86.44* | 1.382 | 51 | 2.889 | 83 | 14.47 | 115 |

TABLE 14-continued

In Vitro Cell Proliferation Assays Using 518B562, 560, and 561 Compounds with Summary of $IC_{50}$ Results

| Cell Line | Tissue Type | Mean $IC_{50}$ (μM) 518F014 | Mean $IC_{50}$ (μM) 518B562 | FIG. No. | Mean $IC_{50}$ (μM) 560 | FIG. No. | Mean $IC_{50}$ (μM) 561 | FIG. No. |
|---|---|---|---|---|---|---|---|---|
| Jeko-1 Parental | Mantle Cell | 89.39* | 4.405 | 52 | 4.696 | 84 | 32.85 | 116 |
| Jeko-1 Lenalidomide Resistant | Lymphoma | 79.38* | 6.193 | 53 | 5.070 | 85 | 40.79 | 117 |
| Jeko-1 Bortezomib Resistant | | 87.62* | 4.811 | 54 | 4.083 | 86 | 31.34 | 118 |

*Value was calculated by averaging using 100 μM for trial value.
In cases where one trial value was >100 μM or <0.005 μM, 100 μM or 0.005M was used to average the values and obtain an $IC_{50}$.

This data demonstrates that the preferred 560, 561, and 562 diharmaline compounds have significantly lower $IC_{50}$ values as compared with the monoharmaline 518F014 compound. This phenomenon has been found consistent throughout the tested compounds of the invention, namely that the diharmaline compounds are markedly superior as compared with the monoharmaline compounds.

Example 9

In this Example, a compound mixture was prepared by reacting 2:1 by weight harmaline and 3-phenoxybenzaldehyde (3-phenoxybenzaldehyde:harmaline). The reaction mixture had three components, namely fractions having molecular weights of 608 (47% by weight), 788 (32% by weight), and 394 (21% by weight). The MW 608 product contained two moieties of harmaline and one of 3-phenoxybenzaldehyde, with one removed water molecule; the MW 788 product contained two moieties of harmaline and two moieties of 3-phenoxybenzaldehyde, with two removed molecules of water; and the MW 394 product contained one mole each of harmaline and 3-phenoxybenzaldehyde with one water molecule removed. The following table sets forth the results of a series of assays using this compound mixture against 31 different cell lines, where the assays were performed as set forth in Example 2. Two $IC_{50}$ trials were run in each case, and the results thereof were averaged to give the mean $IC_{50}$ values.

TABLE 15

| | | 594 | | |
|---|---|---|---|---|
| | | Trial A (μg/mL) | Trial B (μg/mL) | Mean (μg/mL) |
| MIA PaCa-2 | Pancreatic | 3.815 | 3.169 | 3.492 |
| ASPC-1 | | 2.941 | 3.993 | 3.467 |
| BxPC-3 | | 3.448 | 3.325 | 3.387 |
| AN3CA | Endometrial | 2.793 | 2.796 | 2.795 |
| HEC-1a | | 3.147 | 3.425 | 3.286 |
| MDA-MB-231 | TNBC | 3.099 | 3.084 | 3.092 |
| MDA-MB-468 | | 2.898 | 2.682 | 2.790 |
| HCC70 | | 6.146 | 7.590 | 6.868 |
| H1975 (EGFR mut) | NSCLC | 2.924 | 2.867 | 2.896 |
| H1650 (EGFR mut) | | 2.606 | 2.548 | 2.577 |
| A2780 | Ovarian | 2.667 | 2.489 | 2.578 |
| A2780CP | | 3.570 | 2.965 | 3.268 |
| RXF-393 | RCC | 3.16 | 3.161 | 3.161 |
| A498 | | 2.911 | 2.995 | 2.953 |
| N87 | Gastric | 3.482 | 5.037 | 4.260 |
| SiHA | Cervical - SCC | 8.561 | 8.894 | 8.728 |

TABLE 15-continued

| | | 594 | | |
|---|---|---|---|---|
| | | Trial A (μg/mL) | Trial B (μg/mL) | Mean (μg/mL) |
| FaDu | H&N - SCC | 3.782 | 5.453 | 4.618 |
| DOHH-2 | DLBCL | 2.577 | 2.707 | 2.642 |
| SU-DHL-4 | | 2.769 | 2.701 | 2.735 |
| SU-DHL-6 | | 2.480 | 2.234 | 2.36 |
| OCI-LY3 | | 3.865 | 7.536 | 5.701 |
| JIM1 | human | 7.414 | 7.923 | 7.669 |
| KHM-1B | myeloma | | | |
| KMM-1 | | 2.527 | 2.607 | 2.567 |
| KMS-11 | | 6.433 | 5.640 | 6.037 |
| KMS-27 | | 5.538 | 2.733 | 4.136 |
| KMS-34 | | 4.226 | 3.551 | 3.889 |
| H929 | | 6.498 | 5.415 | 5.957 |
| L363 | | 3.673 | 3.603 | 3.638 |
| MM.1S | | 2.482 | 2.656 | 2.569 |
| MOLP-8 | | 2.734 | 2.703 | 2.719 |

Example 10

In this Example, pancreatic cancer cells (S2-007 and Mia-PaCa2) were treated with the previously described compound 518B562 at different times and concentrations, followed by generation of proliferation assays using the techniques described above. This product significantly inhibited the proliferation of the cells in doses of 1-25 μg/mL and in a time-dependent manner of 24-72 hours. After 72 hours of treatment, the $IC_{50}$ values of the compound against S2-007 and Mia-PaCa2 cells was determined as 3 μg/mL and 5 μg/mL, respectively.

Example 11

In this Example, a clustergram/heat map of RNA sequences for cancer stem cell (CSC) markers was performed before and after treatment of S2-007 human pancreatic cancer cells with 518B562. This experiment was conducted using a Whole Transcriptome Shotgun Sequence (WTSS), followed by bioinformatics data analysis of CSC markers. An RNA-Seq/heat map was generated to obtain a genome-wide gene expression profile of the pancreatic cancer cells.

One sample of the pancreatic cancer cell line was untreated, while an identical sample was treated with 5 micro-g/mL of 518B562. Comparative RNA sequences were performed on the samples using an Illumina HISeq 2500 sequencer at a 100 bp single read resolution. The sequence readings were mapped to the human genome (assembly GRCh38.re177) using the STAR software (Dobin et al. 2012). Transcript abundance estimates were generated using the Cufflinks software (Trapnell et al. 2010) and differential gene expression estimates were calculated using the Cuffdiff software (Trapnell et al. 2013). RNA-Seq generated around 48.6 and 60.1 reads, of which between 97.2% and 98.3% of the reads mapped to the reference genome.

The clustergram or heat map suggested that 518B562 significantly inhibited clusters of genes on proliferative, anti-apoptotic, and angiogenic markers, while up-regulating anti-proliferative and apoptotic markers. Specifically, 518B562 up-regulated apoptotic markers [ICAM5, WNK4, ALPP, LTRC26, SHBG, MT1X] and anti-proliferative markers [NRP1, ATF2A, CYP1b1, ALPP, DEPTOR, MT1F]. Also, 518B562 down-regulated angiogenesis markers [OXTR, SYCP2, CRHR1, SPEG], anti-apoptotic markers [TUG1, FABP1, PI3, DOKS] and proliferation signaling markers [FOXj1, SPP1, C3].

Example 12

6 g of benzaldehyde, 3 g of harmaline, and 50 mL of ethanol were placed in a 250 mL round-bottom flask. This dispersion was refluxed for approximately 4 hours at a temperature of about 78° C., after which it was allowed to cool gradually to room temperature. The resultant solids were collected by vacuum filtration, rinsed with approximately 200 mL of cold water, and dried at room temperature to yield multiply twinned racemic crystalline clumps. A single-domain piece was cut from one of the clumps and gave usable diffraction data, making it possible to locate and refine all of the hydrogen atoms as independent isotropic atoms; two nitrogen atoms also appeared to be protonated. The resultant two-dimensional structure of the 560 compound was determined to be:

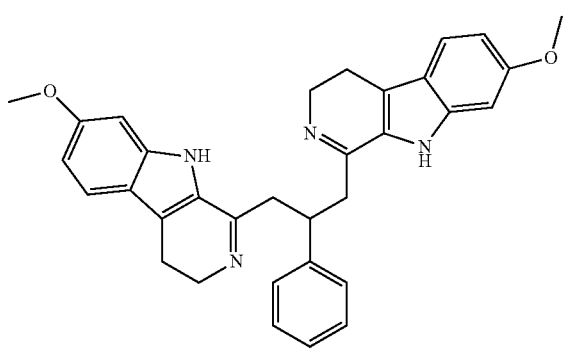

The above structure is referred to herein as the "confirmed 560 compound."

A three-dimensional representation of the above 560 compound is shown below, with the large circles representing carbon atoms, and the small circles representing hydrogen atoms; the double bonds are not shown in this representation. In addition, a hydrogen bond is illustrated in dotted lines between the nitrogens N1 and N4. It is believed that this hydrogen bond may be important to the functionality of the compound. The other numbered atoms are provided for reference.

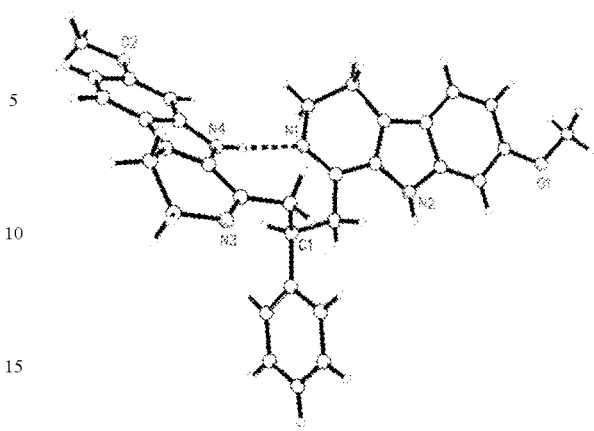

The above compound may be subject to isomerization, particularly during NMR analysis, to give the following two-dimensional isomeric structure:

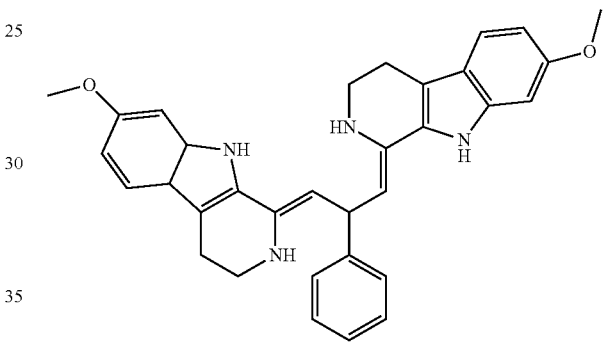

A reduced form of either of the above isomers may be less prone to additional isomerization. The two-dimensional structure of this reduced compound (produced by hydrogenation of the above compounds) is set forth below.

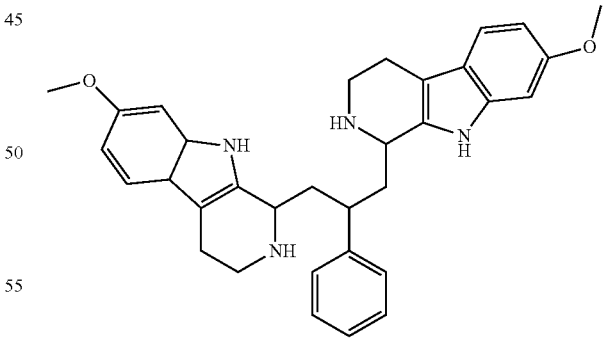

Example 13

In this example, several 560 compounds were prepared by mixing together 6 g of benzaldehyde and 3 g of harmaline in closed 40 mL vials, followed by shaking for several minutes. The closed vials were then placed in a water bath at 40° C. for 1-5 days. After cooling, the vials were opened and placed in a Labconco FreeZone 4.5 L freeze dryer at 0.028 kPa and −48° C. for 1 week. The contents of the vials were then mixed with water/methanol combinations, and the resultant solids were collected by vacuum filtration. The molecular weights of the compounds were found to be 302, 320, 514, and 516.

Example 14

6 g of vanillin, 3 g of harmaline, and 50 mL of ethanol were placed in a 250 mL round-bottom flask. This dispersion was refluxed for approximately 4 hours at a temperature of about 78° C., after which it was allowed to cool gradually to room temperature. The resultant solids were collected by vacuum filtration, rinsed with approximately 200 mL of cold water, and dried at room temperature to yield multiply twinned racemic crystalline clumps. A single-domain piece was cut from one of the clumps and gave usable diffraction data, making it possible to locate and refine all of the hydrogen atoms as independent isotropic atoms; two nitrogen atoms also appeared to be protonated. The resultant two-dimensional structure of the 562 compound was determined to be:

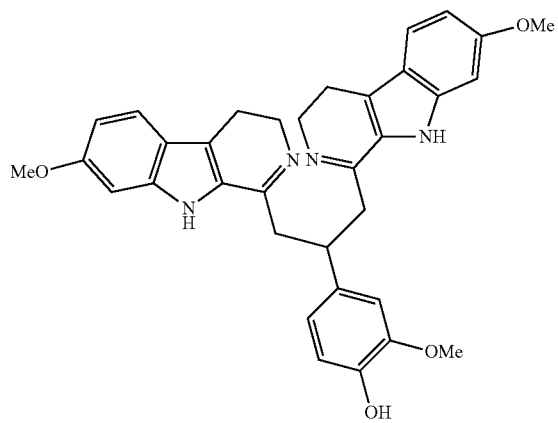 [SMILES: COc1ccc2c3c([nH]c2c1)C(CC(CC1=NCCc2c1[nH]c1cc(OC)ccc21)c1ccc(O)c(OC)c1)=NCC3]

Example 15

Figure 119:
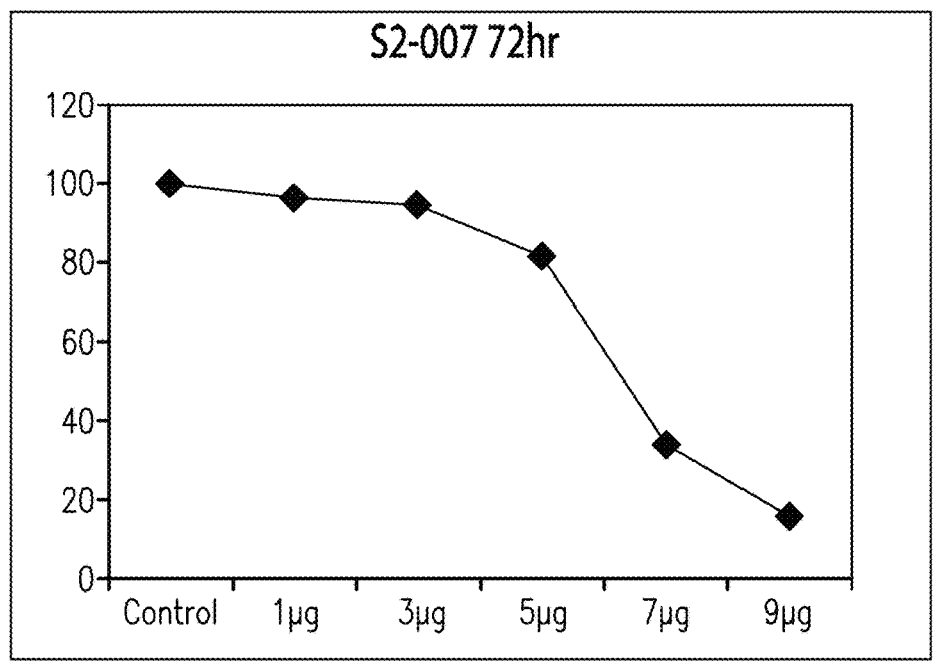
FIG. 119 is a graph illustrating cell growth as a function of the concentration of the confirmed 560 compound, in the S2-007 pancreatic ductal adenocarcinoma cell proliferation assay described in Example 15.
Figure 120:
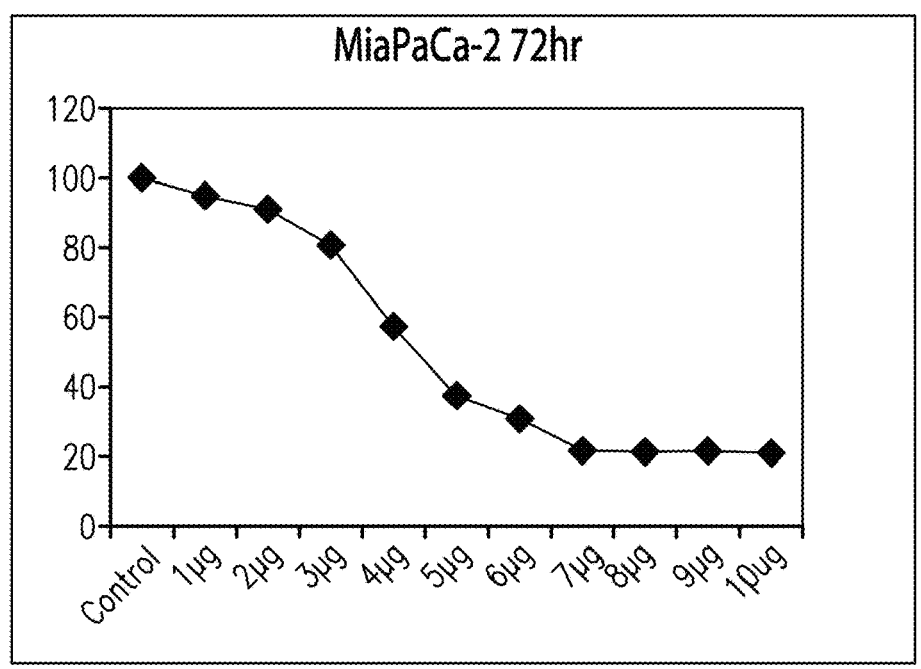
Figure 121:
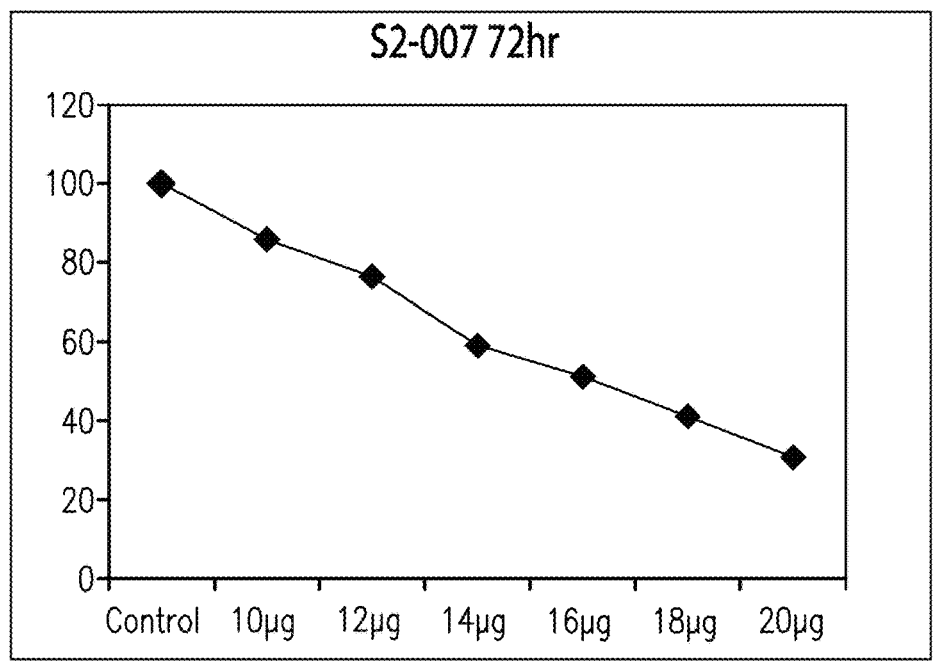
Figure 122:
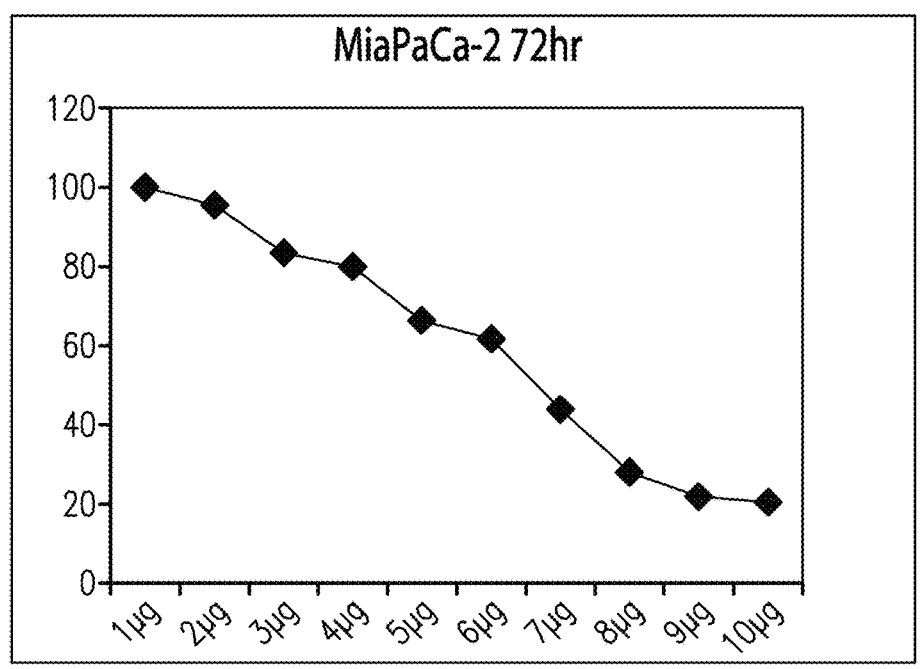

In this example, the 560 and 562 compounds of Examples 12 and 14, respectively, were tested in cell proliferation assays using two pancreatic cancer cells, S2-007 and MiaCaPa-2. In each assay, 5×10⁴ cells were seeded in 96-well culture plates. After incubation for 24 hours, the cells were treated at various concentrations of the 560 or 562 compounds, and allowed to incubate for further periods of 72 hours. Cell proliferation values were determined by enzymatic hexoseaminidase assay. The results of these tests are set forth in FIGS. 119 and 120 (560 compound), and FIGS. 121 and 122 (562 compound). These Figures also provide the IC50 values for each assay.

Example 16

In this example, the 560 and 562 compounds of Examples 12 and 14, respectively, were tested using cell colony formation assays. 500 viable S2-007 and MiaCaPa-2 cells were plated in six-well dishes and allowed to grow for 24 hours. The cells were then incubated in the presence or absence of the 560 and 562 compounds for 72 hours. The compound-containing media were then removed, and the cells were washed in PBS and incubated for an additional 10 days in complete media. The resultant colonies were then washed in PBS and fixed using 10% formalin for 10 minutes at room temperature, followed by washing with PBS and staining with Crystal Violet. The colonies of the control and compound-supplemented assays were then counted and compared.

Figure 123:
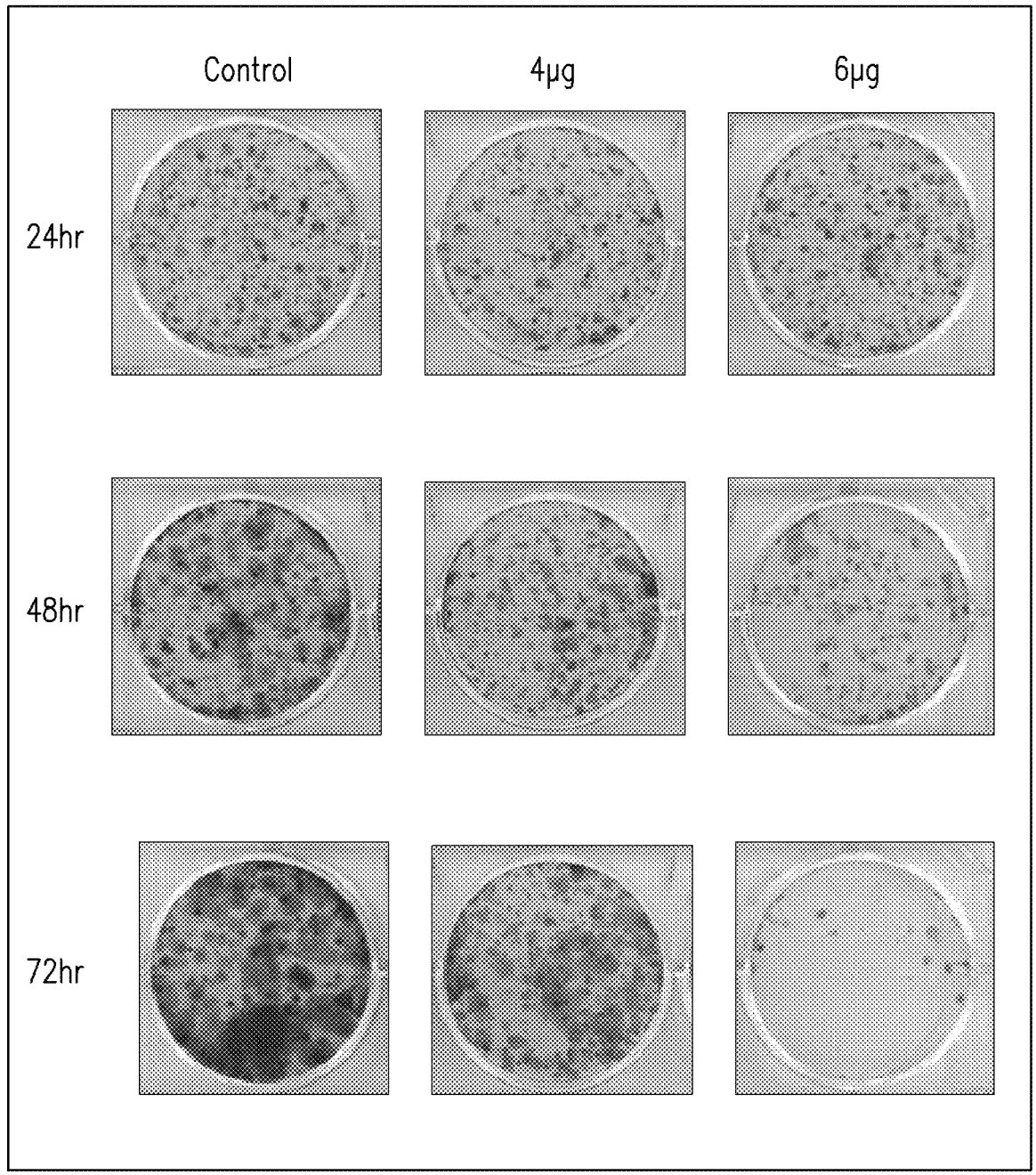

FIG. 123 (560 compound, S2-007 cells) illustrates the colony formation with control (no 560 compound), and 4 µg and 6 µg 560 compound at 24, 48, and 72 hours. The 560 compound significantly disrupted colony formation, particularly at the 6 µg level of use.

Figure 124:
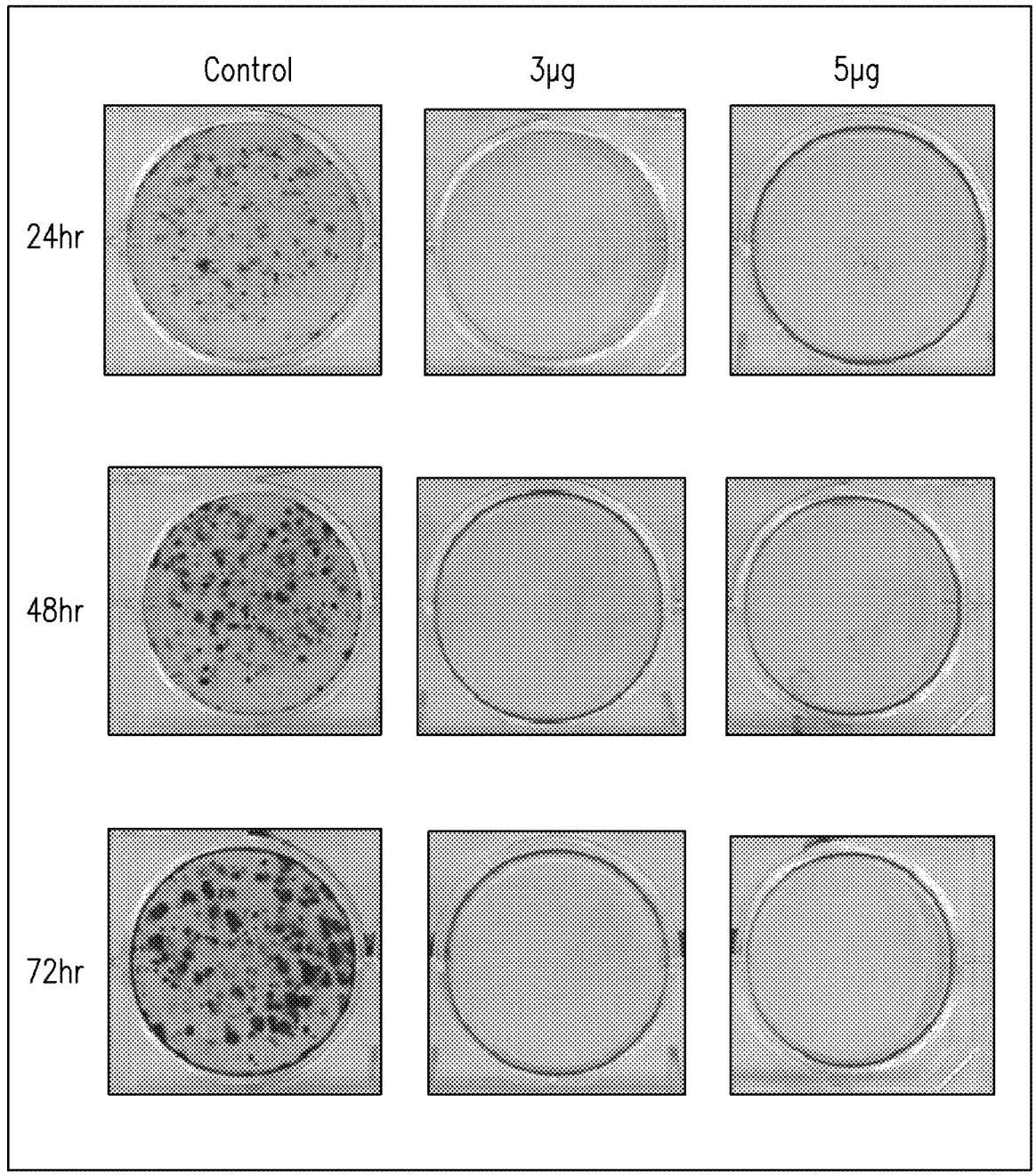

FIG. 124 (560 compound, MiaPaCa-2 cells) illustrates the colony formation with control (no 560 compound), and 3 µg and 5 µg 560 compound at 24, 48, and 72 hours. The 560 compound significantly disrupted colony formation at both levels of use.

Figure 125:
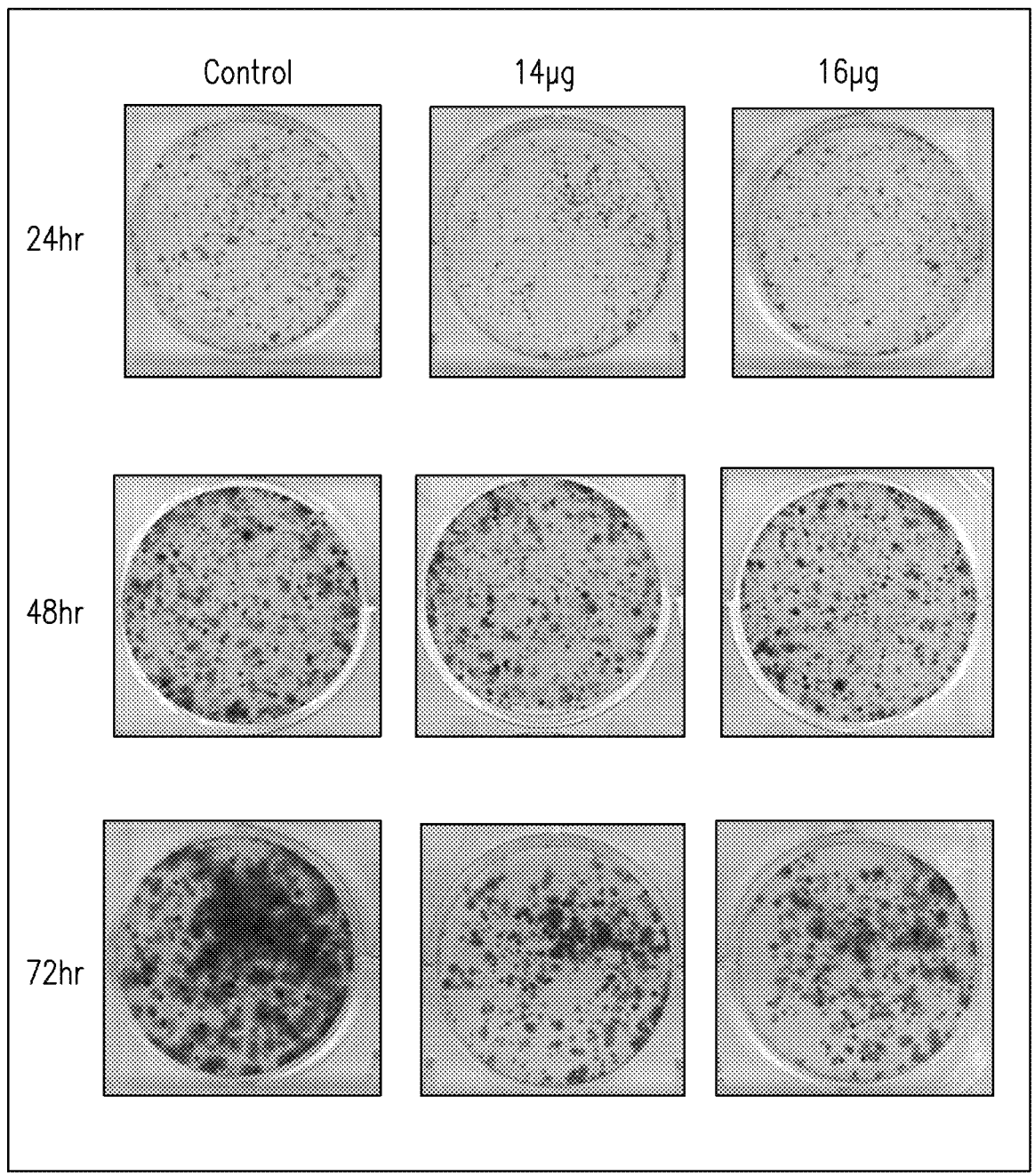

FIG. 125 (562 compound, S2-007 cells) illustrates the colony formation with control (no 562 compound), and 14 µg and 16 µg 562 compound at 24, 48, and 72 hours.

Figure 126:
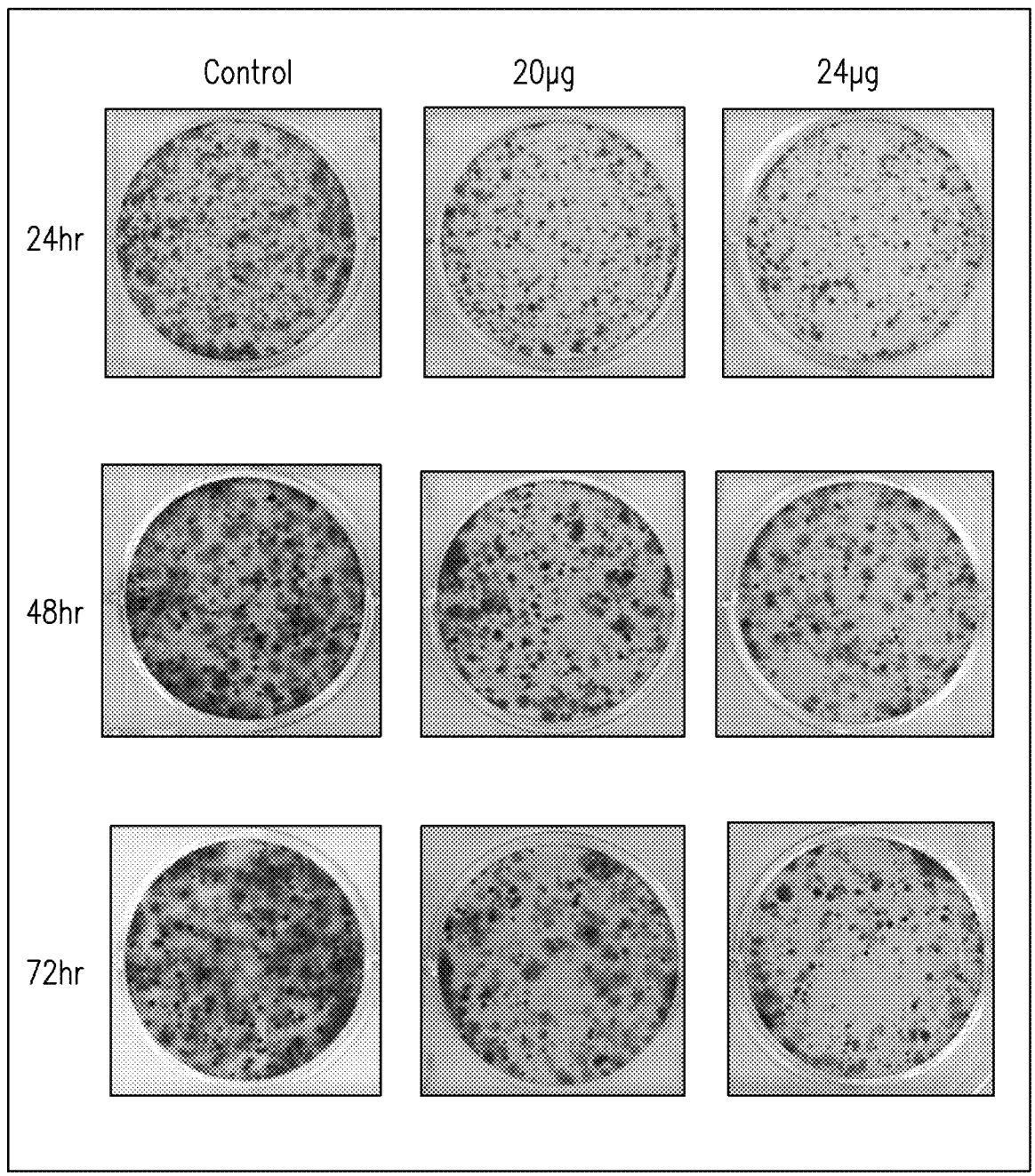

FIG. 126 (562 compound, S2-007 cells) illustrates the colony formation with control (no 562 compound), and 20 µg and 24 µg 562 compound at 24, 48, and 72 hours.

Figure 127:
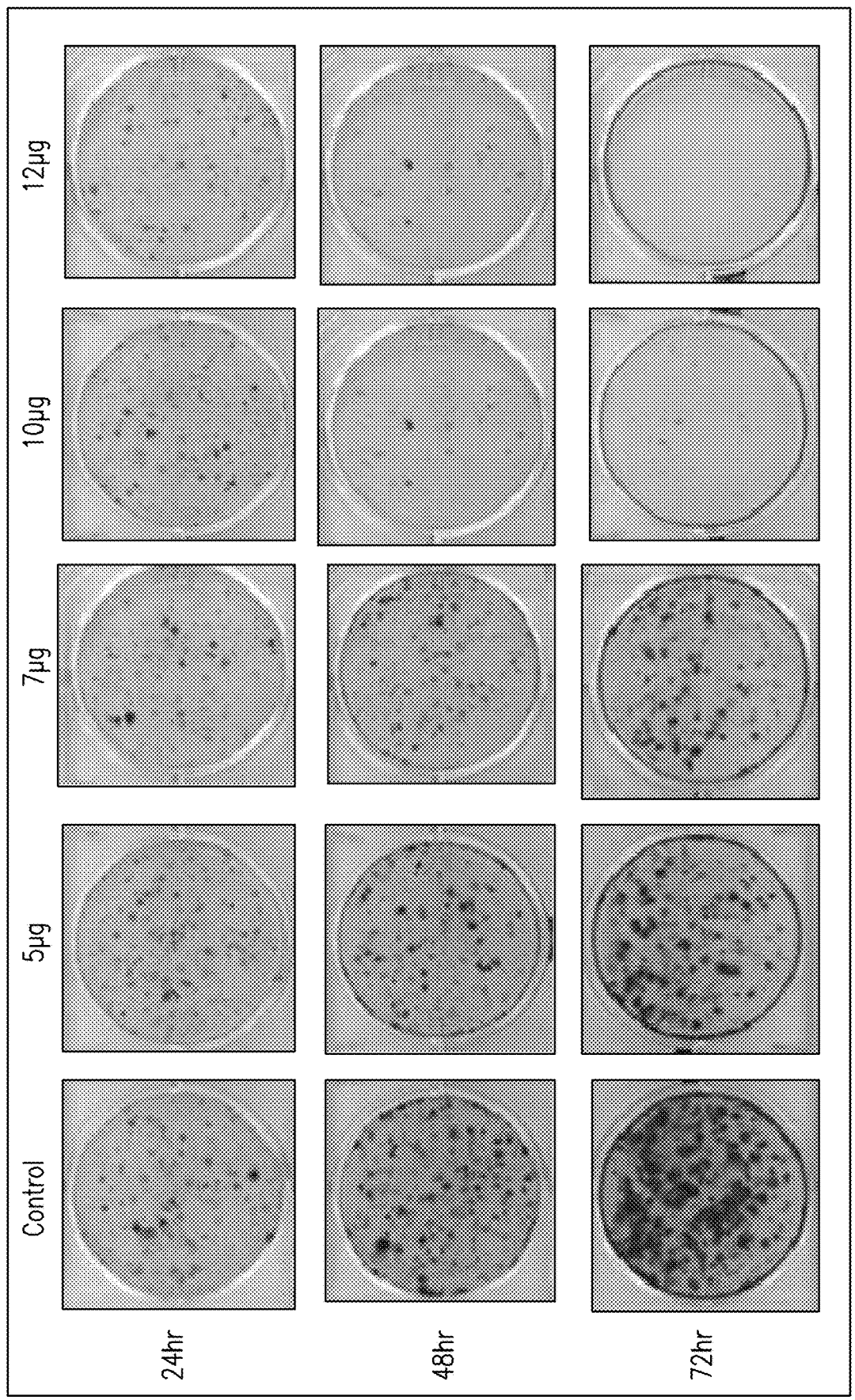

FIG. 127 (562 compound, MiaPaCa-2 cells) illustrates the colony formation with control (no 562 compound), and 3 µg, 7 µg, 10 µg, and 12 µg 562 compound at 24, 48, and 72 hours. The 562 compound significantly disrupted colony formation, particularly at the higher levels of use.

Example 17

In this example, the 560 and 562 compounds of Examples 12 and 14, respectively were used in cell cycle assays against S2-07 and MiaPaCa02 cells. In each instance, cells treated with the 560 and 562 compounds for 72 hours were trypsinized and suspended in PBS. The single-cell suspensions were fixed using pre-chilled 70% ethanol for 3 hours, and were subsequently permeabilized with PBS containing 0.1% Triton X-100, 1 mg/mL propidium iodide, and 2 mg DNase-free RNase at room temperature. Flow cytometry assays were then performed using a FASCalibur analyzer (Becton Dickinson), capturing 10,000 events for each sample. The results were analyzed using ModFit LT™ software (Verity Software House). These results were carried out using a Sub G0 gating window, alternately open (with Sub G0) and closed (without Sub G0), to give quiescent state and active state cell data.

FIGS. 128 and 128A (compound 560 S2-007 cells) illustrates the cell cycle results at 24 and 48 hours with and without Sub G0.

FIGS. 129 and 129A (compound 560 MiaPaCa-2 cells) illustrates the cell cycle results at 24, 48, and 72 hours with and without Sub G0.

FIGS. 130 and 130A (compound 562 S2-007 cells) illustrates the cell cycle results at 24, 48, and 72 hours with and without Sub G0.

FIGS. 131 and 131A (compound 562 MiaPaCa-2 cells) illustrates the cell cycle results at 24, 48, and 72 hours with and without Sub G0.

Example 18

2200 mg of benzaldehyde plus 1100 mg harmaline were placed in a 50 mL beaker and mixed slightly. The beaker was heated for several minutes until a color change was observed, whereupon the mixture was transferred to a 250 mL round-bottom flask with the aid of 50 mL of isopropyl alcohol. Next, 50 µL of 37% HCl was added, and the mixture was refluxed for 1.5 hours. After about 1 hour, crystals began to form. After refluxing, the reaction mixture was allowed to sit and cool to ambient temperature, and was filtered using a Buchner funnel, with cold isopropyl alcohol rinsing. The weight of the collected product was about 700 mg, which was beet red in color. Analysis of the compound indicated that it contained approximately 18% of the confirmed 560 compound (mw=516), and approximately 80% of a dimer (mw=604).

Example 19

3000 mg of benzaldehyde plus 1500 mg harmaline were placed in a 50 mL beaker and mixed slightly. The beaker was heated until the color of the mixture changed to light brown. The mixture was then transferred to a 250 mL round-bottom flask with the aid of 30 mL of isopropyl alcohol. Next, 50 μL of 37% HCl was added, and the mixture was refluxed for 30 minutes. After refluxing, the reaction mixture was allowed to sit and cool to ambient temperature, and was filtered using a Buchner funnel, with cold isopropyl alcohol rinsing. The weight of the collected product was about 1325 mg, which was yellow in color. Analysis of the compound indicated that it contained approximately 80% of the confirmed 560 compound (mw=516).

Example 20

8000 mg of benzaldehyde plus 4000 mg harmaline were placed in a 50 mL beaker and mixed slightly. The mixture was then transferred to a 250 mL round-bottom flask with the aid of 40 mL of methyl alcohol. Next, 50 μL of 37% HCl was added, and the mixture was refluxed for 45 minutes. After refluxing, the reaction mixture was allowed to sit and cool overnight. After cooling, the mixture was filtered using a Buchner funnel, with methyl alcohol rinsing. The product was yellow in color. Analysis of the compound indicated that it contained approximately 93% of the confirmed 560 compound (mw=516), the remainder being unreacted harmaline.

Example 21

8000 mg of vanillin plus 4000 mg harmaline were placed in a 50 mL beaker. The mixture was heated by application of 40° C. water to the outside of the beaker, which initiated a reaction and caused the mixture to change from yellow to light brown in color. The mixture was then transferred to a 250 mL round-bottom flask with the aid of 50 mL of isopropyl alcohol, causing the mixture to turn to a yellow-green color. Once all of the reactants were solubilized, the color changed from yellow-green to yellow-brown. Next, 150 μL of 37% HCl was added, with heating until the mixture turned dark brown in color and produced a bluish precipitate. The mixture was then refluxed for 25 minutes, and the vessel was cooled using tap water. The reaction mixture was then filtered using a Buchner funnel and rinsed with isopropyl alcohol. Thereupon, the mixture was oven-dried, producing an ashy grey-blue color. Analysis of the compound indicated that it contained approximately 85% of the Example 14 562 compound (mw=562).

Example 22

4000 mg of vanillin plus 2000 mg harmaline were placed in a 50 mL beaker. The mixture was heated by application of 40° C. water to the outside of the beaker, which initiated a reaction and caused the mixture to change from yellow to dark brown in color. The mixture was then transferred to a 250 mL round-bottom flask with the aid of 50 mL of isopropyl alcohol. Once all of the reactants were solubilized, the color changed to dark red-brown. Next, 500 μL of 37% HCl was added, with heating until the mixture turned dark brown in color and produced a bluish precipitate. The mixture was then refluxed for 45 minutes, and the vessel was cooled using tap water. The reaction mixture was then filtered using a Buchner funnel and rinsed with isopropyl alcohol. Thereupon, the mixture was oven-dried, to yield approximately 1500 mg of dark brown product. Analysis of the compound indicated that it contained approximately 60% of the Example 14 562 compound (mw=562), about 23% dehydrated adduct (mw=348), and about 17% dimer (mw=696).

Example 23

2 g of cuminaldehyde, 1 g of harmaline, and 40 mL of ethanol were placed in a 250 mL round-bottom flask. This dispersion was refluxed for approximately 30 minutes at a temperature of about 65° C., after which the mixture was allowed to cool gradually overnight to room temperature. The resultant bottom liquid products were then analyzed. The principal compound, referred to herein as the 561 product, has the following structure:

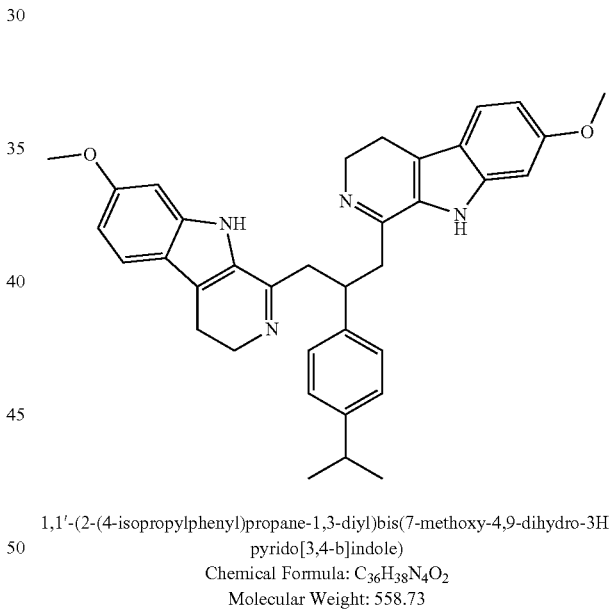

1,1'-(2-(4-isopropylphenyl)propane-1,3-diyl)bis(7-methoxy-4,9-dihydro-3H-pyrido[3,4-b]indole)
Chemical Formula: $C_{36}H_{38}N_4O_2$
Molecular Weight: 558.73

Example 24

In this test, a related diharmaline compound 594, diharmaline 3-phenoxybenzaldehyde was tested using the same cell lines and procedures as described in Example 8. The structure of the 594 compound is set forth below, and the collected cell proliferation assay data is given in the following table.

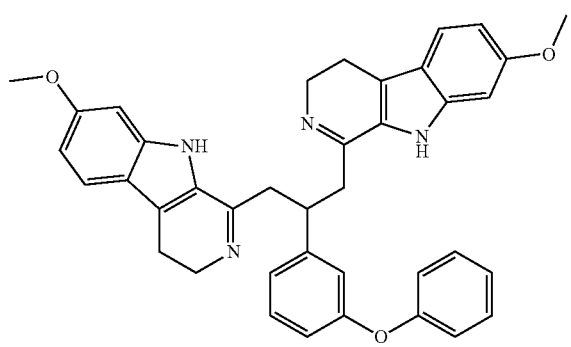

1,1'-(2-(3-phenoxyphenyl)propane-1,3-diyl)bis(7-methoxy-
4,9-dihydro-3H-pyrido[3,4-b]indole)
Chemical Formula: $C_{39}H_{36}N_4O_3$
Exact Mass: 608.28

TABLE 16

| Cell line | Tissue Type | Trial A (µg/mL) | Trial B (µg/mL) | Mean (µg/mL) |
|---|---|---|---|---|
| MIA PaCa-2 | Pancreatic | 3.815 | 3.169 | 3.492 |
| ASPC-1 | | 2.941 | 3.993 | 3.467 |
| BxPC-3 | | 3.448 | 3.325 | 3.387 |
| AN3CA | Endometrial | 2.793 | 2.796 | 2.795 |
| HEC-1a | | 3.147 | 3.425 | 3.286 |
| MDA-MB-231 | Triple | 3.099 | 3.084 | 3.092 |
| MDA-MB-468 | Negative | 2.898 | 2.682 | 2.790 |
| HCC70 | Breast | 6.146 | 7.590 | 6.868 |
| H1975 (EGFR mut) | Non Small | 2.924 | 2.867 | 2.896 |
| H1650 (EGFR mut) | Cell Lung | 2.606 | 2.548 | 2.577 |
| A2780 | Ovarian | 2.667 | 2.489 | 2.578 |
| A2780CP | | 3.570 | 2.965 | 3.268 |
| RXF-393 | RCC | 3.16 | 3.161 | 3.161 |
| A498 | | 4.817 | 4.561 | 4.689 |
| N87 | Gastric | 3.482 | 5.037 | 4.260 |
| SiHA | Squamous | 8.561 | 8.894 | 8.728 |
| FaDu | | 3.782 | 5.453 | 4.618 |
| DOHH-2 | Diffuse | 2.577 | 2.707 | 2.642 |
| SU-DHL-4 | Large B-Cell | 2.769 | 2.701 | 2.735 |
| SU-DHL-6 | Lymphoma | 2.480 | 2.234 | 2.357 |
| OCI-LY3 | | 3.865 | 7.536 | 5.701 |
| JIM1 | human | 7.414 | 7.923 | 7.669 |
| KHM-1B | myeloma | 6.483 | 6.810 | 6.647 |
| KMM-1 | | 2.527 | 2.607 | 2.567 |
| KMS-11 | | 6.433 | 5.640 | 6.037 |
| KMS-27 | | 5.538 | 2.733 | 4.136 |
| KMS-34 | | 4.226 | 3.551 | 3.889 |
| H929 | | 6.498 | 5.415 | 5.957 |
| L363 | | 3.673 | 3.603 | 3.638 |
| MM.1S | | 2.482 | 2.656 | 2.569 |
| MOLP-8 | | 2.734 | 2.703 | 2.719 |

TABLE 16-continued

As evidenced by the above data, the 594 compound is effective against a wide variety of cancer cells.

Example 25

In this example, different cell lines were subjected to in vitro cell proliferation assays as described in Example 8. In particular, the cell lines are identified in the following Table 17, and the tissue types were: Pancreatic; Endometrial; Triple-Negative Breast Cancer (TNBC); Non-Small-Cell Lung Carcinoma (NSCLC); Ovarian; Renal Cell Carcinoma (RCC); Cervical-Squamous Cell; Hemagglutinin and Neuraminidase (H&N-Squamous Cell); Germinal Center B Cell-Like Novo Diffuse Large B-Cell Lymphoma (GCB-DLBCL); Activated B-Cell—Diffuse Large B Cell Lymphoma (ABC-DLBCL); Human Myeloma; Human Myeloma Cell Line Lymphocyte-Like; Human Myeloma Cell Line Lymphocyte-Like Myeloma Pleural Effusion Infiltration; Human Multiple Myeloma; Plasma Cell Leukemia/Multiple Myeloma Epstein-Barr Nuclear Antigen-Negative (EBNA-Negative) and to Express mRNA for Proto-Oncogene B-Cell Lymphoma 2 (BCL2); Multiple Myeloma from Peripheral Blood Type IgD Lmabda.

These cell lines were tested with a series of diharmaline/aldehyde compounds in accordance with the invention. The aldehydes reacted with harmaline are listed in Table 17 as nos. 1-2, 4-15, 17-24, and 27-30, and the similarly numbered corresponding compounds are set forth after Table 17. See the Key below for details. The compounds are identified in the section following Table 17. In each case, the compounds were prepared by reacting overnight one part by weight harmaline and two parts by weight aldehyde in ethanol at 50° C.

| Key - Tables 17-19 | |
|---|---|
| * | Value was averaged using 100 µM trial value |
| HMCL | Human myeloma cell line |
| HMCL-A | Human myeloma cell line lymphocyte-like |
| HMCL-B | Human myeloma cell line lymphocyte-like myeloma pleural effusion infiltration (IgAk) |
| HMM | Human Multiple Myeloma |
| MMIgD | Multiple myeloma from peripheral blood type IgD lmabda |
| PCL/MM | Plasma cell leukemia/multiple myeloma EBNA-negative and to express mRNA for proto-oncogene BCL2 |
| SC | Squamous Cell |

TABLE 17

| Cell Line | Tissue Type (see Key) | Mean $IC_{50}$ (µM) Compounds | | | | | |
|---|---|---|---|---|---|---|---|
| | | 1 | 2 | 4 | 5 | 6 | 7 |
| MIA PaCa-2 | Pancreatic | 3.67 | 7.51 | 4.37 | 19.94 | 13.64 | 16.21 |
| ASPC-1 | Pancreatic | 6.44 | 15.25 | 10.99 | 15.73 | 100* | 40.91 |
| BxPC-3 | Pancreatic | 4.30 | 7.88 | 6.05 | 21.24 | 15.82 | 12.32 |
| AN3CA | Endometrial | 2.50 | 6.72 | 5.10 | 11.39 | 21.45 | 11.46 |
| HEC-1a | Endometrial | 9.27 | 21.61 | 16.26 | 26.98 | 100* | 71.10 |
| MDA-MB-231 | TNBC | 5.72 | 14.35 | 11.99 | 23.73 | 60.51 | 31.70 |
| MDA-MB-468 | TNBC | 4.39 | 9.90 | 6.27 | 14.73 | 14.54 | 11.18 |

TABLE 17-continued

| Cell Line | Tissue Type | | | | | |
|---|---|---|---|---|---|---|
| HCC70 | TNBC | 8.02 | 21.18 | 11.55 | 15.09 | 100* | 23.45 |
| H1975 (EGFR mut) | NSCLC | 6.54 | 19.49 | 14.09 | 28.11 | 100* | 60.83 |
| H1650 (EGFR mut) | NSCLC | 8.18 | 21.60 | 13.60 | 23.40 | 100* | 64.17 |
| A2780 | Ovarian | 5.90 | 16.95 | 11.50 | 24.12 | 100* | 32.96 |
| A2780CP | Ovarian | 4.45 | 20.22 | 10.78 | 24.62 | 70.66 | 33.68 |
| A498 | RCC | 9.91 | 16.76 | 12.71 | 22.76 | 100* | 29.34 |
| SiHA | Cervical - SC | 9.44 | 17.07 | 17.09 | 36.85 | 74.79 | 48.07 |
| FaDu | H&N - SC | 5.36 | 13.54 | 7.69 | 22.26 | 15.76 | 13.70 |
| DoHH-2 | GCB-DLBCL | 2.25 | 3.66 | 3.17 | 9.31 | 6.91 | 6.48 |
| OCI-LY3 | ABC-DLBCL | 3.42 | 6.58 | 5.57 | 12.35 | 11.30 | 11.42 |
| JIM1 | HMCL | 4.51 | 11.54 | 6.89 | 17.73 | 18.00 | 14.41 |
| KMM-1 | HMCL-A | 4.20 | 9.40 | 6.32 | 20.33 | 16.89 | 19.89 |
| KMS-34 | HMCL-B | 4.15 | 9.35 | 4.75 | 17.40 | 10.97 | 11.13 |
| RPMI-8226 | HMM | 1.87 | 8.51 | 4.09 | 19.31 | 10.35 | 11.79 |
| L363 | PCL/MM | 2.62 | 6.26 | 6.38 | 22.15 | 16.33 | 11.75 |
| MOLP-8 | MM IgD | 1.98 | 5.30 | 5.03 | 14.44 | 11.48 | 11.74 |

| Cell Line | Tissue Type (see Key) | Mean IC$_{50}$ (µM) Compounds | | | | |
|---|---|---|---|---|---|---|
| | | 8 | 9 | 10 | 11 | 12 |
| MIA PaCa-2 | Pancreatic | 24.16 | 52.61 | 11.88 | 11.67 | 11.66 |
| ASPC-1 | Pancreatic | 55.59 | 69.99 | 23.76 | 21.93 | 31.31 |
| BxPC-3 | Pancreatic | 21.95 | 30.00 | 27.62 | 11.53 | 11.26 |
| AN3CA | Endometrial | 20.21 | 29.33 | 31.66 | 8.74 | 5.36 |
| HEC-1a | Endometrial | 65.84 | 95.60 | 88.11 | 36.27 | 24.84 |
| MDA-MB-231 | TNBC | 24.35 | 45.82 | 43.67 | 13.47 | 11.35 |
| MDA-MB-468 | TNBC | 8.45 | 12.69 | 11.39 | 12.20 | 11.64 |
| HCC70 | TNBC | 24.92 | 38.95 | 50.24 | 27.23 | 22.03 |
| H1975 (EGFR mut) | NSCLC | 55.14 | 54.62 | 64.03 | 19.47 | 13.00 |
| H1650 (EGFR mut) | NSCLC | 59.92 | 79.70 | 13.27 | 26.18 | 21.58 |
| A2780 | Ovarian | 18.72 | 35.66 | 65.05 | 18.30 | 21.25 |
| A2780CP | Ovarian | 49.81 | 60.32 | 29.41 | 24.87 | 20.47 |
| A498 | RCC | 78.66 | 100* | 79.22* | 51.27 | 40.94 |
| SiHA | Cervical - SC | 100* | 100* | 100* | 15.86 | 50.19 |
| FaDu | H&N - SC | 16.11 | 72.34* | 49.71 | 16.45 | 18.20 |
| DoHH-2 | GCB-DLBCL | 6.37 | 9.76 | 2.78 | 4.32 | 3.72 |
| OCI-LY3 | ABC-DLBCL | 11.34 | 11.94 | 7.57 | 11.34 | 11.29 |
| JIM1 | HMCL | 14.29 | 40.60 | 20.09 | 11.53 | 6.04 |
| KMM-1 | HMCL-A | 13.23 | 16.01 | 11.08 | 12.05 | 10.61 |
| KMS-34 | HMCL-B | 11.05 | 11.37 | 4.87 | 11.14 | 7.19 |
| RPMI-8226 | HMM | 11.51 | 11.52 | 3.98 | 11.10 | 10.17 |
| L363 | PCL/MM | 12.59 | 19.73 | 35.62 | 11.58 | 10.91 |
| MOLP-8 | MM IgD | 10.09 | 6.59 | 8.28 | 10.75 | 3.88 |

| Cell Line | Tissue Type (see Key) | Mean IC$_{50}$ (µM) Compounds | | | | |
|---|---|---|---|---|---|---|
| | | 13 | 14 | 15 | 17 | 18 |
| MIA PaCa-2 | Pancreatic | 15.82 | 22.17 | 3.63 | 29.05 | 32.49 |
| ASPC-1 | Pancreatic | 82.50 | 53.09 | 5.45 | 37.85 | 43.78 |
| BxPC-3 | Pancreatic | 16.55 | 21.03 | 4.22 | 23.27 | 36.19 |
| AN3CA | Endometrial | 7.82 | 9.05 | 3.45 | 29.72 | 28.80 |
| HEC-1a | Endometrial | 17.43 | 28.71 | 13.14 | 46.90 | 49.81 |
| MDA-MB-231 | TNBC | 25.81 | 32.39 | 6.77 | 56.18 | 43.88 |
| MDA-MB-468 | TNBC | 12.62 | 16.85 | 6.70 | 42.23 | 48.66 |
| HCC70 | TNBC | 28.51 | 33.33 | 11.67 | 45.41 | 36.28 |
| H1975 (EGFR mut) | NSCLC | 14.03 | 33.61 | 12.09 | 44.48 | 59.06 |
| H1650 (EGFR mut) | NSCLC | 21.20 | 25.45 | 9.60 | 48.68 | 45.40 |
| A2780 | Ovarian | 11.76 | 21.24 | 8.45 | 40.55 | 26.34 |
| A2780CP | Ovarian | 23.45 | 24.27 | 7.63 | 39.07 | 31.23 |
| A498 | RCC | 91.59* | 54.70 | 15.24 | 89.27 | 93.43* |
| SiHA | Cervical - SC | 100* | 51.89 | 12.34 | 100* | 100* |
| FaDu | H&N-SC | 13.48 | 19.18 | 6.62 | 42.89 | 49.24 |
| DoHH-2 | GCB-DLBCL | 6.52 | 7.90 | 5.05 | 12.07 | 8.55 |
| OCI-LY3 | ABC-DLBCL | 11.69 | 15.39 | 6.32 | 33.77 | 24.97 |
| JIM1 | HMCL | 11.53 | 17.90 | 6.26 | 37.17 | 39.83 |
| KMM-1 | HMCL-A | 13.11 | 23.94 | 7.36 | 37.72 | 33.58 |
| KMS-34 | HMCL-B | 11.12 | 14.64 | 3.50 | 12.49 | 17.80 |
| RPMI-8226 | HMM | 9.10 | 7.53 | 2.95 | 11.97 | 12.27 |
| L363 | PCL/MM | 12.93 | 23.40 | 6.58 | 46.74 | 34.78 |
| MOLP-8 | MM IgD | 10.99 | 10.07 | 3.19 | 16.98 | 12.25 |

| Cell Line | Tissue Type (see Key) | Mean IC$_{50}$ (µM) Compounds | | | | |
|---|---|---|---|---|---|---|
| | | 19 | 20 | 21 | 22 | 23 |
| MIA PaCa-2 | Pancreatic | 36.62 | 2.72 | 4.41 | 5.93 | 5.64 |
| ASPC-1 | Pancreatic | 45.46 | 3.66 | 5.11 | 8.61 | 9.26 |
| BxPC-3 | Pancreatic | 36.21 | 2.25 | 3.58 | 5.37 | 4.97 |

TABLE 17-continued

| Cell Line | Tissue Type | | | | |
|---|---|---|---|---|---|
| AN3CA | Endometrial | 22.78 | 1.86 | 3.93 | 4.15 | 2.38 |
| HEC-1a | Endometrial | 45.04 | 10.99 | 11.67 | 11.78 | 12.52 |
| MDA-MB-231 | TNBC | 41.75 | 4.71 | 5.95 | 7.12 | 5.94 |
| MDA-MB-468 | TNBC | 48.89 | 5.12 | 6.74 | 11.45 | 6.54 |
| HCC70 | TNBC | 50.90 | 6.35 | 10.86 | 13.18 | 10.87 |
| H1975 (EGFR mut) | NSCLC | 54.97 | 6.41 | 11.36 | 11.49 | 8.23 |
| H1650 (EGFR mut) | NSCLC | 56.84 | 4.44 | 8.22 | 11.12 | 5.89 |
| A2780 | Ovarian | 22.06 | 3.75 | 7.51 | 9.16 | 5.07 |
| A2780CP | Ovarian | 27.51 | 5.06 | 9.87 | 9.30 | 6.49 |
| A498 | RCC | 89.50 | 11.28 | 11.69 | 21.57 | 21.44 |
| SiHA | Cervical - SC | 75.94 | 6.73 | 11.46 | 11.68 | 11.66 |
| FaDu | H&N - SC | 44.44 | 4.05 | 6.26 | 11.09 | 6.14 |
| DoHH-2 | GCB-DLBCL | 10.22 | 1.88 | 3.61 | 4.26 | 3.73 |
| OCI-LY3 | ABC-DLBCL | 20.56 | 3.85 | 4.94 | 9.73 | 5.45 |
| JIM1 | HMCL | 42.85 | 4.28 | 5.55 | 7.35 | 6.32 |
| KMM-1 | HMCL-A | 25.60 | 3.66 | 6.41 | 6.21 | 3.98 |
| KMS-34 | HMCL-B | 31.17 | 3.26 | 3.82 | 3.90 | 3.47 |
| RPMI-8226 | HMM | 10.58 | 1.27 | 3.56 | 2.06 | 1.28 |
| L363 | PCL/MM | 36.82 | 3.89 | 5.15 | 6.12 | 4.72 |
| MOLP-8 | MM IgD | 9.81 | 2.28 | 3.69 | 3.83 | 3.19 |

| Cell Line | Tissue Type (see Key) | Mean IC$_{50}$ (µM) Compounds | | | | |
|---|---|---|---|---|---|---|
| | | 24 | 27 | 28 | 29 | 30 |
| MIA PaCa-2 | Pancreatic | 12.98 | 5.83 | 4.51 | 11.27 | 5.47 |
| ASPC-1 | Pancreatic | 32.67 | 7.34 | 7.22 | 10.77 | 10.97 |
| BxPC-3 | Pancreatic | 10.76 | 4.61 | 6.58 | 11.46 | 7.73 |
| AN3CA | Endometrial | 11.23 | 4.36 | 4.49 | 8.07 | 5.01 |
| HEC-1a | Endometrial | 48.18 | 11.65 | 10.55 | 100* | 9.91 |
| MDA-MB-231 | TNBC | 20.67 | 7.39 | 10.14 | 13.94 | 11.06 |
| MDA-MB-468 | TNBC | 16.55 | 10.76 | 8.43 | 100* | 7.46 |
| HCC70 | TNBC | 25.74 | 11.37 | 11.92 | 39.98 | 18.53 |
| H1975 (EGFR mut) | NSCLC | 11.66 | 11.50 | 100* | 13.64 | 11.39 |
| H1650 (EGFR mut) | NSCLC | 12.48 | 11.34 | 11.34 | 13.88 | 16.58 |
| A2780 | Ovarian | 10.62 | 8.09 | 100* | 12.11 | 6.45 |
| A2780CP | Ovarian | 17.80 | 11.10 | 7.02 | 11.45 | 8.55 |
| A498 | RCC | 83.81* | 11.74 | 16.31 | 42.53 | 17.11 |
| SiHA | Cervical - SC | 58.90 | 11.60 | 13.32 | 46.86 | 17.76 |
| FaDu | H&N-SC | 11.68 | 11.15 | 5.64 | 11.41 | 6.82 |
| DoHH-2 | GCB-DLBCL | 5.58 | 2.52 | 2.50 | 2.09 | 5.36 |
| OCI-LY3 | ABC-DLBCL | 11.43 | 9.27 | 6.17 | 9.63 | 7.28 |
| JIM1 | HMCL | 56.09 | 11.36 | 8.08 | 16.58 | 7.07 |
| KMM-1 | HMCL-A | 11.26 | 7.18 | 6.43 | 7.71 | 5.81 |
| KMS-34 | HMCL-B | 7.84 | 4.44 | 4.44 | 4.40 | 4.81 |
| RPMI-8226 | HMM | 5.05 | 3.21 | 3.50 | 4.44 | 4.30 |
| L363 | PCL/MM | 13.19 | 7.83 | 4.75 | 11.43 | 5.57 |
| MOLP-8 | MM IgD | 10.57 | 3.97 | 3.71 | 5.89 | 2.70 |

Compounds:

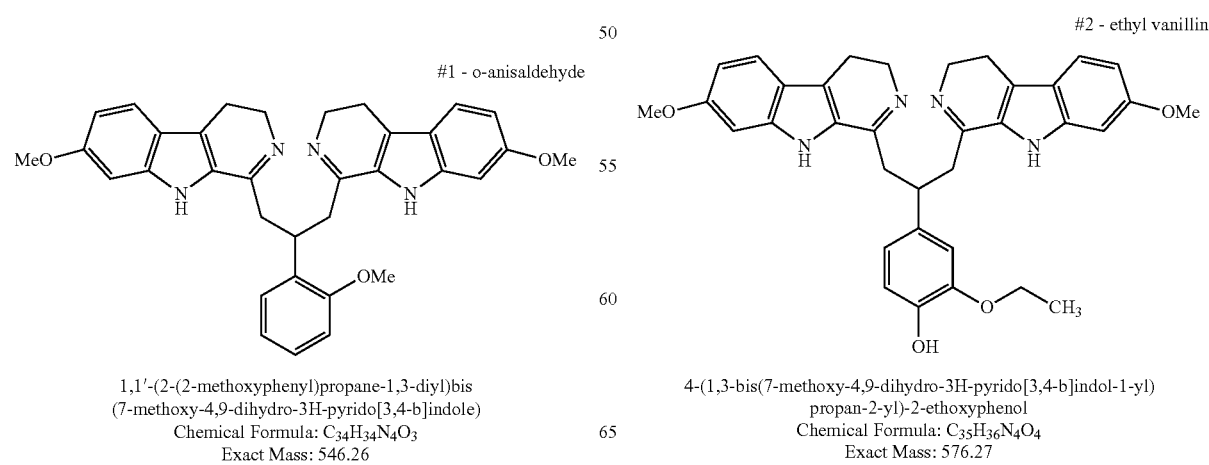

1 - o-anisaldehyde 1,1'-(2-(2-methoxyphenyl)propane-1,3-diyl)bis(7-methoxy-4,9-dihydro-3H-pyrido[3,4-b]indole)
Chemical Formula: C$_{34}$H$_{34}$N$_4$O$_3$
Exact Mass: 546.26

2 - ethyl vanillin 4-(1,3-bis(7-methoxy-4,9-dihydro-3H-pyrido[3,4-b]indol-1-yl)propan-2-yl)-2-ethoxyphenol
Chemical Formula: C$_{35}$H$_{36}$N$_4$O$_4$
Exact Mass: 576.27

-continued

4 -veratraldehyde

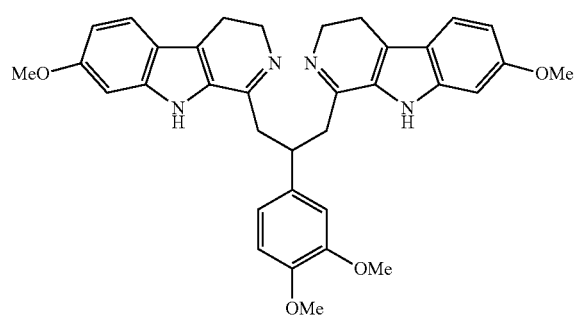

1,1'-(2-(3,4-dimethoxyphenyl)propane-1,3-diyl)bis
(7-methoxy-4,9-dihydro-3H-pyrido[3,4-b]indole)
Chemical Formula: $C_{35}H_{36}N_4O_4$
Exact Mass: 576.27

5 - 5-nitrovanillin

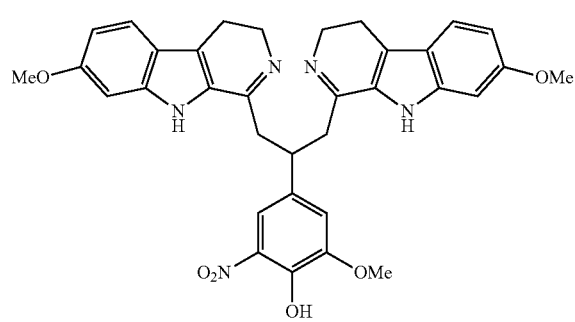

4-(1,3-bis(7-methoxy-4,9-dihydro-3H-pyrido[3,4-b]indol-1-yl)
propan-2-yl)-2-methoxy-6-nitrophenol
Chemical Formula: $C_{34}H_{33}N_5O_6$
Exact Mass: 607.24

6 -- vanillin acetate

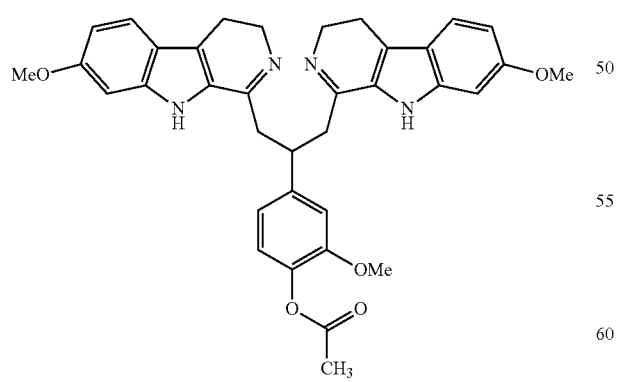

4-(1,3-bis(7-methoxy-4,9-dihydro-3H-pyrido[3,4-b]indol-1-yl)
propan-2-yl)-2-methoxyphenyl acetate
Chemical Formula: $C_{36}H_{36}N_4O_5$
Exact Mass: 604.27

-continued

7 - 3-hydroxy-4-methoxybenzaldehyde

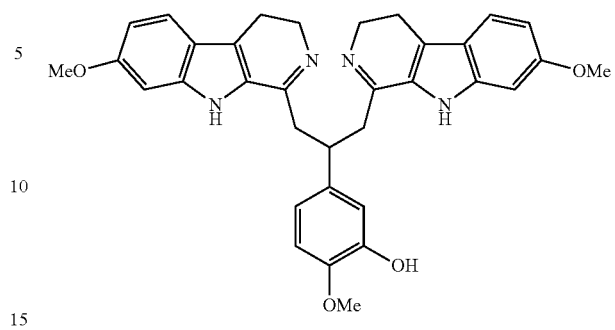

5-(1,3-bis(7-methoxy-4,9-dihydro-3H-pyrido[3,4-b]indol-1-yl)
propan-2-yl)-2-methoxyphenol
Chemical Formula: $C_{34}H_{34}N_4O_4$
Exact Mass: 562.26

8 -2 -hydroxy-4-methoxybenzaldehyde

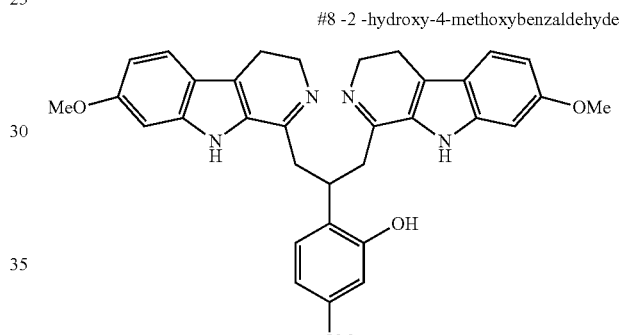

2-(1,3-bis(7-methoxy-4,9-dihydro-3H-pyrido[3,4-b]indol-1-yl)
propan-2-yl)-5-methoxyphenol
Chemical Formula: $C_{34}H_{34}N_4O_4$
Exact Mass: 562.26

9 - 3-chloro-4-hydroxy-5-methoxybenzaldehyde

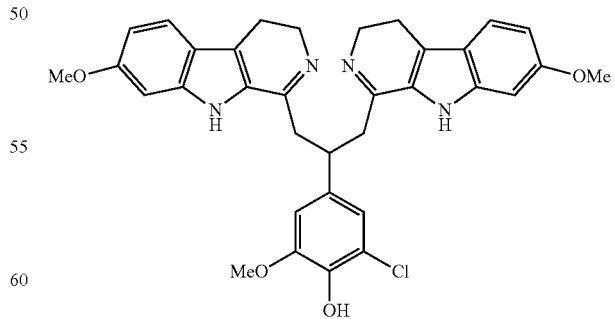

4-(1,3-bis(7-methoxy-4,9-dihydro-3H-pyrido[3,4-b]indol-1-yl)
propan-2-yl)-2-chloro-6-methoxyphenol
Chemical Formula: $C_{34}H_{33}ClN_4O_4$
Exact Mass: 596.22

-continued

10 - 3-benzyloxy-4-methoxybenzaldehyde

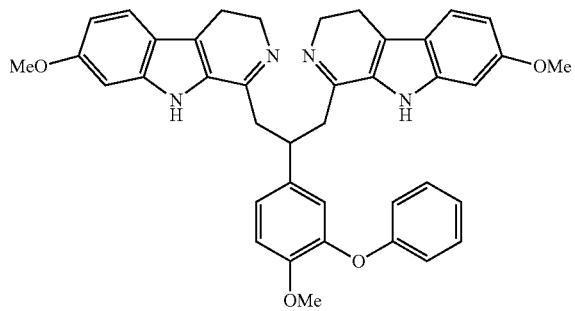

1,1'-(2-(4-methoxy-3-phenoxyphenyl)propane-1,3-diyl)bis
(7-methoxy-4,9-dihydro-3H-pyrido[3,4-b]indole)
Chemical Formula: $C_{40}H_{38}N_4O_4$
Exact Mass: 638.29

11 -- 5-hydroxy-3,4dimethoxybenzaldehyde

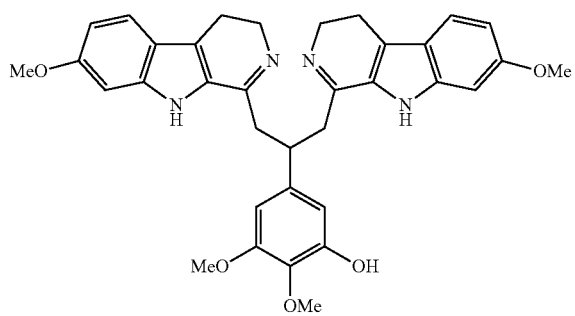

5-(1,3-bis(7-methoxy-4,9-dihydro-3H-pyrido[3,4-b]indol-1-yl)
propan-2-yl)-2,3-dimethoxyphenol
Chemical Formula: $C_{35}H_{36}N_4O_5$
Exact Mass: 592.27

12 -- 5-bromovanillin

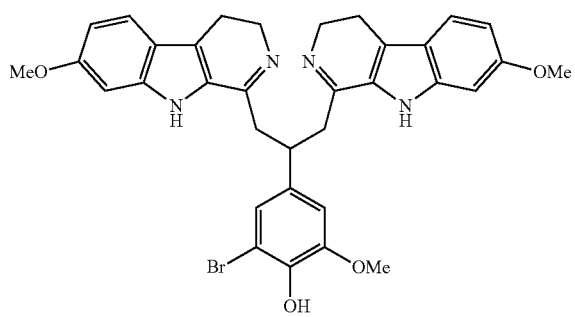

4-(1,3-bis(7-methoxy-4,9-dihydro-3H-pyrido[3,4-b]indol-1-yl)
propan-2-yl)-2-bromo-6-methoxyphenol
Chemical Formula: $C_{34}H_{33}BrN_4O_4$
Exact Mass: 640.17

-continued

13 - 2-bromo-3-hydroxy-4-methoxybenzaldehyde

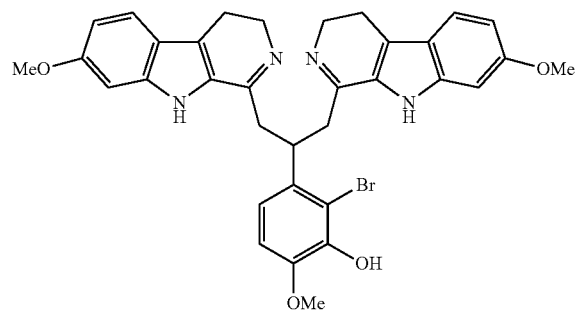

3-(1,3-bis(7-methoxy-4,9-dihydro-3H-pyrido[3,4-b]indol-1-yl)
propan-2-yl)-2-bromo-6-methoxyphenol
Chemical Formula: $C_{34}H_{33}BrN_4O_4$
Exact Mass: 640.17

14 --3-hydroxy-2-iodo-4-methoxybenzaldehyde

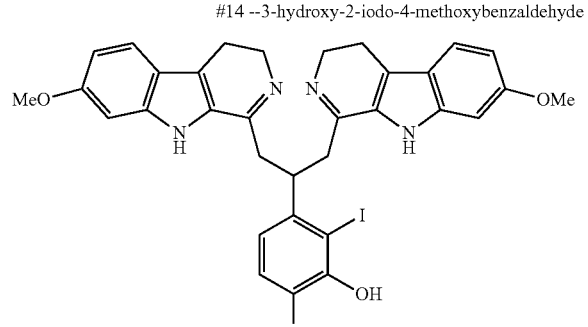

3-(1,3-bis(7-methoxy-4,9-dihydro-3H-pyrido[3,4-b]indol-1-yl)
propan-2-yl)-2-iodo-6-methoxyphenol
Chemical Formula: $C_{34}H_{33}IN_4O_4$
Exact Mass: 688.15

15 -m-anisaldehyde

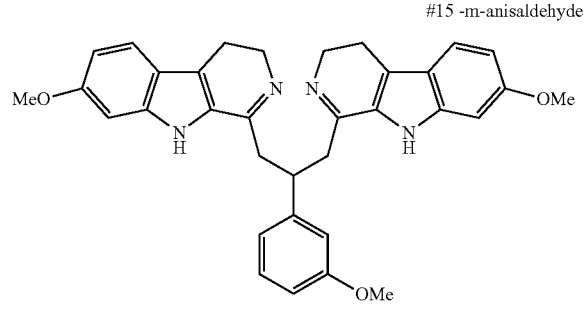

1,1'-(2-(3-methoxyphenyl)propane-1,3-diyl)bis
(7-methoxy-4,9-dihydro-3H-pyrido[3,4-b]indole)
Chemical Formula: $C_{34}H_{34}N_4O_3$
Exact Mass: 546.26

123
-continued

17 -- 4-phenoxybenzaldehyde

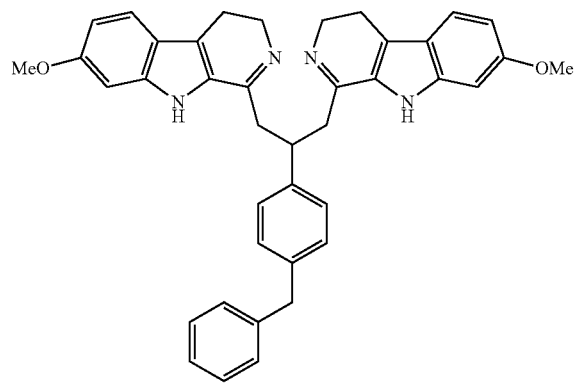

1,1'-(2-(4-phenoxyphenyl)propane-1,3-diyl)bis
(7-methoxy-4,9-dihydro-3H-pyrido[3,4-b]indole)
Chemical Formula: $C_{39}H_{36}N_4O_3$
Exact Mass: 608.28

18 -- biphenyl-3-carboxaldehyde

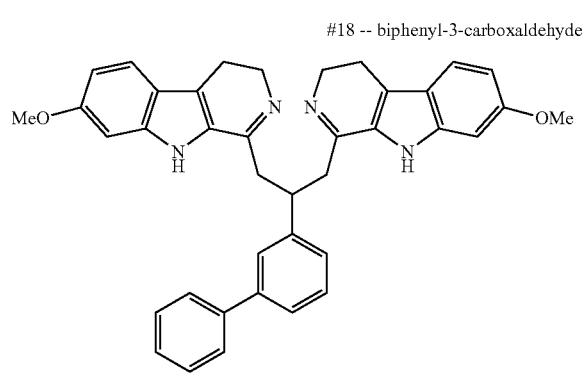

1,1'-(2-([1,1'-biphenyl]-3-yl)propane-1,3-diyl)bis
(7-methoxy-4,9-dihydro-3H-pyrido[3,4-b]indole)
Chemical Formula: $C_{39}H_{36}N_4O_2$
Exact Mass: 592.28

19 -4-fluoro-3-phenoxybenzaldehyde

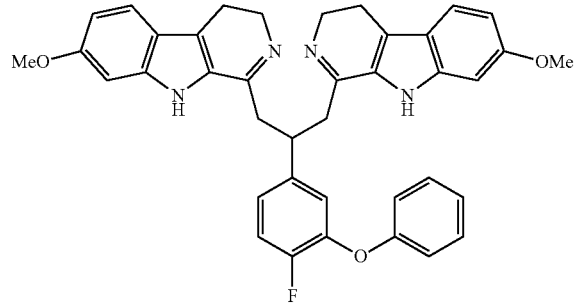

1,1'-(2-(4-fluoro-3-phenoxyphenyl)propane-1,3-diyl)bis
(7-methoxy-4,9-dihydro-3H-pyrido[3,4-b]indole)
Chemical Formula: $C_{39}H_{35}FN_4O_3$
Exact Mass: 626.27

124
-continued

20 -3-fluorobenzaldehyde

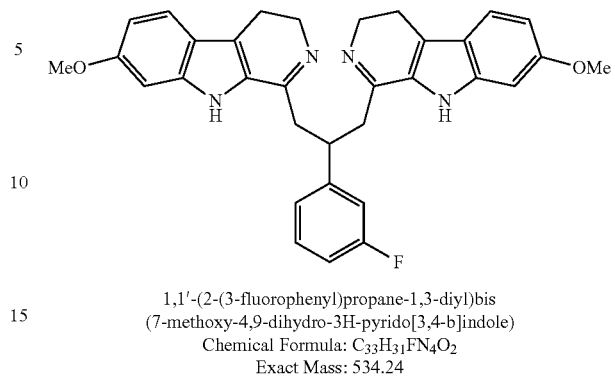

1,1'-(2-(3-fluorophenyl)propane-1,3-diyl)bis
(7-methoxy-4,9-dihydro-3H-pyrido[3,4-b]indole)
Chemical Formula: $C_{33}H_{31}FN_4O_2$
Exact Mass: 534.24

21 -4-fluorobenzaldehyde 1,1'-(2-(4-fluorophenyl)propane-1,3-diyl)bis
(7-methoxy-4,9-dihydro-3H-pyrido[3,4-b]indole)
Chemical Formula: $C_{33}H_{31}FN_4O_2$
Exact Mass: 534.24

22 - 3,5-difluorobenzaldehyde 1,1'-(2-(3,5-difluorophenyl)propane-1,3-diyl)bis
(7-methoxy-4,9-dihydro-3H-pyrido[3,4-b]indole)
Chemical Formula: $C_{33}H_{30}F_2N_4O_2$
Exact Mass: 552.23

23 -2,4,5trifluorobenzaldehyd

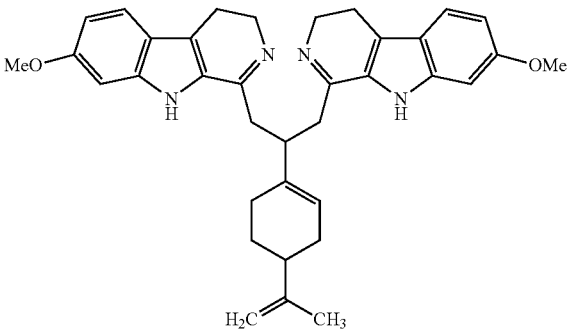

1,1'-(2-(2,4,5-trifluorophenyl)propane-1,3-diyl)bis
(7-methoxy-4,9-dihydro-3H-pyrido[3,4-b]indole)
Chemical Formula: $C_{33}H_{29}F_3N_4O_2$
Exact Mass: 570.22

24

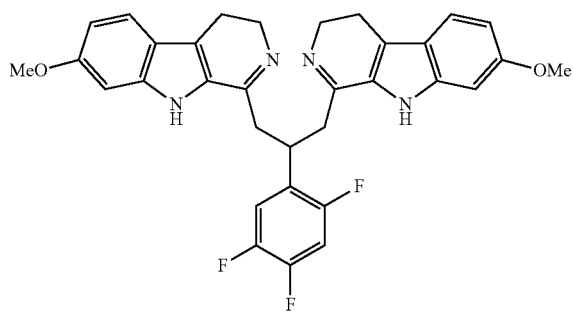

1,1'-(2-(perfluorophenyl)propane-1,3-diyl)bis
(7-methoxy-4,9-dihydro-3H-pyrido[3,4-b]indole)
Chemical Formula: $C_{33}H_{27}F_5N_4O_2$
Exact Mass: 606.21

27 -4-chlorobenzaldehyde

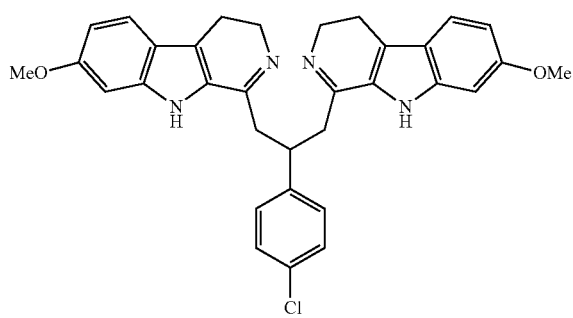

1,1'-(2-(4-chlorophenyl)propane-1,3-diyl)bis
(7-methoxy-4,9-dihydro-3H-pyrido[3,4-b]indole)
Chemical Formula: $C_{33}H_{31}ClN_4O_2$
Exact Mass: 550.21

28 - perillaldehyde

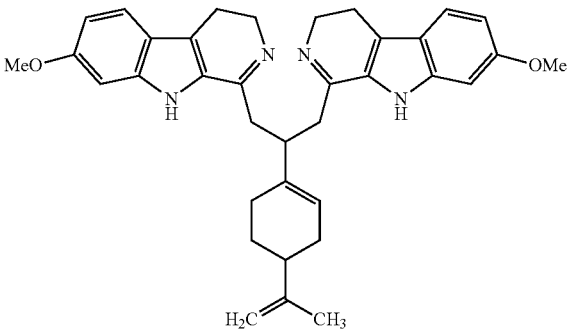

1,1'-(2-(4-(prop-1-en-2-yl)cyclohex-1-en-1-yl)propane-1,3-diyl)bis
(7-methoxy-4,9-dihydro-3H-pyrido[3,4-b]indole)
Chemical Formula: $C_{36}H_{40}N_4O_2$
Exact Mass: 560.32

29 -- cuminaldehyde

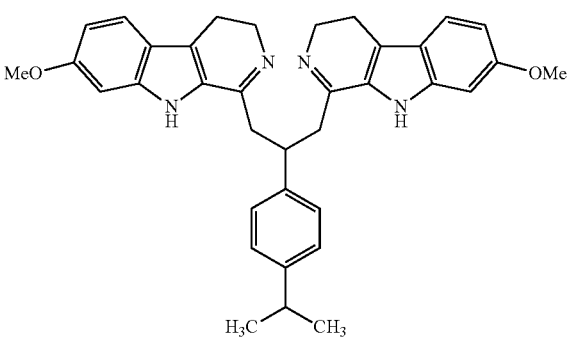

1,1'-(2-(4-isopropylphenyl)propane-1,3-diyl)bis
(7-methoxy-4,9-dihydro-3H-pyrido[3,4-b]indole)
Chemical Formula: $C_{36}H_{38}N_4O_2$
Exact Mass: 558.30

30 -cyclohexane carboxaldehyde

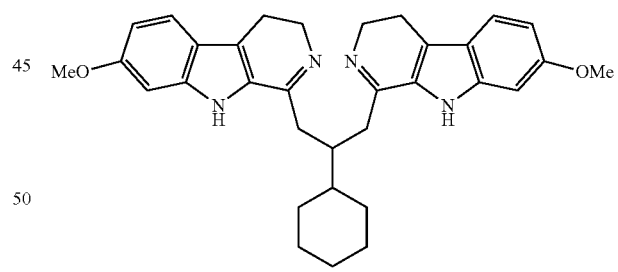

1,1'-(2-cyclohexylpropane-1,3-diyl)bis
(7-methoxy-4,9-dihydro-3H-pyrido[3,4-b]indole)
Chemical Formula: $C_{33}H_{38}N_4O_2$
Exact Mass: 522.30

Example 26

In this Example, a compound was produced via the reaction between a fused bicyclic compound, namely 1-methyl-3,4-dihydroisoquinoline and vanillin, as described in Example 25. This compound was tested against the same cell lines of Example 25, giving the following results.

TABLE 18

| Cell Line | Tissue Type (see Key) | Mean IC$_{50}$ (µM)SAR02 |
|---|---|---|
| MIA PaCa-2 | Pancreatic | 14.67 |
| ASPC-1 | Pancreatic | 18.68 |
| BxPC-3 | Pancreatic | 10.74 |
| AN3CA | Endometrial | 14.16 |
| HEC-1a | Endometrial | 23.35 |
| MDA-MB-231 | TNBC | 22.02 |
| MDA-MB-468 | TNBC | 13.23 |
| HCC70 | TNBC | 27.82 |
| H1975 (EGFR mut) | NSCLC | 17.88 |
| H1650 (EGFR mut) | NSCLC | 8.85 |
| A2780 | Ovarian | 10.41 |
| A2780CP | Ovarian | 23.82 |
| A498 | RCC | 31.12 |
| SiHA | Cervical - SC | 35.90 |
| FaDu | H&N - SC | 14.30 |
| DoHH-2 | GCB-DLBCL | 10.06 |
| OCI-LY3 | ABC-DLBCL | 7.28 |
| JIM1 | HMCL | 14.97 |
| KMM-1 | HMCL-A | 12.32 |
| KMS-34 | HMCL-B | 5.31 |
| RPMI-8226 | HMM | 6.06 |
| L363 | PCL/MM | 12.21 |
| MOLP-8 | MM IgD | 9.82 |

Example 27

In this Example, 200 mg of 4-methyl-6,7-dihydrothienol[3,2-c]pyridine of the formula

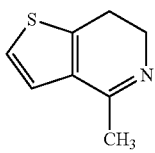

was reacted with an excess of vanillin in methanol at 100° C. by microwaving the reaction mixture for 30 minutes. Unexpectedly, a spirocyclic solid compound was recovered having the formula

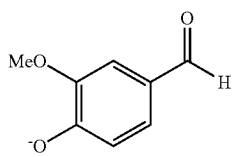

4-formyl-2-methoxyphenolate
Chemical Formula: C$_8$H$_7$O$_3^-$
Exact Mass: 151.04
Molecular Weight: 151.14

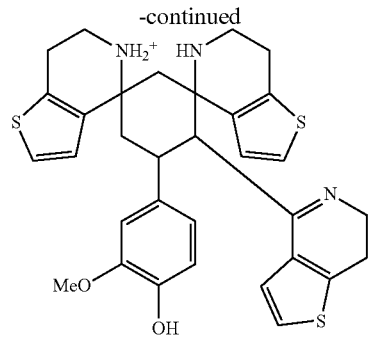

4'-(6,7-dihydrothieno[3,2-c]pyridin-4-yl)-5'-(4-hydroxy-3-methoxyphenyl)6,6'',7,7''-tetrahydro-5H,5''H-dispiro[thieno[3,2-c]pyridine-4,1'-cyclohexane-3',4''-thieno[3,2-c]pyridin]-5-ium
Chemical Formula: C$_{32}$H$_{34}$N$_3$O$_2$S$_3^+$
Exact Mass: 588.18
Molecular Weight: 588.82 which was the MW 588.82 species hydrogen bonded with the MW 151.14 species. Note that the MW 588.82 species comprised a single vanillin moiety with three moieties of 4-methyl-6,7-dihydrothienol[3,2-c]pyridine. The spirocyclic compound (designated HRM 05) was tested by the above in vitro cell proliferation assay against a number of different tissue types, with the following results:

TABLE 19

| Cell Line | Tissue Type (see Key) | Mean IC$_{50}$ (µM)HRM05 |
|---|---|---|
| MIA PaCa-2 | Pancreatic | 12.20 |
| ASPC-1 | Pancreatic | 20.22 |
| BxPC-3 | Pancreatic | TBD |
| AN3CA | Endometrial | TBD |
| HEC-1a | Endometrial | TBD |
| MDA-MB-231 | TNBC | TBD |
| MDA-MB-468 | TNBC | TBD |
| HCC70 | TNBC | TBD |
| H1975 (EGFR mut) | NSCLC | TBD |
| H1650 (EGFR mut) | NSCLC | TBD |
| A2780 | Ovarian | 15.86 |
| A2780CP | Ovarian | TBD |
| A498 | RCC | TBD |
| SiHA | Cervical - SC | TBD |
| FaDu | H&N - SC | 13.97 |
| DoHH-2 | GCB-DLBCL | 17.59 |
| OCI-LY3 | ABC-DLBCL | TBD |
| JIM1 | HMCL | 17.58 |
| KMM-1 | HMCL-A | 12.45 |
| KMS-34 | HMCL-B | TBD |
| RPMI-8226 | HMM | TBD |
| L363 | PCL/MM | 13.66 |
| MOLP-8 | MM IgD | TBD |

TBD = To Be Determined

While the anti-cancer properties of the compositions of the invention have been demonstrated against certain cancers, it is considered that the invention may be applicable to virtually all cancers, such as the following: Acute Lymphoblastic Leukemia, Adult; Acute Lymphoblastic Leukemia, Childhood; Acute Myeloid Leukemia, Adult; Acute Myeloid Leukemia, Childhood; Adrenocortical Carcinoma; Adrenocortical Carcinoma, Childhood; Adolescents, Cancer in; AIDS-Related Cancers; AIDS-Related Lymphoma; Anal Cancer; Appendix Cancer; Astrocytomas, Childhood; Atypical Teratoid/Rhabdoid Tumor, Childhood, Central Nervous System; Basal Cell Carcinoma; Bile Duct Cancer, Extrahepatic; Bladder Cancer; Bladder Cancer, Childhood; Bone Cancer, Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Brain Tumor, Central Nervous System Embryonal Tumors, Childhood; Brain Tumor, Astrocytomas, Childhood; Brain Tumor, Craniopharyngioma, Childhood; Brain Tumor, Ependymoblastoma, Childhood; Brain Tumor, Ependymoma, Childhood; Brain Tumor, Medulloblastoma, Childhood; Brain Tumor, Medulloepithelioma, Childhood; Brain Tumor, Pineal Parenchymal Tumors of Intermediate Differentiation, Childhood; Brain Tumor, Supratentorial Primitive Neuroectodermal Tumors and Pineoblastoma, Childhood; Brain and Spinal Cord Tumors, Childhood (Other); Breast Cancer; Breast Cancer and Pregnancy; Breast Cancer, Childhood; Breast Cancer, Male; Bronchial Tumors, Childhood; Burkitt Lymphoma; Carcinoid Tumor, Childhood; Carcinoid Tumor, Gastrointestinal; Carcinoma of Unknown Primary; Central Nervous System Atypical Teratoid/Rhabdoid Tumor, Childhood; Central Nervous System Embryonal Tumors, Childhood; Central Nervous System (CNS) Lymphoma, Primary; Cervical Cancer; Cervical Cancer, Childhood; Childhood Cancers; Chordoma, Childhood; Chronic Lymphocytic Leukemia; Chronic Myelogenous Leukemia; Chronic Myeloproliferative Disorders; Colon Cancer; Colorectal Cancer, Childhood; Craniopharyngioma, Childhood; Cutaneous T-Cell Lymphoma; Embryonal Tumors, Central Nervous System, Childhood; Endometrial Cancer; Ependymoblastoma, Childhood; Ependymoma, Childhood; Esophageal Cancer; Esophageal Cancer, Childhood; Esthesioneuroblastoma, Childhood; Ewing Sarcoma Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Gastrointestinal Stromal Tumor (GIST); Gastrointestinal Stromal Cell Tumor, Childhood; Germ Cell Tumor, Extracranial, Childhood; Germ Cell Tumor, Extragonadal; Germ Cell Tumor, Ovarian; Gestational Trophoblastic Tumor; Glioma, Adult; Glioma, Childhood Brain Stem; Hairy Cell Leukemia; Head and Neck Cancer; Heart Cancer, Childhood; Hepatocellular (Liver) Cancer, Adult (Primary); Hepatocellular (Liver) Cancer, Childhood (Primary); Histiocytosis, Langerhans Cell; Hodgkin Lymphoma, Adult; Hodgkin Lymphoma, Childhood; Hypopharyngeal Cancer; Intraocular Melanoma; Islet Cell Tumors (Endocrine Pancreas); Kaposi Sarcoma; Kidney (Renal Cell) Cancer; Kidney Cancer, Childhood; Langerhans Cell Histiocytosis; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin, Adult; Lymphoma, Hodgkin, Childhood; Lymphoma, Non-Hodgkin, Adult; Lymphoma, Non-Hodgkin, Childhood; Lymphoma, Primary Central Nervous System (CNS); Macroglobulinemia, Waldenstrom; Malignant Fibrous Histiocytoma of Bone and Osteosarcoma; Medulloblastoma, Childhood; Medulloepithelioma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndromes, Childhood; Multiple Myeloma/Plasma Cell Neoplasm; Mycosis Fungoides; Myelodysplastic Syndromes; Myelodysplastic/Myeloproliferative Neoplasms; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin Lymphoma, Adult; Non-Hodgkin Lymphoma, Childhood; Non-Small Cell Lung Cancer; Oral Cancer, Childhood; Oral Cavity Cancer, Lip and; Oropharyngeal Cancer; Osteosarcoma and Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell Tumors; Papillomatosis, Childhood; Paranasal Sinus and Nasal Cavity Cancer; Parathyroid Cancer; Penile Cancer; Pharyngeal Cancer; Pineal Parenchymal Tumors of Intermediate Differentiation, Childhood; Pineoblastoma and Supratentorial Primitive Neuroectodermal Tumors, Childhood; Pituitary Tumor; Plasma Cell Neoplasm/Multiple Myeloma; Pleuropulmonary Blastoma, Childhood; Pregnancy and Breast Cancer; Primary Central Nervous System (CNS) Lymphoma; Prostate Cancer; Rectal Cancer; Renal Cell (Kidney) Cancer; Renal Pelvis and Ureter, Transitional Cell Cancer; Respiratory Tract Cancer with Chromosome 15 Changes; Retinoblastoma; Rhabdomyosarcoma, Childhood; Salivary Gland Cancer; Salivary Gland Cancer, Childhood; Sarcoma, Ewing Sarcoma Family of Tumors; Sarcoma, Kaposi; Sarcoma, Soft Tissue, Adult; Sarcoma, Soft Tissue, Childhood; Sarcoma, Uterine; Sézary Syndrome; Skin Cancer (Nonmelanoma); Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Cell Carcinoma; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Testicular Cancer, Childhood; Throat Cancer; Thymoma and Thymic Carcinoma; Thymoma and Thymic Carcinoma, Childhood; Thyroid Cancer; Thyroid Cancer, Childhood; Transitional Cell Cancer of the Renal Pelvis and Ureter; Trophoblastic Tumor, Gestational; Unknown Primary Site, Carcinoma of, Adult; Unknown Primary Site, Cancer of, Childhood; Unusual Cancers of Childhood; Ureter and Renal Pelvis, Transitional Cell Cancer; Urethral Cancer; Uterine Cancer, Endometrial; Uterine Sarcoma; Vaginal Cancer; Vaginal Cancer, Childhood; Vulvar Cancer; Waldenström Macroglobulinemia; Wilms Tumor; Women's Cancers.

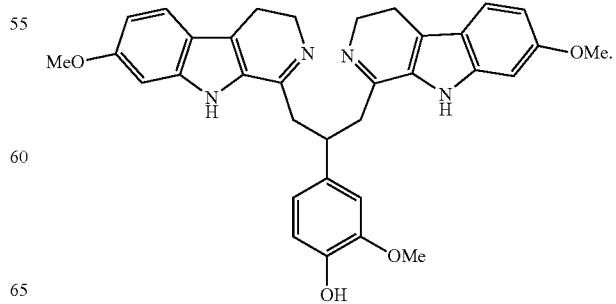

7. The compound of claim 5, said compound having the structure
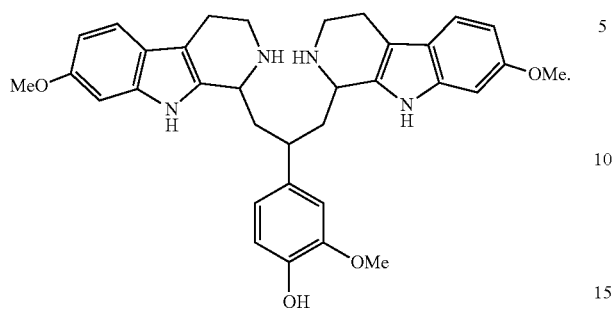

We claim:

1. An anti-cancer composition comprising a therapeutic compound selected from

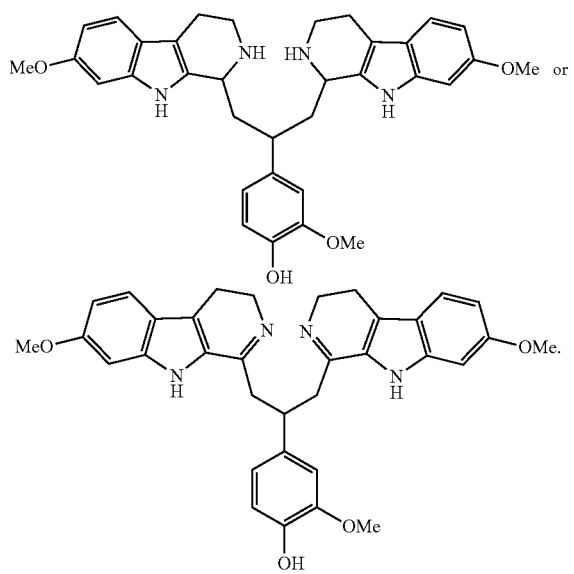

2. The composition of claim 1, said composition including another ingredient selected from the group consisting of active agents, preservatives, buffering agents, salts, carriers, excipients, diluents, and other pharmaceutically acceptable ingredients, and combinations thereof, wherein the designation ═══ refers to the fact that there may optionally be: 1) zero, one, or two non-fused double bonds at one or two valence-permitted positions around either or both of the six-membered, N-containing rings; 2) a double bond between either or both of the N-containing rings and the adjacent carbons of the central moiety, with or without an additional non-fused double bond at any valence-permitted position around the corresponding N-containing ring, provided that in instances 2) where there is a double bond between the nitrogen atom of either N-containing ring and an adjacent carbon atom thereof, R4 is nothing, provided, if there is no such nitrogen double bond, the corresponding R4 is selected from the group consisting of H, OH, and C1-C12 alkyl groups; or 3) either or both of the N-containing rings are free of non-fused double bonds and each R4 is independently selected from the group consisting of H, OH, and C1-C12 alkyl groups.

3. The composition of claim 1, said structure being

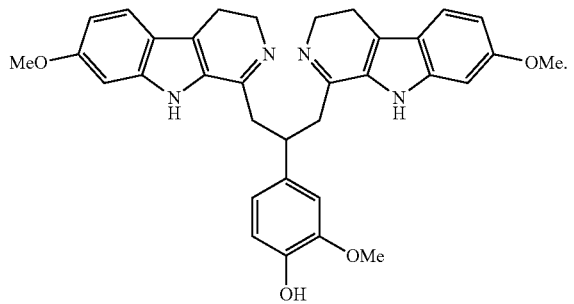 [SMILES: COc1ccc2c3c([nH]c2c1)C(CC(CC1=NCCc2c1[nH]c1cc(OC)ccc21)c1ccc(O)c(OC)c1)=NCC3]

4. The composition of claim 1, said therapeutic compound having the structure

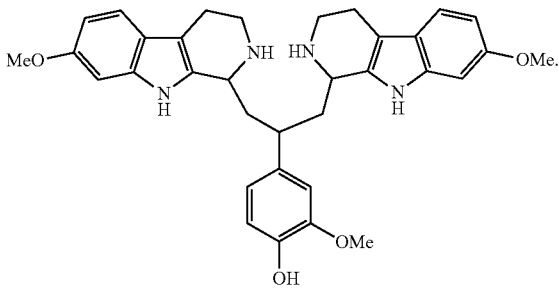 [SMILES: COc1ccc2c3c([nH]c2c1)C(CC(CC1NCCc2c1[nH]c1cc(OC)ccc21)c1ccc(O)c(OC)c1)NCC3]

5. A compound selected from

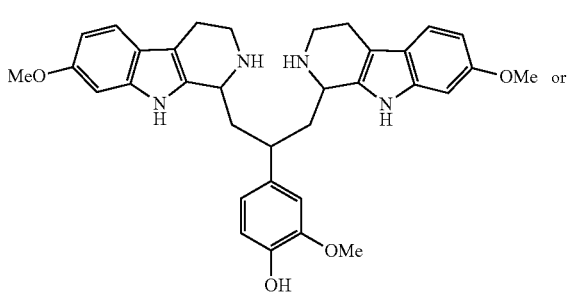

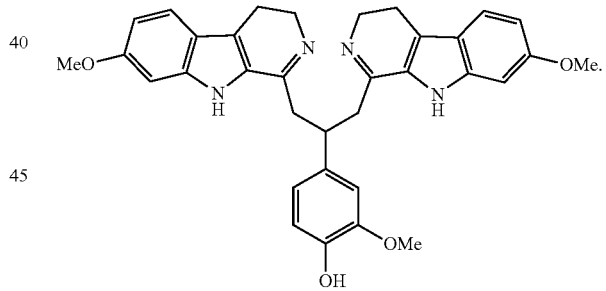

6. The compound of claim 5, said structure being